(12) United States Patent
An et al.

(10) Patent No.: US 12,416,042 B2
(45) Date of Patent: Sep. 16, 2025

(54) METHOD FOR DETECTING METHYLATION OF SDC2 GENE

(71) Applicant: GENOMICTREE, INC., Daejeon (KR)

(72) Inventors: Sungwhan An, Daejeon (KR); Taejeong Oh, Daejeon (KR)

(73) Assignee: GENOMICTREE, INC., Daejeon (KR)

( * ) Notice: Subject to any disclaimer, the term of this patent is extended or adjusted under 35 U.S.C. 154(b) by 915 days.

(21) Appl. No.: 17/616,211

(22) PCT Filed: May 22, 2020

(86) PCT No.: PCT/KR2020/006692
§ 371 (c)(1),
(2) Date: Dec. 3, 2021

(87) PCT Pub. No.: WO2020/256293
PCT Pub. Date: Dec. 24, 2020

(65) Prior Publication Data
US 2022/0325335 A1   Oct. 13, 2022

(30) Foreign Application Priority Data
Jun. 18, 2019   (KR) .................. 10-2019-0072080

(51) Int. Cl.
*C12Q 1/6848* (2018.01)
*C12Q 1/6827* (2018.01)
*C12Q 1/6886* (2018.01)

(52) U.S. Cl.
CPC .......... *C12Q 1/6848* (2013.01); *C12Q 1/6827* (2013.01); *C12Q 1/6886* (2013.01); *C12Q 2600/154* (2013.01)

(58) Field of Classification Search
CPC ............ C12Q 2600/154; C12Q 1/6876; C12Q 1/6827; C12Q 2531/113; C12Q 2523/125
See application file for complete search history.

(56) References Cited

U.S. PATENT DOCUMENTS

| 2012/0264640 A1 | 10/2012 | An et al. |
| 2017/0335405 A1 | 11/2017 | An et al. |
| 2019/0010557 A1 | 1/2019 | Zou et al. |

FOREIGN PATENT DOCUMENTS

| CN | 104812899 A | 7/2015 |
| CN | 105452485 A | 3/2016 |
| CN | 108410980 A | 8/2018 |
| CN | 108642180 A | 10/2018 |
| CN | 109486955 A | 3/2019 |
| JP | 2016500521 A | 1/2016 |
| KR | 1020110084487 A | 7/2011 |
| KR | 1020150114844 A | 10/2015 |
| KR | 20180038252 A | 4/2018 |
| WO | 2017114150 A1 | 7/2017 |
| WO | 2018066910 A1 | 4/2018 |
| WO | 2018194280 A1 | 10/2018 |

OTHER PUBLICATIONS

Oh et al. The Journal of Molecular Diagnostics. 2013. 15(4):498-507. (Year: 2013).*
Chen, Y., et al., "Performance of a Novel Blood-Based Early Colorectal Cancer Screening Assay in Remaining Serum after the Blood Biochemical Test", Disease Markers, 2019, doi.org/10.1155/2019/5232780, vol. 2019, No. 5232780, Publisher: Hindawi.
Office Action issued in Chinese Patent Application 2020800450609 on Nov. 30, 2023.
English translation of Office Action issued in Chinese Patent Application 2020800450609 on Nov. 30, 2023.
Search Report issued in Chinese Patent Application 2020800450609 on Nov. 28, 2023.
Evdokimov, A. A., et al., "GLAD-PCR Assay of DNA Methylation Markers Associated with Colorectal Cancer", Biology and Medicine, 2016, 1000342; DOI: 10.4172/0974-8369.1000342, vol. 8, No. 7.
Liu, X., et al., "Research progress of Syndecan-2 methylation in colorectal cancer screening", The World's Latest Medical Information Digest, 2019, pp. 167-168, vol. 19, No. 08, Publisher: China Academic Journal Electronic Publishing House.
Liu, X., et al., "Research progress of Syndecan-2 methylation in colorectal cancer screening", The World's Latest Medical Information Digest, 2019, pp. 167-168, vol. 19, No. 08, Publisher: China Academic Journal Electronic Publishing House, English Translation.
Office Action issued in counterpart Japanese Patent Application No. 2021574933 on Feb. 2, 2023.
English Translation of Office Action issued in counterpart Japanese Patent Application No. 2021574933 on Feb. 2, 2023.
EESR Issued in European Patent Application No. 20827018.1 on Oct. 9, 2023.
Oh, TJ, et al., "Genome-Wide Identification and Validation of a Novel Methylation Biomarker, SDC2, for Blood-Based Detection of Colorectal Cancer", The Journal of Molecular Diagnostics, 2013, pp. 1-10; http://dx.doi.org/10.1016/j.jmoldx.2013.03.004, vol. 15, No. 4, Publisher: Elsevier.

(Continued)

*Primary Examiner* — Joseph G. Dauner
(74) *Attorney, Agent, or Firm* — HULTQUIST, PLLC; Steven J. Hultquist

(57) ABSTRACT

The present invention relates to a method of detecting methylation of an SDC2 gene, a composition for detecting methylation of an SDC2 gene, and a kit comprising same and, more particularly, to: a method of detecting methylation of an SDC2 gene by using primers for specifically amplifying a methylated SDC2 gene and a probe capable of complementarily hybridizing with a methylated SDC2 gene that has been specifically amplified by the primers; a composition for detecting methylation of an SDC2 gene; and a kit comprising same.

4 Claims, 1 Drawing Sheet
Specification includes a Sequence Listing.

(56) References Cited

OTHER PUBLICATIONS

Ahlquist, D.A., et al., "Colorectal Cancer Screening by Detection of Altered Human DNA in Stool: Feasibility of a Multitarget Assay Panel", Gastroenterology, 2000, pp. 1219-1227, vol. 119, Publisher: American Gastroenterological Association.

Cross, S.H., et al., "CpG islands and genes", Current Opinion in Gene Development, 1995, pp. 309-314, vol. 5, Publisher: Current Biology Ltd.

"Hints for Optimizing Bisulfate Primer Design", epigenie website, Sep. 12, 2024.

Kristensen, E., et al., "Organic carbon dynamics in mangrove ecosystems: A review", Aquatic botany, 2008, pp. 201-219, vol. 89, Publisher: Elsevier.

Thomassin, H., et al., "MethylQuant: a sensitive method for quantifying methylation of specific cytosines within the genome", Nucleic Acids Research, 2004, Page(s) doi: 10.1093/nar/gnh166, vol. 32, No. 21, Publisher: Oxford University Press.

\* cited by examiner

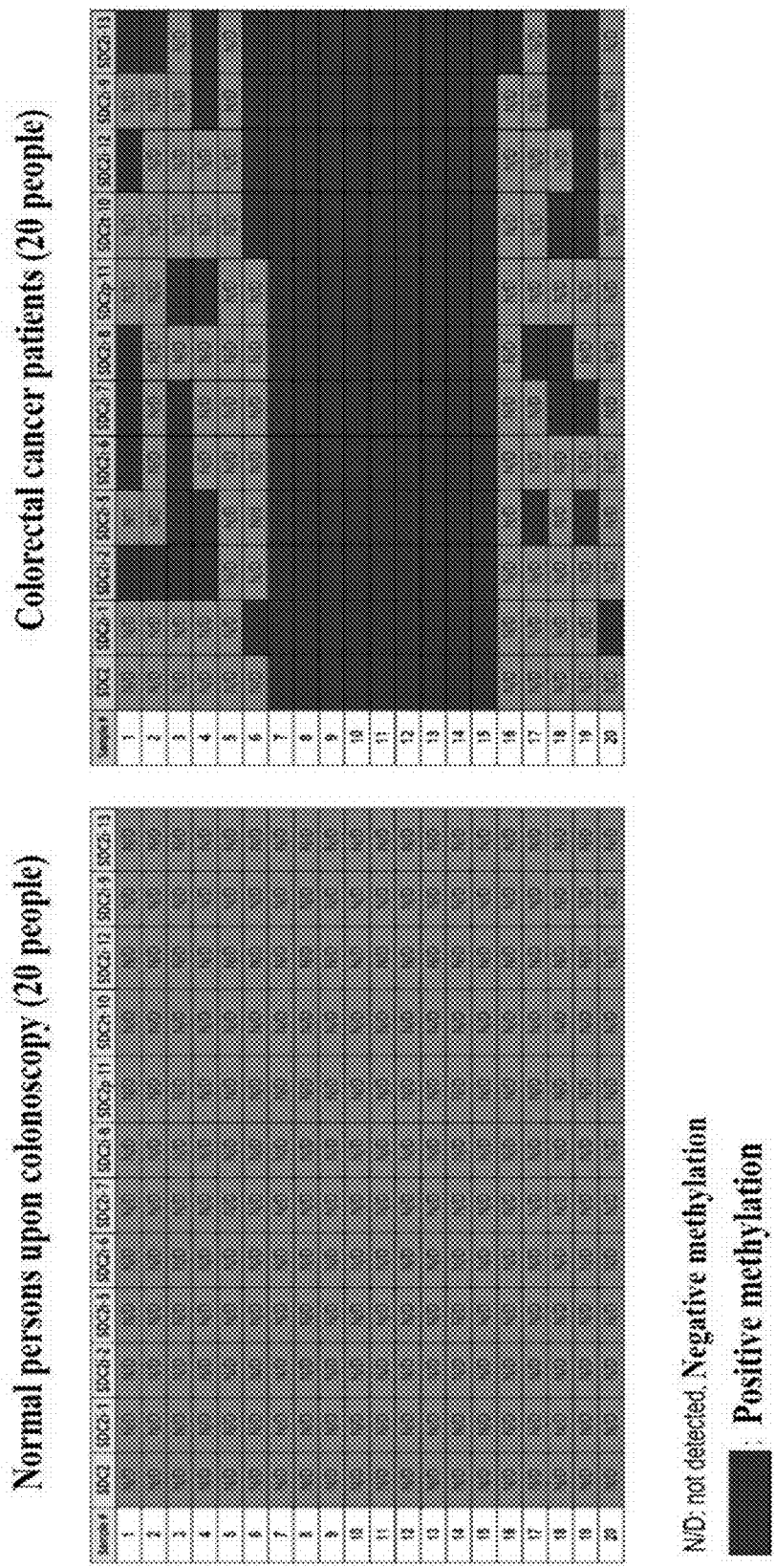

METHOD FOR DETECTING METHYLATION OF SDC2 GENE

CROSS-REFERENCE TO RELATED APPLICATIONS

This is a U.S. national phase under 35 USC § 371 of International Patent Application No. PCT/KR2020/006692 filed May 22, 2020, which in turn claims priority under 35 USC § 119 of Korean Patent Application No. 10-2019-0072080 filed Jun. 18, 2019. The disclosures of all such applications are hereby incorporated herein by reference in their respective entireties, for all purposes.

REFERENCE TO SEQUENCE LISTING SUBMITTED VIA PATENT CENTER

This application includes an electronically submitted sequence listing in .txt format. The .txt file contains a sequence listing entitled "602_UpdatedSeqListing_ST25.txt" created on May 12, 2025 and is 229,401 bytes in size. The sequence listing contained in this .txt file is part of the specification and is hereby incorporated by reference herein in its entirety.

TECHNICAL FIELD

The present invention relates to a method of detecting methylation of an SDC2 gene, a composition for detecting methylation of an SDC2 gene, and a kit comprising the same, and more particularly to a method of detecting methylation of an SDC2 gene using a primer specifically amplifying a methylated SDC2 gene and a probe capable of complementary hybridization to the methylated SDC2 gene specifically amplified by the primer, a composition for detecting methylation of an SDC2 gene, and a kit comprising the same.

BACKGROUND ART

The genomic DNA of mammalian cells, has a fifth base in addition to A, C, G, and T, which is 5-methylcytosine (5-mC), in which a methyl group is attached to the fifth carbon of a cytosine ring. 5-mC is always attached only to C of a CG dinucleotide (5'-mCG-3'), and this CG is often denoted as CpG. C in CpG is mostly methylated, with a methyl group attached thereto. This methylation of CpG inhibits the expression of repetitive sequences in the genome, such as Alu or transposons, and CpG is the site where extragenic changes most frequently occur in mammalian cells. 5-mC of this CpG is naturally converted into T through deamination. Accordingly, CpG in the mammalian genome appears only with a frequency of 1%, which is much lower than a normal frequency ($¼×¼=6.25\%$).

There is a region in which CpGs are exceptionally dense, which is called a CpG site (CpG island). The CpG site is 0.2-3 kb in length, and is a highly concentrated region in which the distribution percentage of C and G bases is greater than 50% and the distribution percentage of CpG is 3.75% or more. About 45,000 CpG sites appear in the entire human genome, and are intensively found in the promoter region, which regulates gene expression. Indeed, CpG sites appear in promoters of housekeeping genes, which account for about half of human genes (Cross, S. et al., Curr. Opin. Gene Develop., 5:309, 1995). Abnormal DNA methylation is known to occur mainly in the 5' regulatory region of the corresponding gene, thereby reducing expression of the corresponding gene.

On the other hand, in somatic cells of normal persons, the CpG islands of these housekeeping gene promoter regions are not methylated, but imprinted genes and inactivated genes on the X chromosome are methylated so as to prevent the expression thereof during development.

During the carcinogenesis process, methylation occurs in the promoter CpG island, and expression of the corresponding gene is impaired. In particular, when methylation occurs in the promoter CpG islands of tumor suppressor genes, which regulate cell cycles or apoptosis, repair DNA, participate in cell adhesion and intercellular interaction, and inhibit invasion and metastasis, the expression and function of these genes are blocked, like mutations in coding sequences, thereby promoting the development and progression of cancer. Partial methylation may also appear on CpG islands due to aging.

Promoter methylation of tumor-related genes is an important indicator of cancer, so it may be used in various ways, such as diagnosis and early diagnosis of cancer, prediction of cancer risk, prediction of cancer prognosis, follow-up after treatment, prediction of response to chemotherapy, and the like. Indeed, recent attempts have been actively made to investigate the promoter methylation of tumor-related genes in the blood, sputum, saliva, stool, urine, and the like, and to use the results thereof in the treatment of various types of cancer (Ahlquist, D. A. et al., Gastroenterol., 119:1219, 2000).

Against this technical background, the inventors of the present application have ascertained that methylation of an SDC2 gene may be detected with high detection limit and accuracy using a primer specifically amplifying a methylated SDC2 gene and a probe capable of complementary hybridization to the methylated SDC2 gene specifically amplified by the primer, thus the present invention has been completed.

DISCLOSURE

It is an object of the present invention to provide a method of detecting methylation of an SDC2 gene using a primer and a probe.

It is another object of the present invention to provide a composition for detecting methylation of an SDC2 gene including a primer and a probe.

It is still another object of the present invention to provide a kit for detecting methylation of an SDC2 gene including the composition.

In order to accomplish the above objects, the present invention provides a method of detecting methylation of an SDC2 gene comprising (a) treating a sample with at least one reagent differently modifying a methylated SDC2 gene and a non-methylated SDC2 gene, (b) performing treatment with a primer specifically amplifying the methylated SDC2 gene, and (c) performing treatment with a probe capable of complementary hybridization to the methylated SDC2 gene specifically amplified by the primer in step (b).

In addition, the present invention provides a composition for detecting methylation of an SDC2 gene comprising at least one reagent differently modifying a methylated SDC2 gene and a non-methylated SDC2 gene, a primer specifically amplifying the methylated SDC2 gene, and a probe capable of complementary hybridization to the methylated SDC2 gene specifically amplified by the primer.

In addition, the present invention provides a kit for detecting methylation of an SDC2 gene comprising the composition.

DESCRIPTION OF DRAWING

FIG. 1 shows the results of verification of methylation of multiple primer sets on stool DNA.

MODE FOR INVENTION

Unless otherwise defined, all technical and scientific terms used herein have the same meanings as those typically understood by those skilled in the art to which the present invention belongs. Generally, the nomenclature used herein is well known in the art and is typical.

The inventors of the present application designed methylation-specific detection primers and probes capable of representing the entire CpG island of the SDC2 gene, and ascertained that methylation may be specifically detected only in methylated DNA through methylation-specific amplification. In addition, the ability of the SDC2 gene to diagnose colorectal cancer in colorectal cancer tissues, stool, and blood was evaluated using methylation-specific detection primers and probes. Based on the results thereof, it was confirmed that the sensitivity and specificity for the diagnosis of colorectal cancer were very high, so usefulness in the diagnosis of colorectal cancer was high.

Accordingly, an aspect of the present invention pertains to a method of detecting methylation of an SDC2 gene comprising (a) treating a sample with at least one reagent differently modifying a methylated SDC2 gene and a non-methylated SDC2 gene, (b) performing treatment with a primer specifically amplifying the methylated SDC2 gene, and (c) performing treatment with a probe capable of complementary hybridization to the methylated SDC2 gene specifically amplified by the primer in step (b).

According to the present invention, the step (a) is treating the sample containing target DNA with at least one reagent differently modifying the methylated DNA region and the non-methylated DNA region.

As used herein, the term "methylation" refers to modification into 5-methylcytosine (5-mC) in which a methyl group is attached to the fifth carbon of a cytosine base ring, and 5-methylcytosine is always attached only to C of the CG dinucleotide (5'-mCG-3'), and this CG is often referred to as CpG. Methylation of CpG inhibits the expression of repetitive sequences in the genome, such as Alu or transposons, and CpG is the site where extragenic changes most frequently occur in mammalian cells. 5-mC of this CpG is naturally converted into T through deamination, and thus, CpG in the mammalian genome is present only at a frequency of 1%, which is much lower than a normal frequency ($\frac{1}{4} \times \frac{1}{4} = 6.25\%$).

There is a region in which CpGs are exceptionally dense, which is called a CpG island. The CpG island is 0.2-3 kb in length, and is a highly concentrated site in which the distribution percentage of C and G bases is greater than 50% and the distribution percentage of CpG is 3.75% or more. About 45,000 CpG islands appear in the entire human genome, and are intensively found in the promoter region, which regulates gene expression. CpG islands actually appear in promoters of housekeeping genes, which account for about half of human genes.

The nucleic acid isolated from a specimen is obtained from a biological sample of the specimen. In order to diagnose colorectal cancer or the stage of progression of colorectal cancer, the nucleic acid has to be isolated from colorectal tissue by scraping or biopsy. Such a sample may be obtained by various medical procedures known in the art.

The extent of methylation of the nucleic acid of the sample obtained from the specimen is measured through comparison with the same portion of the nucleic acid from a specimen without a colorectal tissue cell growth abnormality. Hypermethylation indicates the presence of a methylated allele in at least one nucleic acid. When the same nucleic acid is tested in a specimen without a colorectal tissue cell growth abnormality, the methylation allele does not appear.

"Normal" cells are cells that do not show abnormal cell morphology or a change in cytological properties. "Tumor" cells are cancer cells, and "non-tumor" cells are cells that are part of the diseased tissue but are not the site of the tumor.

According to the present invention, early diagnosis of cell growth abnormalities in the colorectal tissue of a specimen is possible by determining the methylation stage of at least one nucleic acid isolated from the specimen. The methylation stage of at least one nucleic acid may be compared with the methylation stage of at least one nucleic acid isolated from a specimen not exhibiting abnormal colorectal tissue cell growth. Preferably, the nucleic acid is a CpG-containing nucleic acid such as a CpG island.

According to the present invention, it is possible to diagnose a predisposition to cell growth abnormalities in the colorectal tissue of a specimen, including determining the methylation of at least one nucleic acid isolated from the specimen. The methylation stage of at least one nucleic acid may be compared with the methylation stage of at least one nucleic acid isolated from a specimen having no predisposition to abnormal cell growth in colorectal tissue.

As used herein, the term "predisposition" refers to the property of being susceptible to the above-mentioned cell growth abnormality. A specimen having a predisposition is a specimen which does not yet exhibit a cell growth abnormality, but in which a cell growth abnormality is present or the likelihood of developing a cell growth abnormality is increased.

The presence of CpG methylation in target DNA may be an indicator of a disease, and, for example, CpG methylation of any one of a promoter, a 5' untranslated region, and an intron of target DNA may be measured.

The CpG-containing gene is typically DNA. However, the method of the present invention may be performed using a sample containing, for example, DNA, or DNA and RNA including mRNA, in which the DNA or RNA may be single-stranded or double-stranded, or a sample containing a DNA-RNA hybrid may be used.

A nucleic acid mixture may also be used. As used herein, the term "multiple" includes both the case in which there is a plurality of specific nucleic acid sequence sites to be detected in a kind of gene and the case in which a plurality of target DNA sequences is included in one tube (a single reactor). The specific nucleic acid sequence to be detected may be a fraction of a large molecule, or may be present initially in the form of a discrete molecule in which the specific sequence constitutes the entire nucleic acid sequence. The nucleic acid sequence need not be a nucleic acid present in a pure form, and the nucleic acid may be a minor fraction of a complex mixture, such as one contained in whole human DNA.

Particularly, the present invention is directed to detecting methylation of a plurality of target DNA sequences in a sample in a single reactor, in which the sample may include multiple target DNA sequences, and any target DNA may be used without limitation, so long as it is a gene that affects the development or progression of cancer when the expression thereof is suppressed due to abnormal methylation, as well as a control gene.

In the present invention, the sample may be derived from a human body, and the sample may include, for example, colorectal cancer tissue, cells, stool, urine, blood, serum, or plasma.

At least one reagent differently modifying the methylated DNA and the non-methylated DNA may be used without limitation, so long as it is able to distinguish between the non-methylated cytosine base and the methylated cytosine base, and examples of the reagent may include, but are not limited to, bisulfite, hydrogen sulfite, disulfite, and combinations thereof. Particularly, the cytosine base methylated by the reagent is not converted, and the non-methylated cytosine base may be converted into uracil or a base other than cytosine.

In the present invention, step (b) is performing treatment with a primer specifically amplifying the methylated SDC2 gene.

The primer may include at least one CpG dinucleotide. For example, for PCR, forward and reverse primers may be paired and used simultaneously. The forward primer may include, for example, a sequence selected from the group consisting of SEQ ID NOS: 1, 4, 7, 10, 13, 16, 19, 22, 25, 28, 31, and 34 to 1140. The reverse primer may include, for example, a sequence selected from the group consisting of SEQ ID NOS: 2, 5, 8, 11, 14, 17, 20, 23, 26, 29, 32, and 1141 to 1159. The particular primer pair for the primer that specifically amplifies the methylated SDC2 gene is set forth in Table 1 of Example 1 and in Table 5 of Example 4.

In the present invention, step (c) is performing treatment with a probe capable of complementary hybridization to the methylated SDC2 gene specifically amplified by the primer.

In a hybridization reaction, the conditions used to achieve a certain stringent level vary depending on the properties of the nucleic acid to be hybridized. For example, the length of the nucleic acid site to be hybridized, the extent of homology, the nucleotide sequence composition (e.g. GC/AT ratio), and the nucleic acid type (e.g. RNA, DNA) are taken into consideration in selecting the hybridization conditions. An additional consideration is whether the nucleic acid is immobilized on, for example, a filter or the like.

Examples of very stringent conditions are as follows: 2×SSC/0.1% SDS at room temperature (hybridization conditions), 0.2×SSC/0.1% SDS at room temperature (low-stringency conditions), 0.2×SSC/0.1% SDS at 42° C. (moderate-stringency conditions), and 0.1×SSC at 68° C. (high-stringency conditions). The washing process may be performed using any one of these conditions, and, for example, high-stringency conditions or each of the above conditions may be used. The conditions may be applied for 10 to 15 minutes each time in the order described above, or all or some of the conditions described above may be repeatedly applied. As described above, however, the optimal conditions vary depending on the special hybridization reaction involved, and may be determined experimentally. Generally, high-stringency conditions are used for the hybridization of the probe of interest.

The probe may include, for example, at least one CpG dinucleotide. Particularly, the probe may include a sequence selected from the group consisting of SEQ ID NOS: 3, 6, 9, 12, 15, 18, 21, 24, 27, 30, 33, and 1160 to 1178.

In some cases, the probe may be detectably labeled, and may be labeled with, for example, a radioactive isotope, a fluorescent compound, a bioluminescent compound, a chemiluminescent compound, a metal chelate, or an enzyme. Appropriate labeling of the probe as described above is a technique well known in the art, and may be performed through a typical method.

The amount of the amplification product may be detected based on a fluorescence signal. The detection method may include an intercalating method using an intercalator that exhibits fluorescence by binding to the double-stranded DNA of the amplification product to which the probe is bound, a method of using an oligonucleotide in which the 5' end is labeled with a fluorescent material and the 3' end is labeled with a quencher, or the like.

The amplification according to the present invention may be performed through real-time quantitative amplification, for example, real-time polymerase chain reaction (PCR), and in real-time PCR, the amount of a PCR amplification product may be detected using a fluorescence signal. As real-time PCR proceeds, the intensity of the fluorescence signal increases in proportion to an increase in the amount of polynucleotide, and an amplification profile curve showing the intensity of the fluorescence signal depending on the number of amplification cycles is obtained.

In general, the amplification profile curve is divided into a baseline region which shows a fluorescence signal in the background that does not substantially reflect the amount of polynucleotide, an exponential region in which the fluorescence signal increases with an increase in the amount of a polynucleotide product, and a plateau region in which PCR reaches saturation and thus the intensity of the fluorescence signal no longer increases.

Typically, the fluorescence signal intensity at the transition point from the baseline region to the exponential region, namely at the point when the amount of a PCR amplification product reaches an amount detectable by fluorescence, is referred to as a threshold, and the number of amplification cycles corresponding to the threshold value on the amplification profile curve is referred to as a threshold cycle (Ct) value.

By measuring the Ct value, analyzing the standard curve in which the concentration is determined based on the Ct (threshold cycle) value for a standard material, and confirming the concentration of the amplified gene, the methylation-specific sensitivity and/or specificity may be determined.

In one embodiment, the methylation may be detected using any method selected from the group consisting of PCR, methylation-specific PCR, real-time methylation-specific PCR, PCR using a methylated-DNA-specific binding protein, PCR using a methylated-DNA-specific binding antibody, quantitative PCR, gene chip, sequencing, sequencing by synthesis, and sequencing by ligation.

(1) Methylation-specific PCR: For detection by methylation-specific PCR, when treated with a bisulfate, the cytosine in the 5'-CpG'-3 region remains as cytosine in the case of methylation, and is converted into uracil in the case of non-methylation. Therefore, a primer corresponding to a region in which the 5'-CpG-3' nucleotide sequence exists may be prepared for the nucleotide sequence converted after treatment with bisulfite. When PCR is performed using primers, in the case of methylation, a PCR product is made due to the use of the primers corresponding to the methylated nucleotide sequence, and methylation may be confirmed through agarose gel electrophoresis. Here, the methylation detection probe may be TaqMan, Molecular Beacon, or a probe having a self-reporting function or an energy-transfer labeling function, but is not limited thereto.

(2) Real-time methylation-specific PCR: Real-time methylation-specific PCR is a real-time measurement method modified from methylation-specific PCR, and includes treating genomic DNA with bisulfite, designing PCR primers corresponding to the methylated nucleotide sequence, and performing real-time PCR using the primers. Here, there are two detection methods: a detection method using a TaqMan probe complementary to the amplified nucleotide sequence and a detection method using SYBR Green. Therefore, real-time methylation-specific PCR is capable of selectively quantitatively analyzing only methylated DNA. As such, a standard curve is created using an in-vitro methylated DNA sample, and a gene having no 5'-CpG-3' sequence in the nucleotide sequence is also amplified as a negative control for standardization, thus quantitatively analyzing the extent of methylation.

(3) PCR using methylated-DNA-specific binding protein, quantitative PCR, and DNA chip assay: In the PCR using a methylated-DNA-specific binding protein or the DNA chip method, when a protein that specifically binds only to methylated DNA is mixed with DNA, the protein specifically binds only to methylated DNA, so methylated DNA may be selectively isolated.

In addition, methylation may be measured through quantitative PCR, and methylated DNA isolated with the methylated-DNA-specific binding protein is labeled with a fluorescent dye and hybridized to a DNA chip integrated with complementary probes, thereby measuring methylation.

(4) Detection of differential methylation-bisulfite sequencing method: Another method of detecting a nucleic acid containing methylated CpG includes bringing a nucleic-acid-containing sample into contact with an agent that modifies non-methylated cytosine and amplifying the CpG-containing nucleic acid in the sample using CpG-specific oligonucleotide primers. Here, the oligonucleotide primers may be characterized in that the methylated nucleic acid is detected by distinguishing between modified methylated and non-methylated nucleic acids. The amplification step is optional and preferable, but not essential. The method relies on the PCR reaction to distinguish between modified (e.g. chemically modified) methylated DNA and non-methylated DNA.

(5) Bisulfite sequencing method: Another method of detecting nucleic acid containing methylated CpG includes bringing a nucleic-acid-containing sample into contact with an agent that modifies non-methylated cytosine and amplifying the CpG-containing nucleic acid in the sample using methylation-independent oligonucleotide primers. Here, the oligonucleotide primers may be characterized in that the nucleic acid is amplified without distinguishing between modified methylated and non-methylated nucleic acids. The amplified product has been described in connection with bisulfite sequencing for detection of methylated nucleic acids by next-generation sequencing methods or for sequencing by the Sanger method using a sequencing primer.

(6) Next-generation sequencing methods include a sequencing-by-synthesis method and a sequencing-by-ligation method. These methods are characterized in that, instead of creating a bacterial clone, a single DNA fragment is spatially separated, amplified in situ (clonal amplification), and sequenced. Here, since hundreds of thousands of fragments are read simultaneously, such a method is also called a massively parallel sequencing method.

Basically, a sequencing-by-synthesis method is performed, a method of obtaining signals by sequentially attaching mono- or di-nucleotides is used, and examples thereof may include pyrosequencing, ion torrent, and Solexa methods.

Examples of NGS devices based on the sequencing-by-synthesis method include Roche's 454 platform, Illumina's HiSeq platform, Life Technology's Ion PGM platform, and Pacific BioSciences' PacBio platform. 454 and Ion PGM use emersion PCR as a clonal amplification method, and HiSeq uses bridge amplification. The sequencing-by-synthesis method reads the sequence by detecting phosphate, protons, or pre-attached fluorescence generated when DNA is synthesized by sequentially attaching one nucleotide. In the method of detecting the sequence, 454 uses a pyrosequencing method using phosphoric acid, and Ion PGM uses proton detection. HiSeq and PacBio detect fluorescence to decode the sequence.

A sequencing-by-ligation method is a sequencing technique using DNA ligase, which identifies nucleotides at certain positions in a DNA nucleotide sequence. Unlike most sequencing techniques using a polymerase, the sequencing-by-ligation method does not use a polymerase and is characterized in that DNA ligase does not ligate mismatched sequences. An example thereof is the SOLiD system. In this technique, two bases are read with spacing, which is repeated five times independently through primer reset, so accuracy is improved by reading each base twice in duplicate.

In the sequencing-by-ligation method, among the dinucleotide primer sets made of 16 combinations, dinucleotide primers corresponding to the nucleotide sequences are sequentially ligated, the combination of these ligations is finally analyzed, and the nucleotide sequence of the corresponding DNA is completed.

Here, the next-generation sequencing method may be exemplified by a sequencing-by-synthesis method or a sequencing-by-ligation method. The methylated-DNA-specific binding protein is not limited to MBD2bt, and the antibody is a 5'-methyl-cytosine antibody, but is not limited thereto.

With regard to the primer used in the present invention, when a reagent such as bisulfite is used in step (a), the cytosine in the 5'-CpG'-3 site remains as cytosine in the case of methylation, and is converted into uracil in the case of non-methylation. Therefore, a primer corresponding to a region in which the 5'-CpG-3' nucleotide sequence exists may be prepared for the nucleotide sequence converted after treatment with a reagent, such as bisulfite.

The primer may be designed to have "substantial" complementarity with each strand of the locus to be amplified in the SDC2 gene. This means that the primer has sufficient complementarity to hybridize with the corresponding nucleic acid strand under the conditions for the polymerization reaction.

Another aspect of the present invention pertains to a composition for detecting methylation of an SDC2 gene including at least one reagent differently modifying a methylated SDC2 gene and a non-methylated SDC2 gene, a primer specifically amplifying the methylated SDC2 gene, and a probe capable of complementary hybridization to the methylated SDC2 gene specifically amplified by the primer.

Since the components contained in the composition according to the present invention overlap the components described above, a description thereof is equally applied.

Still another aspect of the present invention pertains to a kit for detecting methylation of target DNA including the composition described above.

In one embodiment, the kit includes compartmentalized carrier means that accommodates a sample therein, a container including a reagent, a container including a primer capable of amplifying the SDC2 gene 5'-CpG-3', and a container including a probe for detecting the amplification product.

The carrier means is suitable for accommodating one or more individual containers, such as bottles and tubes, containing independent components for use in the method of the present invention. In the specification of the present invention, one of ordinary skill in the art may readily determine the apportionment of the necessary agents in the containers.

A better understanding of the present invention may be obtained through the following examples. These examples are merely set forth to illustrate the present invention, and are not to be construed as limiting the scope of the present invention, as will be apparent to those of ordinary skill in the art.

Example 1: Evaluation of Ability of SDC2 Gene to Diagnose Colorectal Cancer in Colorectal Cancer Tissue In order to evaluate the ability of the SDC2 gene to diagnose colorectal cancer, 11 sets of methylation-specific detection primers and probes capable of representing the entire CpG island of the SDC2 gene were designed (Table 1), and methylation-specific real-time PCR (qMSP) was performed. To this end, genomic DNA was isolated from the surgical tissue of 20 colorectal cancer patients using cancer tissue and normal tissue adjacent thereto (QIAAMP® DNA mini kit, Qiagen), and genomic DNA (2.0 µg) was treated with bisulfate using an EZ DNA methylation-Gold kit (Zymo Research, USA), dissolved in 10 µl of sterile distilled water, and used for methylation-specific real-time PCR (qMSP). qMSP was performed using bisulfite-treated genomic DNA as a template and using the methylation-specific primers and probes designed in Table 1 below. For qMSP, a ROTOR-GENE® Q PCR machine (Qiagen) was used. A total of 20 µl of a PCR reaction solution (20 ng of template DNA, 4 µl of 5×AptaTaq DNA Master (Roche Diagnostics), 2 µl (2 pmol/µl) of PCR primer, 2 µl (2 pmol/µl) of TaqMan probe, and 10 µl of D.W.) was prepared, and PCR was performed under conditions of 95° C. for 5 minutes followed by 95° C. for 15 seconds and an appropriate annealing temperature (58° C. to 61° C.) for 1 minute for a total of 40 cycles. Whether the PCR product was amplified was confirmed by measuring the cycle threshold ($C_T$) value. Methylated and non-methylated control DNAs were tested along with the sample DNA using an EPI-TECT® PCR control DNA set (Qiagen, cat. no. 59695). As an internal control gene, a COL2A1 gene (Kristensen et al., 2008) was used. The extent of methylation of each sample was measured using a $C_T$ (cycle threshold) value.

The sensitivity and specificity for colorectal cancer diagnosis of each primer and probe set were calculated through ROC curve analysis (MedCalc program, Belgium) using the $C_T$ values of colorectal cancer tissue and normal tissue adjacent thereto (Table 2).

TABLE 1

Primer and probe sequences for SDC2 gene qMSP

| Set | Primer | Sequence (5'-->3') | Amplification product size (bp) | SEQ ID NO: |
|---|---|---|---|---|
| SDC2 i-1 | F | GATTCGTTGGGATAAATGCGTTCGTTC | 111 | 1 |
| | R | CTCGATACCCCATTCCCGCG | | 2 |
| | Probe | AAGCGTTGTTCGTTGGCGTTATTTCGCGG | | 3 |
| SDC2 i-2 | F | GCGTTATTTCGCGGTTCGC | 114 | 4 |
| | R | CCACGCAACAAAACCCGCCG | | 5 |
| | Probe | CGAGAATTGCGGTTTGGTTTAGTCGTAGAG | | 6 |
| SDC2 i-5 | F | GTATCGCGGGGCGTTAGGGAC | 108 | 7 |
| | R | CGACCCGAAACCGAACGCCG | | 8 |
| | Probe | CGGGAGTTCGTAAGTAGGGCGAGGCG | | 9 |
| SDC2 i-6 | F | GGCGGGGTACGTGTGATAC | 98 | 10 |
| | R | GCCAAAACCAAAAAAAACGAACGTAACG | | 11 |
| | Probe | CGGTTTCGGGTCGTTTGGTCGTTGG | | 12 |
| SDC2 i-7 | F | GATAGAGGTTTTTTTTCGTTACGTTC | 96 | 13 |
| | R | CGACAAACGCTCCGCCGAAAACG | | 14 |
| | Probe | TTTGGCGGGGCGTTTTTGGGGTCGGGA | | 15 |
| SDC2 i-8 | F | CGGGTTCGCGAGGGAAC | 105 | 16 |
| | R | CTTACATACAATCAAACAAAAAAACTAACGCG | | 17 |
| | Probe | CGCGCGTTTTTCGAGATTAGGGATGATTTG | | 18 |
| SDC2 i-9 | F | CGTTTTGGCGGTGGGAATTTG | 93 | 19 |
| | R | ACGCCCAAATAAAAACAACTACGAACG | | 20 |
| | Probe | TGGTCGCGTTTCGGGGGTTGGAG | | 21 |
| SDC2 t-10 | F | GATTCGGGGAGGGAGGC | 128 | 22 |
| | R | ACGACGAAAACGCGCGATCCG | | 23 |
| | Probe | CGTAGTCGCGGAGTTAGTGGTTTCGTT | | 24 |
| SDC2 p-11 | F | GTCGGTGAGTAGAGTCGGC | 122 | 25 |
| | R | CGACAATATAACTCCCAAATAAACCCG | | 26 |
| | Probe | CGGAGTCGCGGCGTTTATTGGTTTTC | | 27 |

TABLE 1-continued

Primer and probe sequences for SDC2 gene qMSP

| Set | Primer | Sequence (5'-->3') | Amplification product size (bp) | SEQ ID NO: |
|---|---|---|---|---|
| SDC2 i-12 | F | CGGAGGATGCGCGCGTC | 129 bp | 28 |
| | R | CGAACGAACGCATTTATCCCAACG | | 29 |
| | Probe | AGTTACGAGAGGAGTTCGTAGGGAA TAGG | | 30 |
| SDC2 i-13 | F | CGGTTAGGGCGAGGTAATCG | 122 bp | 31 |
| | R | CGACGTCCCAACATTTTCGAACG | | 32 |
| | Probe | CGTGGAATCGTAGTAGGCGATTTTT TAAGG | | 33 |

Based on the results of verification of SDC2 gene methylation using colorectal cancer tissue and normal tissue DNA adjacent thereto, the sensitivity for colorectal cancer diagnosis was 80% (16/20) to 95.0% (19/20) and the specificity therefor was 85.0% (3/20) to 95.0% (1/20), which was evaluated to be superior. Therefore, it was confirmed that the usefulness of SDC2 gene methylation in the diagnosis of colorectal cancer was high.

TABLE 2

Evaluation of ability of SDC2 gene to diagnose colorectal cancer in colorectal cancer tissue

| Primer and probe set | Cut-off ($C_T$) | Sensitivity (%), n = 20 | Specificity(%), n = 20 |
|---|---|---|---|
| SDC2i-1 | <35 | 80 | 95 |
| SDC2i-2 | | 95 | 95 |
| SDC2i-5 | | 85 | 90 |
| SDC2i-6 | | 90 | 95 |
| SDC2i-7 | | 90 | 85 |
| SDC2i-8 | | 80 | 90 |
| SDC2i-9 | | 80 | 90 |
| SDC2t-10 | | 80 | 95 |
| SDC2p-11 | | 85 | 90 |
| SDC2i-12 | | 90 | 95 |
| SDC2i-13 | | 95 | 90 |

Example 2: Evaluation of Ability of SDC2 Gene to Diagnose Colorectal Cancer Using Stool DNA In order to evaluate the ability of the SDC2 gene to diagnose colorectal cancer, methylation-specific real-time PCR (qMSP) was performed using the SDC2 gene methylation-specific detection primers and probes (Table 1) described in Example 1. To this end, genomic DNA was isolated from stool DNA of 20 colorectal cancer patients (Yonsei Medical Center Severance Hospital) and 20 normal persons (Yonsei Medical Center Severance Hospital check-up) (Stool DNA mini kit, Qiagen), and genomic DNA (2.0 µg) was treated with bisulfite using the EZ DNA methylation-Gold kit (Zymo Research, USA), dissolved in 10 µl of sterile distilled water, and used for methylation-specific real-time PCR (qMSP). qMSP was performed by the method described in Example 1.

The sensitivity and specificity for colorectal cancer diagnosis of each primer and probe set were calculated through ROC curve analysis (MedCalc program, Belgium) using $C_T$ values from stool DNA of colorectal cancer patients and normal persons (Table 3).

TABLE 3

Evaluation of ability of SDC2 gene to diagnose colorectal cancer in stool DNA

| Primer and probe set | Cut-off ($C_T$) | Sensitivity(%), n = 20 | Specificity(%), n = 20 |
|---|---|---|---|
| SDC2i-1 | <40 | 80 | 90 |
| SDC2i-2 | | 90 | 90 |
| SDC2i-5 | | 80 | 85 |
| SDC2i-6 | | 90 | 90 |
| SDC2i-7 | | 80 | 85 |
| SDC2i-8 | | 80 | 90 |
| SDC2i-9 | | 80 | 85 |
| SDC2t-10 | | 80 | 90 |
| SDC2p-11 | | 85 | 90 |
| SDC2i-12 | | 80 | 90 |
| SDC2i-13 | | 85 | 90 |

Based on the results of verification of SDC2 gene methylation using stool DNA from colorectal cancer patients (20 people) and normal persons (20 people), the sensitivity for colorectal cancer diagnosis was 80% (16/20) to 90.0% (18/20), and the specificity therefor was 85.0% (3/20) to 90.0% (2/20), which was evaluated to be superior. Therefore, it was confirmed that the usefulness of SDC2 gene methylation in the diagnosis of colorectal cancer in stool DNA was high.

Example 3: Evaluation of Ability of SDC2 Gene to Diagnose Colorectal Cancer in Blood In order to evaluate the ability of the SDC2 gene to diagnose colorectal cancer, methylation-specific real-time PCR (qMSP) was performed using the SDC2 gene methylation-specific detection primers and probes (Table 1) described in Example 1. To this end, DNA was isolated from 1 mL of serum of each of 10 colorectal cancer patients (Chungnam National University Hospital) and 10 normal persons (Innovative Research, USA) (Dynabead, Thermo Fisher), and the DNA was treated with bisulfate using the EZ DNA methylation-Gold kit (Zymo Research, USA), dissolved in 10 µl of sterile distilled water, and used for methylation-specific real-time PCR (qMSP). qMSP was performed by the method described in Example 1.

The sensitivity and specificity for colorectal cancer diagnosis of each primer and probe set were calculated through ROC curve analysis (MedCalc program, Belgium) using the $C_T$ values resulting from qMMSP using serum DNA from colorectal cancer patients and normal persons (Table 4).

TABLE 4

Evaluation of ability of SDC2 gene to diagnose colorectal cancer in blood (serum) DNA

| Primer and probe set | Cut-off ($C_T$) | Sensitivity(%), n = 20 | Specificity(%), n = 20 |
|---|---|---|---|
| SDC2i-1 | <40 | 75 | 90 |
| SDC2i-2 |  | 85 | 90 |
| SDC2i-5 |  | 85 | 90 |
| SDC2i-6 |  | 70 | 90 |
| SDC2i-7 |  | 70 | 85 |
| SDC2i-8 |  | 80 | 90 |
| SDC2i-9 |  | 70 | 85 |
| SDC2t-10 |  | 80 | 90 |
| SDC2p-11 |  | 75 | 90 |
| SDC2i-12 |  | 80 | 90 |
| SDC2i-13 |  | 85 | 85 |

Based on the results of verification of SDC2 gene methylation using blood DNA from colorectal cancer patients (10 people) and normal persons (10 people), the sensitivity for colorectal cancer diagnosis was 70% (14/20) to 90.0% (18/20), and the specificity therefor was 85.0% (3/20) to 90.0% (2/20), which was evaluated to be superior. Therefore, it was confirmed that the usefulness of SDC2 gene methylation in the diagnosis of colorectal cancer in blood DNA was high.

Example 4: Evaluation of ability of SDC2 gene to diagnose colorectal cancer using stool DNA In order to evaluate the ability of the SDC2 gene to diagnose colorectal cancer, methylation-specific real-time PCR (qMSP) was performed using the SDC2 gene methylation-specific detection primers and probes (Table 1) described in Example 1. To this end, genomic DNA was isolated from stool DNA of 20 colorectal cancer patients (Yonsei Medical Center Severance Hospital) and 20 normal persons (Yonsei Medical Center Severance Hospital checkup) (Stool DNA mini kit, Qiagen), and the genomic DNA (2.0 µg) was treated with bisulfite using the EZ DNA methylation-Gold kit (Zymo Research, USA), dissolved in 10 µl of sterile distilled water, and used for methylation-specific real-time PCR (qMSP). qMSP was performed by the method described in Example 1.

The positivity frequency for colorectal cancer diagnosis of each primer and probe set was calculated using $C_T$ values from stool DNA of colorectal cancer patients and normal persons (FIG. 1).

As shown in FIG. 1, all primer sets exhibited negative methylation in normal persons upon colonoscopy (specificity: 100%). In colorectal cancer patients, the positive methylation frequency of the newly designed primers was higher than that of SEQ ID NO: 1179 (TAGAAATTAATAAGT-GAGAGGGCGT) and SEQ ID NO: 1180 (GACT-CAAACTCGAAAACTCGAA) SDC2 primer set described in Korean Patent No. 1142131 (in FIG. 1, the SDC2 item showed positive methylation frequency on the primers of Korean Patent No. 1142131).

The positive methylation frequency in colorectal cancer patients of primer and probe sets is shown in Table 5 below.

TABLE 5

Positive methylation frequency of primer and probe sets in stool DNA

| Primer and probe set | Cut-off (CT) | Positive methylation frequency (%), n = 20 |
|---|---|---|
| SDC2* | <40 | 45 |
| SDC2i-1 |  | 55 |
| SDC2i-2 |  | 65 |
| SDC2i-5 |  | 65 |
| SDC2i-6 |  | 55 |
| SDC2i-7 |  | 65 |
| SDC2i-8 |  | 60 |
| SDC2i-9 |  | 65 |
| SDC2t-10 |  | 60 |
| SDC2p-11 |  | 55 |
| SDC2i-12 |  | 60 |
| SDC2i-13 |  | 80 |

*Positive methylation frequency in SEQ ID NO: 1127 (TAGAAAT-TAATAAGTGAGAGGGCGT) and SEQ ID NO: 1180 (GACT-CAAACTCGAAAACTCGAA) SDC2 primer set described in Korean Patent No. 1142131

Based on the results thereof, it was confirmed that all newly designed primer and probe sets exhibited high positive methylation frequency in colorectal cancer patients.

Example 5: Evaluation of Detection of SDC2 Gene Methylation Through Multiple Methylation-Specific Primer And Probe Design In order to evaluate the ability of the SDC2 gene to diagnose colorectal cancer, 1,107 sets of methylation-specific detection primers and probes capable of representing the entire CpG island of the SDC2 gene were designed (Table 6), and methylation-specific real-time PCR (qMSP) was performed. To this end, the abilities of these primers and probes to detect SDC2 gene methylation were evaluated using bisulfite-treated human methylated DNA and non-methylated DNA (EPITECT® PCR control DNA set, Qiagen, Cat. no. 59695). 20 ng of the DNA was dissolved in 10 µl of sterile distilled water and then used for methylation-specific real-time PCR (qMSP). For qMSP, a ROTOR-GENE® Q PCR machine (Qiagen) was used. A total of 20 µl of a PCR reaction solution (20 ng of template DNA, 4 µl of 5×AptaTaq DNA Master (Roche Diagnostics), 2 µl (2 pmol/µl) of PCR primer, 2 µl (2 pmol/µl) of TaqMan probe, and 10 µl of D.W.) was prepared, and PCR was performed under conditions of 95° C. for 5 minutes followed by 95° C. for 15 seconds and an appropriate annealing temperature (58° C. to 61° C.) for 1 minute for a total of 40 cycles. Whether the PCR product was amplified was confirmed by measuring the cycle threshold (CT) value. As an internal control gene, a COL2A1 gene (Kristensen et al., 2008) was used. For the extent of methylation of each sample, the sensitivity and specificity for colorectal cancer diagnosis of each primer and probe set were calculated through ROC curve analysis (MedCalc program, Belgium) using CT (cycle t) values.

TABLE 6

Primer and probe sequences for SDC2 gene qMSP

| Set | Primer | Sequence (5'-->3') |
|---|---|---|
| 1 to 61 | F1-F61 | SEQ ID NOS: 34 to 94, respectively |
| | R1 | GAACGCATTTATCC (SEQ ID NO: 1141) |
| | P1 | TTTAAGTATATATCGGAGATTCGTTG (SEQ ID NO: 1160) |
| 62 to 122 | F62-F122 | SEQ ID NOS: 95 to 155, respectively |
| | R2 | AAATAACGCCAACG (SEQ ID NO: 1142) |
| | P2 | TTTTTTTTTTTAGAAAAGCGTTGTT (SEQ ID NO: 1161) |
| 123 to 183 | F123-F183 | SEQ ID NOS: 156 to 216, respectively |
| | R3 | CAAAAACCTCTACG (SEQ ID NO: 1143) |
| | P3 | TATCGAGAATTGCGGTTTGGTTTAGT (SEQ ID NO: 1162) |
| 184 to 244 | F184-244 | SEQ ID NOS: 217 to 277, respectively |
| | R4 | CTCCGTCCTTCCCA (SEQ ID NO: 1144) |
| | P4 | TTTTCGGCGGGTTTTGTTGCGTGGTT (SEQ ID NO: 1163) |
| 245 to 305 | F245-F305 | SEQ ID NOS: 278 to 338, respectively |
| | R5 | CGAAATAAAACCGT (SEQ ID NO: 1145) |
| | P5 | GGAGTTTGGGTCGGGTTCGCGAGGGA (SEQ ID NO: 1164) |
| 306 to 366 | F306-F366 | SEQ ID NOS: 339 to 399, respectively |
| | R6 | AATAATATACGAAA (SEQ ID NO: 1146) |
| | P6 | TGATTTGGAAATTTCGGGGTTTTTT (SEQ ID NO: 1165) |
| 367 to 447 | F367 to F447 | SEQ ID NOS: 400 to 480, respectively |
| | R7 | AAACACTCGCGAAT (SEQ ID NO: 1147) |
| | P7 | GGGGAGATGGGGGTTAGATTTAAGAG (SEQ ID NO: 1166) |
| 448 to 508 | F448 to F508 | SEQ ID NOS: 481 to 541, respectively |
| | R8 | ATTACCTCGCCCTA (SEQ ID NO: 1148) |
| | P8 | TTTTTTTGTTTGATGTTTTTTGCGGT (SEQ ID NO: 1167) |
| 509 to 569 | F509 to F569 | SEQ ID NOS: 542 to 602, respectively |
| | R9 | GTTCCGTACCTCCC (SEQ ID NO: 1149) |
| | P9 | TAGGCGATTTTTTAAGGGGATATTGG (SEQ ID NO: 1168) |
| 570 to 630 | F570 to F630 | SEQ ID NOS: 603 to 663, respectively |
| | R10 | GAAAAAAAAATCGC (SEQ ID NO: 1150) |
| | P10 | TCGGTTATTGGATTTTTAGTTTTGCG (SEQ ID NO: 1169) |
| 631 to 681 | F631 to F681 | SEQ ID NOS: 664 to 714, respectively |
| | R11 | AAAATATCCTCCCG (SEQ ID NO: 1151) |
| | P11 | GAGGTTGTATCGCGGGGCGTTAGGGA (SEQ ID NO: 1170) |
| 682 to 742 | F682 to F742 | SEQ ID NOS: 715 to 775, respectively |
| | R12 | AACGCCGTATCACA (SEQ ID NO: 1152) |
| | P12 | TCGTAAGTAGGGCGAGGCGGGGTACG (SEQ ID NO: 1171) |
| 743 to 803 | F743 to F803 | SEQ ID NOS: 776 to 836, respectively |
| | R13 | AAAAAACGAACGTA (SEQ ID NO: 1153) |
| | P13 | TTGGGGATAGAGGTTTTTTTTTCGT (SEQ ID NO: 1172) |
| 804 to 864 | F804 to F864 | SEQ ID NOS: 837 to 897, respectively |
| | R14 | GACAAACGCTCCGC (SEQ ID NO: 1154) |
| | P14 | TGGGGTCGGGAGGAGTTTCGTTTTCG (SEQ ID NO: 1173 ) |
| 865 to 925 | F865 to F925 | SEQ ID NOS: 898 to 958, respectively |
| | R15 | ACGCGACCAAAAAA (SEQ ID NO: 1155) |
| | P15 | GTTTTGGCGGTGGGAATTTGATTTTT (SEQ ID NO: 1174) |
| 926 to 976 | F926 to F976 | SEQ ID NOS: 959 to 1009, respectively |
| | R16 | TTTAAAAAACGCTC (SEQ ID NO: 1156) |
| | P16 | GAGTTTGTTTTTTACGTCGTTTAAT (SEQ ID NO: 1175) |
| 977 to 1037 | F977 to F1037 | SEQ ID NOS: 1010 to 1070, respectively |
| | R17 | AAACTCCTAACGCC (SEQ ID NO: 1157) |
| | P17 | TTTTCGTTCGTAGTTGTTTTTATTTG (SEQ ID NO: 1176) |
| 1038 to 1098 | F1038 to F1098 | SEQ ID NOS: 1071 to 1131, respectively |
| | R18 | AAACGAAATCTAAA (SEQ ID NO 1158) |
| | 18 | GTTGGGTTAGGTGGAAGTTTGAGTAT (SEQ ID NO: 1177) |
| 1099 to 1107 | F1099 to F1107 | SEQ ID NOS: 1132 to 1140, respectively |
| | R19 | AAAAAACGTAAAAA (SEQ ID NO: 1159) |
| | P19 | GTGCGGTTGTTTTGGTTTTTTTGGT (SEQ ID NO: 1178) |

Based on the results of measurement of the SDC2 gene methylation of the primers and probes, no methylation was detected in the non-methylated DNA and methylation was detected only in the methylated DNA (Table 6), indicating that these primers and probes are suitable for detecting SDC2 methylation.

TABLE 7

Results of detection of methylation of primers and probes specific to SDC2 gene methylation

| set | qMSP $C_T$ value | |
|---|---|---|
| | Methylated DNA | Non-methylated DNA |
| 1 | 24.6 | N.D |
| 2 | 24.4 | N.D |
| 3 | 24.2 | N.D |
| 4 | 25.1 | N.D |
| 5 | 24.9 | N.D |
| 6 | 25.9 | N.D |
| 7 | 27.6 | N.D |
| 8 | 24.3 | N.D |
| 9 | 24.3 | N.D |
| 10 | 23.9 | N.D |
| 11 | 25.3 | N.D |
| 12 | 26.4 | N.D |
| 13 | 27.4 | N.D |
| 14 | 26.3 | N.D |
| 15 | 25.2 | N.D |
| 16 | 24.3 | N.D |
| 17 | 24.3 | N.D |
| 18 | 28.3 | N.D |
| 19 | 25.3 | N.D |
| 20 | 26.4 | N.D |
| 21 | 27.4 | N.D |
| 22 | 26.3 | N.D |
| 23 | 25.2 | N.D |
| 24 | 25.7 | N.D |
| 25 | 27.6 | N.D |
| 26 | 27.8 | N.D |
| 27 | 29.3 | N.D |
| 28 | 25.4 | N.D |
| 29 | 25.7 | N.D |
| 30 | 27.4 | N.D |
| 31 | 24.3 | N.D |
| 32 | 28.3 | N.D |
| 33 | 25.3 | N.D |
| 34 | 26.4 | N.D |
| 35 | 27.4 | N.D |
| 36 | 26.3 | N.D |
| 37 | 25.2 | N.D |
| 38 | 25.7 | N.D |
| 39 | 27.6 | N.D |
| 40 | 27.8 | N.D |
| 41 | 29.3 | N.D |
| 42 | 25.4 | N.D |
| 43 | 25.7 | N.D |
| 44 | 27.4 | N.D |
| 45 | 28.2 | N.D |
| 46 | 27.7 | N.D |
| 47 | 24.2 | N.D |
| 48 | 27.9 | N.D |
| 49 | 28.6 | N.D |
| 50 | 28.4 | N.D |
| 51 | 24.4 | N.D |
| 52 | 24.2 | N.D |
| 53 | 25.1 | N.D |
| 54 | 24.9 | N.D |
| 55 | 25.9 | N.D |
| 56 | 27.6 | N.D |
| 57 | 24.3 | N.D |
| 58 | 24.3 | N.D |
| 59 | 25.7 | N.D |
| 60 | 27.4 | N.D |
| 61 | 28.2 | N.D |
| 62 | 27.2 | N.D |
| 63 | 24.2 | N.D |
| 64 | 27.9 | N.D |
| 65 | 28.6 | N.D |
| 66 | 28.4 | N.D |
| 67 | 24.4 | N.D |
| 68 | 24.2 | N.D |
| 69 | 25.1 | N.D |
| 70 | 24.9 | N.D |
| 71 | 25.9 | N.D |
| 72 | 27.6 | N.D |
| 73 | 24.3 | N.D |
| 74 | 24.3 | N.D |
| 75 | 28.3 | N.D |
| 76 | 25.3 | N.D |
| 77 | 26.4 | N.D |
| 78 | 27.4 | N.D |
| 79 | 26.3 | N.D |
| 80 | 25.2 | N.D |
| 81 | 25.7 | N.D |
| 82 | 28.2 | N.D |
| 83 | 27.2 | N.D |
| 84 | 24.2 | N.D |
| 85 | 27.9 | N.D |
| 86 | 28.6 | N.D |
| 87 | 28.4 | N.D |
| 88 | 24.4 | N.D |
| 89 | 24.2 | N.D |
| 90 | 25.1 | N.D |
| 91 | 24.9 | N.D |
| 92 | 25.9 | N.D |
| 93 | 27.6 | N.D |
| 94 | 24.3 | N.D |
| 95 | 24.2 | N.D |
| 96 | 25.2 | N.D |
| 97 | 25.7 | N.D |
| 98 | 27.6 | N.D |
| 99 | 27.8 | N.D |
| 100 | 29.1 | N.D |
| 101 | 25.4 | N.D |
| 102 | 25.7 | N.D |
| 103 | 27.4 | N.D |
| 104 | 28.2 | N.D |
| 105 | 27.2 | N.D |
| 106 | 24.2 | N.D |
| 107 | 27.9 | N.D |
| 108 | 28.6 | N.D |
| 109 | 28.4 | N.D |
| 110 | 24.4 | N.D |
| 111 | 24.2 | N.D |
| 112 | 25.1 | N.D |
| 113 | 24.9 | N.D |
| 114 | 25.9 | N.D |
| 115 | 27.6 | N.D |
| 116 | 24.3 | N.D |
| 117 | 24.3 | N.D |
| 118 | 28.3 | N.D |
| 119 | 25.3 | N.D |
| 120 | 26.4 | N.D |
| 121 | 27.8 | N.D |
| 122 | 29.3 | N.D |
| 123 | 25.4 | N.D |
| 124 | 25.7 | N.D |
| 125 | 27.4 | N.D |
| 126 | 28.2 | N.D |
| 127 | 27.2 | N.D |
| 128 | 24.2 | N.D |
| 129 | 27.9 | N.D |
| 130 | 28.6 | N.D |
| 131 | 28.4 | N.D |
| 132 | 24.4 | N.D |
| 133 | 24.2 | N.D |
| 134 | 25.1 | N.D |
| 135 | 24.9 | N.D |
| 136 | 28.4 | N.D |
| 137 | 24.4 | N.D |
| 138 | 24.2 | N.D |
| 139 | 25.1 | N.D |
| 140 | 24.9 | N.D |
| 141 | 25.9 | N.D |
| 142 | 27.6 | N.D |
| 143 | 24.3 | N.D |
| 144 | 24.3 | N.D |
| 145 | 28.3 | N.D |
| 146 | 25.3 | N.D |

TABLE 7-continued

Results of detection of methylation of primers and probes specific to SDC2 gene methylation

| set | qMSP $C_T$ value | |
|---|---|---|
| | Methylated DNA | Non-methylated DNA |
| 147 | 26.4 | N.D |
| 148 | 27.4 | N.D |
| 149 | 26.3 | N.D |
| 150 | 25.2 | N.D |
| 151 | 25.7 | N.D |
| 152 | 27.6 | N.D |
| 153 | 27.8 | N.D |
| 154 | 29.3 | N.D |
| 155 | 25.4 | N.D |
| 156 | 27.4 | N.D |
| 157 | 26.3 | N.D |
| 158 | 25.2 | N.D |
| 159 | 25.7 | N.D |
| 160 | 27.6 | N.D |
| 161 | 27.8 | N.D |
| 162 | 29.3 | N.D |
| 163 | 25.4 | N.D |
| 164 | 25.7 | N.D |
| 165 | 27.4 | N.D |
| 166 | 28.2 | N.D |
| 167 | 27.2 | N.D |
| 168 | 24.2 | N.D |
| 169 | 27.9 | N.D |
| 170 | 28.6 | N.D |
| 171 | 28.4 | N.D |
| 172 | 24.4 | N.D |
| 173 | 24.2 | N.D |
| 174 | 25.1 | N.D |
| 175 | 24.9 | N.D |
| 176 | 25.9 | N.D |
| 177 | 27.6 | N.D |
| 178 | 24.3 | N.D |
| 179 | 24.2 | N.D |
| 180 | 27.6 | N.D |
| 181 | 27.8 | N.D |
| 182 | 29.3 | N.D |
| 183 | 25.4 | N.D |
| 184 | 25.7 | N.D |
| 185 | 27.4 | N.D |
| 186 | 28.2 | N.D |
| 187 | 27.2 | N.D |
| 188 | 24.2 | N.D |
| 189 | 27.9 | N.D |
| 190 | 28.6 | N.D |
| 191 | 28.4 | N.D |
| 192 | 24.4 | N.D |
| 193 | 24.2 | N.D |
| 194 | 25.1 | N.D |
| 195 | 24.9 | N.D |
| 196 | 25.9 | N.D |
| 197 | 27.6 | N.D |
| 198 | 24.3 | N.D |
| 199 | 24.3 | N.D |
| 200 | 28.4 | N.D |
| 201 | 28.2 | N.D |
| 202 | 27.2 | N.D |
| 203 | 24.2 | N.D |
| 204 | 27.9 | N.D |
| 205 | 28.6 | N.D |
| 206 | 28.4 | N.D |
| 207 | 24.4 | N.D |
| 208 | 24.2 | N.D |
| 209 | 25.1 | N.D |
| 210 | 24.9 | N.D |
| 211 | 25.9 | N.D |
| 212 | 27.6 | N.D |
| 213 | 24.3 | N.D |
| 214 | 24.3 | N.D |
| 215 | 28.3 | N.D |
| 216 | 25.3 | N.D |
| 217 | 26.4 | N.D |
| 218 | 27.4 | N.D |
| 219 | 26.3 | N.D |
| 220 | 25.2 | N.D |
| 221 | 25.7 | N.D |
| 222 | 27.6 | N.D |
| 223 | 27.8 | N.D |
| 224 | 29.3 | N.D |
| 225 | 24.4 | N.D |
| 226 | 24.2 | N.D |
| 227 | 25.1 | N.D |
| 228 | 24.9 | N.D |
| 229 | 25.9 | N.D |
| 230 | 27.6 | N.D |
| 231 | 24.3 | N.D |
| 232 | 24.3 | N.D |
| 233 | 28.3 | N.D |
| 234 | 25.3 | N.D |
| 235 | 26.4 | N.D |
| 236 | 27.4 | N.D |
| 237 | 26.3 | N.D |
| 238 | 25.2 | N.D |
| 239 | 25.7 | N.D |
| 240 | 27.6 | N.D |
| 241 | 27.8 | N.D |
| 242 | 29.3 | N.D |
| 243 | 25.4 | N.D |
| 244 | 25.7 | N.D |
| 245 | 27.4 | N.D |
| 246 | 28.2 | N.D |
| 247 | 27.2 | N.D |
| 248 | 24.2 | N.D |
| 249 | 25.3 | N.D |
| 250 | 26.3 | N.D |
| 251 | 25.9 | N.D |
| 252 | 26.4 | N.D |
| 253 | 27.4 | N.D |
| 254 | 26.3 | N.D |
| 255 | 25.2 | N.D |
| 256 | 25.7 | N.D |
| 257 | 27.6 | N.D |
| 258 | 27.8 | N.D |
| 259 | 29.3 | N.D |
| 260 | 25.4 | N.D |
| 261 | 25.7 | N.D |
| 262 | 27.4 | N.D |
| 263 | 27.4 | N.D |
| 264 | 26.3 | N.D |
| 265 | 25.2 | N.D |
| 266 | 25.7 | N.D |
| 267 | 27.6 | N.D |
| 268 | 27.8 | N.D |
| 269 | 29.3 | N.D |
| 270 | 25.4 | N.D |
| 271 | 25.7 | N.D |
| 272 | 27.4 | N.D |
| 273 | 26.3 | N.D |
| 274 | 25.2 | N.D |
| 275 | 25.7 | N.D |
| 276 | 27.6 | N.D |
| 277 | 27.8 | N.D |
| 278 | 29.3 | N.D |
| 279 | 25.4 | N.D |
| 280 | 25.7 | N.D |
| 281 | 27.4 | N.D |
| 282 | 28.2 | N.D |
| 283 | 27.2 | N.D |
| 284 | 27.4 | N.D |
| 285 | 26.3 | N.D |
| 286 | 25.2 | N.D |
| 287 | 25.7 | N.D |
| 288 | 27.6 | N.D |
| 289 | 27.8 | N.D |
| 290 | 29.3 | N.D |
| 291 | 27.3 | N.D |
| 292 | 25.2 | N.D |

TABLE 7-continued

Results of detection of methylation of primers and probes specific to SDC2 gene methylation

| set | qMSP $C_T$ value | |
|---|---|---|
| | Methylated DNA | Non-methylated DNA |
| 293 | 26.2 | N.D |
| 294 | 27.4 | N.D |
| 295 | 26.3 | N.D |
| 296 | 25.2 | N.D |
| 297 | 25.7 | N.D |
| 298 | 27.6 | N.D |
| 299 | 27.8 | N.D |
| 300 | 24 | N.D |
| 301 | 26.3 | N.D |
| 302 | 25.2 | N.D |
| 303 | 25.7 | N.D |
| 304 | 27.6 | N.D |
| 305 | 27.8 | N.D |
| 306 | 29.3 | N.D |
| 307 | 25.4 | N.D |
| 308 | 25.7 | N.D |
| 309 | 27.4 | N.D |
| 310 | 24.2 | N.D |
| 311 | 27.9 | N.D |
| 312 | 28.6 | N.D |
| 313 | 28.4 | N.D |
| 314 | 24.4 | N.D |
| 315 | 24.2 | N.D |
| 316 | 25.1 | N.D |
| 317 | 24.9 | N.D |
| 318 | 25.9 | N.D |
| 319 | 27.6 | N.D |
| 320 | 24.3 | N.D |
| 321 | 24.3 | N.D |
| 322 | 28.3 | N.D |
| 323 | 25.3 | N.D |
| 324 | 26.4 | N.D |
| 325 | 27.4 | N.D |
| 326 | 26.3 | N.D |
| 327 | 25.2 | N.D |
| 328 | 27.6 | N.D |
| 329 | 27.8 | N.D |
| 330 | 29.3 | N.D |
| 331 | 25.4 | N.D |
| 332 | 27.4 | N.D |
| 333 | 26.3 | N.D |
| 334 | 25.2 | N.D |
| 335 | 25.7 | N.D |
| 336 | 27.6 | N.D |
| 337 | 27.8 | N.D |
| 338 | 29.3 | N.D |
| 339 | 24.3 | N.D |
| 340 | 25.2 | N.D |
| 341 | 26.8 | N.D |
| 342 | 27.4 | N.D |
| 343 | 28.2 | N.D |
| 344 | 27.2 | N.D |
| 345 | 24.2 | N.D |
| 346 | 27.9 | N.D |
| 347 | 28.6 | N.D |
| 348 | 28.4 | N.D |
| 349 | 24.4 | N.D |
| 350 | 24.2 | N.D |
| 351 | 25.1 | N.D |
| 352 | 27.4 | N.D |
| 353 | 26.3 | N.D |
| 354 | 25.2 | N.D |
| 355 | 25.7 | N.D |
| 356 | 27.6 | N.D |
| 357 | 27.9 | N.D |
| 358 | 28.6 | N.D |
| 359 | 28.4 | N.D |
| 360 | 24.4 | N.D |
| 361 | 24.2 | N.D |
| 362 | 25.1 | N.D |
| 363 | 24.9 | N.D |
| 364 | 25.9 | N.D |
| 365 | 27.6 | N.D |
| 366 | 24.3 | N.D |
| 367 | 25.8 | N.D |
| 368 | 26.1 | N.D |
| 369 | 27.7 | N.D |
| 370 | 25.3 | N.D |
| 371 | 27.9 | N.D |
| 372 | 28.6 | N.D |
| 373 | 28.4 | N.D |
| 374 | 24.4 | N.D |
| 375 | 24.2 | N.D |
| 376 | 25.1 | N.D |
| 377 | 24.9 | N.D |
| 378 | 25.9 | N.D |
| 379 | 27.6 | N.D |
| 380 | 24.3 | N.D |
| 381 | 27.4 | N.D |
| 382 | 26.3 | N.D |
| 383 | 25.2 | N.D |
| 384 | 25.7 | N.D |
| 385 | 27.6 | N.D |
| 386 | 27.8 | N.D |
| 387 | 29.3 | N.D |
| 388 | 25.1 | N.D |
| 389 | 26.3 | N.D |
| 390 | 27.4 | N.D |
| 391 | 26.3 | N.D |
| 392 | 25.2 | N.D |
| 393 | 25.7 | N.D |
| 394 | 27.6 | N.D |
| 395 | 27.8 | N.D |
| 396 | 29.3 | N.D |
| 397 | 25.4 | N.D |
| 398 | 25.7 | N.D |
| 399 | 27.4 | N.D |
| 400 | 24.4 | N.D |
| 401 | 27.2 | N.D |
| 402 | 24.2 | N.D |
| 403 | 27.9 | N.D |
| 404 | 27.6 | N.D |
| 405 | 24.2 | N.D |
| 406 | 27.9 | N.D |
| 407 | 28.6 | N.D |
| 408 | 28.4 | N.D |
| 409 | 24.4 | N.D |
| 410 | 24.2 | N.D |
| 411 | 25.1 | N.D |
| 412 | 24.9 | N.D |
| 413 | 25.9 | N.D |
| 414 | 27.6 | N.D |
| 415 | 24.3 | N.D |
| 416 | 24.3 | N.D |
| 417 | 28.3 | N.D |
| 418 | 25.3 | N.D |
| 419 | 27.4 | N.D |
| 420 | 26.3 | N.D |
| 421 | 25.2 | N.D |
| 422 | 25.7 | N.D |
| 423 | 27.6 | N.D |
| 424 | 27.8 | N.D |
| 425 | 29.3 | N.D |
| 426 | 27.9 | N.D |
| 427 | 28.6 | N.D |
| 428 | 28.4 | N.D |
| 429 | 24.4 | N.D |
| 430 | 24.2 | N.D |
| 431 | 25.1 | N.D |
| 432 | 24.9 | N.D |
| 433 | 25.9 | N.D |
| 434 | 27.6 | N.D |
| 435 | 24.3 | N.D |
| 436 | 27.4 | N.D |
| 437 | 26.3 | N.D |
| 438 | 25.2 | N.D |

TABLE 7-continued

Results of detection of methylation of primers and probes specific to SDC2 gene methylation

| set | qMSP $C_T$ value Methylated DNA | Non-methylated DNA |
|---|---|---|
| 439 | 25.7 | N.D |
| 440 | 27.6 | N.D |
| 441 | 27.8 | N.D |
| 442 | 29.3 | N.D |
| 443 | 25.4 | N.D |
| 444 | 27.4 | N.D |
| 445 | 26.3 | N.D |
| 446 | 25.2 | N.D |
| 447 | 25.7 | N.D |
| 448 | 27.6 | N.D |
| 449 | 27.8 | N.D |
| 450 | 29.3 | N.D |
| 451 | 28.2 | N.D |
| 452 | 27.2 | N.D |
| 453 | 24.2 | N.D |
| 454 | 27.9 | N.D |
| 455 | 28.6 | N.D |
| 456 | 28.4 | N.D |
| 457 | 24.4 | N.D |
| 458 | 24.2 | N.D |
| 459 | 25.1 | N.D |
| 460 | 24.9 | N.D |
| 461 | 24.2 | N.D |
| 462 | 27.9 | N.D |
| 463 | 28.6 | N.D |
| 464 | 28.4 | N.D |
| 465 | 24.4 | N.D |
| 466 | 24.2 | N.D |
| 467 | 25.1 | N.D |
| 468 | 24.9 | N.D |
| 469 | 25.9 | N.D |
| 470 | 27.6 | N.D |
| 471 | 24.3 | N.D |
| 472 | 24.3 | N.D |
| 473 | 28.3 | N.D |
| 474 | 25.3 | N.D |
| 475 | 26.4 | N.D |
| 476 | 27.4 | N.D |
| 477 | 26.3 | N.D |
| 478 | 25.2 | N.D |
| 479 | 27.8 | N.D |
| 480 | 29.3 | N.D |
| 481 | 25.4 | N.D |
| 482 | 25.7 | N.D |
| 483 | 27.4 | N.D |
| 484 | 28.2 | N.D |
| 485 | 27.4 | N.D |
| 486 | 26.3 | N.D |
| 487 | 25.2 | N.D |
| 488 | 25.7 | N.D |
| 489 | 27.6 | N.D |
| 490 | 27.8 | N.D |
| 491 | 29.3 | N.D |
| 492 | 25.4 | N.D |
| 493 | 27.4 | N.D |
| 494 | 26.3 | N.D |
| 495 | 25.2 | N.D |
| 496 | 25.7 | N.D |
| 497 | 27.6 | N.D |
| 498 | 27.8 | N.D |
| 499 | 29.3 | N.D |
| 500 | 25.4 | N.D |
| 501 | 27.9 | N.D |
| 502 | 28.6 | N.D |
| 503 | 28.4 | N.D |
| 504 | 24.4 | N.D |
| 505 | 24.2 | N.D |
| 506 | 25.1 | N.D |
| 507 | 24.9 | N.D |
| 508 | 25.9 | N.D |
| 509 | 27.6 | N.D |
| 510 | 24.3 | N.D |
| 511 | 25.5 | N.D |
| 512 | 27.8 | N.D |
| 513 | 28.2 | N.D |
| 514 | 26.1 | N.D |
| 515 | 27.4 | N.D |
| 516 | 26.3 | N.D |
| 517 | 25.2 | N.D |
| 518 | 25.7 | N.D |
| 519 | 27.6 | N.D |
| 520 | 27.8 | N.D |
| 521 | 29.3 | N.D |
| 522 | 26.2 | N.D |
| 523 | 25.3 | N.D |
| 524 | 28.2 | N.D |
| 525 | 27.4 | N.D |
| 526 | 28.2 | N.D |
| 527 | 27.2 | N.D |
| 528 | 24.2 | N.D |
| 529 | 27.9 | N.D |
| 530 | 28.6 | N.D |
| 531 | 28.4 | N.D |
| 532 | 24.4 | N.D |
| 533 | 24.2 | N.D |
| 534 | 25.4 | N.D |
| 535 | 24.9 | N.D |
| 536 | 25.9 | N.D |
| 537 | 27.6 | N.D |
| 538 | 25.2 | N.D |
| 539 | 25.7 | N.D |
| 540 | 27.6 | N.D |
| 541 | 27.4 | N.D |
| 542 | 26.3 | N.D |
| 543 | 25.2 | N.D |
| 544 | 25.7 | N.D |
| 545 | 27.6 | N.D |
| 546 | 27.8 | N.D |
| 547 | 29.3 | N.D |
| 548 | 25.4 | N.D |
| 549 | 25.7 | N.D |
| 550 | 27.4 | N.D |
| 551 | 28.2 | N.D |
| 552 | 27.2 | N.D |
| 553 | 24.2 | N.D |
| 554 | 27.4 | N.D |
| 555 | 26.3 | N.D |
| 556 | 25.2 | N.D |
| 557 | 25.7 | N.D |
| 558 | 27.6 | N.D |
| 559 | 27.8 | N.D |
| 560 | 29.3 | N.D |
| 561 | 28.4 | N.D |
| 562 | 24.4 | N.D |
| 563 | 24.2 | N.D |
| 564 | 25.1 | N.D |
| 565 | 24.9 | N.D |
| 566 | 25.9 | N.D |
| 567 | 27.6 | N.D |
| 568 | 24.3 | N.D |
| 569 | 24.3 | N.D |
| 570 | 28.3 | N.D |
| 571 | 25.3 | N.D |
| 572 | 26.4 | N.D |
| 573 | 27.4 | N.D |
| 574 | 26.3 | N.D |
| 575 | 25.2 | N.D |
| 576 | 25.7 | N.D |
| 577 | 27.6 | N.D |
| 578 | 27.8 | N.D |
| 579 | 29.3 | N.D |
| 580 | 25.4 | N.D |
| 581 | 25.7 | N.D |
| 582 | 27.4 | N.D |
| 583 | 28.2 | N.D |
| 584 | 27.2 | N.D |

TABLE 7-continued

Results of detection of methylation of primers and probes specific to SDC2 gene methylation

| set | qMSP $C_T$ value Methylated DNA | Non-methylated DNA |
|---|---|---|
| 585 | 24.2 | N.D |
| 586 | 24.2 | N.D |
| 587 | 26.3 | N.D |
| 588 | 25.2 | N.D |
| 589 | 25.7 | N.D |
| 590 | 27.6 | N.D |
| 591 | 27.8 | N.D |
| 592 | 29.3 | N.D |
| 593 | 27.4 | N.D |
| 594 | 28.2 | N.D |
| 595 | 27.2 | N.D |
| 596 | 24.2 | N.D |
| 597 | 27.9 | N.D |
| 598 | 28.6 | N.D |
| 599 | 28.4 | N.D |
| 600 | 27 | N.D |
| 601 | 24.2 | N.D |
| 602 | 25.1 | N.D |
| 603 | 24.9 | N.D |
| 604 | 25.9 | N.D |
| 605 | 24.2 | N.D |
| 606 | 27.9 | N.D |
| 607 | 28.6 | N.D |
| 608 | 28.4 | N.D |
| 609 | 24.4 | N.D |
| 610 | 24.2 | N.D |
| 611 | 25.1 | N.D |
| 612 | 24.9 | N.D |
| 613 | 25.9 | N.D |
| 614 | 27.6 | N.D |
| 615 | 24.3 | N.D |
| 616 | 24.3 | N.D |
| 617 | 28.3 | N.D |
| 618 | 25.3 | N.D |
| 619 | 26.4 | N.D |
| 620 | 27.4 | N.D |
| 621 | 26.3 | N.D |
| 622 | 25.2 | N.D |
| 623 | 26.3 | N.D |
| 624 | 25.2 | N.D |
| 625 | 25.7 | N.D |
| 626 | 27.6 | N.D |
| 627 | 27.8 | N.D |
| 628 | 29.3 | N.D |
| 629 | 25.4 | N.D |
| 630 | 25.7 | N.D |
| 631 | 27.4 | N.D |
| 632 | 28.2 | N.D |
| 633 | 27.2 | N.D |
| 634 | 24.2 | N.D |
| 635 | 27.4 | N.D |
| 636 | 26.3 | N.D |
| 637 | 25.2 | N.D |
| 638 | 25.7 | N.D |
| 639 | 27.6 | N.D |
| 640 | 27.8 | N.D |
| 641 | 29.3 | N.D |
| 642 | 24.2 | N.D |
| 643 | 27.9 | N.D |
| 644 | 28.6 | N.D |
| 645 | 28.4 | N.D |
| 646 | 24.4 | N.D |
| 647 | 24.2 | N.D |
| 648 | 25.1 | N.D |
| 649 | 24.9 | N.D |
| 650 | 25.9 | N.D |
| 651 | 27.9 | N.D |
| 652 | 26.1 | N.D |
| 653 | 24.8 | N.D |
| 654 | 25.5 | N.D |
| 655 | 25.7 | N.D |
| 656 | 24.9 | N.D |
| 657 | 24.2 | N.D |
| 658 | 25.5 | N.D |
| 659 | 25.4 | N.D |
| 660 | 26.8 | N.D |
| 661 | 26.8 | N.D |
| 662 | 24.7 | N.D |
| 663 | 25.5 | N.D |
| 664 | 27.4 | N.D |
| 665 | 24.6 | N.D |
| 666 | 24.4 | N.D |
| 667 | 24.2 | N.D |
| 668 | 25.1 | N.D |
| 669 | 24.9 | N.D |
| 670 | 25.9 | N.D |
| 671 | 27.6 | N.D |
| 672 | 24.3 | N.D |
| 673 | 24.3 | N.D |
| 674 | 23.9 | N.D |
| 675 | 25.3 | N.D |
| 676 | 26.4 | N.D |
| 677 | 27.4 | N.D |
| 678 | 26.3 | N.D |
| 679 | 25.2 | N.D |
| 680 | 24.3 | N.D |
| 681 | 24.3 | N.D |
| 682 | 28.3 | N.D |
| 683 | 25.3 | N.D |
| 684 | 26.4 | N.D |
| 685 | 27.4 | N.D |
| 686 | 26.3 | N.D |
| 687 | 25.2 | N.D |
| 688 | 25.7 | N.D |
| 689 | 27.6 | N.D |
| 690 | 27.8 | N.D |
| 691 | 29.3 | N.D |
| 692 | 25.4 | N.D |
| 693 | 25.7 | N.D |
| 694 | 27.4 | N.D |
| 695 | 24.3 | N.D |
| 696 | 28.3 | N.D |
| 697 | 25.3 | N.D |
| 698 | 26.4 | N.D |
| 699 | 27.4 | N.D |
| 700 | 26.3 | N.D |
| 701 | 25.2 | N.D |
| 702 | 25.7 | N.D |
| 703 | 27.6 | N.D |
| 704 | 27.8 | N.D |
| 705 | 29.3 | N.D |
| 706 | 25.4 | N.D |
| 707 | 25.7 | N.D |
| 708 | 27.4 | N.D |
| 709 | 28.2 | N.D |
| 710 | 27.2 | N.D |
| 711 | 24.2 | N.D |
| 712 | 27.9 | N.D |
| 713 | 28.6 | N.D |
| 714 | 28.4 | N.D |
| 715 | 24.4 | N.D |
| 716 | 24.2 | N.D |
| 717 | 25.1 | N.D |
| 718 | 24.9 | N.D |
| 719 | 25.9 | N.D |
| 720 | 27.6 | N.D |
| 721 | 24.3 | N.D |
| 722 | 24.3 | N.D |
| 723 | 25.7 | N.D |
| 724 | 27.4 | N.D |
| 725 | 28.2 | N.D |
| 726 | 27.2 | N.D |
| 727 | 24.2 | N.D |
| 728 | 27.9 | N.D |
| 729 | 28.6 | N.D |
| 730 | 28.4 | N.D |

TABLE 7-continued

Results of detection of methylation of primers and probes specific to SDC2 gene methylation

| set | qMSP C$_T$ value | |
|---|---|---|
| | Methylated DNA | Non-methylated DNA |
| 731 | 24.4 | N.D |
| 732 | 24.2 | N.D |
| 733 | 25.1 | N.D |
| 734 | 24.9 | N.D |
| 735 | 25.9 | N.D |
| 736 | 27.6 | N.D |
| 737 | 24.3 | N.D |
| 738 | 24.3 | N.D |
| 739 | 28.3 | N.D |
| 740 | 25.3 | N.D |
| 741 | 26.4 | N.D |
| 742 | 27.4 | N.D |
| 743 | 26.3 | N.D |
| 744 | 25.2 | N.D |
| 745 | 25.7 | N.D |
| 746 | 28.2 | N.D |
| 747 | 27.2 | N.D |
| 748 | 24.2 | N.D |
| 749 | 27.9 | N.D |
| 750 | 28.6 | N.D |
| 751 | 28.4 | N.D |
| 752 | 24.4 | N.D |
| 753 | 24.2 | N.D |
| 754 | 25.1 | N.D |
| 755 | 24.9 | N.D |
| 756 | 25.9 | N.D |
| 757 | 27.6 | N.D |
| 758 | 24.3 | N.D |
| 759 | 24.2 | N.D |
| 760 | 25.2 | N.D |
| 761 | 25.7 | N.D |
| 762 | 27.6 | N.D |
| 763 | 27.8 | N.D |
| 764 | 29.1 | N.D |
| 765 | 25.4 | N.D |
| 766 | 25.7 | N.D |
| 767 | 27.4 | N.D |
| 768 | 28.2 | N.D |
| 769 | 27.2 | N.D |
| 770 | 24.2 | N.D |
| 771 | 27.9 | N.D |
| 772 | 28.6 | N.D |
| 773 | 28.4 | N.D |
| 774 | 24.4 | N.D |
| 775 | 24.2 | N.D |
| 776 | 25.1 | N.D |
| 777 | 24.9 | N.D |
| 778 | 25.9 | N.D |
| 779 | 27.6 | N.D |
| 780 | 24.3 | N.D |
| 781 | 24.3 | N.D |
| 782 | 28.3 | N.D |
| 783 | 25.3 | N.D |
| 784 | 26.4 | N.D |
| 785 | 27.8 | N.D |
| 786 | 29.3 | N.D |
| 787 | 25.4 | N.D |
| 788 | 25.7 | N.D |
| 789 | 27.4 | N.D |
| 790 | 28.2 | N.D |
| 791 | 27.2 | N.D |
| 792 | 24.2 | N.D |
| 793 | 27.9 | N.D |
| 794 | 28.6 | N.D |
| 795 | 28.4 | N.D |
| 796 | 24.4 | N.D |
| 797 | 24.2 | N.D |
| 798 | 25.1 | N.D |
| 799 | 24.9 | N.D |
| 800 | 28.4 | N.D |
| 801 | 24.4 | N.D |
| 802 | 24.2 | N.D |
| 803 | 25.1 | N.D |
| 804 | 24.9 | N.D |
| 805 | 25.9 | N.D |
| 806 | 27.6 | N.D |
| 807 | 24.3 | N.D |
| 808 | 24.3 | N.D |
| 809 | 28.3 | N.D |
| 810 | 25.3 | N.D |
| 811 | 26.4 | N.D |
| 812 | 27.4 | N.D |
| 813 | 26.3 | N.D |
| 814 | 25.2 | N.D |
| 815 | 25.7 | N.D |
| 816 | 27.6 | N.D |
| 817 | 27.8 | N.D |
| 818 | 29.3 | N.D |
| 819 | 25.4 | N.D |
| 820 | 27.4 | N.D |
| 821 | 26.3 | N.D |
| 822 | 25.2 | N.D |
| 823 | 25.7 | N.D |
| 824 | 27.6 | N.D |
| 825 | 27.8 | N.D |
| 826 | 29.3 | N.D |
| 827 | 25.4 | N.D |
| 828 | 25.7 | N.D |
| 829 | 27.4 | N.D |
| 830 | 28.2 | N.D |
| 831 | 27.2 | N.D |
| 832 | 24.2 | N.D |
| 833 | 27.9 | N.D |
| 834 | 28.6 | N.D |
| 835 | 28.4 | N.D |
| 836 | 24.4 | N.D |
| 837 | 24.2 | N.D |
| 838 | 25.1 | N.D |
| 839 | 24.9 | N.D |
| 840 | 25.9 | N.D |
| 841 | 27.6 | N.D |
| 842 | 24.3 | N.D |
| 843 | 24.2 | N.D |
| 844 | 27.6 | N.D |
| 845 | 27.8 | N.D |
| 846 | 29.3 | N.D |
| 847 | 25.4 | N.D |
| 848 | 25.7 | N.D |
| 849 | 27.4 | N.D |
| 850 | 28.2 | N.D |
| 851 | 27.2 | N.D |
| 852 | 24.2 | N.D |
| 853 | 27.9 | N.D |
| 854 | 28.6 | N.D |
| 855 | 28.4 | N.D |
| 856 | 24.4 | N.D |
| 857 | 24.2 | N.D |
| 858 | 25.1 | N.D |
| 859 | 24.9 | N.D |
| 860 | 25.9 | N.D |
| 861 | 27.6 | N.D |
| 862 | 24.3 | N.D |
| 863 | 24.3 | N.D |
| 864 | 28.4 | N.D |
| 865 | 28.2 | N.D |
| 866 | 27.2 | N.D |
| 867 | 24.2 | N.D |
| 868 | 27.9 | N.D |
| 869 | 28.6 | N.D |
| 870 | 28.4 | N.D |
| 871 | 24.4 | N.D |
| 872 | 24.2 | N.D |
| 873 | 25.1 | N.D |
| 874 | 24.9 | N.D |
| 875 | 25.9 | N.D |
| 876 | 27.6 | N.D |

TABLE 7-continued

Results of detection of methylation of primers and probes specific to SDC2 gene methylation

| set | qMSP C$_T$ value Methylated DNA | Non-methylated DNA |
|---|---|---|
| 877 | 24.3 | N.D |
| 878 | 24.3 | N.D |
| 879 | 28.3 | N.D |
| 880 | 25.3 | N.D |
| 881 | 26.4 | N.D |
| 882 | 27.4 | N.D |
| 883 | 26.3 | N.D |
| 884 | 25.2 | N.D |
| 885 | 25.7 | N.D |
| 886 | 27.6 | N.D |
| 887 | 27.8 | N.D |
| 888 | 29.3 | N.D |
| 889 | 24.4 | N.D |
| 890 | 24.2 | N.D |
| 891 | 25.1 | N.D |
| 892 | 24.9 | N.D |
| 893 | 25.9 | N.D |
| 894 | 27.6 | N.D |
| 895 | 24.3 | N.D |
| 896 | 24.3 | N.D |
| 897 | 28.3 | N.D |
| 898 | 25.3 | N.D |
| 899 | 26.4 | N.D |
| 900 | 27.4 | N.D |
| 901 | 26.3 | N.D |
| 902 | 25.2 | N.D |
| 903 | 25.7 | N.D |
| 904 | 27.6 | N.D |
| 905 | 27.8 | N.D |
| 906 | 29.3 | N.D |
| 907 | 25.4 | N.D |
| 908 | 25.7 | N.D |
| 909 | 27.4 | N.D |
| 910 | 28.2 | N.D |
| 911 | 27.2 | N.D |
| 912 | 24.2 | N.D |
| 913 | 25.3 | N.D |
| 914 | 26.3 | N.D |
| 915 | 25.9 | N.D |
| 916 | 26.4 | N.D |
| 917 | 27.4 | N.D |
| 918 | 26.3 | N.D |
| 919 | 25.2 | N.D |
| 920 | 25.7 | N.D |
| 921 | 27.6 | N.D |
| 922 | 27.8 | N.D |
| 923 | 29.3 | N.D |
| 924 | 25.4 | N.D |
| 925 | 25.7 | N.D |
| 926 | 27.4 | N.D |
| 927 | 27.4 | N.D |
| 928 | 26.3 | N.D |
| 929 | 25.2 | N.D |
| 930 | 25.7 | N.D |
| 931 | 27.6 | N.D |
| 932 | 27.8 | N.D |
| 933 | 29.3 | N.D |
| 934 | 25.4 | N.D |
| 935 | 25.7 | N.D |
| 936 | 27.4 | N.D |
| 937 | 26.3 | N.D |
| 938 | 25.2 | N.D |
| 939 | 25.7 | N.D |
| 940 | 27.6 | N.D |
| 941 | 27.8 | N.D |
| 942 | 29.3 | N.D |
| 943 | 25.4 | N.D |
| 944 | 25.7 | N.D |
| 945 | 27.4 | N.D |
| 946 | 28.2 | N.D |
| 947 | 27.2 | N.D |
| 948 | 27.4 | N.D |
| 949 | 26.3 | N.D |
| 950 | 25.2 | N.D |
| 951 | 25.7 | N.D |
| 952 | 27.6 | N.D |
| 953 | 27.8 | N.D |
| 954 | 29.3 | N.D |
| 955 | 27.3 | N.D |
| 956 | 25.2 | N.D |
| 957 | 26.2 | N.D |
| 958 | 27.4 | N.D |
| 959 | 26.3 | N.D |
| 960 | 25.2 | N.D |
| 961 | 25.7 | N.D |
| 962 | 27.6 | N.D |
| 963 | 27.8 | N.D |
| 964 | 24 | N.D |
| 965 | 26.3 | N.D |
| 966 | 25.2 | N.D |
| 967 | 25.7 | N.D |
| 968 | 27.6 | N.D |
| 969 | 27.8 | N.D |
| 970 | 29.3 | N.D |
| 971 | 25.4 | N.D |
| 972 | 25.7 | N.D |
| 973 | 27.4 | N.D |
| 974 | 24.2 | N.D |
| 975 | 27.9 | N.D |
| 976 | 28.6 | N.D |
| 977 | 28.4 | N.D |
| 978 | 24.4 | N.D |
| 979 | 24.2 | N.D |
| 980 | 25.1 | N.D |
| 981 | 24.9 | N.D |
| 982 | 25.9 | N.D |
| 983 | 27.6 | N.D |
| 984 | 24.3 | N.D |
| 985 | 24.3 | N.D |
| 986 | 28.3 | N.D |
| 987 | 25.3 | N.D |
| 988 | 26.4 | N.D |
| 989 | 27.4 | N.D |
| 990 | 26.3 | N.D |
| 991 | 25.2 | N.D |
| 992 | 27.6 | N.D |
| 993 | 27.8 | N.D |
| 994 | 29.3 | N.D |
| 995 | 25.4 | N.D |
| 996 | 27.4 | N.D |
| 997 | 26.3 | N.D |
| 998 | 25.2 | N.D |
| 999 | 25.7 | N.D |
| 1000 | 27.6 | N.D |
| 1001 | 27.8 | N.D |
| 1002 | 29.3 | N.D |
| 1003 | 24.3 | N.D |
| 1004 | 25.2 | N.D |
| 1005 | 26.8 | N.D |
| 1006 | 27.4 | N.D |
| 1007 | 28.2 | N.D |
| 1008 | 27.2 | N.D |
| 1009 | 24.2 | N.D |
| 1010 | 27.9 | N.D |
| 1011 | 28.6 | N.D |
| 1012 | 28.4 | N.D |
| 1013 | 24.4 | N.D |
| 1014 | 24.2 | N.D |
| 1015 | 25.1 | N.D |
| 1016 | 27.4 | N.D |
| 1017 | 26.3 | N.D |
| 1018 | 25.2 | N.D |
| 1019 | 25.7 | N.D |
| 1020 | 27.6 | N.D |
| 1021 | 27.9 | N.D |
| 1022 | 28.6 | N.D |

TABLE 7-continued

Results of detection of methylation of primers and probes specific to SDC2 gene methylation

| set | qMSP C$_T$ value Methylated DNA | Non-methylated DNA |
|---|---|---|
| 1023 | 28.4 | N.D |
| 1024 | 24.4 | N.D |
| 1025 | 24.4 | N.D |
| 1026 | 25.1 | N.D |
| 1027 | 24.9 | N.D |
| 1028 | 25.9 | N.D |
| 1029 | 27.6 | N.D |
| 1030 | 24.3 | N.D |
| 1031 | 25.8 | N.D |
| 1032 | 26.1 | N.D |
| 1033 | 27.7 | N.D |
| 1034 | 25.3 | N.D |
| 1035 | 27.9 | N.D |
| 1036 | 28.6 | N.D |
| 1037 | 28.4 | N.D |
| 1038 | 24.4 | N.D |
| 1039 | 24.2 | N.D |
| 1040 | 25.1 | N.D |
| 1041 | 24.9 | N.D |
| 1042 | 25.9 | N.D |
| 1043 | 27.6 | N.D |
| 1044 | 24.3 | N.D |
| 1045 | 27.4 | N.D |
| 1046 | 26.3 | N.D |
| 1047 | 25.2 | N.D |
| 1048 | 25.7 | N.D |
| 1049 | 27.6 | N.D |
| 1050 | 27.8 | N.D |
| 1051 | 29.3 | N.D |
| 1052 | 25.1 | N.D |
| 1053 | 26.4 | N.D |
| 1054 | 27.4 | N.D |
| 1055 | 26.3 | N.D |
| 1056 | 25.2 | N.D |
| 1057 | 25.7 | N.D |
| 1058 | 27.6 | N.D |
| 1059 | 27.8 | N.D |
| 1060 | 29.3 | N.D |
| 1061 | 25.4 | N.D |
| 1062 | 25.7 | N.D |
| 1063 | 27.4 | N.D |
| 1064 | 24.4 | N.D |
| 1065 | 27.2 | N.D |
| 1066 | 24.2 | N.D |
| 1067 | 27.9 | N.D |
| 1068 | 27.6 | N.D |
| 1069 | 24.2 | N.D |
| 1070 | 27.9 | N.D |
| 1071 | 28.6 | N.D |
| 1072 | 28.4 | N.D |
| 1073 | 24.4 | N.D |
| 1074 | 24.2 | N.D |
| 1075 | 25.1 | N.D |
| 1076 | 24.9 | N.D |
| 1077 | 25.9 | N.D |
| 1078 | 27.6 | N.D |
| 1079 | 24.3 | N.D |
| 1080 | 24.3 | N.D |
| 1081 | 28.3 | N.D |
| 1082 | 25.3 | N.D |
| 1083 | 27.4 | N.D |
| 1084 | 26.3 | N.D |
| 1085 | 25.2 | N.D |
| 1086 | 25.7 | N.D |
| 1087 | 27.6 | N.D |
| 1088 | 27.8 | N.D |
| 1089 | 29.3 | N.D |
| 1090 | 27.9 | N.D |
| 1091 | 28.6 | N.D |
| 1092 | 28.4 | N.D |
| 1093 | 24.4 | N.D |
| 1094 | 24.2 | N.D |
| 1095 | 25.1 | N.D |
| 1096 | 24.9 | N.D |
| 1097 | 25.9 | N.D |
| 1098 | 27.6 | N.D |
| 1099 | 24.3 | N.D |
| 1100 | 27.4 | N.D |
| 1101 | 26.3 | N.D |
| 1102 | 25.2 | N.D |
| 1103 | 25.7 | N.D |
| 1104 | 27.6 | N.D |
| 1105 | 27.8 | N.D |
| 1106 | 29.3 | N.D |
| 1107 | 25.4 | N.D |

INDUSTRIAL APPLICABILITY

The present invention has the effect of providing a method of conferring information for the diagnosis of colorectal cancer by detecting methylation of the CpG island of an SDC2 gene, which is a colorectal-cancer-specific marker gene, with high detection sensitivity. Since colorectal cancer can be diagnosed at the initial transformation stage, early diagnosis is possible, and the method of the present invention is capable of diagnosing colorectal cancer more accurately and quickly than typical methods and is thus useful.

Although specific embodiments of the present invention have been disclosed in detail as described above, it will be obvious to those of ordinary skill in the art that the description is merely of preferable exemplary embodiments, and is not to be construed as limiting the scope of the present invention. Therefore, the substantial scope of the present invention will be defined by the appended claims and equivalents thereof.

SEQUENCE LIST FREE TEXT

An electronic file is attached.

The invention claimed is:

1. A method of detecting methylation of an SDC2 gene, comprising:
   (a) treating genomic DNA from a stool sample with a reagent comprising bisulfite, hydrogen sulfite, modifies or disulfite, which differently modifies a methylated SDC2 gene and a non-methylated SDC2 gene;
   (b) performing treatment with a primer pair comprising the sequence of SEQ ID NOs: 31 and 32 specifically amplifying the methylated SDC2 gene; and
   (c) detecting the methylation of the SDC2 gene using a probe comprising the sequence of SEQ ID NO: 33 that hybridizes to the amplified methylated SDC2 gene specifically amplified in step (b).

2. The method according to claim 1, wherein at least one cytosine base is converted into uracil through treatment with the reagent.

3. The method according to claim 1, wherein the detecting the methylation is performed using a process selected from the group consisting of PCR, methylation-specific PCR, real-time methylation-specific PCR, PCR using a methylated-DNA-specific binding protein, PCR using a methylated-DNA-specific binding antibody, quantitative PCR, gene chip, sequencing, sequencing by synthesis, and sequencing by ligation.

4. The method according to claim 1, wherein the methylation of the SDC2 gene is detected by detecting a material that binds to the probe and exhibits fluorescence.

* * * * *

UNITED STATES PATENT AND TRADEMARK OFFICE
CERTIFICATE OF CORRECTION

PATENT NO. : 12,416,042 B2  
APPLICATION NO. : 17/616211  
DATED : September 16, 2025  
INVENTOR(S) : Sungwhan An et al.

Page 1 of 1

It is certified that error appears in the above-identified patent and that said Letters Patent is hereby corrected as shown below:

In the Claims

Column 391, Lines 18-19, Claim 1 "bisulfite, hydrogen sulfite, modifies or disulfite, which differently modifies" should be -- bisulfite, hydrogen sulfite, or disulfite, which differently modifies --.

Signed and Sealed this  
Eleventh Day of November, 2025

John A. Squires  
*Director of the United States Patent and Trademark Office*

SEQUENCE LISTING

<160> NUMBER OF SEQ ID NOS: 1180

<210> SEQ ID NO 1
<211> LENGTH: 27
<212> TYPE: DNA
<213> ORGANISM: Artificial Sequence
<220> FEATURE:
<223> OTHER INFORMATION: Synthetic Construct

```
<400> SEQUENCE: 1
gattcgttgg gataaatgcg ttcgttc                                    27

<210> SEQ ID NO 2
<211> LENGTH: 21
<212> TYPE: DNA
<213> ORGANISM: Artificial Sequence
<220> FEATURE:
<223> OTHER INFORMATION: Synthetic Construct

<400> SEQUENCE: 2
ctcgataccc ccattcccgc g                                          21

<210> SEQ ID NO 3
<211> LENGTH: 29
<212> TYPE: DNA
<213> ORGANISM: Artificial Sequence
<220> FEATURE:
<223> OTHER INFORMATION: Synthetic Construct

<400> SEQUENCE: 3
aagcgttgtt cgttggcgtt atttcgcgg                                  29

<210> SEQ ID NO 4
<211> LENGTH: 19
<212> TYPE: DNA
<213> ORGANISM: Artificial Sequence
<220> FEATURE:
<223> OTHER INFORMATION: Synthetic Construct

<400> SEQUENCE: 4
gcgttatttc gcggttcgc                                             19

<210> SEQ ID NO 5
<211> LENGTH: 20
<212> TYPE: DNA
<213> ORGANISM: Artificial Sequence
<220> FEATURE:
<223> OTHER INFORMATION: Synthetic Construct

<400> SEQUENCE: 5
ccacgcaaca aaacccgccg                                            20

<210> SEQ ID NO 6
<211> LENGTH: 30
<212> TYPE: DNA
<213> ORGANISM: Artificial Sequence
<220> FEATURE:
<223> OTHER INFORMATION: Synthetic Construct

<400> SEQUENCE: 6
cgagaattgc ggtttggttt agtcgtagag                                 30

<210> SEQ ID NO 7
<211> LENGTH: 21
<212> TYPE: DNA
<213> ORGANISM: Artificial Sequence
<220> FEATURE:
<223> OTHER INFORMATION: Synthetic Construct

<400> SEQUENCE: 7
gtatcgcggg gcgttaggga c                                          21

<210> SEQ ID NO 8
<211> LENGTH: 20
```

```
<212> TYPE: DNA
<213> ORGANISM: Artificial Sequence
<220> FEATURE:
<223> OTHER INFORMATION: Synthetic Construct

<400> SEQUENCE: 8
cgacccgaaa ccgaacgccg                                              20

<210> SEQ ID NO 9
<211> LENGTH: 27
<212> TYPE: DNA
<213> ORGANISM: Artificial Sequence
<220> FEATURE:
<223> OTHER INFORMATION: Synthetic Construct

<400> SEQUENCE: 9
cgggagtgtc gtaagtaggg cgaggcg                                      27

<210> SEQ ID NO 10
<211> LENGTH: 19
<212> TYPE: DNA
<213> ORGANISM: Artificial Sequence
<220> FEATURE:
<223> OTHER INFORMATION: Synthetic Construct

<400> SEQUENCE: 10
ggcggggtac gtgtgatac                                               19

<210> SEQ ID NO 11
<211> LENGTH: 28
<212> TYPE: DNA
<213> ORGANISM: Artificial Sequence
<220> FEATURE:
<223> OTHER INFORMATION: Synthetic Construct

<400> SEQUENCE: 11
gccaaaacca aaaaaaacga acgtaacg                                     28

<210> SEQ ID NO 12
<211> LENGTH: 25
<212> TYPE: DNA
<213> ORGANISM: Artificial Sequence
<220> FEATURE:
<223> OTHER INFORMATION: Synthetic Construct

<400> SEQUENCE: 12
cggtttcggg tcgtttggtc gttgg                                        25

<210> SEQ ID NO 13
<211> LENGTH: 27
<212> TYPE: DNA
<213> ORGANISM: Artificial Sequence
<220> FEATURE:
<223> OTHER INFORMATION: Synthetic Construct

<400> SEQUENCE: 13
gatagaggtt tttttttcgt tacgttc                                      27

<210> SEQ ID NO 14
<211> LENGTH: 23
<212> TYPE: DNA
<213> ORGANISM: Artificial Sequence
<220> FEATURE:
<223> OTHER INFORMATION: Synthetic Construct

<400> SEQUENCE: 14
```

```
cgacaaacgc tccgccgaaa acg                                           23

<210> SEQ ID NO 15
<211> LENGTH: 27
<212> TYPE: DNA
<213> ORGANISM: Artificial Sequence
<220> FEATURE:
<223> OTHER INFORMATION: Synthetic Construct

<400> SEQUENCE: 15
tttggcgggg cgttttgggg gtcggga                                       27

<210> SEQ ID NO 16
<211> LENGTH: 17
<212> TYPE: DNA
<213> ORGANISM: Artificial Sequence
<220> FEATURE:
<223> OTHER INFORMATION: Synthetic Construct

<400> SEQUENCE: 16
cgggttcgcg agggaac                                                  17

<210> SEQ ID NO 17
<211> LENGTH: 32
<212> TYPE: DNA
<213> ORGANISM: Artificial Sequence
<220> FEATURE:
<223> OTHER INFORMATION: Synthetic Construct

<400> SEQUENCE: 17
cttacataca atcaaacaaa aaaactaacg cg                                 32

<210> SEQ ID NO 18
<211> LENGTH: 30
<212> TYPE: DNA
<213> ORGANISM: Artificial Sequence
<220> FEATURE:
<223> OTHER INFORMATION: Synthetic Construct

<400> SEQUENCE: 18
cgcgcgtttt tcgagattag ggatgatttg                                    30

<210> SEQ ID NO 19
<211> LENGTH: 21
<212> TYPE: DNA
<213> ORGANISM: Artificial Sequence
<220> FEATURE:
<223> OTHER INFORMATION: Synthetic Construct

<400> SEQUENCE: 19
cgttttggcg gtgggaattt g                                             21

<210> SEQ ID NO 20
<211> LENGTH: 27
<212> TYPE: DNA
<213> ORGANISM: Artificial Sequence
<220> FEATURE:
<223> OTHER INFORMATION: Synthetic Construct

<400> SEQUENCE: 20
acgcccaaat aaaaacaact acgaacg                                       27

<210> SEQ ID NO 21
<211> LENGTH: 23
<212> TYPE: DNA
<213> ORGANISM: Artificial Sequence
```

```
<220> FEATURE:
<223> OTHER INFORMATION: Synthetic Construct

<400> SEQUENCE: 21
tggtcgcgtt tcggggttg gag                                         23

<210> SEQ ID NO 22
<211> LENGTH: 17
<212> TYPE: DNA
<213> ORGANISM: Artificial Sequence
<220> FEATURE:
<223> OTHER INFORMATION: Synthetic Construct

<400> SEQUENCE: 22
gattcgggga gggaggc                                               17

<210> SEQ ID NO 23
<211> LENGTH: 21
<212> TYPE: DNA
<213> ORGANISM: Artificial Sequence
<220> FEATURE:
<223> OTHER INFORMATION: Synthetic Construct

<400> SEQUENCE: 23
acgacgaaaa cgcgcgatcc g                                          21

<210> SEQ ID NO 24
<211> LENGTH: 27
<212> TYPE: DNA
<213> ORGANISM: Artificial Sequence
<220> FEATURE:
<223> OTHER INFORMATION: Synthetic Construct

<400> SEQUENCE: 24
cgtagtcgcg gagttagtgg tttcgtt                                    27

<210> SEQ ID NO 25
<211> LENGTH: 19
<212> TYPE: DNA
<213> ORGANISM: Artificial Sequence
<220> FEATURE:
<223> OTHER INFORMATION: Synthetic Construct

<400> SEQUENCE: 25
gtcggtgagt agagtcggc                                             19

<210> SEQ ID NO 26
<211> LENGTH: 27
<212> TYPE: DNA
<213> ORGANISM: Artificial Sequence
<220> FEATURE:
<223> OTHER INFORMATION: Synthetic Construct

<400> SEQUENCE: 26
cgacaatata actcccaaat aaacccg                                    27

<210> SEQ ID NO 27
<211> LENGTH: 26
<212> TYPE: DNA
<213> ORGANISM: Artificial Sequence
<220> FEATURE:
<223> OTHER INFORMATION: Synthetic Construct

<400> SEQUENCE: 27
cggagtcgcg gcgtttattg gttttc                                     26
```

<210> SEQ ID NO 28
<211> LENGTH: 17
<212> TYPE: DNA
<213> ORGANISM: Artificial Sequence
<220> FEATURE:
<223> OTHER INFORMATION: Synthetic Construct

<400> SEQUENCE: 28
cggaggatgc gcgcgtc                                                    17

<210> SEQ ID NO 29
<211> LENGTH: 24
<212> TYPE: DNA
<213> ORGANISM: Artificial Sequence
<220> FEATURE:
<223> OTHER INFORMATION: Synthetic Construct

<400> SEQUENCE: 29
cgaacgaacg catttatccc aacg                                            24

<210> SEQ ID NO 30
<211> LENGTH: 29
<212> TYPE: DNA
<213> ORGANISM: Artificial Sequence
<220> FEATURE:
<223> OTHER INFORMATION: Synthetic Construct

<400> SEQUENCE: 30
agttacgaga ggagttcgta gggaatagg                                       29

<210> SEQ ID NO 31
<211> LENGTH: 20
<212> TYPE: DNA
<213> ORGANISM: Artificial Sequence
<220> FEATURE:
<223> OTHER INFORMATION: Synthetic Construct

<400> SEQUENCE: 31
cggttagggc gaggtaatcg                                                 20

<210> SEQ ID NO 32
<211> LENGTH: 23
<212> TYPE: DNA
<213> ORGANISM: Artificial Sequence
<220> FEATURE:
<223> OTHER INFORMATION: Synthetic Construct

<400> SEQUENCE: 32
cgacgtccca acattttcga acg                                             23

<210> SEQ ID NO 33
<211> LENGTH: 30
<212> TYPE: DNA
<213> ORGANISM: Artificial Sequence
<220> FEATURE:
<223> OTHER INFORMATION: Synthetic Construct

<400> SEQUENCE: 33
cgtggaatcg tagtaggcga tttttttaagg                                     30

<210> SEQ ID NO 34
<211> LENGTH: 14
<212> TYPE: DNA
<213> ORGANISM: Artificial Sequence
<220> FEATURE:
<223> OTHER INFORMATION: Synthetic Construct -continued

<400> SEQUENCE: 34
gagtgggtta ggcg                                                    14

<210> SEQ ID NO 35
<211> LENGTH: 14
<212> TYPE: DNA
<213> ORGANISM: Artificial Sequence
<220> FEATURE:
<223> OTHER INFORMATION: Synthetic Construct

<400> SEQUENCE: 35
agtgggttag gcgg                                                    14

<210> SEQ ID NO 36
<211> LENGTH: 14
<212> TYPE: DNA
<213> ORGANISM: Artificial Sequence
<220> FEATURE:
<223> OTHER INFORMATION: Synthetic Construct

<400> SEQUENCE: 36
gtgggttagg cgga                                                    14

<210> SEQ ID NO 37
<211> LENGTH: 14
<212> TYPE: DNA
<213> ORGANISM: Artificial Sequence
<220> FEATURE:
<223> OTHER INFORMATION: Synthetic Construct

<400> SEQUENCE: 37
tgggttaggc ggag                                                    14

<210> SEQ ID NO 38
<211> LENGTH: 14
<212> TYPE: DNA
<213> ORGANISM: Artificial Sequence
<220> FEATURE:
<223> OTHER INFORMATION: Synthetic Construct

<400> SEQUENCE: 38
gggttaggcg gagg                                                    14

<210> SEQ ID NO 39
<211> LENGTH: 14
<212> TYPE: DNA
<213> ORGANISM: Artificial Sequence
<220> FEATURE:
<223> OTHER INFORMATION: Synthetic Construct

<400> SEQUENCE: 39
ggttaggcgg agga                                                    14

<210> SEQ ID NO 40
<211> LENGTH: 14
<212> TYPE: DNA
<213> ORGANISM: Artificial Sequence
<220> FEATURE:
<223> OTHER INFORMATION: Synthetic Construct

<400> SEQUENCE: 40
gttaggcgga ggat                                                    14

<210> SEQ ID NO 41

```
<211> LENGTH: 14
<212> TYPE: DNA
<213> ORGANISM: Artificial Sequence
<220> FEATURE:
<223> OTHER INFORMATION: Synthetic Construct

<400> SEQUENCE: 41
ttaggcggag gatg                                                       14

<210> SEQ ID NO 42
<211> LENGTH: 14
<212> TYPE: DNA
<213> ORGANISM: Artificial Sequence
<220> FEATURE:
<223> OTHER INFORMATION: Synthetic Construct

<400> SEQUENCE: 42
taggcggagg atgc                                                       14

<210> SEQ ID NO 43
<211> LENGTH: 14
<212> TYPE: DNA
<213> ORGANISM: Artificial Sequence
<220> FEATURE:
<223> OTHER INFORMATION: Synthetic Construct

<400> SEQUENCE: 43
aggcggagga tgcg                                                       14

<210> SEQ ID NO 44
<211> LENGTH: 14
<212> TYPE: DNA
<213> ORGANISM: Artificial Sequence
<220> FEATURE:
<223> OTHER INFORMATION: Synthetic Construct

<400> SEQUENCE: 44
ggcggaggat gcgc                                                       14

<210> SEQ ID NO 45
<211> LENGTH: 14
<212> TYPE: DNA
<213> ORGANISM: Artificial Sequence
<220> FEATURE:
<223> OTHER INFORMATION: Synthetic Construct

<400> SEQUENCE: 45
gcggaggatg cgcg                                                       14

<210> SEQ ID NO 46
<211> LENGTH: 14
<212> TYPE: DNA
<213> ORGANISM: Artificial Sequence
<220> FEATURE:
<223> OTHER INFORMATION: Synthetic Construct

<400> SEQUENCE: 46
cggaggatgc gcgc                                                       14

<210> SEQ ID NO 47
<211> LENGTH: 14
<212> TYPE: DNA
<213> ORGANISM: Artificial Sequence
<220> FEATURE:
<223> OTHER INFORMATION: Synthetic Construct

<400> SEQUENCE: 47
```
ggaggatgcg cgcg                    14

<210> SEQ ID NO 48
<211> LENGTH: 14
<212> TYPE: DNA
<213> ORGANISM: Artificial Sequence
<220> FEATURE:
<223> OTHER INFORMATION: Synthetic Construct

<400> SEQUENCE: 48
gaggatgcgc gcgt                    14

<210> SEQ ID NO 49
<211> LENGTH: 14
<212> TYPE: DNA
<213> ORGANISM: Artificial Sequence
<220> FEATURE:
<223> OTHER INFORMATION: Synthetic Construct

<400> SEQUENCE: 49
aggatgcgcg cgtc                    14

<210> SEQ ID NO 50
<211> LENGTH: 14
<212> TYPE: DNA
<213> ORGANISM: Artificial Sequence
<220> FEATURE:
<223> OTHER INFORMATION: Synthetic Construct

<400> SEQUENCE: 50
ggatgcgcgc gtcg                    14

<210> SEQ ID NO 51
<211> LENGTH: 14
<212> TYPE: DNA
<213> ORGANISM: Artificial Sequence
<220> FEATURE:
<223> OTHER INFORMATION: Synthetic Construct

<400> SEQUENCE: 51
gatgcgcgcg tcgt                    14

<210> SEQ ID NO 52
<211> LENGTH: 14
<212> TYPE: DNA
<213> ORGANISM: Artificial Sequence
<220> FEATURE:
<223> OTHER INFORMATION: Synthetic Construct

<400> SEQUENCE: 52
atgcgcgcgt cgtt                    14

<210> SEQ ID NO 53
<211> LENGTH: 14
<212> TYPE: DNA
<213> ORGANISM: Artificial Sequence
<220> FEATURE:
<223> OTHER INFORMATION: Synthetic Construct

<400> SEQUENCE: 53
tgcgcgcgtc gttt                    14

<210> SEQ ID NO 54
<211> LENGTH: 14
<212> TYPE: DNA

```
<213> ORGANISM: Artificial Sequence
<220> FEATURE:
<223> OTHER INFORMATION: Synthetic Construct

<400> SEQUENCE: 54
gcgcgcgtcg ttta                                                        14

<210> SEQ ID NO 55
<211> LENGTH: 14
<212> TYPE: DNA
<213> ORGANISM: Artificial Sequence
<220> FEATURE:
<223> OTHER INFORMATION: Synthetic Construct

<400> SEQUENCE: 55
cgcgcgtcgt ttag                                                        14

<210> SEQ ID NO 56
<211> LENGTH: 14
<212> TYPE: DNA
<213> ORGANISM: Artificial Sequence
<220> FEATURE:
<223> OTHER INFORMATION: Synthetic Construct

<400> SEQUENCE: 56
gcgcgtcgtt tagg                                                        14

<210> SEQ ID NO 57
<211> LENGTH: 14
<212> TYPE: DNA
<213> ORGANISM: Artificial Sequence
<220> FEATURE:
<223> OTHER INFORMATION: Synthetic Construct

<400> SEQUENCE: 57
cgcgtcgttt aggg                                                        14

<210> SEQ ID NO 58
<211> LENGTH: 14
<212> TYPE: DNA
<213> ORGANISM: Artificial Sequence
<220> FEATURE:
<223> OTHER INFORMATION: Synthetic Construct

<400> SEQUENCE: 58
gcgtcgttta gggt                                                        14

<210> SEQ ID NO 59
<211> LENGTH: 14
<212> TYPE: DNA
<213> ORGANISM: Artificial Sequence
<220> FEATURE:
<223> OTHER INFORMATION: Synthetic Construct

<400> SEQUENCE: 59
cgtcgtttag ggtg                                                        14

<210> SEQ ID NO 60
<211> LENGTH: 14
<212> TYPE: DNA
<213> ORGANISM: Artificial Sequence
<220> FEATURE:
<223> OTHER INFORMATION: Synthetic Construct

<400> SEQUENCE: 60
gtcgtttagg gtgt                                                        14
```

<210> SEQ ID NO 61
<211> LENGTH: 14
<212> TYPE: DNA
<213> ORGANISM: Artificial Sequence
<220> FEATURE:
<223> OTHER INFORMATION: Synthetic Construct

<400> SEQUENCE: 61
tcgtttaggg tgtt                                                      14

<210> SEQ ID NO 62
<211> LENGTH: 14
<212> TYPE: DNA
<213> ORGANISM: Artificial Sequence
<220> FEATURE:
<223> OTHER INFORMATION: Synthetic Construct

<400> SEQUENCE: 62
cgtttagggt gttt                                                      14

<210> SEQ ID NO 63
<211> LENGTH: 14
<212> TYPE: DNA
<213> ORGANISM: Artificial Sequence
<220> FEATURE:
<223> OTHER INFORMATION: Synthetic Construct

<400> SEQUENCE: 63
gtttagggtg tttg                                                      14

<210> SEQ ID NO 64
<211> LENGTH: 14
<212> TYPE: DNA
<213> ORGANISM: Artificial Sequence
<220> FEATURE:
<223> OTHER INFORMATION: Synthetic Construct

<400> SEQUENCE: 64
tttagggtgt ttga                                                      14

<210> SEQ ID NO 65
<211> LENGTH: 14
<212> TYPE: DNA
<213> ORGANISM: Artificial Sequence
<220> FEATURE:
<223> OTHER INFORMATION: Synthetic Construct

<400> SEQUENCE: 65
ttagggtgtt tgaa                                                      14

<210> SEQ ID NO 66
<211> LENGTH: 14
<212> TYPE: DNA
<213> ORGANISM: Artificial Sequence
<220> FEATURE:
<223> OTHER INFORMATION: Synthetic Construct

<400> SEQUENCE: 66
tagggtgttt gaag                                                      14

<210> SEQ ID NO 67
<211> LENGTH: 14
<212> TYPE: DNA
<213> ORGANISM: Artificial Sequence
<220> FEATURE:

<223> OTHER INFORMATION: Synthetic Construct

<400> SEQUENCE: 67
agggtgtttg aagt                                                         14

<210> SEQ ID NO 68
<211> LENGTH: 14
<212> TYPE: DNA
<213> ORGANISM: Artificial Sequence
<220> FEATURE:
<223> OTHER INFORMATION: Synthetic Construct

<400> SEQUENCE: 68
gggtgtttga agtt                                                         14

<210> SEQ ID NO 69
<211> LENGTH: 14
<212> TYPE: DNA
<213> ORGANISM: Artificial Sequence
<220> FEATURE:
<223> OTHER INFORMATION: Synthetic Construct

<400> SEQUENCE: 69
ggtgtttgaa gtta                                                         14

<210> SEQ ID NO 70
<211> LENGTH: 14
<212> TYPE: DNA
<213> ORGANISM: Artificial Sequence
<220> FEATURE:
<223> OTHER INFORMATION: Synthetic Construct

<400> SEQUENCE: 70
gtgtttgaag ttac                                                         14

<210> SEQ ID NO 71
<211> LENGTH: 14
<212> TYPE: DNA
<213> ORGANISM: Artificial Sequence
<220> FEATURE:
<223> OTHER INFORMATION: Synthetic Construct

<400> SEQUENCE: 71
tgtttgaagt tacg                                                         14

<210> SEQ ID NO 72
<211> LENGTH: 14
<212> TYPE: DNA
<213> ORGANISM: Artificial Sequence
<220> FEATURE:
<223> OTHER INFORMATION: Synthetic Construct

<400> SEQUENCE: 72
gtttgaagtt acga                                                         14

<210> SEQ ID NO 73
<211> LENGTH: 14
<212> TYPE: DNA
<213> ORGANISM: Artificial Sequence
<220> FEATURE:
<223> OTHER INFORMATION: Synthetic Construct

<400> SEQUENCE: 73
tttgaagtta cgag                                                         14

```
<210> SEQ ID NO 74
<211> LENGTH: 14
<212> TYPE: DNA
<213> ORGANISM: Artificial Sequence
<220> FEATURE:
<223> OTHER INFORMATION: Synthetic Construct

<400> SEQUENCE: 74
ttgaagttac gaga                                                    14

<210> SEQ ID NO 75
<211> LENGTH: 14
<212> TYPE: DNA
<213> ORGANISM: Artificial Sequence
<220> FEATURE:
<223> OTHER INFORMATION: Synthetic Construct

<400> SEQUENCE: 75
tgaagttacg agag                                                    14

<210> SEQ ID NO 76
<211> LENGTH: 14
<212> TYPE: DNA
<213> ORGANISM: Artificial Sequence
<220> FEATURE:
<223> OTHER INFORMATION: Synthetic Construct

<400> SEQUENCE: 76
gaagttacga gagg                                                    14

<210> SEQ ID NO 77
<211> LENGTH: 14
<212> TYPE: DNA
<213> ORGANISM: Artificial Sequence
<220> FEATURE:
<223> OTHER INFORMATION: Synthetic Construct

<400> SEQUENCE: 77
aagttacgag agga                                                    14

<210> SEQ ID NO 78
<211> LENGTH: 14
<212> TYPE: DNA
<213> ORGANISM: Artificial Sequence
<220> FEATURE:
<223> OTHER INFORMATION: Synthetic Construct

<400> SEQUENCE: 78
agttacgaga ggag                                                    14

<210> SEQ ID NO 79
<211> LENGTH: 14
<212> TYPE: DNA
<213> ORGANISM: Artificial Sequence
<220> FEATURE:
<223> OTHER INFORMATION: Synthetic Construct

<400> SEQUENCE: 79
gttacgagag gagt                                                    14

<210> SEQ ID NO 80
<211> LENGTH: 14
<212> TYPE: DNA
<213> ORGANISM: Artificial Sequence
<220> FEATURE:
<223> OTHER INFORMATION: Synthetic Construct
```

```
<400> SEQUENCE: 80
ttacgagagg agtt                                                    14

<210> SEQ ID NO 81
<211> LENGTH: 14
<212> TYPE: DNA
<213> ORGANISM: Artificial Sequence
<220> FEATURE:
<223> OTHER INFORMATION: Synthetic Construct

<400> SEQUENCE: 81
tacgagagga gttc                                                    14

<210> SEQ ID NO 82
<211> LENGTH: 14
<212> TYPE: DNA
<213> ORGANISM: Artificial Sequence
<220> FEATURE:
<223> OTHER INFORMATION: Synthetic Construct

<400> SEQUENCE: 82
acgagaggag ttcg                                                    14

<210> SEQ ID NO 83
<211> LENGTH: 14
<212> TYPE: DNA
<213> ORGANISM: Artificial Sequence
<220> FEATURE:
<223> OTHER INFORMATION: Synthetic Construct

<400> SEQUENCE: 83
cgagaggagt tcgt                                                    14

<210> SEQ ID NO 84
<211> LENGTH: 14
<212> TYPE: DNA
<213> ORGANISM: Artificial Sequence
<220> FEATURE:
<223> OTHER INFORMATION: Synthetic Construct

<400> SEQUENCE: 84
gagaggagtt cgta                                                    14

<210> SEQ ID NO 85
<211> LENGTH: 14
<212> TYPE: DNA
<213> ORGANISM: Artificial Sequence
<220> FEATURE:
<223> OTHER INFORMATION: Synthetic Construct

<400> SEQUENCE: 85
agaggagttc gtag                                                    14

<210> SEQ ID NO 86
<211> LENGTH: 14
<212> TYPE: DNA
<213> ORGANISM: Artificial Sequence
<220> FEATURE:
<223> OTHER INFORMATION: Synthetic Construct

<400> SEQUENCE: 86
gaggagttcg tagg                                                    14

<210> SEQ ID NO 87
<211> LENGTH: 14
```

```
<212> TYPE: DNA
<213> ORGANISM: Artificial Sequence
<220> FEATURE:
<223> OTHER INFORMATION: Synthetic Construct

<400> SEQUENCE: 87
aggagttcgt aggg                                                    14

<210> SEQ ID NO 88
<211> LENGTH: 14
<212> TYPE: DNA
<213> ORGANISM: Artificial Sequence
<220> FEATURE:
<223> OTHER INFORMATION: Synthetic Construct

<400> SEQUENCE: 88
ggagttcgta ggga                                                    14

<210> SEQ ID NO 89
<211> LENGTH: 14
<212> TYPE: DNA
<213> ORGANISM: Artificial Sequence
<220> FEATURE:
<223> OTHER INFORMATION: Synthetic Construct

<400> SEQUENCE: 89
gagttcgtag ggaa                                                    14

<210> SEQ ID NO 90
<211> LENGTH: 14
<212> TYPE: DNA
<213> ORGANISM: Artificial Sequence
<220> FEATURE:
<223> OTHER INFORMATION: Synthetic Construct

<400> SEQUENCE: 90
agttcgtagg gaat                                                    14

<210> SEQ ID NO 91
<211> LENGTH: 14
<212> TYPE: DNA
<213> ORGANISM: Artificial Sequence
<220> FEATURE:
<223> OTHER INFORMATION: Synthetic Construct

<400> SEQUENCE: 91
gttcgtaggg aata                                                    14

<210> SEQ ID NO 92
<211> LENGTH: 14
<212> TYPE: DNA
<213> ORGANISM: Artificial Sequence
<220> FEATURE:
<223> OTHER INFORMATION: Synthetic Construct

<400> SEQUENCE: 92
ttcgtaggga atag                                                    14

<210> SEQ ID NO 93
<211> LENGTH: 14
<212> TYPE: DNA
<213> ORGANISM: Artificial Sequence
<220> FEATURE:
<223> OTHER INFORMATION: Synthetic Construct

<400> SEQUENCE: 93
```
tcgtagggaa tagg                                                        14

<210> SEQ ID NO 94
<211> LENGTH: 14
<212> TYPE: DNA
<213> ORGANISM: Artificial Sequence
<220> FEATURE:
<223> OTHER INFORMATION: Synthetic Construct

<400> SEQUENCE: 94
cgtagggaat aggg                                                        14

<210> SEQ ID NO 95
<211> LENGTH: 14
<212> TYPE: DNA
<213> ORGANISM: Artificial Sequence
<220> FEATURE:
<223> OTHER INFORMATION: Synthetic Construct

<400> SEQUENCE: 95
gtagggaata gggg                                                        14

<210> SEQ ID NO 96
<211> LENGTH: 14
<212> TYPE: DNA
<213> ORGANISM: Artificial Sequence
<220> FEATURE:
<223> OTHER INFORMATION: Synthetic Construct

<400> SEQUENCE: 96
tagggaatag ggga                                                        14

<210> SEQ ID NO 97
<211> LENGTH: 14
<212> TYPE: DNA
<213> ORGANISM: Artificial Sequence
<220> FEATURE:
<223> OTHER INFORMATION: Synthetic Construct

<400> SEQUENCE: 97
agggaatagg ggag                                                        14

<210> SEQ ID NO 98
<211> LENGTH: 14
<212> TYPE: DNA
<213> ORGANISM: Artificial Sequence
<220> FEATURE:
<223> OTHER INFORMATION: Synthetic Construct

<400> SEQUENCE: 98
gggaataggg gagc                                                        14

<210> SEQ ID NO 99
<211> LENGTH: 14
<212> TYPE: DNA
<213> ORGANISM: Artificial Sequence
<220> FEATURE:
<223> OTHER INFORMATION: Synthetic Construct

<400> SEQUENCE: 99
ggaatagggg agcg                                                        14

<210> SEQ ID NO 100
<211> LENGTH: 14
<212> TYPE: DNA
<213> ORGANISM: Artificial Sequence

```
<220> FEATURE:
<223> OTHER INFORMATION: Synthetic Construct

<400> SEQUENCE: 100
gaatagggga gcgt                                                    14

<210> SEQ ID NO 101
<211> LENGTH: 14
<212> TYPE: DNA
<213> ORGANISM: Artificial Sequence
<220> FEATURE:
<223> OTHER INFORMATION: Synthetic Construct

<400> SEQUENCE: 101 aatagggag cgtt                                                    14

<210> SEQ ID NO 102
<211> LENGTH: 14
<212> TYPE: DNA
<213> ORGANISM: Artificial Sequence
<220> FEATURE:
<223> OTHER INFORMATION: Synthetic Construct

<400> SEQUENCE: 102 atagggagc gtta                                                    14

<210> SEQ ID NO 103
<211> LENGTH: 14
<212> TYPE: DNA
<213> ORGANISM: Artificial Sequence
<220> FEATURE:
<223> OTHER INFORMATION: Synthetic Construct

<400> SEQUENCE: 103 tagggagcg ttat                                                    14

<210> SEQ ID NO 104
<211> LENGTH: 14
<212> TYPE: DNA
<213> ORGANISM: Artificial Sequence
<220> FEATURE:
<223> OTHER INFORMATION: Synthetic Construct

<400> SEQUENCE: 104
aggggagcgt tatt                                                    14

<210> SEQ ID NO 105
<211> LENGTH: 14
<212> TYPE: DNA
<213> ORGANISM: Artificial Sequence
<220> FEATURE:
<223> OTHER INFORMATION: Synthetic Construct

<400> SEQUENCE: 105
ggggagcgtt attt                                                    14

<210> SEQ ID NO 106
<211> LENGTH: 14
<212> TYPE: DNA
<213> ORGANISM: Artificial Sequence
<220> FEATURE:
<223> OTHER INFORMATION: Synthetic Construct

<400> SEQUENCE: 106
gggagcgtta tttg                                                    14
```

```
<210> SEQ ID NO 107
<211> LENGTH: 14
<212> TYPE: DNA
<213> ORGANISM: Artificial Sequence
<220> FEATURE:
<223> OTHER INFORMATION: Synthetic Construct

<400> SEQUENCE: 107
ggagcgttat ttgg                                                       14

<210> SEQ ID NO 108
<211> LENGTH: 14
<212> TYPE: DNA
<213> ORGANISM: Artificial Sequence
<220> FEATURE:
<223> OTHER INFORMATION: Synthetic Construct

<400> SEQUENCE: 108
gagcgttatt tggg                                                       14

<210> SEQ ID NO 109
<211> LENGTH: 14
<212> TYPE: DNA
<213> ORGANISM: Artificial Sequence
<220> FEATURE:
<223> OTHER INFORMATION: Synthetic Construct

<400> SEQUENCE: 109
agcgttattt gggg                                                       14

<210> SEQ ID NO 110
<211> LENGTH: 14
<212> TYPE: DNA
<213> ORGANISM: Artificial Sequence
<220> FEATURE:
<223> OTHER INFORMATION: Synthetic Construct

<400> SEQUENCE: 110
gcgttatttg ggga                                                       14

<210> SEQ ID NO 111
<211> LENGTH: 14
<212> TYPE: DNA
<213> ORGANISM: Artificial Sequence
<220> FEATURE:
<223> OTHER INFORMATION: Synthetic Construct

<400> SEQUENCE: 111
cgttatttgg ggaa                                                       14

<210> SEQ ID NO 112
<211> LENGTH: 14
<212> TYPE: DNA
<213> ORGANISM: Artificial Sequence
<220> FEATURE:
<223> OTHER INFORMATION: Synthetic Construct

<400> SEQUENCE: 112
gttatttggg gaat                                                       14

<210> SEQ ID NO 113
<211> LENGTH: 14
<212> TYPE: DNA
<213> ORGANISM: Artificial Sequence
<220> FEATURE:
<223> OTHER INFORMATION: Synthetic Construct
```

```
<400> SEQUENCE: 113
ttatttgggg aatt                                                    14

<210> SEQ ID NO 114
<211> LENGTH: 14
<212> TYPE: DNA
<213> ORGANISM: Artificial Sequence
<220> FEATURE:
<223> OTHER INFORMATION: Synthetic Construct

<400> SEQUENCE: 114 tatttggga attt                                                     14

<210> SEQ ID NO 115
<211> LENGTH: 14
<212> TYPE: DNA
<213> ORGANISM: Artificial Sequence
<220> FEATURE:
<223> OTHER INFORMATION: Synthetic Construct

<400> SEQUENCE: 115
atttggggaa tttt                                                    14

<210> SEQ ID NO 116
<211> LENGTH: 14
<212> TYPE: DNA
<213> ORGANISM: Artificial Sequence
<220> FEATURE:
<223> OTHER INFORMATION: Synthetic Construct

<400> SEQUENCE: 116
tttggggaat tttt                                                    14

<210> SEQ ID NO 117
<211> LENGTH: 14
<212> TYPE: DNA
<213> ORGANISM: Artificial Sequence
<220> FEATURE:
<223> OTHER INFORMATION: Synthetic Construct

<400> SEQUENCE: 117
ttggggaatt ttta                                                    14

<210> SEQ ID NO 118
<211> LENGTH: 14
<212> TYPE: DNA
<213> ORGANISM: Artificial Sequence
<220> FEATURE:
<223> OTHER INFORMATION: Synthetic Construct

<400> SEQUENCE: 118
tggggaattt ttag                                                    14

<210> SEQ ID NO 119
<211> LENGTH: 14
<212> TYPE: DNA
<213> ORGANISM: Artificial Sequence
<220> FEATURE:
<223> OTHER INFORMATION: Synthetic Construct

<400> SEQUENCE: 119
ggggaatttt tagt                                                    14

<210> SEQ ID NO 120
```

```
<211> LENGTH: 14
<212> TYPE: DNA
<213> ORGANISM: Artificial Sequence
<220> FEATURE:
<223> OTHER INFORMATION: Synthetic Construct

<400> SEQUENCE: 120
gggaattttt agtt                                                    14

<210> SEQ ID NO 121
<211> LENGTH: 14
<212> TYPE: DNA
<213> ORGANISM: Artificial Sequence
<220> FEATURE:
<223> OTHER INFORMATION: Synthetic Construct

<400> SEQUENCE: 121
ggaattttta gttt                                                    14

<210> SEQ ID NO 122
<211> LENGTH: 14
<212> TYPE: DNA
<213> ORGANISM: Artificial Sequence
<220> FEATURE:
<223> OTHER INFORMATION: Synthetic Construct

<400> SEQUENCE: 122
gaatttttag tttt                                                    14

<210> SEQ ID NO 123
<211> LENGTH: 14
<212> TYPE: DNA
<213> ORGANISM: Artificial Sequence
<220> FEATURE:
<223> OTHER INFORMATION: Synthetic Construct

<400> SEQUENCE: 123 aattttagt tttt                                                     14

<210> SEQ ID NO 124
<211> LENGTH: 14
<212> TYPE: DNA
<213> ORGANISM: Artificial Sequence
<220> FEATURE:
<223> OTHER INFORMATION: Synthetic Construct

<400> SEQUENCE: 124 attttagtt ttta                                                     14

<210> SEQ ID NO 125
<211> LENGTH: 14
<212> TYPE: DNA
<213> ORGANISM: Artificial Sequence
<220> FEATURE:
<223> OTHER INFORMATION: Synthetic Construct

<400> SEQUENCE: 125
tttttagttt ttaa                                                    14

<210> SEQ ID NO 126
<211> LENGTH: 14
<212> TYPE: DNA
<213> ORGANISM: Artificial Sequence
<220> FEATURE:
<223> OTHER INFORMATION: Synthetic Construct

<400> SEQUENCE: 126
``` ttttagttttt taag                                          14

<210> SEQ ID NO 127
<211> LENGTH: 14
<212> TYPE: DNA
<213> ORGANISM: Artificial Sequence
<220> FEATURE:
<223> OTHER INFORMATION: Synthetic Construct

<400> SEQUENCE: 127
tttagttttt aagt                                           14

<210> SEQ ID NO 128
<211> LENGTH: 14
<212> TYPE: DNA
<213> ORGANISM: Artificial Sequence
<220> FEATURE:
<223> OTHER INFORMATION: Synthetic Construct

<400> SEQUENCE: 128
ttagttttta agta                                           14

<210> SEQ ID NO 129
<211> LENGTH: 14
<212> TYPE: DNA
<213> ORGANISM: Artificial Sequence
<220> FEATURE:
<223> OTHER INFORMATION: Synthetic Construct

<400> SEQUENCE: 129
tagtttttaa gtat                                           14

<210> SEQ ID NO 130
<211> LENGTH: 14
<212> TYPE: DNA
<213> ORGANISM: Artificial Sequence
<220> FEATURE:
<223> OTHER INFORMATION: Synthetic Construct

<400> SEQUENCE: 130
agtttttaag tata                                           14

<210> SEQ ID NO 131
<211> LENGTH: 14
<212> TYPE: DNA
<213> ORGANISM: Artificial Sequence
<220> FEATURE:
<223> OTHER INFORMATION: Synthetic Construct

<400> SEQUENCE: 131
gtttttaagt atat                                           14

<210> SEQ ID NO 132
<211> LENGTH: 14
<212> TYPE: DNA
<213> ORGANISM: Artificial Sequence
<220> FEATURE:
<223> OTHER INFORMATION: Synthetic Construct

<400> SEQUENCE: 132
tttttaagta tata                                           14

<210> SEQ ID NO 133
<211> LENGTH: 14
<212> TYPE: DNA

<213> ORGANISM: Artificial Sequence
<220> FEATURE:
<223> OTHER INFORMATION: Synthetic Construct

<400> SEQUENCE: 133
ttttaagtat atat                                                14

<210> SEQ ID NO 134
<211> LENGTH: 14
<212> TYPE: DNA
<213> ORGANISM: Artificial Sequence
<220> FEATURE:
<223> OTHER INFORMATION: Synthetic Construct

<400> SEQUENCE: 134
tttaagtata tatc                                                14

<210> SEQ ID NO 135
<211> LENGTH: 14
<212> TYPE: DNA
<213> ORGANISM: Artificial Sequence
<220> FEATURE:
<223> OTHER INFORMATION: Synthetic Construct

<400> SEQUENCE: 135
ttaagtatat atcg                                                14

<210> SEQ ID NO 136
<211> LENGTH: 14
<212> TYPE: DNA
<213> ORGANISM: Artificial Sequence
<220> FEATURE:
<223> OTHER INFORMATION: Synthetic Construct

<400> SEQUENCE: 136
taagtatata tcgg                                                14

<210> SEQ ID NO 137
<211> LENGTH: 14
<212> TYPE: DNA
<213> ORGANISM: Artificial Sequence
<220> FEATURE:
<223> OTHER INFORMATION: Synthetic Construct

<400> SEQUENCE: 137
aagtatatat cgga                                                14

<210> SEQ ID NO 138
<211> LENGTH: 14
<212> TYPE: DNA
<213> ORGANISM: Artificial Sequence
<220> FEATURE:
<223> OTHER INFORMATION: Synthetic Construct

<400> SEQUENCE: 138
agtatatatc ggag                                                14

<210> SEQ ID NO 139
<211> LENGTH: 14
<212> TYPE: DNA
<213> ORGANISM: Artificial Sequence
<220> FEATURE:
<223> OTHER INFORMATION: Synthetic Construct

<400> SEQUENCE: 139
gtatatatcg gaga                                                14

```
<210> SEQ ID NO 140
<211> LENGTH: 14
<212> TYPE: DNA
<213> ORGANISM: Artificial Sequence
<220> FEATURE:
<223> OTHER INFORMATION: Synthetic Construct

<400> SEQUENCE: 140
tatatatcgg agat                                                        14

<210> SEQ ID NO 141
<211> LENGTH: 14
<212> TYPE: DNA
<213> ORGANISM: Artificial Sequence
<220> FEATURE:
<223> OTHER INFORMATION: Synthetic Construct

<400> SEQUENCE: 141
atatatcgga gatt                                                        14

<210> SEQ ID NO 142
<211> LENGTH: 14
<212> TYPE: DNA
<213> ORGANISM: Artificial Sequence
<220> FEATURE:
<223> OTHER INFORMATION: Synthetic Construct

<400> SEQUENCE: 142
tatatcggag attc                                                        14

<210> SEQ ID NO 143
<211> LENGTH: 14
<212> TYPE: DNA
<213> ORGANISM: Artificial Sequence
<220> FEATURE:
<223> OTHER INFORMATION: Synthetic Construct

<400> SEQUENCE: 143
atatcggaga ttcg                                                        14

<210> SEQ ID NO 144
<211> LENGTH: 14
<212> TYPE: DNA
<213> ORGANISM: Artificial Sequence
<220> FEATURE:
<223> OTHER INFORMATION: Synthetic Construct

<400> SEQUENCE: 144
tatcggagat tcgt                                                        14

<210> SEQ ID NO 145
<211> LENGTH: 14
<212> TYPE: DNA
<213> ORGANISM: Artificial Sequence
<220> FEATURE:
<223> OTHER INFORMATION: Synthetic Construct

<400> SEQUENCE: 145
atcggagatt cgtt                                                        14

<210> SEQ ID NO 146
<211> LENGTH: 14
<212> TYPE: DNA
<213> ORGANISM: Artificial Sequence
<220> FEATURE:
```

<223> OTHER INFORMATION: Synthetic Construct

<400> SEQUENCE: 146
tcggagattc gttg                                                      14

<210> SEQ ID NO 147
<211> LENGTH: 14
<212> TYPE: DNA
<213> ORGANISM: Artificial Sequence
<220> FEATURE:
<223> OTHER INFORMATION: Synthetic Construct

<400> SEQUENCE: 147
cggagattcg ttgg                                                      14

<210> SEQ ID NO 148
<211> LENGTH: 14
<212> TYPE: DNA
<213> ORGANISM: Artificial Sequence
<220> FEATURE:
<223> OTHER INFORMATION: Synthetic Construct

<400> SEQUENCE: 148
ggagattcgt tggg                                                      14

<210> SEQ ID NO 149
<211> LENGTH: 14
<212> TYPE: DNA
<213> ORGANISM: Artificial Sequence
<220> FEATURE:
<223> OTHER INFORMATION: Synthetic Construct

<400> SEQUENCE: 149
gagattcgtt ggga                                                      14

<210> SEQ ID NO 150
<211> LENGTH: 14
<212> TYPE: DNA
<213> ORGANISM: Artificial Sequence
<220> FEATURE:
<223> OTHER INFORMATION: Synthetic Construct

<400> SEQUENCE: 150
agattcgttg ggat                                                      14

<210> SEQ ID NO 151
<211> LENGTH: 14
<212> TYPE: DNA
<213> ORGANISM: Artificial Sequence
<220> FEATURE:
<223> OTHER INFORMATION: Synthetic Construct

<400> SEQUENCE: 151
gattcgttgg gata                                                      14

<210> SEQ ID NO 152
<211> LENGTH: 14
<212> TYPE: DNA
<213> ORGANISM: Artificial Sequence
<220> FEATURE:
<223> OTHER INFORMATION: Synthetic Construct

<400> SEQUENCE: 152
attcgttggg ataa                                                      14

```
<210> SEQ ID NO 153
<211> LENGTH: 14
<212> TYPE: DNA
<213> ORGANISM: Artificial Sequence
<220> FEATURE:
<223> OTHER INFORMATION: Synthetic Construct

<400> SEQUENCE: 153
ttcgttggga taaa                                                        14

<210> SEQ ID NO 154
<211> LENGTH: 14
<212> TYPE: DNA
<213> ORGANISM: Artificial Sequence
<220> FEATURE:
<223> OTHER INFORMATION: Synthetic Construct

<400> SEQUENCE: 154
tcgttgggat aaat                                                        14

<210> SEQ ID NO 155
<211> LENGTH: 14
<212> TYPE: DNA
<213> ORGANISM: Artificial Sequence
<220> FEATURE:
<223> OTHER INFORMATION: Synthetic Construct

<400> SEQUENCE: 155
cgttgggata aatg                                                        14

<210> SEQ ID NO 156
<211> LENGTH: 14
<212> TYPE: DNA
<213> ORGANISM: Artificial Sequence
<220> FEATURE:
<223> OTHER INFORMATION: Synthetic Construct

<400> SEQUENCE: 156
gttgggataa atgc                                                        14

<210> SEQ ID NO 157
<211> LENGTH: 14
<212> TYPE: DNA
<213> ORGANISM: Artificial Sequence
<220> FEATURE:
<223> OTHER INFORMATION: Synthetic Construct

<400> SEQUENCE: 157
ttgggataaa tgcg                                                        14

<210> SEQ ID NO 158
<211> LENGTH: 14
<212> TYPE: DNA
<213> ORGANISM: Artificial Sequence
<220> FEATURE:
<223> OTHER INFORMATION: Synthetic Construct

<400> SEQUENCE: 158
tgggataaat gcgt                                                        14

<210> SEQ ID NO 159
<211> LENGTH: 14
<212> TYPE: DNA
<213> ORGANISM: Artificial Sequence
<220> FEATURE:
<223> OTHER INFORMATION: Synthetic Construct
```

```
<400> SEQUENCE: 159
gggataaatg cgtt                                                       14

<210> SEQ ID NO 160
<211> LENGTH: 14
<212> TYPE: DNA
<213> ORGANISM: Artificial Sequence
<220> FEATURE:
<223> OTHER INFORMATION: Synthetic Construct

<400> SEQUENCE: 160
ggataaatgc gttc                                                       14

<210> SEQ ID NO 161
<211> LENGTH: 14
<212> TYPE: DNA
<213> ORGANISM: Artificial Sequence
<220> FEATURE:
<223> OTHER INFORMATION: Synthetic Construct

<400> SEQUENCE: 161
gataaatgcg ttcg                                                       14

<210> SEQ ID NO 162
<211> LENGTH: 14
<212> TYPE: DNA
<213> ORGANISM: Artificial Sequence
<220> FEATURE:
<223> OTHER INFORMATION: Synthetic Construct

<400> SEQUENCE: 162
ataaatgcgt tcgt                                                       14

<210> SEQ ID NO 163
<211> LENGTH: 14
<212> TYPE: DNA
<213> ORGANISM: Artificial Sequence
<220> FEATURE:
<223> OTHER INFORMATION: Synthetic Construct

<400> SEQUENCE: 163
taaatgcgtt cgtt                                                       14

<210> SEQ ID NO 164
<211> LENGTH: 14
<212> TYPE: DNA
<213> ORGANISM: Artificial Sequence
<220> FEATURE:
<223> OTHER INFORMATION: Synthetic Construct

<400> SEQUENCE: 164
aaatgcgttc gttc                                                       14

<210> SEQ ID NO 165
<211> LENGTH: 14
<212> TYPE: DNA
<213> ORGANISM: Artificial Sequence
<220> FEATURE:
<223> OTHER INFORMATION: Synthetic Construct

<400> SEQUENCE: 165
aatgcgttcg ttcg                                                       14

<210> SEQ ID NO 166
<211> LENGTH: 14
```

```
<212> TYPE: DNA
<213> ORGANISM: Artificial Sequence
<220> FEATURE:
<223> OTHER INFORMATION: Synthetic Construct

<400> SEQUENCE: 166
atgcgttcgt tcgg                                                        14

<210> SEQ ID NO 167
<211> LENGTH: 14
<212> TYPE: DNA
<213> ORGANISM: Artificial Sequence
<220> FEATURE:
<223> OTHER INFORMATION: Synthetic Construct

<400> SEQUENCE: 167
tgcgttcgtt cggt                                                        14

<210> SEQ ID NO 168
<211> LENGTH: 14
<212> TYPE: DNA
<213> ORGANISM: Artificial Sequence
<220> FEATURE:
<223> OTHER INFORMATION: Synthetic Construct

<400> SEQUENCE: 168
gcgttcgttc ggtt                                                        14

<210> SEQ ID NO 169
<211> LENGTH: 14
<212> TYPE: DNA
<213> ORGANISM: Artificial Sequence
<220> FEATURE:
<223> OTHER INFORMATION: Synthetic Construct

<400> SEQUENCE: 169
cgttcgttcg gtta                                                        14

<210> SEQ ID NO 170
<211> LENGTH: 14
<212> TYPE: DNA
<213> ORGANISM: Artificial Sequence
<220> FEATURE:
<223> OTHER INFORMATION: Synthetic Construct

<400> SEQUENCE: 170
gttcgttcgg ttat                                                        14

<210> SEQ ID NO 171
<211> LENGTH: 14
<212> TYPE: DNA
<213> ORGANISM: Artificial Sequence
<220> FEATURE:
<223> OTHER INFORMATION: Synthetic Construct

<400> SEQUENCE: 171
ttcgttcggt tatt                                                        14

<210> SEQ ID NO 172
<211> LENGTH: 14
<212> TYPE: DNA
<213> ORGANISM: Artificial Sequence
<220> FEATURE:
<223> OTHER INFORMATION: Synthetic Construct

<400> SEQUENCE: 172
```
tcgttcggtt attt         14

<210> SEQ ID NO 173
<211> LENGTH: 14
<212> TYPE: DNA
<213> ORGANISM: Artificial Sequence
<220> FEATURE:
<223> OTHER INFORMATION: Synthetic Construct

<400> SEQUENCE: 173
cgttcggtta tttt         14

<210> SEQ ID NO 174
<211> LENGTH: 14
<212> TYPE: DNA
<213> ORGANISM: Artificial Sequence
<220> FEATURE:
<223> OTHER INFORMATION: Synthetic Construct

<400> SEQUENCE: 174
gttcggttat tttt         14

<210> SEQ ID NO 175
<211> LENGTH: 14
<212> TYPE: DNA
<213> ORGANISM: Artificial Sequence
<220> FEATURE:
<223> OTHER INFORMATION: Synthetic Construct

<400> SEQUENCE: 175
ttcggttatt tttt         14

<210> SEQ ID NO 176
<211> LENGTH: 14
<212> TYPE: DNA
<213> ORGANISM: Artificial Sequence
<220> FEATURE:
<223> OTHER INFORMATION: Synthetic Construct

<400> SEQUENCE: 176
tcggttattt tttt         14

<210> SEQ ID NO 177
<211> LENGTH: 14
<212> TYPE: DNA
<213> ORGANISM: Artificial Sequence
<220> FEATURE:
<223> OTHER INFORMATION: Synthetic Construct

<400> SEQUENCE: 177
cggttatttt tttt         14

<210> SEQ ID NO 178
<211> LENGTH: 14
<212> TYPE: DNA
<213> ORGANISM: Artificial Sequence
<220> FEATURE:
<223> OTHER INFORMATION: Synthetic Construct

<400> SEQUENCE: 178
ggttattttt tttt         14

<210> SEQ ID NO 179
<211> LENGTH: 14
<212> TYPE: DNA
<213> ORGANISM: Artificial Sequence

```
<220> FEATURE:
<223> OTHER INFORMATION: Synthetic Construct

<400> SEQUENCE: 179 gttattttt tttt                                                          14

<210> SEQ ID NO 180
<211> LENGTH: 14
<212> TYPE: DNA
<213> ORGANISM: Artificial Sequence
<220> FEATURE:
<223> OTHER INFORMATION: Synthetic Construct

<400> SEQUENCE: 180 ttatttttt tttt                                                          14

<210> SEQ ID NO 181
<211> LENGTH: 14
<212> TYPE: DNA
<213> ORGANISM: Artificial Sequence
<220> FEATURE:
<223> OTHER INFORMATION: Synthetic Construct

<400> SEQUENCE: 181 tattttttt tttt                                                          14

<210> SEQ ID NO 182
<211> LENGTH: 14
<212> TYPE: DNA
<213> ORGANISM: Artificial Sequence
<220> FEATURE:
<223> OTHER INFORMATION: Synthetic Construct

<400> SEQUENCE: 182 atttttttt tttt                                                          14

<210> SEQ ID NO 183
<211> LENGTH: 14
<212> TYPE: DNA
<213> ORGANISM: Artificial Sequence
<220> FEATURE:
<223> OTHER INFORMATION: Synthetic Construct

<400> SEQUENCE: 183 ttttttttt tttt                                                          14

<210> SEQ ID NO 184
<211> LENGTH: 14
<212> TYPE: DNA
<213> ORGANISM: Artificial Sequence
<220> FEATURE:
<223> OTHER INFORMATION: Synthetic Construct

<400> SEQUENCE: 184 ttttttttt tttt                                                          14

<210> SEQ ID NO 185
<211> LENGTH: 14
<212> TYPE: DNA
<213> ORGANISM: Artificial Sequence
<220> FEATURE:
<223> OTHER INFORMATION: Synthetic Construct

<400> SEQUENCE: 185 ttttttttt tttt                                                          14
```

```
<210> SEQ ID NO 186
<211> LENGTH: 14
<212> TYPE: DNA
<213> ORGANISM: Artificial Sequence
<220> FEATURE:
<223> OTHER INFORMATION: Synthetic Construct

<400> SEQUENCE: 186 ttttttttttt tttt                                                      14

<210> SEQ ID NO 187
<211> LENGTH: 14
<212> TYPE: DNA
<213> ORGANISM: Artificial Sequence
<220> FEATURE:
<223> OTHER INFORMATION: Synthetic Construct

<400> SEQUENCE: 187 ttttttttttt tttt                                                      14

<210> SEQ ID NO 188
<211> LENGTH: 14
<212> TYPE: DNA
<213> ORGANISM: Artificial Sequence
<220> FEATURE:
<223> OTHER INFORMATION: Synthetic Construct

<400> SEQUENCE: 188 ttttttttttt tttt                                                      14

<210> SEQ ID NO 189
<211> LENGTH: 14
<212> TYPE: DNA
<213> ORGANISM: Artificial Sequence
<220> FEATURE:
<223> OTHER INFORMATION: Synthetic Construct

<400> SEQUENCE: 189 ttttttttttt tttt                                                      14

<210> SEQ ID NO 190
<211> LENGTH: 14
<212> TYPE: DNA
<213> ORGANISM: Artificial Sequence
<220> FEATURE:
<223> OTHER INFORMATION: Synthetic Construct

<400> SEQUENCE: 190 ttttttttttt tttt                                                      14

<210> SEQ ID NO 191
<211> LENGTH: 14
<212> TYPE: DNA
<213> ORGANISM: Artificial Sequence
<220> FEATURE:
<223> OTHER INFORMATION: Synthetic Construct

<400> SEQUENCE: 191 ttttttttttt tttt                                                      14

<210> SEQ ID NO 192
<211> LENGTH: 14
<212> TYPE: DNA
<213> ORGANISM: Artificial Sequence
<220> FEATURE:
<223> OTHER INFORMATION: Synthetic Construct
```

```
<400> SEQUENCE: 192
tttttttttt tttt                                                14

<210> SEQ ID NO 193
<211> LENGTH: 14
<212> TYPE: DNA
<213> ORGANISM: Artificial Sequence
<220> FEATURE:
<223> OTHER INFORMATION: Synthetic Construct

<400> SEQUENCE: 193
tttttttttt tttt                                                14

<210> SEQ ID NO 194
<211> LENGTH: 14
<212> TYPE: DNA
<213> ORGANISM: Artificial Sequence
<220> FEATURE:
<223> OTHER INFORMATION: Synthetic Construct

<400> SEQUENCE: 194
tttttttttt ttta                                                14

<210> SEQ ID NO 195
<211> LENGTH: 14
<212> TYPE: DNA
<213> ORGANISM: Artificial Sequence
<220> FEATURE:
<223> OTHER INFORMATION: Synthetic Construct

<400> SEQUENCE: 195
tttttttttt ttag                                                14

<210> SEQ ID NO 196
<211> LENGTH: 14
<212> TYPE: DNA
<213> ORGANISM: Artificial Sequence
<220> FEATURE:
<223> OTHER INFORMATION: Synthetic Construct

<400> SEQUENCE: 196
tttttttttt taga                                                14

<210> SEQ ID NO 197
<211> LENGTH: 14
<212> TYPE: DNA
<213> ORGANISM: Artificial Sequence
<220> FEATURE:
<223> OTHER INFORMATION: Synthetic Construct

<400> SEQUENCE: 197
tttttttttt agaa                                                14

<210> SEQ ID NO 198
<211> LENGTH: 14
<212> TYPE: DNA
<213> ORGANISM: Artificial Sequence
<220> FEATURE:
<223> OTHER INFORMATION: Synthetic Construct

<400> SEQUENCE: 198
ttttttttta gaaa                                                14

<210> SEQ ID NO 199
```

```
<211> LENGTH: 14
<212> TYPE: DNA
<213> ORGANISM: Artificial Sequence
<220> FEATURE:
<223> OTHER INFORMATION: Synthetic Construct

<400> SEQUENCE: 199 tttttttag aaaa                                                          14

<210> SEQ ID NO 200
<211> LENGTH: 14
<212> TYPE: DNA
<213> ORGANISM: Artificial Sequence
<220> FEATURE:
<223> OTHER INFORMATION: Synthetic Construct

<400> SEQUENCE: 200
tttttttaga aaag                                                         14

<210> SEQ ID NO 201
<211> LENGTH: 14
<212> TYPE: DNA
<213> ORGANISM: Artificial Sequence
<220> FEATURE:
<223> OTHER INFORMATION: Synthetic Construct

<400> SEQUENCE: 201 tttttttagaa aagc                                                        14

<210> SEQ ID NO 202
<211> LENGTH: 14
<212> TYPE: DNA
<213> ORGANISM: Artificial Sequence
<220> FEATURE:
<223> OTHER INFORMATION: Synthetic Construct

<400> SEQUENCE: 202
tttttagaaa agcg                                                         14

<210> SEQ ID NO 203
<211> LENGTH: 14
<212> TYPE: DNA
<213> ORGANISM: Artificial Sequence
<220> FEATURE:
<223> OTHER INFORMATION: Synthetic Construct

<400> SEQUENCE: 203
ttttagaaaa gcgt                                                         14

<210> SEQ ID NO 204
<211> LENGTH: 14
<212> TYPE: DNA
<213> ORGANISM: Artificial Sequence
<220> FEATURE:
<223> OTHER INFORMATION: Synthetic Construct

<400> SEQUENCE: 204
tttagaaaag cgtt                                                         14

<210> SEQ ID NO 205
<211> LENGTH: 14
<212> TYPE: DNA
<213> ORGANISM: Artificial Sequence
<220> FEATURE:
<223> OTHER INFORMATION: Synthetic Construct

<400> SEQUENCE: 205
```
ttagaaaagc gttg                                                        14

<210> SEQ ID NO 206
<211> LENGTH: 14
<212> TYPE: DNA
<213> ORGANISM: Artificial Sequence
<220> FEATURE:
<223> OTHER INFORMATION: Synthetic Construct

<400> SEQUENCE: 206
tagaaaagcg ttgt                                                        14

<210> SEQ ID NO 207
<211> LENGTH: 14
<212> TYPE: DNA
<213> ORGANISM: Artificial Sequence
<220> FEATURE:
<223> OTHER INFORMATION: Synthetic Construct

<400> SEQUENCE: 207
agaaaagcgt tgtt                                                        14

<210> SEQ ID NO 208
<211> LENGTH: 14
<212> TYPE: DNA
<213> ORGANISM: Artificial Sequence
<220> FEATURE:
<223> OTHER INFORMATION: Synthetic Construct

<400> SEQUENCE: 208
gaaaagcgtt gttc                                                        14

<210> SEQ ID NO 209
<211> LENGTH: 14
<212> TYPE: DNA
<213> ORGANISM: Artificial Sequence
<220> FEATURE:
<223> OTHER INFORMATION: Synthetic Construct

<400> SEQUENCE: 209
aaaagcgttg ttcg                                                        14

<210> SEQ ID NO 210
<211> LENGTH: 14
<212> TYPE: DNA
<213> ORGANISM: Artificial Sequence
<220> FEATURE:
<223> OTHER INFORMATION: Synthetic Construct

<400> SEQUENCE: 210
aaagcgttgt tcgt                                                        14

<210> SEQ ID NO 211
<211> LENGTH: 14
<212> TYPE: DNA
<213> ORGANISM: Artificial Sequence
<220> FEATURE:
<223> OTHER INFORMATION: Synthetic Construct

<400> SEQUENCE: 211
aagcgttgtt cgtt                                                        14

<210> SEQ ID NO 212
<211> LENGTH: 14
<212> TYPE: DNA

```
<213> ORGANISM: Artificial Sequence
<220> FEATURE:
<223> OTHER INFORMATION: Synthetic Construct

<400> SEQUENCE: 212
agcgttgttc gttg                                                        14

<210> SEQ ID NO 213
<211> LENGTH: 14
<212> TYPE: DNA
<213> ORGANISM: Artificial Sequence
<220> FEATURE:
<223> OTHER INFORMATION: Synthetic Construct

<400> SEQUENCE: 213
gcgttgttcg ttgg                                                        14

<210> SEQ ID NO 214
<211> LENGTH: 14
<212> TYPE: DNA
<213> ORGANISM: Artificial Sequence
<220> FEATURE:
<223> OTHER INFORMATION: Synthetic Construct

<400> SEQUENCE: 214
cgttgttcgt tggc                                                        14

<210> SEQ ID NO 215
<211> LENGTH: 14
<212> TYPE: DNA
<213> ORGANISM: Artificial Sequence
<220> FEATURE:
<223> OTHER INFORMATION: Synthetic Construct

<400> SEQUENCE: 215
gttgttcgtt ggcg                                                        14

<210> SEQ ID NO 216
<211> LENGTH: 14
<212> TYPE: DNA
<213> ORGANISM: Artificial Sequence
<220> FEATURE:
<223> OTHER INFORMATION: Synthetic Construct

<400> SEQUENCE: 216
ttgttcgttg gcgt                                                        14

<210> SEQ ID NO 217
<211> LENGTH: 14
<212> TYPE: DNA
<213> ORGANISM: Artificial Sequence
<220> FEATURE:
<223> OTHER INFORMATION: Synthetic Construct

<400> SEQUENCE: 217
tgttcgttgg cgtt                                                        14

<210> SEQ ID NO 218
<211> LENGTH: 14
<212> TYPE: DNA
<213> ORGANISM: Artificial Sequence
<220> FEATURE:
<223> OTHER INFORMATION: Synthetic Construct

<400> SEQUENCE: 218
gttcgttggc gtta                                                        14
```

```
<210> SEQ ID NO 219
<211> LENGTH: 14
<212> TYPE: DNA
<213> ORGANISM: Artificial Sequence
<220> FEATURE:
<223> OTHER INFORMATION: Synthetic Construct

<400> SEQUENCE: 219
ttcgttggcg ttat                                                        14

<210> SEQ ID NO 220
<211> LENGTH: 14
<212> TYPE: DNA
<213> ORGANISM: Artificial Sequence
<220> FEATURE:
<223> OTHER INFORMATION: Synthetic Construct

<400> SEQUENCE: 220
tcgttggcgt tatt                                                        14

<210> SEQ ID NO 221
<211> LENGTH: 14
<212> TYPE: DNA
<213> ORGANISM: Artificial Sequence
<220> FEATURE:
<223> OTHER INFORMATION: Synthetic Construct

<400> SEQUENCE: 221
cgttggcgtt attt                                                        14

<210> SEQ ID NO 222
<211> LENGTH: 14
<212> TYPE: DNA
<213> ORGANISM: Artificial Sequence
<220> FEATURE:
<223> OTHER INFORMATION: Synthetic Construct

<400> SEQUENCE: 222
gttggcgtta tttc                                                        14

<210> SEQ ID NO 223
<211> LENGTH: 14
<212> TYPE: DNA
<213> ORGANISM: Artificial Sequence
<220> FEATURE:
<223> OTHER INFORMATION: Synthetic Construct

<400> SEQUENCE: 223
ttggcgttat ttcg                                                        14

<210> SEQ ID NO 224
<211> LENGTH: 14
<212> TYPE: DNA
<213> ORGANISM: Artificial Sequence
<220> FEATURE:
<223> OTHER INFORMATION: Synthetic Construct

<400> SEQUENCE: 224
tggcgttatt tcgc                                                        14

<210> SEQ ID NO 225
<211> LENGTH: 14
<212> TYPE: DNA
<213> ORGANISM: Artificial Sequence
<220> FEATURE:
```

<223> OTHER INFORMATION: Synthetic Construct

<400> SEQUENCE: 225
ggcgttattt cgcg                                                              14

<210> SEQ ID NO 226
<211> LENGTH: 14
<212> TYPE: DNA
<213> ORGANISM: Artificial Sequence
<220> FEATURE:
<223> OTHER INFORMATION: Synthetic Construct

<400> SEQUENCE: 226
gcgttatttc gcgg                                                              14

<210> SEQ ID NO 227
<211> LENGTH: 14
<212> TYPE: DNA
<213> ORGANISM: Artificial Sequence
<220> FEATURE:
<223> OTHER INFORMATION: Synthetic Construct

<400> SEQUENCE: 227
cgttatttcg cggt                                                              14

<210> SEQ ID NO 228
<211> LENGTH: 14
<212> TYPE: DNA
<213> ORGANISM: Artificial Sequence
<220> FEATURE:
<223> OTHER INFORMATION: Synthetic Construct

<400> SEQUENCE: 228
gttatttcgc ggtt                                                              14

<210> SEQ ID NO 229
<211> LENGTH: 14
<212> TYPE: DNA
<213> ORGANISM: Artificial Sequence
<220> FEATURE:
<223> OTHER INFORMATION: Synthetic Construct

<400> SEQUENCE: 229
ttatttcgcg gttc                                                              14

<210> SEQ ID NO 230
<211> LENGTH: 14
<212> TYPE: DNA
<213> ORGANISM: Artificial Sequence
<220> FEATURE:
<223> OTHER INFORMATION: Synthetic Construct

<400> SEQUENCE: 230
tatttcgcgg ttcg                                                              14

<210> SEQ ID NO 231
<211> LENGTH: 14
<212> TYPE: DNA
<213> ORGANISM: Artificial Sequence
<220> FEATURE:
<223> OTHER INFORMATION: Synthetic Construct

<400> SEQUENCE: 231
atttcgcggt tcgc                                                              14

```
<210> SEQ ID NO 232
<211> LENGTH: 14
<212> TYPE: DNA
<213> ORGANISM: Artificial Sequence
<220> FEATURE:
<223> OTHER INFORMATION: Synthetic Construct

<400> SEQUENCE: 232
tttcgcggtt cgcg                                                        14

<210> SEQ ID NO 233
<211> LENGTH: 14
<212> TYPE: DNA
<213> ORGANISM: Artificial Sequence
<220> FEATURE:
<223> OTHER INFORMATION: Synthetic Construct

<400> SEQUENCE: 233
ttcgcggttc gcgg                                                        14

<210> SEQ ID NO 234
<211> LENGTH: 14
<212> TYPE: DNA
<213> ORGANISM: Artificial Sequence
<220> FEATURE:
<223> OTHER INFORMATION: Synthetic Construct

<400> SEQUENCE: 234
tcgcggttcg cggg                                                        14

<210> SEQ ID NO 235
<211> LENGTH: 14
<212> TYPE: DNA
<213> ORGANISM: Artificial Sequence
<220> FEATURE:
<223> OTHER INFORMATION: Synthetic Construct

<400> SEQUENCE: 235
cgcggttcgc ggga                                                        14

<210> SEQ ID NO 236
<211> LENGTH: 14
<212> TYPE: DNA
<213> ORGANISM: Artificial Sequence
<220> FEATURE:
<223> OTHER INFORMATION: Synthetic Construct

<400> SEQUENCE: 236
gcggttcgcg ggaa                                                        14

<210> SEQ ID NO 237
<211> LENGTH: 14
<212> TYPE: DNA
<213> ORGANISM: Artificial Sequence
<220> FEATURE:
<223> OTHER INFORMATION: Synthetic Construct

<400> SEQUENCE: 237
cggttcgcgg gaat                                                        14

<210> SEQ ID NO 238
<211> LENGTH: 14
<212> TYPE: DNA
<213> ORGANISM: Artificial Sequence
<220> FEATURE:
<223> OTHER INFORMATION: Synthetic Construct
```

```
<400> SEQUENCE: 238
ggttcgcggg aatg                                                    14

<210> SEQ ID NO 239
<211> LENGTH: 14
<212> TYPE: DNA
<213> ORGANISM: Artificial Sequence
<220> FEATURE:
<223> OTHER INFORMATION: Synthetic Construct

<400> SEQUENCE: 239
gttcgcggga atgg                                                    14

<210> SEQ ID NO 240
<211> LENGTH: 14
<212> TYPE: DNA
<213> ORGANISM: Artificial Sequence
<220> FEATURE:
<223> OTHER INFORMATION: Synthetic Construct

<400> SEQUENCE: 240
ttcgcgggaa tggg                                                    14

<210> SEQ ID NO 241
<211> LENGTH: 14
<212> TYPE: DNA
<213> ORGANISM: Artificial Sequence
<220> FEATURE:
<223> OTHER INFORMATION: Synthetic Construct

<400> SEQUENCE: 241
tcgcgggaat gggg                                                    14

<210> SEQ ID NO 242
<211> LENGTH: 14
<212> TYPE: DNA
<213> ORGANISM: Artificial Sequence
<220> FEATURE:
<223> OTHER INFORMATION: Synthetic Construct

<400> SEQUENCE: 242
cgcgggaatg gggg                                                    14

<210> SEQ ID NO 243
<211> LENGTH: 14
<212> TYPE: DNA
<213> ORGANISM: Artificial Sequence
<220> FEATURE:
<223> OTHER INFORMATION: Synthetic Construct

<400> SEQUENCE: 243
gcgggaatgg gggt                                                    14

<210> SEQ ID NO 244
<211> LENGTH: 14
<212> TYPE: DNA
<213> ORGANISM: Artificial Sequence
<220> FEATURE:
<223> OTHER INFORMATION: Synthetic Construct

<400> SEQUENCE: 244
cgggaatggg ggta                                                    14

<210> SEQ ID NO 245
<211> LENGTH: 14
```

<212> TYPE: DNA
<213> ORGANISM: Artificial Sequence
<220> FEATURE:
<223> OTHER INFORMATION: Synthetic Construct

<400> SEQUENCE: 245
gggaatgggg gtat                                                              14

<210> SEQ ID NO 246
<211> LENGTH: 14
<212> TYPE: DNA
<213> ORGANISM: Artificial Sequence
<220> FEATURE:
<223> OTHER INFORMATION: Synthetic Construct

<400> SEQUENCE: 246
ggaatggggg tatc                                                              14

<210> SEQ ID NO 247
<211> LENGTH: 14
<212> TYPE: DNA
<213> ORGANISM: Artificial Sequence
<220> FEATURE:
<223> OTHER INFORMATION: Synthetic Construct

<400> SEQUENCE: 247 gaatggggt atcg                                                              14

<210> SEQ ID NO 248
<211> LENGTH: 14
<212> TYPE: DNA
<213> ORGANISM: Artificial Sequence
<220> FEATURE:
<223> OTHER INFORMATION: Synthetic Construct

<400> SEQUENCE: 248 aatggggta tcga                                                              14

<210> SEQ ID NO 249
<211> LENGTH: 14
<212> TYPE: DNA
<213> ORGANISM: Artificial Sequence
<220> FEATURE:
<223> OTHER INFORMATION: Synthetic Construct

<400> SEQUENCE: 249 atggggtat cgag                                                              14

<210> SEQ ID NO 250
<211> LENGTH: 14
<212> TYPE: DNA
<213> ORGANISM: Artificial Sequence
<220> FEATURE:
<223> OTHER INFORMATION: Synthetic Construct

<400> SEQUENCE: 250 tggggtatc gaga                                                              14

<210> SEQ ID NO 251
<211> LENGTH: 14
<212> TYPE: DNA
<213> ORGANISM: Artificial Sequence
<220> FEATURE:
<223> OTHER INFORMATION: Synthetic Construct

<400> SEQUENCE: 251

```
gggggtatcg agaa                                            14

<210> SEQ ID NO 252
<211> LENGTH: 14
<212> TYPE: DNA
<213> ORGANISM: Artificial Sequence
<220> FEATURE:
<223> OTHER INFORMATION: Synthetic Construct

<400> SEQUENCE: 252
ggggtatcga gaat                                            14

<210> SEQ ID NO 253
<211> LENGTH: 14
<212> TYPE: DNA
<213> ORGANISM: Artificial Sequence
<220> FEATURE:
<223> OTHER INFORMATION: Synthetic Construct

<400> SEQUENCE: 253
gggtatcgag aatt                                            14

<210> SEQ ID NO 254
<211> LENGTH: 14
<212> TYPE: DNA
<213> ORGANISM: Artificial Sequence
<220> FEATURE:
<223> OTHER INFORMATION: Synthetic Construct

<400> SEQUENCE: 254
ggtatcgaga attg                                            14

<210> SEQ ID NO 255
<211> LENGTH: 14
<212> TYPE: DNA
<213> ORGANISM: Artificial Sequence
<220> FEATURE:
<223> OTHER INFORMATION: Synthetic Construct

<400> SEQUENCE: 255
gtatcgagaa ttgc                                            14

<210> SEQ ID NO 256
<211> LENGTH: 14
<212> TYPE: DNA
<213> ORGANISM: Artificial Sequence
<220> FEATURE:
<223> OTHER INFORMATION: Synthetic Construct

<400> SEQUENCE: 256
tatcgagaat tgcg                                            14

<210> SEQ ID NO 257
<211> LENGTH: 14
<212> TYPE: DNA
<213> ORGANISM: Artificial Sequence
<220> FEATURE:
<223> OTHER INFORMATION: Synthetic Construct

<400> SEQUENCE: 257
atcgagaatt gcgg                                            14

<210> SEQ ID NO 258
<211> LENGTH: 14
<212> TYPE: DNA
<213> ORGANISM: Artificial Sequence
```

```
<220> FEATURE:
<223> OTHER INFORMATION: Synthetic Construct

<400> SEQUENCE: 258
tcgagaattg cggt                                                    14

<210> SEQ ID NO 259
<211> LENGTH: 14
<212> TYPE: DNA
<213> ORGANISM: Artificial Sequence
<220> FEATURE:
<223> OTHER INFORMATION: Synthetic Construct

<400> SEQUENCE: 259
cgagaattgc ggtt                                                    14

<210> SEQ ID NO 260
<211> LENGTH: 14
<212> TYPE: DNA
<213> ORGANISM: Artificial Sequence
<220> FEATURE:
<223> OTHER INFORMATION: Synthetic Construct

<400> SEQUENCE: 260
gagaattgcg gttt                                                    14

<210> SEQ ID NO 261
<211> LENGTH: 14
<212> TYPE: DNA
<213> ORGANISM: Artificial Sequence
<220> FEATURE:
<223> OTHER INFORMATION: Synthetic Construct

<400> SEQUENCE: 261
agaattgcgg tttg                                                    14

<210> SEQ ID NO 262
<211> LENGTH: 14
<212> TYPE: DNA
<213> ORGANISM: Artificial Sequence
<220> FEATURE:
<223> OTHER INFORMATION: Synthetic Construct

<400> SEQUENCE: 262
gaattgcggt ttgg                                                    14

<210> SEQ ID NO 263
<211> LENGTH: 14
<212> TYPE: DNA
<213> ORGANISM: Artificial Sequence
<220> FEATURE:
<223> OTHER INFORMATION: Synthetic Construct

<400> SEQUENCE: 263
aattgcggtt tggt                                                    14

<210> SEQ ID NO 264
<211> LENGTH: 14
<212> TYPE: DNA
<213> ORGANISM: Artificial Sequence
<220> FEATURE:
<223> OTHER INFORMATION: Synthetic Construct

<400> SEQUENCE: 264
attgcggttt ggtt                                                    14
```

<210> SEQ ID NO 265
<211> LENGTH: 14
<212> TYPE: DNA
<213> ORGANISM: Artificial Sequence
<220> FEATURE:
<223> OTHER INFORMATION: Synthetic Construct

<400> SEQUENCE: 265
ttgcggtttg gttt                                                          14

<210> SEQ ID NO 266
<211> LENGTH: 14
<212> TYPE: DNA
<213> ORGANISM: Artificial Sequence
<220> FEATURE:
<223> OTHER INFORMATION: Synthetic Construct

<400> SEQUENCE: 266
tgcggtttgg ttta                                                          14

<210> SEQ ID NO 267
<211> LENGTH: 14
<212> TYPE: DNA
<213> ORGANISM: Artificial Sequence
<220> FEATURE:
<223> OTHER INFORMATION: Synthetic Construct

<400> SEQUENCE: 267
gcggtttggt ttag                                                          14

<210> SEQ ID NO 268
<211> LENGTH: 14
<212> TYPE: DNA
<213> ORGANISM: Artificial Sequence
<220> FEATURE:
<223> OTHER INFORMATION: Synthetic Construct

<400> SEQUENCE: 268
cggtttggtt tagt                                                          14

<210> SEQ ID NO 269
<211> LENGTH: 14
<212> TYPE: DNA
<213> ORGANISM: Artificial Sequence
<220> FEATURE:
<223> OTHER INFORMATION: Synthetic Construct

<400> SEQUENCE: 269
ggtttggttt agtc                                                          14

<210> SEQ ID NO 270
<211> LENGTH: 14
<212> TYPE: DNA
<213> ORGANISM: Artificial Sequence
<220> FEATURE:
<223> OTHER INFORMATION: Synthetic Construct

<400> SEQUENCE: 270
gtttggttta gtcg                                                          14

<210> SEQ ID NO 271
<211> LENGTH: 14
<212> TYPE: DNA
<213> ORGANISM: Artificial Sequence
<220> FEATURE:
<223> OTHER INFORMATION: Synthetic Construct

```
<400> SEQUENCE: 271
tttggtttag tcgt                                                        14

<210> SEQ ID NO 272
<211> LENGTH: 14
<212> TYPE: DNA
<213> ORGANISM: Artificial Sequence
<220> FEATURE:
<223> OTHER INFORMATION: Synthetic Construct

<400> SEQUENCE: 272
ttggtttagt cgta                                                        14

<210> SEQ ID NO 273
<211> LENGTH: 14
<212> TYPE: DNA
<213> ORGANISM: Artificial Sequence
<220> FEATURE:
<223> OTHER INFORMATION: Synthetic Construct

<400> SEQUENCE: 273
tggtttagtc gtag                                                        14

<210> SEQ ID NO 274
<211> LENGTH: 14
<212> TYPE: DNA
<213> ORGANISM: Artificial Sequence
<220> FEATURE:
<223> OTHER INFORMATION: Synthetic Construct

<400> SEQUENCE: 274
ggtttagtcg taga                                                        14

<210> SEQ ID NO 275
<211> LENGTH: 14
<212> TYPE: DNA
<213> ORGANISM: Artificial Sequence
<220> FEATURE:
<223> OTHER INFORMATION: Synthetic Construct

<400> SEQUENCE: 275
gtttagtcgt agag                                                        14

<210> SEQ ID NO 276
<211> LENGTH: 14
<212> TYPE: DNA
<213> ORGANISM: Artificial Sequence
<220> FEATURE:
<223> OTHER INFORMATION: Synthetic Construct

<400> SEQUENCE: 276
tttagtcgta gagg                                                        14

<210> SEQ ID NO 277
<211> LENGTH: 14
<212> TYPE: DNA
<213> ORGANISM: Artificial Sequence
<220> FEATURE:
<223> OTHER INFORMATION: Synthetic Construct

<400> SEQUENCE: 277
ttagtcgtag aggt                                                        14

<210> SEQ ID NO 278
```

-continued

```
<211> LENGTH: 14
<212> TYPE: DNA
<213> ORGANISM: Artificial Sequence
<220> FEATURE:
<223> OTHER INFORMATION: Synthetic Construct

<400> SEQUENCE: 278
tagtcgtaga ggtt                                                      14

<210> SEQ ID NO 279
<211> LENGTH: 14
<212> TYPE: DNA
<213> ORGANISM: Artificial Sequence
<220> FEATURE:
<223> OTHER INFORMATION: Synthetic Construct

<400> SEQUENCE: 279
agtcgtagag gttt                                                      14

<210> SEQ ID NO 280
<211> LENGTH: 14
<212> TYPE: DNA
<213> ORGANISM: Artificial Sequence
<220> FEATURE:
<223> OTHER INFORMATION: Synthetic Construct

<400> SEQUENCE: 280
gtcgtagagg tttt                                                      14

<210> SEQ ID NO 281
<211> LENGTH: 14
<212> TYPE: DNA
<213> ORGANISM: Artificial Sequence
<220> FEATURE:
<223> OTHER INFORMATION: Synthetic Construct

<400> SEQUENCE: 281
tcgtagaggt tttt                                                      14

<210> SEQ ID NO 282
<211> LENGTH: 14
<212> TYPE: DNA
<213> ORGANISM: Artificial Sequence
<220> FEATURE:
<223> OTHER INFORMATION: Synthetic Construct

<400> SEQUENCE: 282
cgtagaggtt tttg                                                      14

<210> SEQ ID NO 283
<211> LENGTH: 14
<212> TYPE: DNA
<213> ORGANISM: Artificial Sequence
<220> FEATURE:
<223> OTHER INFORMATION: Synthetic Construct

<400> SEQUENCE: 283
gtagaggttt ttga                                                      14

<210> SEQ ID NO 284
<211> LENGTH: 14
<212> TYPE: DNA
<213> ORGANISM: Artificial Sequence
<220> FEATURE:
<223> OTHER INFORMATION: Synthetic Construct

<400> SEQUENCE: 284
``` tagaggttttt tgaa                                        14

<210> SEQ ID NO 285
<211> LENGTH: 14
<212> TYPE: DNA
<213> ORGANISM: Artificial Sequence
<220> FEATURE:
<223> OTHER INFORMATION: Synthetic Construct

<400> SEQUENCE: 285
agaggttttt gaag                                         14

<210> SEQ ID NO 286
<211> LENGTH: 14
<212> TYPE: DNA
<213> ORGANISM: Artificial Sequence
<220> FEATURE:
<223> OTHER INFORMATION: Synthetic Construct

<400> SEQUENCE: 286 gaggttttg aagt                                          14

<210> SEQ ID NO 287
<211> LENGTH: 14
<212> TYPE: DNA
<213> ORGANISM: Artificial Sequence
<220> FEATURE:
<223> OTHER INFORMATION: Synthetic Construct

<400> SEQUENCE: 287
aggtttttga agtt                                         14

<210> SEQ ID NO 288
<211> LENGTH: 14
<212> TYPE: DNA
<213> ORGANISM: Artificial Sequence
<220> FEATURE:
<223> OTHER INFORMATION: Synthetic Construct

<400> SEQUENCE: 288
ggtttttgaa gtta                                         14

<210> SEQ ID NO 289
<211> LENGTH: 14
<212> TYPE: DNA
<213> ORGANISM: Artificial Sequence
<220> FEATURE:
<223> OTHER INFORMATION: Synthetic Construct

<400> SEQUENCE: 289
gtttttgaag ttat                                         14

<210> SEQ ID NO 290
<211> LENGTH: 14
<212> TYPE: DNA
<213> ORGANISM: Artificial Sequence
<220> FEATURE:
<223> OTHER INFORMATION: Synthetic Construct

<400> SEQUENCE: 290
tttttgaagt tatt                                         14

<210> SEQ ID NO 291
<211> LENGTH: 14
<212> TYPE: DNA

```
<213> ORGANISM: Artificial Sequence
<220> FEATURE:
<223> OTHER INFORMATION: Synthetic Construct

<400> SEQUENCE: 291
ttttgaagtt attt                                                        14

<210> SEQ ID NO 292
<211> LENGTH: 14
<212> TYPE: DNA
<213> ORGANISM: Artificial Sequence
<220> FEATURE:
<223> OTHER INFORMATION: Synthetic Construct

<400> SEQUENCE: 292
tttgaagtta tttt                                                        14

<210> SEQ ID NO 293
<211> LENGTH: 14
<212> TYPE: DNA
<213> ORGANISM: Artificial Sequence
<220> FEATURE:
<223> OTHER INFORMATION: Synthetic Construct

<400> SEQUENCE: 293
ttgaagttat tttt                                                        14

<210> SEQ ID NO 294
<211> LENGTH: 14
<212> TYPE: DNA
<213> ORGANISM: Artificial Sequence
<220> FEATURE:
<223> OTHER INFORMATION: Synthetic Construct

<400> SEQUENCE: 294
tgaagttatt ttta                                                        14

<210> SEQ ID NO 295
<211> LENGTH: 14
<212> TYPE: DNA
<213> ORGANISM: Artificial Sequence
<220> FEATURE:
<223> OTHER INFORMATION: Synthetic Construct

<400> SEQUENCE: 295
gaagttattt ttaa                                                        14

<210> SEQ ID NO 296
<211> LENGTH: 14
<212> TYPE: DNA
<213> ORGANISM: Artificial Sequence
<220> FEATURE:
<223> OTHER INFORMATION: Synthetic Construct

<400> SEQUENCE: 296
aagttatttt taat                                                        14

<210> SEQ ID NO 297
<211> LENGTH: 14
<212> TYPE: DNA
<213> ORGANISM: Artificial Sequence
<220> FEATURE:
<223> OTHER INFORMATION: Synthetic Construct

<400> SEQUENCE: 297
agttattttt aatt                                                        14
```

<210> SEQ ID NO 298
<211> LENGTH: 14
<212> TYPE: DNA
<213> ORGANISM: Artificial Sequence
<220> FEATURE:
<223> OTHER INFORMATION: Synthetic Construct

<400> SEQUENCE: 298
gttattttta attt                                                    14

<210> SEQ ID NO 299
<211> LENGTH: 14
<212> TYPE: DNA
<213> ORGANISM: Artificial Sequence
<220> FEATURE:
<223> OTHER INFORMATION: Synthetic Construct

<400> SEQUENCE: 299
ttatttttaa tttt                                                    14

<210> SEQ ID NO 300
<211> LENGTH: 14
<212> TYPE: DNA
<213> ORGANISM: Artificial Sequence
<220> FEATURE:
<223> OTHER INFORMATION: Synthetic Construct

<400> SEQUENCE: 300 tattttttaat tttt                                                   14

<210> SEQ ID NO 301
<211> LENGTH: 14
<212> TYPE: DNA
<213> ORGANISM: Artificial Sequence
<220> FEATURE:
<223> OTHER INFORMATION: Synthetic Construct

<400> SEQUENCE: 301 attttttaatt tttt                                                   14

<210> SEQ ID NO 302
<211> LENGTH: 14
<212> TYPE: DNA
<213> ORGANISM: Artificial Sequence
<220> FEATURE:
<223> OTHER INFORMATION: Synthetic Construct

<400> SEQUENCE: 302
tttttaattt tttc                                                    14

<210> SEQ ID NO 303
<211> LENGTH: 14
<212> TYPE: DNA
<213> ORGANISM: Artificial Sequence
<220> FEATURE:
<223> OTHER INFORMATION: Synthetic Construct

<400> SEQUENCE: 303
ttttaatttt ttcg                                                    14

<210> SEQ ID NO 304
<211> LENGTH: 14
<212> TYPE: DNA
<213> ORGANISM: Artificial Sequence
<220> FEATURE:

```
<223> OTHER INFORMATION: Synthetic Construct

<400> SEQUENCE: 304
tttaattttt tcgt                                                          14

<210> SEQ ID NO 305
<211> LENGTH: 14
<212> TYPE: DNA
<213> ORGANISM: Artificial Sequence
<220> FEATURE:
<223> OTHER INFORMATION: Synthetic Construct

<400> SEQUENCE: 305
ttaatttttt cgtt                                                          14

<210> SEQ ID NO 306
<211> LENGTH: 14
<212> TYPE: DNA
<213> ORGANISM: Artificial Sequence
<220> FEATURE:
<223> OTHER INFORMATION: Synthetic Construct

<400> SEQUENCE: 306
taattttttc gttt                                                          14

<210> SEQ ID NO 307
<211> LENGTH: 14
<212> TYPE: DNA
<213> ORGANISM: Artificial Sequence
<220> FEATURE:
<223> OTHER INFORMATION: Synthetic Construct

<400> SEQUENCE: 307
aattttttcg tttt                                                          14

<210> SEQ ID NO 308
<211> LENGTH: 14
<212> TYPE: DNA
<213> ORGANISM: Artificial Sequence
<220> FEATURE:
<223> OTHER INFORMATION: Synthetic Construct

<400> SEQUENCE: 308
attttttcgt tttc                                                          14

<210> SEQ ID NO 309
<211> LENGTH: 14
<212> TYPE: DNA
<213> ORGANISM: Artificial Sequence
<220> FEATURE:
<223> OTHER INFORMATION: Synthetic Construct

<400> SEQUENCE: 309
ttttttcgtt ttcg                                                          14

<210> SEQ ID NO 310
<211> LENGTH: 14
<212> TYPE: DNA
<213> ORGANISM: Artificial Sequence
<220> FEATURE:
<223> OTHER INFORMATION: Synthetic Construct

<400> SEQUENCE: 310
tttttcgttt tcgg                                                          14
```

```
<210> SEQ ID NO 311
<211> LENGTH: 14
<212> TYPE: DNA
<213> ORGANISM: Artificial Sequence
<220> FEATURE:
<223> OTHER INFORMATION: Synthetic Construct

<400> SEQUENCE: 311
ttttcgtttt cggc                                                         14

<210> SEQ ID NO 312
<211> LENGTH: 14
<212> TYPE: DNA
<213> ORGANISM: Artificial Sequence
<220> FEATURE:
<223> OTHER INFORMATION: Synthetic Construct

<400> SEQUENCE: 312
tttcgttttc ggcg                                                         14

<210> SEQ ID NO 313
<211> LENGTH: 14
<212> TYPE: DNA
<213> ORGANISM: Artificial Sequence
<220> FEATURE:
<223> OTHER INFORMATION: Synthetic Construct

<400> SEQUENCE: 313
ttcgttttcg gcgg                                                         14

<210> SEQ ID NO 314
<211> LENGTH: 14
<212> TYPE: DNA
<213> ORGANISM: Artificial Sequence
<220> FEATURE:
<223> OTHER INFORMATION: Synthetic Construct

<400> SEQUENCE: 314
tcgttttcgg cggg                                                         14

<210> SEQ ID NO 315
<211> LENGTH: 14
<212> TYPE: DNA
<213> ORGANISM: Artificial Sequence
<220> FEATURE:
<223> OTHER INFORMATION: Synthetic Construct

<400> SEQUENCE: 315
cgttttcggc gggt                                                         14

<210> SEQ ID NO 316
<211> LENGTH: 14
<212> TYPE: DNA
<213> ORGANISM: Artificial Sequence
<220> FEATURE:
<223> OTHER INFORMATION: Synthetic Construct

<400> SEQUENCE: 316
gttttcggcg ggtt                                                         14

<210> SEQ ID NO 317
<211> LENGTH: 14
<212> TYPE: DNA
<213> ORGANISM: Artificial Sequence
<220> FEATURE:
<223> OTHER INFORMATION: Synthetic Construct
```

<400> SEQUENCE: 317
ttttcggcgg gttt                                                    14

<210> SEQ ID NO 318
<211> LENGTH: 14
<212> TYPE: DNA
<213> ORGANISM: Artificial Sequence
<220> FEATURE:
<223> OTHER INFORMATION: Synthetic Construct

<400> SEQUENCE: 318
tttcggcggg tttt                                                    14

<210> SEQ ID NO 319
<211> LENGTH: 14
<212> TYPE: DNA
<213> ORGANISM: Artificial Sequence
<220> FEATURE:
<223> OTHER INFORMATION: Synthetic Construct

<400> SEQUENCE: 319
ttcggcgggt tttg                                                    14

<210> SEQ ID NO 320
<211> LENGTH: 14
<212> TYPE: DNA
<213> ORGANISM: Artificial Sequence
<220> FEATURE:
<223> OTHER INFORMATION: Synthetic Construct

<400> SEQUENCE: 320
tcggcgggtt ttgt                                                    14

<210> SEQ ID NO 321
<211> LENGTH: 14
<212> TYPE: DNA
<213> ORGANISM: Artificial Sequence
<220> FEATURE:
<223> OTHER INFORMATION: Synthetic Construct

<400> SEQUENCE: 321
cggcgggttt tgtt                                                    14

<210> SEQ ID NO 322
<211> LENGTH: 14
<212> TYPE: DNA
<213> ORGANISM: Artificial Sequence
<220> FEATURE:
<223> OTHER INFORMATION: Synthetic Construct

<400> SEQUENCE: 322
ggcgggtttt gttg                                                    14

<210> SEQ ID NO 323
<211> LENGTH: 14
<212> TYPE: DNA
<213> ORGANISM: Artificial Sequence
<220> FEATURE:
<223> OTHER INFORMATION: Synthetic Construct

<400> SEQUENCE: 323
gcgggttttg ttgc                                                    14

<210> SEQ ID NO 324
<211> LENGTH: 14

```
<212> TYPE: DNA
<213> ORGANISM: Artificial Sequence
<220> FEATURE:
<223> OTHER INFORMATION: Synthetic Construct

<400> SEQUENCE: 324
cgggttttgt tgcg                                                        14

<210> SEQ ID NO 325
<211> LENGTH: 14
<212> TYPE: DNA
<213> ORGANISM: Artificial Sequence
<220> FEATURE:
<223> OTHER INFORMATION: Synthetic Construct

<400> SEQUENCE: 325
gggttttgtt gcgt                                                        14

<210> SEQ ID NO 326
<211> LENGTH: 14
<212> TYPE: DNA
<213> ORGANISM: Artificial Sequence
<220> FEATURE:
<223> OTHER INFORMATION: Synthetic Construct

<400> SEQUENCE: 326
ggttttgttg cgtg                                                        14

<210> SEQ ID NO 327
<211> LENGTH: 14
<212> TYPE: DNA
<213> ORGANISM: Artificial Sequence
<220> FEATURE:
<223> OTHER INFORMATION: Synthetic Construct

<400> SEQUENCE: 327
gttttgttgc gtgg                                                        14

<210> SEQ ID NO 328
<211> LENGTH: 14
<212> TYPE: DNA
<213> ORGANISM: Artificial Sequence
<220> FEATURE:
<223> OTHER INFORMATION: Synthetic Construct

<400> SEQUENCE: 328
ttttgttgcg tggt                                                        14

<210> SEQ ID NO 329
<211> LENGTH: 14
<212> TYPE: DNA
<213> ORGANISM: Artificial Sequence
<220> FEATURE:
<223> OTHER INFORMATION: Synthetic Construct

<400> SEQUENCE: 329
tttgttgcgt ggtt                                                        14

<210> SEQ ID NO 330
<211> LENGTH: 14
<212> TYPE: DNA
<213> ORGANISM: Artificial Sequence
<220> FEATURE:
<223> OTHER INFORMATION: Synthetic Construct

<400> SEQUENCE: 330
```
ttgttgcgtg gttt                                       14

<210> SEQ ID NO 331
<211> LENGTH: 14
<212> TYPE: DNA
<213> ORGANISM: Artificial Sequence
<220> FEATURE:
<223> OTHER INFORMATION: Synthetic Construct

<400> SEQUENCE: 331
tgttgcgtgg tttg                                       14

<210> SEQ ID NO 332
<211> LENGTH: 14
<212> TYPE: DNA
<213> ORGANISM: Artificial Sequence
<220> FEATURE:
<223> OTHER INFORMATION: Synthetic Construct

<400> SEQUENCE: 332
gttgcgtggt ttgg                                       14

<210> SEQ ID NO 333
<211> LENGTH: 14
<212> TYPE: DNA
<213> ORGANISM: Artificial Sequence
<220> FEATURE:
<223> OTHER INFORMATION: Synthetic Construct

<400> SEQUENCE: 333
ttgcgtggtt tggg                                       14

<210> SEQ ID NO 334
<211> LENGTH: 14
<212> TYPE: DNA
<213> ORGANISM: Artificial Sequence
<220> FEATURE:
<223> OTHER INFORMATION: Synthetic Construct

<400> SEQUENCE: 334
tgcgtggttt ggga                                       14

<210> SEQ ID NO 335
<211> LENGTH: 14
<212> TYPE: DNA
<213> ORGANISM: Artificial Sequence
<220> FEATURE:
<223> OTHER INFORMATION: Synthetic Construct

<400> SEQUENCE: 335
gcgtggtttg ggaa                                       14

<210> SEQ ID NO 336
<211> LENGTH: 14
<212> TYPE: DNA
<213> ORGANISM: Artificial Sequence
<220> FEATURE:
<223> OTHER INFORMATION: Synthetic Construct

<400> SEQUENCE: 336
cgtggtttgg gaag                                       14

<210> SEQ ID NO 337
<211> LENGTH: 14
<212> TYPE: DNA
<213> ORGANISM: Artificial Sequence

```
<220> FEATURE:
<223> OTHER INFORMATION: Synthetic Construct

<400> SEQUENCE: 337
gtggtttggg aagg                                                          14

<210> SEQ ID NO 338
<211> LENGTH: 14
<212> TYPE: DNA
<213> ORGANISM: Artificial Sequence
<220> FEATURE:
<223> OTHER INFORMATION: Synthetic Construct

<400> SEQUENCE: 338
tggtttggga agga                                                          14

<210> SEQ ID NO 339
<211> LENGTH: 14
<212> TYPE: DNA
<213> ORGANISM: Artificial Sequence
<220> FEATURE:
<223> OTHER INFORMATION: Synthetic Construct

<400> SEQUENCE: 339
ggtttgggaa ggac                                                          14

<210> SEQ ID NO 340
<211> LENGTH: 14
<212> TYPE: DNA
<213> ORGANISM: Artificial Sequence
<220> FEATURE:
<223> OTHER INFORMATION: Synthetic Construct

<400> SEQUENCE: 340
gtttgggaag gacg                                                          14

<210> SEQ ID NO 341
<211> LENGTH: 14
<212> TYPE: DNA
<213> ORGANISM: Artificial Sequence
<220> FEATURE:
<223> OTHER INFORMATION: Synthetic Construct

<400> SEQUENCE: 341
tttgggaagg acgg                                                          14

<210> SEQ ID NO 342
<211> LENGTH: 14
<212> TYPE: DNA
<213> ORGANISM: Artificial Sequence
<220> FEATURE:
<223> OTHER INFORMATION: Synthetic Construct

<400> SEQUENCE: 342
ttgggaagga cgga                                                          14

<210> SEQ ID NO 343
<211> LENGTH: 14
<212> TYPE: DNA
<213> ORGANISM: Artificial Sequence
<220> FEATURE:
<223> OTHER INFORMATION: Synthetic Construct

<400> SEQUENCE: 343
tgggaaggac ggag                                                          14
```

```
<210> SEQ ID NO 344
<211> LENGTH: 14
<212> TYPE: DNA
<213> ORGANISM: Artificial Sequence
<220> FEATURE:
<223> OTHER INFORMATION: Synthetic Construct

<400> SEQUENCE: 344
gggaaggacg gagg                                                        14

<210> SEQ ID NO 345
<211> LENGTH: 14
<212> TYPE: DNA
<213> ORGANISM: Artificial Sequence
<220> FEATURE:
<223> OTHER INFORMATION: Synthetic Construct

<400> SEQUENCE: 345
ggaaggacgg aggg                                                        14

<210> SEQ ID NO 346
<211> LENGTH: 14
<212> TYPE: DNA
<213> ORGANISM: Artificial Sequence
<220> FEATURE:
<223> OTHER INFORMATION: Synthetic Construct

<400> SEQUENCE: 346
gaaggacgga gggg                                                        14

<210> SEQ ID NO 347
<211> LENGTH: 14
<212> TYPE: DNA
<213> ORGANISM: Artificial Sequence
<220> FEATURE:
<223> OTHER INFORMATION: Synthetic Construct

<400> SEQUENCE: 347
aaggacggag ggga                                                        14

<210> SEQ ID NO 348
<211> LENGTH: 14
<212> TYPE: DNA
<213> ORGANISM: Artificial Sequence
<220> FEATURE:
<223> OTHER INFORMATION: Synthetic Construct

<400> SEQUENCE: 348
aggacggagg ggaa                                                        14

<210> SEQ ID NO 349
<211> LENGTH: 14
<212> TYPE: DNA
<213> ORGANISM: Artificial Sequence
<220> FEATURE:
<223> OTHER INFORMATION: Synthetic Construct

<400> SEQUENCE: 349
ggacggaggg gaaa                                                        14

<210> SEQ ID NO 350
<211> LENGTH: 14
<212> TYPE: DNA
<213> ORGANISM: Artificial Sequence
<220> FEATURE:
<223> OTHER INFORMATION: Synthetic Construct
```

```
<400> SEQUENCE: 350
gacggagggg aaag                                                       14

<210> SEQ ID NO 351
<211> LENGTH: 14
<212> TYPE: DNA
<213> ORGANISM: Artificial Sequence
<220> FEATURE:
<223> OTHER INFORMATION: Synthetic Construct

<400> SEQUENCE: 351 acggaggggga aagg                                                      14

<210> SEQ ID NO 352
<211> LENGTH: 14
<212> TYPE: DNA
<213> ORGANISM: Artificial Sequence
<220> FEATURE:
<223> OTHER INFORMATION: Synthetic Construct

<400> SEQUENCE: 352
cggaggggaa aggg                                                       14

<210> SEQ ID NO 353
<211> LENGTH: 14
<212> TYPE: DNA
<213> ORGANISM: Artificial Sequence
<220> FEATURE:
<223> OTHER INFORMATION: Synthetic Construct

<400> SEQUENCE: 353
ggaggggaaa gggt                                                       14

<210> SEQ ID NO 354
<211> LENGTH: 14
<212> TYPE: DNA
<213> ORGANISM: Artificial Sequence
<220> FEATURE:
<223> OTHER INFORMATION: Synthetic Construct

<400> SEQUENCE: 354
gaggggaaag ggtg                                                       14

<210> SEQ ID NO 355
<211> LENGTH: 14
<212> TYPE: DNA
<213> ORGANISM: Artificial Sequence
<220> FEATURE:
<223> OTHER INFORMATION: Synthetic Construct

<400> SEQUENCE: 355
aggggaaagg gtgg                                                       14

<210> SEQ ID NO 356
<211> LENGTH: 14
<212> TYPE: DNA
<213> ORGANISM: Artificial Sequence
<220> FEATURE:
<223> OTHER INFORMATION: Synthetic Construct

<400> SEQUENCE: 356
ggggaaaggg tggt                                                       14

<210> SEQ ID NO 357
```

```
<211> LENGTH: 14
<212> TYPE: DNA
<213> ORGANISM: Artificial Sequence
<220> FEATURE:
<223> OTHER INFORMATION: Synthetic Construct

<400> SEQUENCE: 357 gggaagggt ggta                                              14

<210> SEQ ID NO 358
<211> LENGTH: 14
<212> TYPE: DNA
<213> ORGANISM: Artificial Sequence
<220> FEATURE:
<223> OTHER INFORMATION: Synthetic Construct

<400> SEQUENCE: 358
ggaaagggtg gtag                                             14

<210> SEQ ID NO 359
<211> LENGTH: 14
<212> TYPE: DNA
<213> ORGANISM: Artificial Sequence
<220> FEATURE:
<223> OTHER INFORMATION: Synthetic Construct

<400> SEQUENCE: 359
gaaagggtgg tagg                                             14

<210> SEQ ID NO 360
<211> LENGTH: 14
<212> TYPE: DNA
<213> ORGANISM: Artificial Sequence
<220> FEATURE:
<223> OTHER INFORMATION: Synthetic Construct

<400> SEQUENCE: 360
aaagggtggt agga                                             14

<210> SEQ ID NO 361
<211> LENGTH: 14
<212> TYPE: DNA
<213> ORGANISM: Artificial Sequence
<220> FEATURE:
<223> OTHER INFORMATION: Synthetic Construct

<400> SEQUENCE: 361
aagggtggta ggag                                             14

<210> SEQ ID NO 362
<211> LENGTH: 14
<212> TYPE: DNA
<213> ORGANISM: Artificial Sequence
<220> FEATURE:
<223> OTHER INFORMATION: Synthetic Construct

<400> SEQUENCE: 362
agggtggtag gagg                                             14

<210> SEQ ID NO 363
<211> LENGTH: 14
<212> TYPE: DNA
<213> ORGANISM: Artificial Sequence
<220> FEATURE:
<223> OTHER INFORMATION: Synthetic Construct

<400> SEQUENCE: 363
```
gggtggtagg aggg                                              14

<210> SEQ ID NO 364
<211> LENGTH: 14
<212> TYPE: DNA
<213> ORGANISM: Artificial Sequence
<220> FEATURE:
<223> OTHER INFORMATION: Synthetic Construct

<400> SEQUENCE: 364
ggtggtagga gggg                                              14

<210> SEQ ID NO 365
<211> LENGTH: 14
<212> TYPE: DNA
<213> ORGANISM: Artificial Sequence
<220> FEATURE:
<223> OTHER INFORMATION: Synthetic Construct

<400> SEQUENCE: 365
gtggtaggag gggg                                              14

<210> SEQ ID NO 366
<211> LENGTH: 14
<212> TYPE: DNA
<213> ORGANISM: Artificial Sequence
<220> FEATURE:
<223> OTHER INFORMATION: Synthetic Construct

<400> SEQUENCE: 366
tggtaggagg gggg                                              14

<210> SEQ ID NO 367
<211> LENGTH: 14
<212> TYPE: DNA
<213> ORGANISM: Artificial Sequence
<220> FEATURE:
<223> OTHER INFORMATION: Synthetic Construct

<400> SEQUENCE: 367
ggtaggaggg ggga                                              14

<210> SEQ ID NO 368
<211> LENGTH: 14
<212> TYPE: DNA
<213> ORGANISM: Artificial Sequence
<220> FEATURE:
<223> OTHER INFORMATION: Synthetic Construct

<400> SEQUENCE: 368
gtaggagggg ggag                                              14

<210> SEQ ID NO 369
<211> LENGTH: 14
<212> TYPE: DNA
<213> ORGANISM: Artificial Sequence
<220> FEATURE:
<223> OTHER INFORMATION: Synthetic Construct

<400> SEQUENCE: 369
taggaggggg gagt                                              14

<210> SEQ ID NO 370
<211> LENGTH: 14
<212> TYPE: DNA

```
<213> ORGANISM: Artificial Sequence
<220> FEATURE:
<223> OTHER INFORMATION: Synthetic Construct

<400> SEQUENCE: 370 aggaggggg agtt                                                          14

<210> SEQ ID NO 371
<211> LENGTH: 14
<212> TYPE: DNA
<213> ORGANISM: Artificial Sequence
<220> FEATURE:
<223> OTHER INFORMATION: Synthetic Construct

<400> SEQUENCE: 371 ggaggggga gttt                                                          14

<210> SEQ ID NO 372
<211> LENGTH: 14
<212> TYPE: DNA
<213> ORGANISM: Artificial Sequence
<220> FEATURE:
<223> OTHER INFORMATION: Synthetic Construct

<400> SEQUENCE: 372
gaggggggag tttg                                                         14

<210> SEQ ID NO 373
<211> LENGTH: 14
<212> TYPE: DNA
<213> ORGANISM: Artificial Sequence
<220> FEATURE:
<223> OTHER INFORMATION: Synthetic Construct

<400> SEQUENCE: 373
aggggggagt ttgg                                                         14

<210> SEQ ID NO 374
<211> LENGTH: 14
<212> TYPE: DNA
<213> ORGANISM: Artificial Sequence
<220> FEATURE:
<223> OTHER INFORMATION: Synthetic Construct

<400> SEQUENCE: 374 gggggagtt tggg                                                          14

<210> SEQ ID NO 375
<211> LENGTH: 14
<212> TYPE: DNA
<213> ORGANISM: Artificial Sequence
<220> FEATURE:
<223> OTHER INFORMATION: Synthetic Construct

<400> SEQUENCE: 375
gggggagttt gggt                                                         14

<210> SEQ ID NO 376
<211> LENGTH: 14
<212> TYPE: DNA
<213> ORGANISM: Artificial Sequence
<220> FEATURE:
<223> OTHER INFORMATION: Synthetic Construct

<400> SEQUENCE: 376
ggggagtttg ggtc                                                         14
```

<210> SEQ ID NO 377
<211> LENGTH: 14
<212> TYPE: DNA
<213> ORGANISM: Artificial Sequence
<220> FEATURE:
<223> OTHER INFORMATION: Synthetic Construct

<400> SEQUENCE: 377
gggagtttgg gtcg                                                         14

<210> SEQ ID NO 378
<211> LENGTH: 14
<212> TYPE: DNA
<213> ORGANISM: Artificial Sequence
<220> FEATURE:
<223> OTHER INFORMATION: Synthetic Construct

<400> SEQUENCE: 378
ggagtttggg tcgg                                                         14

<210> SEQ ID NO 379
<211> LENGTH: 14
<212> TYPE: DNA
<213> ORGANISM: Artificial Sequence
<220> FEATURE:
<223> OTHER INFORMATION: Synthetic Construct

<400> SEQUENCE: 379
gagtttgggt cggg                                                         14

<210> SEQ ID NO 380
<211> LENGTH: 14
<212> TYPE: DNA
<213> ORGANISM: Artificial Sequence
<220> FEATURE:
<223> OTHER INFORMATION: Synthetic Construct

<400> SEQUENCE: 380
agtttgggtc gggt                                                         14

<210> SEQ ID NO 381
<211> LENGTH: 14
<212> TYPE: DNA
<213> ORGANISM: Artificial Sequence
<220> FEATURE:
<223> OTHER INFORMATION: Synthetic Construct

<400> SEQUENCE: 381
gtttgggtcg ggtt                                                         14

<210> SEQ ID NO 382
<211> LENGTH: 14
<212> TYPE: DNA
<213> ORGANISM: Artificial Sequence
<220> FEATURE:
<223> OTHER INFORMATION: Synthetic Construct

<400> SEQUENCE: 382
tttgggtcgg gttc                                                         14

<210> SEQ ID NO 383
<211> LENGTH: 14
<212> TYPE: DNA
<213> ORGANISM: Artificial Sequence
<220> FEATURE:

<223> OTHER INFORMATION: Synthetic Construct

<400> SEQUENCE: 383
ttgggtcggg ttcg                                                      14

<210> SEQ ID NO 384
<211> LENGTH: 14
<212> TYPE: DNA
<213> ORGANISM: Artificial Sequence
<220> FEATURE:
<223> OTHER INFORMATION: Synthetic Construct

<400> SEQUENCE: 384
tgggtcgggt tcgc                                                      14

<210> SEQ ID NO 385
<211> LENGTH: 14
<212> TYPE: DNA
<213> ORGANISM: Artificial Sequence
<220> FEATURE:
<223> OTHER INFORMATION: Synthetic Construct

<400> SEQUENCE: 385
gggtcgggtt cgcg                                                      14

<210> SEQ ID NO 386
<211> LENGTH: 14
<212> TYPE: DNA
<213> ORGANISM: Artificial Sequence
<220> FEATURE:
<223> OTHER INFORMATION: Synthetic Construct

<400> SEQUENCE: 386
ggtcgggttc gcga                                                      14

<210> SEQ ID NO 387
<211> LENGTH: 14
<212> TYPE: DNA
<213> ORGANISM: Artificial Sequence
<220> FEATURE:
<223> OTHER INFORMATION: Synthetic Construct

<400> SEQUENCE: 387
gtcgggttcg cgag                                                      14

<210> SEQ ID NO 388
<211> LENGTH: 14
<212> TYPE: DNA
<213> ORGANISM: Artificial Sequence
<220> FEATURE:
<223> OTHER INFORMATION: Synthetic Construct

<400> SEQUENCE: 388
tcgggttcgc gagg                                                      14

<210> SEQ ID NO 389
<211> LENGTH: 14
<212> TYPE: DNA
<213> ORGANISM: Artificial Sequence
<220> FEATURE:
<223> OTHER INFORMATION: Synthetic Construct

<400> SEQUENCE: 389
cgggttcgcg aggg                                                      14

```
<210> SEQ ID NO 390
<211> LENGTH: 14
<212> TYPE: DNA
<213> ORGANISM: Artificial Sequence
<220> FEATURE:
<223> OTHER INFORMATION: Synthetic Construct

<400> SEQUENCE: 390
gggttcgcga ggga                                                      14

<210> SEQ ID NO 391
<211> LENGTH: 14
<212> TYPE: DNA
<213> ORGANISM: Artificial Sequence
<220> FEATURE:
<223> OTHER INFORMATION: Synthetic Construct

<400> SEQUENCE: 391
ggttcgcgag ggaa                                                      14

<210> SEQ ID NO 392
<211> LENGTH: 14
<212> TYPE: DNA
<213> ORGANISM: Artificial Sequence
<220> FEATURE:
<223> OTHER INFORMATION: Synthetic Construct

<400> SEQUENCE: 392
gttcgcgagg gaac                                                      14

<210> SEQ ID NO 393
<211> LENGTH: 14
<212> TYPE: DNA
<213> ORGANISM: Artificial Sequence
<220> FEATURE:
<223> OTHER INFORMATION: Synthetic Construct

<400> SEQUENCE: 393
ttcgcgaggg aacg                                                      14

<210> SEQ ID NO 394
<211> LENGTH: 14
<212> TYPE: DNA
<213> ORGANISM: Artificial Sequence
<220> FEATURE:
<223> OTHER INFORMATION: Synthetic Construct

<400> SEQUENCE: 394
tcgcgaggga acgg                                                      14

<210> SEQ ID NO 395
<211> LENGTH: 14
<212> TYPE: DNA
<213> ORGANISM: Artificial Sequence
<220> FEATURE:
<223> OTHER INFORMATION: Synthetic Construct

<400> SEQUENCE: 395
cgcgagggaa cggt                                                      14

<210> SEQ ID NO 396
<211> LENGTH: 14
<212> TYPE: DNA
<213> ORGANISM: Artificial Sequence
<220> FEATURE:
<223> OTHER INFORMATION: Synthetic Construct
```

```
<400> SEQUENCE: 396
gcgagggaac ggtt                                                        14

<210> SEQ ID NO 397
<211> LENGTH: 14
<212> TYPE: DNA
<213> ORGANISM: Artificial Sequence
<220> FEATURE:
<223> OTHER INFORMATION: Synthetic Construct

<400> SEQUENCE: 397
cgagggaacg gttt                                                        14

<210> SEQ ID NO 398
<211> LENGTH: 14
<212> TYPE: DNA
<213> ORGANISM: Artificial Sequence
<220> FEATURE:
<223> OTHER INFORMATION: Synthetic Construct

<400> SEQUENCE: 398
gagggaacgg tttt                                                        14

<210> SEQ ID NO 399
<211> LENGTH: 14
<212> TYPE: DNA
<213> ORGANISM: Artificial Sequence
<220> FEATURE:
<223> OTHER INFORMATION: Synthetic Construct

<400> SEQUENCE: 399
agggaacggt ttta                                                        14

<210> SEQ ID NO 400
<211> LENGTH: 14
<212> TYPE: DNA
<213> ORGANISM: Artificial Sequence
<220> FEATURE:
<223> OTHER INFORMATION: Synthetic Construct

<400> SEQUENCE: 400
gggaacggtt ttat                                                        14

<210> SEQ ID NO 401
<211> LENGTH: 14
<212> TYPE: DNA
<213> ORGANISM: Artificial Sequence
<220> FEATURE:
<223> OTHER INFORMATION: Synthetic Construct

<400> SEQUENCE: 401
ggaacggttt tatt                                                        14

<210> SEQ ID NO 402
<211> LENGTH: 14
<212> TYPE: DNA
<213> ORGANISM: Artificial Sequence
<220> FEATURE:
<223> OTHER INFORMATION: Synthetic Construct

<400> SEQUENCE: 402
gaacggtttt attt                                                        14

<210> SEQ ID NO 403
<211> LENGTH: 14
```

```
<212> TYPE: DNA
<213> ORGANISM: Artificial Sequence
<220> FEATURE:
<223> OTHER INFORMATION: Synthetic Construct

<400> SEQUENCE: 403
aacgttttta tttc                                                      14

<210> SEQ ID NO 404
<211> LENGTH: 14
<212> TYPE: DNA
<213> ORGANISM: Artificial Sequence
<220> FEATURE:
<223> OTHER INFORMATION: Synthetic Construct

<400> SEQUENCE: 404
acggttttat ttcg                                                      14

<210> SEQ ID NO 405
<211> LENGTH: 14
<212> TYPE: DNA
<213> ORGANISM: Artificial Sequence
<220> FEATURE:
<223> OTHER INFORMATION: Synthetic Construct

<400> SEQUENCE: 405
cggttttatt tcgc                                                      14

<210> SEQ ID NO 406
<211> LENGTH: 14
<212> TYPE: DNA
<213> ORGANISM: Artificial Sequence
<220> FEATURE:
<223> OTHER INFORMATION: Synthetic Construct

<400> SEQUENCE: 406
ggttttattt cgcg                                                      14

<210> SEQ ID NO 407
<211> LENGTH: 14
<212> TYPE: DNA
<213> ORGANISM: Artificial Sequence
<220> FEATURE:
<223> OTHER INFORMATION: Synthetic Construct

<400> SEQUENCE: 407
gttttatttc gcgc                                                      14

<210> SEQ ID NO 408
<211> LENGTH: 14
<212> TYPE: DNA
<213> ORGANISM: Artificial Sequence
<220> FEATURE:
<223> OTHER INFORMATION: Synthetic Construct

<400> SEQUENCE: 408
ttttatttcg cgcg                                                      14

<210> SEQ ID NO 409
<211> LENGTH: 14
<212> TYPE: DNA
<213> ORGANISM: Artificial Sequence
<220> FEATURE:
<223> OTHER INFORMATION: Synthetic Construct

<400> SEQUENCE: 409
```
tttatttcgc gcgt                                                14

<210> SEQ ID NO 410
<211> LENGTH: 14
<212> TYPE: DNA
<213> ORGANISM: Artificial Sequence
<220> FEATURE:
<223> OTHER INFORMATION: Synthetic Construct

<400> SEQUENCE: 410
ttatttcgcg cgtt                                                14

<210> SEQ ID NO 411
<211> LENGTH: 14
<212> TYPE: DNA
<213> ORGANISM: Artificial Sequence
<220> FEATURE:
<223> OTHER INFORMATION: Synthetic Construct

<400> SEQUENCE: 411
tatttcgcgc gttt                                                14

<210> SEQ ID NO 412
<211> LENGTH: 14
<212> TYPE: DNA
<213> ORGANISM: Artificial Sequence
<220> FEATURE:
<223> OTHER INFORMATION: Synthetic Construct

<400> SEQUENCE: 412
atttcgcgcg tttt                                                14

<210> SEQ ID NO 413
<211> LENGTH: 14
<212> TYPE: DNA
<213> ORGANISM: Artificial Sequence
<220> FEATURE:
<223> OTHER INFORMATION: Synthetic Construct

<400> SEQUENCE: 413
tttcgcgcgt tttt                                                14

<210> SEQ ID NO 414
<211> LENGTH: 14
<212> TYPE: DNA
<213> ORGANISM: Artificial Sequence
<220> FEATURE:
<223> OTHER INFORMATION: Synthetic Construct

<400> SEQUENCE: 414
ttcgcgcgtt tttc                                                14

<210> SEQ ID NO 415
<211> LENGTH: 14
<212> TYPE: DNA
<213> ORGANISM: Artificial Sequence
<220> FEATURE:
<223> OTHER INFORMATION: Synthetic Construct

<400> SEQUENCE: 415
tcgcgcgttt ttcg                                                14

<210> SEQ ID NO 416
<211> LENGTH: 14
<212> TYPE: DNA
<213> ORGANISM: Artificial Sequence
<220> FEATURE:
<223> OTHER INFORMATION: Synthetic Construct

<400> SEQUENCE: 416 cgcgcgttttt tcga                    14

<210> SEQ ID NO 417
<211> LENGTH: 14
<212> TYPE: DNA
<213> ORGANISM: Artificial Sequence
<220> FEATURE:
<223> OTHER INFORMATION: Synthetic Construct

<400> SEQUENCE: 417
gcgcgttttt cgag                    14

<210> SEQ ID NO 418
<211> LENGTH: 14
<212> TYPE: DNA
<213> ORGANISM: Artificial Sequence
<220> FEATURE:
<223> OTHER INFORMATION: Synthetic Construct

<400> SEQUENCE: 418 cgcgttttttc gaga                   14

<210> SEQ ID NO 419
<211> LENGTH: 14
<212> TYPE: DNA
<213> ORGANISM: Artificial Sequence
<220> FEATURE:
<223> OTHER INFORMATION: Synthetic Construct

<400> SEQUENCE: 419
gcgtttttcg agat                    14

<210> SEQ ID NO 420
<211> LENGTH: 14
<212> TYPE: DNA
<213> ORGANISM: Artificial Sequence
<220> FEATURE:
<223> OTHER INFORMATION: Synthetic Construct

<400> SEQUENCE: 420 cgttttttcga gatt                   14

<210> SEQ ID NO 421
<211> LENGTH: 14
<212> TYPE: DNA
<213> ORGANISM: Artificial Sequence
<220> FEATURE:
<223> OTHER INFORMATION: Synthetic Construct

<400> SEQUENCE: 421 gttttttcgag atta                   14

<210> SEQ ID NO 422
<211> LENGTH: 14
<212> TYPE: DNA
<213> ORGANISM: Artificial Sequence
<220> FEATURE:
<223> OTHER INFORMATION: Synthetic Construct

<400> SEQUENCE: 422
tttttcgaga ttag                    14

<210> SEQ ID NO 423
<211> LENGTH: 14
<212> TYPE: DNA
<213> ORGANISM: Artificial Sequence
<220> FEATURE:
<223> OTHER INFORMATION: Synthetic Construct

<400> SEQUENCE: 423
ttttcgagat tagg                                                         14

<210> SEQ ID NO 424
<211> LENGTH: 14
<212> TYPE: DNA
<213> ORGANISM: Artificial Sequence
<220> FEATURE:
<223> OTHER INFORMATION: Synthetic Construct

<400> SEQUENCE: 424
tttcgagatt aggg                                                         14

<210> SEQ ID NO 425
<211> LENGTH: 14
<212> TYPE: DNA
<213> ORGANISM: Artificial Sequence
<220> FEATURE:
<223> OTHER INFORMATION: Synthetic Construct

<400> SEQUENCE: 425
ttcgagatta ggga                                                         14

<210> SEQ ID NO 426
<211> LENGTH: 14
<212> TYPE: DNA
<213> ORGANISM: Artificial Sequence
<220> FEATURE:
<223> OTHER INFORMATION: Synthetic Construct

<400> SEQUENCE: 426
tcgagattag ggat                                                         14

<210> SEQ ID NO 427
<211> LENGTH: 14
<212> TYPE: DNA
<213> ORGANISM: Artificial Sequence
<220> FEATURE:
<223> OTHER INFORMATION: Synthetic Construct

<400> SEQUENCE: 427
cgagattagg gatg                                                         14

<210> SEQ ID NO 428
<211> LENGTH: 14
<212> TYPE: DNA
<213> ORGANISM: Artificial Sequence
<220> FEATURE:
<223> OTHER INFORMATION: Synthetic Construct

<400> SEQUENCE: 428
gagattaggg atga                                                         14

<210> SEQ ID NO 429
<211> LENGTH: 14
<212> TYPE: DNA
<213> ORGANISM: Artificial Sequence
<220> FEATURE:
<223> OTHER INFORMATION: Synthetic Construct

<400> SEQUENCE: 429
agattaggga tgat                                                         14

<210> SEQ ID NO 430
<211> LENGTH: 14
<212> TYPE: DNA
<213> ORGANISM: Artificial Sequence
<220> FEATURE:
<223> OTHER INFORMATION: Synthetic Construct

<400> SEQUENCE: 430
gattagggat gatt                                                         14

<210> SEQ ID NO 431
<211> LENGTH: 14
<212> TYPE: DNA
<213> ORGANISM: Artificial Sequence
<220> FEATURE:
<223> OTHER INFORMATION: Synthetic Construct

<400> SEQUENCE: 431
attagggatg attt                                                         14

<210> SEQ ID NO 432
<211> LENGTH: 14
<212> TYPE: DNA
<213> ORGANISM: Artificial Sequence
<220> FEATURE:
<223> OTHER INFORMATION: Synthetic Construct

<400> SEQUENCE: 432
ttagggatga tttg                                                         14

<210> SEQ ID NO 433
<211> LENGTH: 14
<212> TYPE: DNA
<213> ORGANISM: Artificial Sequence
<220> FEATURE:
<223> OTHER INFORMATION: Synthetic Construct

<400> SEQUENCE: 433
tagggatgat ttgg                                                         14

<210> SEQ ID NO 434
<211> LENGTH: 14
<212> TYPE: DNA
<213> ORGANISM: Artificial Sequence
<220> FEATURE:
<223> OTHER INFORMATION: Synthetic Construct

<400> SEQUENCE: 434
agggatgatt tgga                                                         14

<210> SEQ ID NO 435
<211> LENGTH: 14
<212> TYPE: DNA
<213> ORGANISM: Artificial Sequence
<220> FEATURE:
<223> OTHER INFORMATION: Synthetic Construct

<400> SEQUENCE: 435
gggatgattt ggaa                                                         14

<210> SEQ ID NO 436

```
<211> LENGTH: 14
<212> TYPE: DNA
<213> ORGANISM: Artificial Sequence
<220> FEATURE:
<223> OTHER INFORMATION: Synthetic Construct

<400> SEQUENCE: 436
ggatgatttg gaaa                                                     14

<210> SEQ ID NO 437
<211> LENGTH: 14
<212> TYPE: DNA
<213> ORGANISM: Artificial Sequence
<220> FEATURE:
<223> OTHER INFORMATION: Synthetic Construct

<400> SEQUENCE: 437
gatgatttgg aaat                                                     14

<210> SEQ ID NO 438
<211> LENGTH: 14
<212> TYPE: DNA
<213> ORGANISM: Artificial Sequence
<220> FEATURE:
<223> OTHER INFORMATION: Synthetic Construct

<400> SEQUENCE: 438
atgatttgga aatt                                                     14

<210> SEQ ID NO 439
<211> LENGTH: 14
<212> TYPE: DNA
<213> ORGANISM: Artificial Sequence
<220> FEATURE:
<223> OTHER INFORMATION: Synthetic Construct

<400> SEQUENCE: 439
tgatttggaa attt                                                     14

<210> SEQ ID NO 440
<211> LENGTH: 14
<212> TYPE: DNA
<213> ORGANISM: Artificial Sequence
<220> FEATURE:
<223> OTHER INFORMATION: Synthetic Construct

<400> SEQUENCE: 440
gatttggaaa tttc                                                     14

<210> SEQ ID NO 441
<211> LENGTH: 14
<212> TYPE: DNA
<213> ORGANISM: Artificial Sequence
<220> FEATURE:
<223> OTHER INFORMATION: Synthetic Construct

<400> SEQUENCE: 441
atttggaaat ttcg                                                     14

<210> SEQ ID NO 442
<211> LENGTH: 14
<212> TYPE: DNA
<213> ORGANISM: Artificial Sequence
<220> FEATURE:
<223> OTHER INFORMATION: Synthetic Construct

<400> SEQUENCE: 442
```
tttggaaatt tcgg                                    14

<210> SEQ ID NO 443
<211> LENGTH: 14
<212> TYPE: DNA
<213> ORGANISM: Artificial Sequence
<220> FEATURE:
<223> OTHER INFORMATION: Synthetic Construct

<400> SEQUENCE: 443
ttggaaattt cggg                                    14

<210> SEQ ID NO 444
<211> LENGTH: 14
<212> TYPE: DNA
<213> ORGANISM: Artificial Sequence
<220> FEATURE:
<223> OTHER INFORMATION: Synthetic Construct

<400> SEQUENCE: 444 tggaaattc gggg                                     14

<210> SEQ ID NO 445
<211> LENGTH: 14
<212> TYPE: DNA
<213> ORGANISM: Artificial Sequence
<220> FEATURE:
<223> OTHER INFORMATION: Synthetic Construct

<400> SEQUENCE: 445
ggaaatttcg gggt                                    14

<210> SEQ ID NO 446
<211> LENGTH: 14
<212> TYPE: DNA
<213> ORGANISM: Artificial Sequence
<220> FEATURE:
<223> OTHER INFORMATION: Synthetic Construct

<400> SEQUENCE: 446
gaaatttcgg ggtt                                    14

<210> SEQ ID NO 447
<211> LENGTH: 14
<212> TYPE: DNA
<213> ORGANISM: Artificial Sequence
<220> FEATURE:
<223> OTHER INFORMATION: Synthetic Construct

<400> SEQUENCE: 447
aaatttcggg gttt                                    14

<210> SEQ ID NO 448
<211> LENGTH: 14
<212> TYPE: DNA
<213> ORGANISM: Artificial Sequence
<220> FEATURE:
<223> OTHER INFORMATION: Synthetic Construct

<400> SEQUENCE: 448
aatttcgggg tttt                                    14

<210> SEQ ID NO 449
<211> LENGTH: 14
<212> TYPE: DNA

```
<213> ORGANISM: Artificial Sequence
<220> FEATURE:
<223> OTHER INFORMATION: Synthetic Construct

<400> SEQUENCE: 449
atttcggggt tttt                                                         14

<210> SEQ ID NO 450
<211> LENGTH: 14
<212> TYPE: DNA
<213> ORGANISM: Artificial Sequence
<220> FEATURE:
<223> OTHER INFORMATION: Synthetic Construct

<400> SEQUENCE: 450
tttcggggtt tttt                                                         14

<210> SEQ ID NO 451
<211> LENGTH: 14
<212> TYPE: DNA
<213> ORGANISM: Artificial Sequence
<220> FEATURE:
<223> OTHER INFORMATION: Synthetic Construct

<400> SEQUENCE: 451
ttcggggttt tttt                                                         14

<210> SEQ ID NO 452
<211> LENGTH: 14
<212> TYPE: DNA
<213> ORGANISM: Artificial Sequence
<220> FEATURE:
<223> OTHER INFORMATION: Synthetic Construct

<400> SEQUENCE: 452
tcggggtttt tttt                                                         14

<210> SEQ ID NO 453
<211> LENGTH: 14
<212> TYPE: DNA
<213> ORGANISM: Artificial Sequence
<220> FEATURE:
<223> OTHER INFORMATION: Synthetic Construct

<400> SEQUENCE: 453
cggggttttt tttt                                                         14

<210> SEQ ID NO 454
<211> LENGTH: 14
<212> TYPE: DNA
<213> ORGANISM: Artificial Sequence
<220> FEATURE:
<223> OTHER INFORMATION: Synthetic Construct

<400> SEQUENCE: 454
ggggtttttt tttt                                                         14

<210> SEQ ID NO 455
<211> LENGTH: 14
<212> TYPE: DNA
<213> ORGANISM: Artificial Sequence
<220> FEATURE:
<223> OTHER INFORMATION: Synthetic Construct

<400> SEQUENCE: 455
gggttttttt tttc                                                         14
```

```
<210> SEQ ID NO 456
<211> LENGTH: 14
<212> TYPE: DNA
<213> ORGANISM: Artificial Sequence
<220> FEATURE:
<223> OTHER INFORMATION: Synthetic Construct

<400> SEQUENCE: 456
ggtttttttt ttcg                                                       14

<210> SEQ ID NO 457
<211> LENGTH: 14
<212> TYPE: DNA
<213> ORGANISM: Artificial Sequence
<220> FEATURE:
<223> OTHER INFORMATION: Synthetic Construct

<400> SEQUENCE: 457 gtttttttttt tcgt                                                      14

<210> SEQ ID NO 458
<211> LENGTH: 14
<212> TYPE: DNA
<213> ORGANISM: Artificial Sequence
<220> FEATURE:
<223> OTHER INFORMATION: Synthetic Construct

<400> SEQUENCE: 458
tttttttttt cgta                                                       14

<210> SEQ ID NO 459
<211> LENGTH: 14
<212> TYPE: DNA
<213> ORGANISM: Artificial Sequence
<220> FEATURE:
<223> OTHER INFORMATION: Synthetic Construct

<400> SEQUENCE: 459 ttttttttttc gtat                                                      14

<210> SEQ ID NO 460
<211> LENGTH: 14
<212> TYPE: DNA
<213> ORGANISM: Artificial Sequence
<220> FEATURE:
<223> OTHER INFORMATION: Synthetic Construct

<400> SEQUENCE: 460 tttttttcg tata                                                        14

<210> SEQ ID NO 461
<211> LENGTH: 14
<212> TYPE: DNA
<213> ORGANISM: Artificial Sequence
<220> FEATURE:
<223> OTHER INFORMATION: Synthetic Construct

<400> SEQUENCE: 461
tttttttcgt atat                                                       14

<210> SEQ ID NO 462
<211> LENGTH: 14
<212> TYPE: DNA
<213> ORGANISM: Artificial Sequence
<220> FEATURE:
```

<223> OTHER INFORMATION: Synthetic Construct

<400> SEQUENCE: 462 tttttcgta tatt                                                      14

<210> SEQ ID NO 463
<211> LENGTH: 14
<212> TYPE: DNA
<213> ORGANISM: Artificial Sequence
<220> FEATURE:
<223> OTHER INFORMATION: Synthetic Construct

<400> SEQUENCE: 463
tttttcgtat atta                                                     14

<210> SEQ ID NO 464
<211> LENGTH: 14
<212> TYPE: DNA
<213> ORGANISM: Artificial Sequence
<220> FEATURE:
<223> OTHER INFORMATION: Synthetic Construct

<400> SEQUENCE: 464
ttttcgtata ttat                                                     14

<210> SEQ ID NO 465
<211> LENGTH: 14
<212> TYPE: DNA
<213> ORGANISM: Artificial Sequence
<220> FEATURE:
<223> OTHER INFORMATION: Synthetic Construct

<400> SEQUENCE: 465
tttcgtatat tatt                                                     14

<210> SEQ ID NO 466
<211> LENGTH: 14
<212> TYPE: DNA
<213> ORGANISM: Artificial Sequence
<220> FEATURE:
<223> OTHER INFORMATION: Synthetic Construct

<400> SEQUENCE: 466
ttcgtatatt attt                                                     14

<210> SEQ ID NO 467
<211> LENGTH: 14
<212> TYPE: DNA
<213> ORGANISM: Artificial Sequence
<220> FEATURE:
<223> OTHER INFORMATION: Synthetic Construct

<400> SEQUENCE: 467
tcgtatatta tttt                                                     14

<210> SEQ ID NO 468
<211> LENGTH: 14
<212> TYPE: DNA
<213> ORGANISM: Artificial Sequence
<220> FEATURE:
<223> OTHER INFORMATION: Synthetic Construct

<400> SEQUENCE: 468
cgtatattat tttt                                                     14

-continued

```
<210> SEQ ID NO 469
<211> LENGTH: 14
<212> TYPE: DNA
<213> ORGANISM: Artificial Sequence
<220> FEATURE:
<223> OTHER INFORMATION: Synthetic Construct

<400> SEQUENCE: 469
gtatattatt tttt                                                          14

<210> SEQ ID NO 470
<211> LENGTH: 14
<212> TYPE: DNA
<213> ORGANISM: Artificial Sequence
<220> FEATURE:
<223> OTHER INFORMATION: Synthetic Construct

<400> SEQUENCE: 470
tatattattt tttt                                                          14

<210> SEQ ID NO 471
<211> LENGTH: 14
<212> TYPE: DNA
<213> ORGANISM: Artificial Sequence
<220> FEATURE:
<223> OTHER INFORMATION: Synthetic Construct

<400> SEQUENCE: 471
atattatttt tttc                                                          14

<210> SEQ ID NO 472
<211> LENGTH: 14
<212> TYPE: DNA
<213> ORGANISM: Artificial Sequence
<220> FEATURE:
<223> OTHER INFORMATION: Synthetic Construct

<400> SEQUENCE: 472
tattattttt ttcg                                                          14

<210> SEQ ID NO 473
<211> LENGTH: 14
<212> TYPE: DNA
<213> ORGANISM: Artificial Sequence
<220> FEATURE:
<223> OTHER INFORMATION: Synthetic Construct

<400> SEQUENCE: 473 attattttttt tcgc                                                         14

<210> SEQ ID NO 474
<211> LENGTH: 14
<212> TYPE: DNA
<213> ORGANISM: Artificial Sequence
<220> FEATURE:
<223> OTHER INFORMATION: Synthetic Construct

<400> SEQUENCE: 474
ttattttttt cgcg                                                          14

<210> SEQ ID NO 475
<211> LENGTH: 14
<212> TYPE: DNA
<213> ORGANISM: Artificial Sequence
<220> FEATURE:
<223> OTHER INFORMATION: Synthetic Construct
```

```
<400> SEQUENCE: 475 tattttttc gcgt                                                      14

<210> SEQ ID NO 476
<211> LENGTH: 14
<212> TYPE: DNA
<213> ORGANISM: Artificial Sequence
<220> FEATURE:
<223> OTHER INFORMATION: Synthetic Construct

<400> SEQUENCE: 476 attttttcg cgtt                                                      14

<210> SEQ ID NO 477
<211> LENGTH: 14
<212> TYPE: DNA
<213> ORGANISM: Artificial Sequence
<220> FEATURE:
<223> OTHER INFORMATION: Synthetic Construct

<400> SEQUENCE: 477
tttttttcgc gtta                                                     14

<210> SEQ ID NO 478
<211> LENGTH: 14
<212> TYPE: DNA
<213> ORGANISM: Artificial Sequence
<220> FEATURE:
<223> OTHER INFORMATION: Synthetic Construct

<400> SEQUENCE: 478 tttttcgcg ttag                                                      14

<210> SEQ ID NO 479
<211> LENGTH: 14
<212> TYPE: DNA
<213> ORGANISM: Artificial Sequence
<220> FEATURE:
<223> OTHER INFORMATION: Synthetic Construct

<400> SEQUENCE: 479
tttttcgcgt tagt                                                     14

<210> SEQ ID NO 480
<211> LENGTH: 14
<212> TYPE: DNA
<213> ORGANISM: Artificial Sequence
<220> FEATURE:
<223> OTHER INFORMATION: Synthetic Construct

<400> SEQUENCE: 480
ttttcgcgtt agtt                                                     14

<210> SEQ ID NO 481
<211> LENGTH: 14
<212> TYPE: DNA
<213> ORGANISM: Artificial Sequence
<220> FEATURE:
<223> OTHER INFORMATION: Synthetic Construct

<400> SEQUENCE: 481
tttcgcgtta gttt                                                     14

<210> SEQ ID NO 482
<211> LENGTH: 14
```

```
<212> TYPE: DNA
<213> ORGANISM: Artificial Sequence
<220> FEATURE:
<223> OTHER INFORMATION: Synthetic Construct

<400> SEQUENCE: 482
ttcgcgttag tttt                                                    14

<210> SEQ ID NO 483
<211> LENGTH: 14
<212> TYPE: DNA
<213> ORGANISM: Artificial Sequence
<220> FEATURE:
<223> OTHER INFORMATION: Synthetic Construct

<400> SEQUENCE: 483
tcgcgttagt tttt                                                    14

<210> SEQ ID NO 484
<211> LENGTH: 14
<212> TYPE: DNA
<213> ORGANISM: Artificial Sequence
<220> FEATURE:
<223> OTHER INFORMATION: Synthetic Construct

<400> SEQUENCE: 484
cgcgttagtt tttt                                                    14

<210> SEQ ID NO 485
<211> LENGTH: 14
<212> TYPE: DNA
<213> ORGANISM: Artificial Sequence
<220> FEATURE:
<223> OTHER INFORMATION: Synthetic Construct

<400> SEQUENCE: 485
gcgttagttt tttt                                                    14

<210> SEQ ID NO 486
<211> LENGTH: 14
<212> TYPE: DNA
<213> ORGANISM: Artificial Sequence
<220> FEATURE:
<223> OTHER INFORMATION: Synthetic Construct

<400> SEQUENCE: 486
cgttagtttt tttg                                                    14

<210> SEQ ID NO 487
<211> LENGTH: 14
<212> TYPE: DNA
<213> ORGANISM: Artificial Sequence
<220> FEATURE:
<223> OTHER INFORMATION: Synthetic Construct

<400> SEQUENCE: 487
gttagttttt ttgt                                                    14

<210> SEQ ID NO 488
<211> LENGTH: 14
<212> TYPE: DNA
<213> ORGANISM: Artificial Sequence
<220> FEATURE:
<223> OTHER INFORMATION: Synthetic Construct

<400> SEQUENCE: 488
```

```
ttagttttttt tgtt                                                        14

<210> SEQ ID NO 489
<211> LENGTH: 14
<212> TYPE: DNA
<213> ORGANISM: Artificial Sequence
<220> FEATURE:
<223> OTHER INFORMATION: Synthetic Construct

<400> SEQUENCE: 489 tagtttttt gttt                                                          14

<210> SEQ ID NO 490
<211> LENGTH: 14
<212> TYPE: DNA
<213> ORGANISM: Artificial Sequence
<220> FEATURE:
<223> OTHER INFORMATION: Synthetic Construct

<400> SEQUENCE: 490 agttttttg tttg                                                          14

<210> SEQ ID NO 491
<211> LENGTH: 14
<212> TYPE: DNA
<213> ORGANISM: Artificial Sequence
<220> FEATURE:
<223> OTHER INFORMATION: Synthetic Construct

<400> SEQUENCE: 491 gttttttgt ttga                                                          14

<210> SEQ ID NO 492
<211> LENGTH: 14
<212> TYPE: DNA
<213> ORGANISM: Artificial Sequence
<220> FEATURE:
<223> OTHER INFORMATION: Synthetic Construct

<400> SEQUENCE: 492 ttttttgtt tgat                                                          14

<210> SEQ ID NO 493
<211> LENGTH: 14
<212> TYPE: DNA
<213> ORGANISM: Artificial Sequence
<220> FEATURE:
<223> OTHER INFORMATION: Synthetic Construct

<400> SEQUENCE: 493 tttttgttt gatt                                                          14

<210> SEQ ID NO 494
<211> LENGTH: 14
<212> TYPE: DNA
<213> ORGANISM: Artificial Sequence
<220> FEATURE:
<223> OTHER INFORMATION: Synthetic Construct

<400> SEQUENCE: 494
tttttgtttg attg                                                         14

<210> SEQ ID NO 495
<211> LENGTH: 14
<212> TYPE: DNA
<213> ORGANISM: Artificial Sequence
```

```
<220> FEATURE:
<223> OTHER INFORMATION: Synthetic Construct

<400> SEQUENCE: 495
ttttgtttga ttgt                                                            14

<210> SEQ ID NO 496
<211> LENGTH: 14
<212> TYPE: DNA
<213> ORGANISM: Artificial Sequence
<220> FEATURE:
<223> OTHER INFORMATION: Synthetic Construct

<400> SEQUENCE: 496
tttgtttgat tgta                                                            14

<210> SEQ ID NO 497
<211> LENGTH: 14
<212> TYPE: DNA
<213> ORGANISM: Artificial Sequence
<220> FEATURE:
<223> OTHER INFORMATION: Synthetic Construct

<400> SEQUENCE: 497
ttgtttgatt gtat                                                            14

<210> SEQ ID NO 498
<211> LENGTH: 14
<212> TYPE: DNA
<213> ORGANISM: Artificial Sequence
<220> FEATURE:
<223> OTHER INFORMATION: Synthetic Construct

<400> SEQUENCE: 498
tgtttgattg tatg                                                            14

<210> SEQ ID NO 499
<211> LENGTH: 14
<212> TYPE: DNA
<213> ORGANISM: Artificial Sequence
<220> FEATURE:
<223> OTHER INFORMATION: Synthetic Construct

<400> SEQUENCE: 499
gtttgattgt atgt                                                            14

<210> SEQ ID NO 500
<211> LENGTH: 14
<212> TYPE: DNA
<213> ORGANISM: Artificial Sequence
<220> FEATURE:
<223> OTHER INFORMATION: Synthetic Construct

<400> SEQUENCE: 500
tttgattgta tgta                                                            14

<210> SEQ ID NO 501
<211> LENGTH: 14
<212> TYPE: DNA
<213> ORGANISM: Artificial Sequence
<220> FEATURE:
<223> OTHER INFORMATION: Synthetic Construct

<400> SEQUENCE: 501
ttgattgtat gtaa                                                            14
```

<210> SEQ ID NO 502
<211> LENGTH: 14
<212> TYPE: DNA
<213> ORGANISM: Artificial Sequence
<220> FEATURE:
<223> OTHER INFORMATION: Synthetic Construct

<400> SEQUENCE: 502
tgattgtatg taag                                                  14

<210> SEQ ID NO 503
<211> LENGTH: 14
<212> TYPE: DNA
<213> ORGANISM: Artificial Sequence
<220> FEATURE:
<223> OTHER INFORMATION: Synthetic Construct

<400> SEQUENCE: 503
gattgtatgt aagt                                                  14

<210> SEQ ID NO 504
<211> LENGTH: 14
<212> TYPE: DNA
<213> ORGANISM: Artificial Sequence
<220> FEATURE:
<223> OTHER INFORMATION: Synthetic Construct

<400> SEQUENCE: 504
attgtatgta agtt                                                  14

<210> SEQ ID NO 505
<211> LENGTH: 14
<212> TYPE: DNA
<213> ORGANISM: Artificial Sequence
<220> FEATURE:
<223> OTHER INFORMATION: Synthetic Construct

<400> SEQUENCE: 505
ttgtatgtaa gttt                                                  14

<210> SEQ ID NO 506
<211> LENGTH: 14
<212> TYPE: DNA
<213> ORGANISM: Artificial Sequence
<220> FEATURE:
<223> OTHER INFORMATION: Synthetic Construct

<400> SEQUENCE: 506
tgtatgtaag tttt                                                  14

<210> SEQ ID NO 507
<211> LENGTH: 14
<212> TYPE: DNA
<213> ORGANISM: Artificial Sequence
<220> FEATURE:
<223> OTHER INFORMATION: Synthetic Construct

<400> SEQUENCE: 507
gtatgtaagt tttg                                                  14

<210> SEQ ID NO 508
<211> LENGTH: 14
<212> TYPE: DNA
<213> ORGANISM: Artificial Sequence
<220> FEATURE:
<223> OTHER INFORMATION: Synthetic Construct

```
<400> SEQUENCE: 508
tatgtaagtt ttgg                                                          14

<210> SEQ ID NO 509
<211> LENGTH: 14
<212> TYPE: DNA
<213> ORGANISM: Artificial Sequence
<220> FEATURE:
<223> OTHER INFORMATION: Synthetic Construct

<400> SEQUENCE: 509
atgtaagttt tggg                                                          14

<210> SEQ ID NO 510
<211> LENGTH: 14
<212> TYPE: DNA
<213> ORGANISM: Artificial Sequence
<220> FEATURE:
<223> OTHER INFORMATION: Synthetic Construct

<400> SEQUENCE: 510
tgtaagtttt gggg                                                          14

<210> SEQ ID NO 511
<211> LENGTH: 14
<212> TYPE: DNA
<213> ORGANISM: Artificial Sequence
<220> FEATURE:
<223> OTHER INFORMATION: Synthetic Construct

<400> SEQUENCE: 511
gtaagttttg ggga                                                          14

<210> SEQ ID NO 512
<211> LENGTH: 14
<212> TYPE: DNA
<213> ORGANISM: Artificial Sequence
<220> FEATURE:
<223> OTHER INFORMATION: Synthetic Construct

<400> SEQUENCE: 512
taagttttgg ggag                                                          14

<210> SEQ ID NO 513
<211> LENGTH: 14
<212> TYPE: DNA
<213> ORGANISM: Artificial Sequence
<220> FEATURE:
<223> OTHER INFORMATION: Synthetic Construct

<400> SEQUENCE: 513
aagttttggg gaga                                                          14

<210> SEQ ID NO 514
<211> LENGTH: 14
<212> TYPE: DNA
<213> ORGANISM: Artificial Sequence
<220> FEATURE:
<223> OTHER INFORMATION: Synthetic Construct

<400> SEQUENCE: 514
agttttgggg agat                                                          14

<210> SEQ ID NO 515
```

```
<211> LENGTH: 14
<212> TYPE: DNA
<213> ORGANISM: Artificial Sequence
<220> FEATURE:
<223> OTHER INFORMATION: Synthetic Construct

<400> SEQUENCE: 515
gttttgggga gatg                                                        14

<210> SEQ ID NO 516
<211> LENGTH: 14
<212> TYPE: DNA
<213> ORGANISM: Artificial Sequence
<220> FEATURE:
<223> OTHER INFORMATION: Synthetic Construct

<400> SEQUENCE: 516 ttttgggag atgg                                                         14

<210> SEQ ID NO 517
<211> LENGTH: 14
<212> TYPE: DNA
<213> ORGANISM: Artificial Sequence
<220> FEATURE:
<223> OTHER INFORMATION: Synthetic Construct

<400> SEQUENCE: 517
tttggggaga tggg                                                        14

<210> SEQ ID NO 518
<211> LENGTH: 14
<212> TYPE: DNA
<213> ORGANISM: Artificial Sequence
<220> FEATURE:
<223> OTHER INFORMATION: Synthetic Construct

<400> SEQUENCE: 518
ttggggagat gggg                                                        14

<210> SEQ ID NO 519
<211> LENGTH: 14
<212> TYPE: DNA
<213> ORGANISM: Artificial Sequence
<220> FEATURE:
<223> OTHER INFORMATION: Synthetic Construct

<400> SEQUENCE: 519
tggggagatg gggg                                                        14

<210> SEQ ID NO 520
<211> LENGTH: 14
<212> TYPE: DNA
<213> ORGANISM: Artificial Sequence
<220> FEATURE:
<223> OTHER INFORMATION: Synthetic Construct

<400> SEQUENCE: 520
ggggagatgg gggt                                                        14

<210> SEQ ID NO 521
<211> LENGTH: 14
<212> TYPE: DNA
<213> ORGANISM: Artificial Sequence
<220> FEATURE:
<223> OTHER INFORMATION: Synthetic Construct

<400> SEQUENCE: 521
```

```
gggagatggg ggtt                                              14

<210> SEQ ID NO 522
<211> LENGTH: 14
<212> TYPE: DNA
<213> ORGANISM: Artificial Sequence
<220> FEATURE:
<223> OTHER INFORMATION: Synthetic Construct

<400> SEQUENCE: 522
ggagatgggg gtta                                              14

<210> SEQ ID NO 523
<211> LENGTH: 14
<212> TYPE: DNA
<213> ORGANISM: Artificial Sequence
<220> FEATURE:
<223> OTHER INFORMATION: Synthetic Construct

<400> SEQUENCE: 523
gagatggggg ttag                                              14

<210> SEQ ID NO 524
<211> LENGTH: 14
<212> TYPE: DNA
<213> ORGANISM: Artificial Sequence
<220> FEATURE:
<223> OTHER INFORMATION: Synthetic Construct

<400> SEQUENCE: 524
agatgggggt taga                                              14

<210> SEQ ID NO 525
<211> LENGTH: 14
<212> TYPE: DNA
<213> ORGANISM: Artificial Sequence
<220> FEATURE:
<223> OTHER INFORMATION: Synthetic Construct

<400> SEQUENCE: 525 gatggggtt agat                                               14

<210> SEQ ID NO 526
<211> LENGTH: 14
<212> TYPE: DNA
<213> ORGANISM: Artificial Sequence
<220> FEATURE:
<223> OTHER INFORMATION: Synthetic Construct

<400> SEQUENCE: 526 atggggtta gatt                                               14

<210> SEQ ID NO 527
<211> LENGTH: 14
<212> TYPE: DNA
<213> ORGANISM: Artificial Sequence
<220> FEATURE:
<223> OTHER INFORMATION: Synthetic Construct

<400> SEQUENCE: 527 tggggttag attt                                               14

<210> SEQ ID NO 528
<211> LENGTH: 14
<212> TYPE: DNA
```

<213> ORGANISM: Artificial Sequence
<220> FEATURE:
<223> OTHER INFORMATION: Synthetic Construct

<400> SEQUENCE: 528
gggggttaga ttta                                                     14

<210> SEQ ID NO 529
<211> LENGTH: 14
<212> TYPE: DNA
<213> ORGANISM: Artificial Sequence
<220> FEATURE:
<223> OTHER INFORMATION: Synthetic Construct

<400> SEQUENCE: 529
ggggttagat ttaa                                                     14

<210> SEQ ID NO 530
<211> LENGTH: 14
<212> TYPE: DNA
<213> ORGANISM: Artificial Sequence
<220> FEATURE:
<223> OTHER INFORMATION: Synthetic Construct

<400> SEQUENCE: 530
gggttagatt taag                                                     14

<210> SEQ ID NO 531
<211> LENGTH: 14
<212> TYPE: DNA
<213> ORGANISM: Artificial Sequence
<220> FEATURE:
<223> OTHER INFORMATION: Synthetic Construct

<400> SEQUENCE: 531
ggttagattt aaga                                                     14

<210> SEQ ID NO 532
<211> LENGTH: 14
<212> TYPE: DNA
<213> ORGANISM: Artificial Sequence
<220> FEATURE:
<223> OTHER INFORMATION: Synthetic Construct

<400> SEQUENCE: 532
gttagattta agag                                                     14

<210> SEQ ID NO 533
<211> LENGTH: 14
<212> TYPE: DNA
<213> ORGANISM: Artificial Sequence
<220> FEATURE:
<223> OTHER INFORMATION: Synthetic Construct

<400> SEQUENCE: 533
ttagatttaa gaga                                                     14

<210> SEQ ID NO 534
<211> LENGTH: 14
<212> TYPE: DNA
<213> ORGANISM: Artificial Sequence
<220> FEATURE:
<223> OTHER INFORMATION: Synthetic Construct

<400> SEQUENCE: 534
tagatttaag agat                                                     14

```
<210> SEQ ID NO 535
<211> LENGTH: 14
<212> TYPE: DNA
<213> ORGANISM: Artificial Sequence
<220> FEATURE:
<223> OTHER INFORMATION: Synthetic Construct

<400> SEQUENCE: 535
agatttaaga gatt                                                         14

<210> SEQ ID NO 536
<211> LENGTH: 14
<212> TYPE: DNA
<213> ORGANISM: Artificial Sequence
<220> FEATURE:
<223> OTHER INFORMATION: Synthetic Construct

<400> SEQUENCE: 536
gatttaagag attc                                                         14

<210> SEQ ID NO 537
<211> LENGTH: 14
<212> TYPE: DNA
<213> ORGANISM: Artificial Sequence
<220> FEATURE:
<223> OTHER INFORMATION: Synthetic Construct

<400> SEQUENCE: 537
atttaagaga ttcg                                                         14

<210> SEQ ID NO 538
<211> LENGTH: 14
<212> TYPE: DNA
<213> ORGANISM: Artificial Sequence
<220> FEATURE:
<223> OTHER INFORMATION: Synthetic Construct

<400> SEQUENCE: 538
tttaagagat tcgc                                                         14

<210> SEQ ID NO 539
<211> LENGTH: 14
<212> TYPE: DNA
<213> ORGANISM: Artificial Sequence
<220> FEATURE:
<223> OTHER INFORMATION: Synthetic Construct

<400> SEQUENCE: 539
ttaagagatt cgcg                                                         14

<210> SEQ ID NO 540
<211> LENGTH: 14
<212> TYPE: DNA
<213> ORGANISM: Artificial Sequence
<220> FEATURE:
<223> OTHER INFORMATION: Synthetic Construct

<400> SEQUENCE: 540
taagagattc gcga                                                         14

<210> SEQ ID NO 541
<211> LENGTH: 14
<212> TYPE: DNA
<213> ORGANISM: Artificial Sequence
<220> FEATURE:
```

<223> OTHER INFORMATION: Synthetic Construct

<400> SEQUENCE: 541
aagagattcg cgag                                                                    14

<210> SEQ ID NO 542
<211> LENGTH: 14
<212> TYPE: DNA
<213> ORGANISM: Artificial Sequence
<220> FEATURE:
<223> OTHER INFORMATION: Synthetic Construct

<400> SEQUENCE: 542
agagattcgc gagt                                                                    14

<210> SEQ ID NO 543
<211> LENGTH: 14
<212> TYPE: DNA
<213> ORGANISM: Artificial Sequence
<220> FEATURE:
<223> OTHER INFORMATION: Synthetic Construct

<400> SEQUENCE: 543
gagattcgcg agtg                                                                    14

<210> SEQ ID NO 544
<211> LENGTH: 14
<212> TYPE: DNA
<213> ORGANISM: Artificial Sequence
<220> FEATURE:
<223> OTHER INFORMATION: Synthetic Construct

<400> SEQUENCE: 544
agattcgcga gtgt                                                                    14

<210> SEQ ID NO 545
<211> LENGTH: 14
<212> TYPE: DNA
<213> ORGANISM: Artificial Sequence
<220> FEATURE:
<223> OTHER INFORMATION: Synthetic Construct

<400> SEQUENCE: 545
gattcgcgag tgtt                                                                    14

<210> SEQ ID NO 546
<211> LENGTH: 14
<212> TYPE: DNA
<213> ORGANISM: Artificial Sequence
<220> FEATURE:
<223> OTHER INFORMATION: Synthetic Construct

<400> SEQUENCE: 546
attcgcgagt gttt                                                                    14

<210> SEQ ID NO 547
<211> LENGTH: 14
<212> TYPE: DNA
<213> ORGANISM: Artificial Sequence
<220> FEATURE:
<223> OTHER INFORMATION: Synthetic Construct

<400> SEQUENCE: 547
ttcgcgagtg ttta                                                                    14

```
<210> SEQ ID NO 548
<211> LENGTH: 14
<212> TYPE: DNA
<213> ORGANISM: Artificial Sequence
<220> FEATURE:
<223> OTHER INFORMATION: Synthetic Construct

<400> SEQUENCE: 548
tcgcgagtgt ttag                                                       14

<210> SEQ ID NO 549
<211> LENGTH: 14
<212> TYPE: DNA
<213> ORGANISM: Artificial Sequence
<220> FEATURE:
<223> OTHER INFORMATION: Synthetic Construct

<400> SEQUENCE: 549
cgcgagtgtt taga                                                       14

<210> SEQ ID NO 550
<211> LENGTH: 14
<212> TYPE: DNA
<213> ORGANISM: Artificial Sequence
<220> FEATURE:
<223> OTHER INFORMATION: Synthetic Construct

<400> SEQUENCE: 550
gcgagtgttt agag                                                       14

<210> SEQ ID NO 551
<211> LENGTH: 14
<212> TYPE: DNA
<213> ORGANISM: Artificial Sequence
<220> FEATURE:
<223> OTHER INFORMATION: Synthetic Construct

<400> SEQUENCE: 551
cgagtgttta gaga                                                       14

<210> SEQ ID NO 552
<211> LENGTH: 14
<212> TYPE: DNA
<213> ORGANISM: Artificial Sequence
<220> FEATURE:
<223> OTHER INFORMATION: Synthetic Construct

<400> SEQUENCE: 552
gagtgtttag agag                                                       14

<210> SEQ ID NO 553
<211> LENGTH: 14
<212> TYPE: DNA
<213> ORGANISM: Artificial Sequence
<220> FEATURE:
<223> OTHER INFORMATION: Synthetic Construct

<400> SEQUENCE: 553
agtgtttaga gaga                                                       14

<210> SEQ ID NO 554
<211> LENGTH: 14
<212> TYPE: DNA
<213> ORGANISM: Artificial Sequence
<220> FEATURE:
<223> OTHER INFORMATION: Synthetic Construct
```

```
<400> SEQUENCE: 554
gtgtttagag agaa                                                 14

<210> SEQ ID NO 555
<211> LENGTH: 14
<212> TYPE: DNA
<213> ORGANISM: Artificial Sequence
<220> FEATURE:
<223> OTHER INFORMATION: Synthetic Construct

<400> SEQUENCE: 555
tgtttagaga gaaa                                                 14

<210> SEQ ID NO 556
<211> LENGTH: 14
<212> TYPE: DNA
<213> ORGANISM: Artificial Sequence
<220> FEATURE:
<223> OTHER INFORMATION: Synthetic Construct

<400> SEQUENCE: 556
gtttagagag aaaa                                                 14

<210> SEQ ID NO 557
<211> LENGTH: 14
<212> TYPE: DNA
<213> ORGANISM: Artificial Sequence
<220> FEATURE:
<223> OTHER INFORMATION: Synthetic Construct

<400> SEQUENCE: 557
tttagagaga aaag                                                 14

<210> SEQ ID NO 558
<211> LENGTH: 14
<212> TYPE: DNA
<213> ORGANISM: Artificial Sequence
<220> FEATURE:
<223> OTHER INFORMATION: Synthetic Construct

<400> SEQUENCE: 558
ttagagagaa aagt                                                 14

<210> SEQ ID NO 559
<211> LENGTH: 14
<212> TYPE: DNA
<213> ORGANISM: Artificial Sequence
<220> FEATURE:
<223> OTHER INFORMATION: Synthetic Construct

<400> SEQUENCE: 559
tagagagaaa agtt                                                 14

<210> SEQ ID NO 560
<211> LENGTH: 14
<212> TYPE: DNA
<213> ORGANISM: Artificial Sequence
<220> FEATURE:
<223> OTHER INFORMATION: Synthetic Construct

<400> SEQUENCE: 560
agagagaaaa gttt                                                 14

<210> SEQ ID NO 561
<211> LENGTH: 14
```

```
<212> TYPE: DNA
<213> ORGANISM: Artificial Sequence
<220> FEATURE:
<223> OTHER INFORMATION: Synthetic Construct

<400> SEQUENCE: 561
gagagaaaag tttg                                                         14

<210> SEQ ID NO 562
<211> LENGTH: 14
<212> TYPE: DNA
<213> ORGANISM: Artificial Sequence
<220> FEATURE:
<223> OTHER INFORMATION: Synthetic Construct

<400> SEQUENCE: 562
agagaaaagt ttgt                                                         14

<210> SEQ ID NO 563
<211> LENGTH: 14
<212> TYPE: DNA
<213> ORGANISM: Artificial Sequence
<220> FEATURE:
<223> OTHER INFORMATION: Synthetic Construct

<400> SEQUENCE: 563
gagaaaagtt tgta                                                         14

<210> SEQ ID NO 564
<211> LENGTH: 14
<212> TYPE: DNA
<213> ORGANISM: Artificial Sequence
<220> FEATURE:
<223> OTHER INFORMATION: Synthetic Construct

<400> SEQUENCE: 564
agaaaagttt gtaa                                                         14

<210> SEQ ID NO 565
<211> LENGTH: 14
<212> TYPE: DNA
<213> ORGANISM: Artificial Sequence
<220> FEATURE:
<223> OTHER INFORMATION: Synthetic Construct

<400> SEQUENCE: 565
gaaaagtttg taaa                                                         14

<210> SEQ ID NO 566
<211> LENGTH: 14
<212> TYPE: DNA
<213> ORGANISM: Artificial Sequence
<220> FEATURE:
<223> OTHER INFORMATION: Synthetic Construct

<400> SEQUENCE: 566
aaaagtttgt aaaa                                                         14

<210> SEQ ID NO 567
<211> LENGTH: 14
<212> TYPE: DNA
<213> ORGANISM: Artificial Sequence
<220> FEATURE:
<223> OTHER INFORMATION: Synthetic Construct

<400> SEQUENCE: 567
```
aaagtttgta aaag                                                     14

<210> SEQ ID NO 568
<211> LENGTH: 14
<212> TYPE: DNA
<213> ORGANISM: Artificial Sequence
<220> FEATURE:
<223> OTHER INFORMATION: Synthetic Construct

<400> SEQUENCE: 568
aagtttgtaa aagt                                                     14

<210> SEQ ID NO 569
<211> LENGTH: 14
<212> TYPE: DNA
<213> ORGANISM: Artificial Sequence
<220> FEATURE:
<223> OTHER INFORMATION: Synthetic Construct

<400> SEQUENCE: 569
agtttgtaaa agtt                                                     14

<210> SEQ ID NO 570
<211> LENGTH: 14
<212> TYPE: DNA
<213> ORGANISM: Artificial Sequence
<220> FEATURE:
<223> OTHER INFORMATION: Synthetic Construct

<400> SEQUENCE: 570
gtttgtaaaa gttt                                                     14

<210> SEQ ID NO 571
<211> LENGTH: 14
<212> TYPE: DNA
<213> ORGANISM: Artificial Sequence
<220> FEATURE:
<223> OTHER INFORMATION: Synthetic Construct

<400> SEQUENCE: 571
tttgtaaaag tttt                                                     14

<210> SEQ ID NO 572
<211> LENGTH: 14
<212> TYPE: DNA
<213> ORGANISM: Artificial Sequence
<220> FEATURE:
<223> OTHER INFORMATION: Synthetic Construct

<400> SEQUENCE: 572
ttgtaaaagt tttt                                                     14

<210> SEQ ID NO 573
<211> LENGTH: 14
<212> TYPE: DNA
<213> ORGANISM: Artificial Sequence
<220> FEATURE:
<223> OTHER INFORMATION: Synthetic Construct

<400> SEQUENCE: 573
tgtaaaagtt tttt                                                     14

<210> SEQ ID NO 574
<211> LENGTH: 14
<212> TYPE: DNA
<213> ORGANISM: Artificial Sequence

```
<220> FEATURE:
<223> OTHER INFORMATION: Synthetic Construct

<400> SEQUENCE: 574
gtaaaagttt tttt                                                          14

<210> SEQ ID NO 575
<211> LENGTH: 14
<212> TYPE: DNA
<213> ORGANISM: Artificial Sequence
<220> FEATURE:
<223> OTHER INFORMATION: Synthetic Construct

<400> SEQUENCE: 575
taaaagtttt tttg                                                          14

<210> SEQ ID NO 576
<211> LENGTH: 14
<212> TYPE: DNA
<213> ORGANISM: Artificial Sequence
<220> FEATURE:
<223> OTHER INFORMATION: Synthetic Construct

<400> SEQUENCE: 576
aaaagttttt ttgt                                                          14

<210> SEQ ID NO 577
<211> LENGTH: 14
<212> TYPE: DNA
<213> ORGANISM: Artificial Sequence
<220> FEATURE:
<223> OTHER INFORMATION: Synthetic Construct

<400> SEQUENCE: 577 aaagttttttt tgtt                                                         14

<210> SEQ ID NO 578
<211> LENGTH: 14
<212> TYPE: DNA
<213> ORGANISM: Artificial Sequence
<220> FEATURE:
<223> OTHER INFORMATION: Synthetic Construct

<400> SEQUENCE: 578
aagttttttt gttt                                                          14

<210> SEQ ID NO 579
<211> LENGTH: 14
<212> TYPE: DNA
<213> ORGANISM: Artificial Sequence
<220> FEATURE:
<223> OTHER INFORMATION: Synthetic Construct

<400> SEQUENCE: 579
agtttttttg tttg                                                          14

<210> SEQ ID NO 580
<211> LENGTH: 14
<212> TYPE: DNA
<213> ORGANISM: Artificial Sequence
<220> FEATURE:
<223> OTHER INFORMATION: Synthetic Construct

<400> SEQUENCE: 580
gtttttttgt ttga                                                          14
```

```
<210> SEQ ID NO 581
<211> LENGTH: 14
<212> TYPE: DNA
<213> ORGANISM: Artificial Sequence
<220> FEATURE:
<223> OTHER INFORMATION: Synthetic Construct

<400> SEQUENCE: 581
tttttttgtt tgat                                                     14

<210> SEQ ID NO 582
<211> LENGTH: 14
<212> TYPE: DNA
<213> ORGANISM: Artificial Sequence
<220> FEATURE:
<223> OTHER INFORMATION: Synthetic Construct

<400> SEQUENCE: 582 tttttgttt gatg                                                      14

<210> SEQ ID NO 583
<211> LENGTH: 14
<212> TYPE: DNA
<213> ORGANISM: Artificial Sequence
<220> FEATURE:
<223> OTHER INFORMATION: Synthetic Construct

<400> SEQUENCE: 583
tttttgtttg atgt                                                     14

<210> SEQ ID NO 584
<211> LENGTH: 14
<212> TYPE: DNA
<213> ORGANISM: Artificial Sequence
<220> FEATURE:
<223> OTHER INFORMATION: Synthetic Construct

<400> SEQUENCE: 584
ttttgtttga tgtt                                                     14

<210> SEQ ID NO 585
<211> LENGTH: 14
<212> TYPE: DNA
<213> ORGANISM: Artificial Sequence
<220> FEATURE:
<223> OTHER INFORMATION: Synthetic Construct

<400> SEQUENCE: 585
tttgtttgat gttt                                                     14

<210> SEQ ID NO 586
<211> LENGTH: 14
<212> TYPE: DNA
<213> ORGANISM: Artificial Sequence
<220> FEATURE:
<223> OTHER INFORMATION: Synthetic Construct

<400> SEQUENCE: 586
ttgtttgatg tttt                                                     14

<210> SEQ ID NO 587
<211> LENGTH: 14
<212> TYPE: DNA
<213> ORGANISM: Artificial Sequence
<220> FEATURE:
<223> OTHER INFORMATION: Synthetic Construct
```

```
<400> SEQUENCE: 587
tgtttgatgt tttt                                                14

<210> SEQ ID NO 588
<211> LENGTH: 14
<212> TYPE: DNA
<213> ORGANISM: Artificial Sequence
<220> FEATURE:
<223> OTHER INFORMATION: Synthetic Construct

<400> SEQUENCE: 588
gtttgatgtt tttt                                                14

<210> SEQ ID NO 589
<211> LENGTH: 14
<212> TYPE: DNA
<213> ORGANISM: Artificial Sequence
<220> FEATURE:
<223> OTHER INFORMATION: Synthetic Construct

<400> SEQUENCE: 589
tttgatgttt tttg                                                14

<210> SEQ ID NO 590
<211> LENGTH: 14
<212> TYPE: DNA
<213> ORGANISM: Artificial Sequence
<220> FEATURE:
<223> OTHER INFORMATION: Synthetic Construct

<400> SEQUENCE: 590
ttgatgtttt ttgc                                                14

<210> SEQ ID NO 591
<211> LENGTH: 14
<212> TYPE: DNA
<213> ORGANISM: Artificial Sequence
<220> FEATURE:
<223> OTHER INFORMATION: Synthetic Construct

<400> SEQUENCE: 591
tgatgttttt tgcg                                                14

<210> SEQ ID NO 592
<211> LENGTH: 14
<212> TYPE: DNA
<213> ORGANISM: Artificial Sequence
<220> FEATURE:
<223> OTHER INFORMATION: Synthetic Construct

<400> SEQUENCE: 592
gatgtttttt gcgg                                                14

<210> SEQ ID NO 593
<211> LENGTH: 14
<212> TYPE: DNA
<213> ORGANISM: Artificial Sequence
<220> FEATURE:
<223> OTHER INFORMATION: Synthetic Construct

<400> SEQUENCE: 593
atgttttttg cggt                                                14

<210> SEQ ID NO 594
```

```
<211> LENGTH: 14
<212> TYPE: DNA
<213> ORGANISM: Artificial Sequence
<220> FEATURE:
<223> OTHER INFORMATION: Synthetic Construct

<400> SEQUENCE: 594
tgttttttgc ggtt                                                         14

<210> SEQ ID NO 595
<211> LENGTH: 14
<212> TYPE: DNA
<213> ORGANISM: Artificial Sequence
<220> FEATURE:
<223> OTHER INFORMATION: Synthetic Construct

<400> SEQUENCE: 595 gtttttgcg gtta                                                          14

<210> SEQ ID NO 596
<211> LENGTH: 14
<212> TYPE: DNA
<213> ORGANISM: Artificial Sequence
<220> FEATURE:
<223> OTHER INFORMATION: Synthetic Construct

<400> SEQUENCE: 596 tttttgcgg ttag                                                          14

<210> SEQ ID NO 597
<211> LENGTH: 14
<212> TYPE: DNA
<213> ORGANISM: Artificial Sequence
<220> FEATURE:
<223> OTHER INFORMATION: Synthetic Construct

<400> SEQUENCE: 597
tttttgcggt tagg                                                         14

<210> SEQ ID NO 598
<211> LENGTH: 14
<212> TYPE: DNA
<213> ORGANISM: Artificial Sequence
<220> FEATURE:
<223> OTHER INFORMATION: Synthetic Construct

<400> SEQUENCE: 598
ttttgcggtt aggg                                                         14

<210> SEQ ID NO 599
<211> LENGTH: 14
<212> TYPE: DNA
<213> ORGANISM: Artificial Sequence
<220> FEATURE:
<223> OTHER INFORMATION: Synthetic Construct

<400> SEQUENCE: 599
tttgcggtta gggc                                                         14

<210> SEQ ID NO 600
<211> LENGTH: 14
<212> TYPE: DNA
<213> ORGANISM: Artificial Sequence
<220> FEATURE:
<223> OTHER INFORMATION: Synthetic Construct

<400> SEQUENCE: 600
```
ttgcggttag ggcg                                                14

<210> SEQ ID NO 601
<211> LENGTH: 14
<212> TYPE: DNA
<213> ORGANISM: Artificial Sequence
<220> FEATURE:
<223> OTHER INFORMATION: Synthetic Construct

<400> SEQUENCE: 601
tgcggttagg gcga                                                14

<210> SEQ ID NO 602
<211> LENGTH: 14
<212> TYPE: DNA
<213> ORGANISM: Artificial Sequence
<220> FEATURE:
<223> OTHER INFORMATION: Synthetic Construct

<400> SEQUENCE: 602
gcggttaggg cgag                                                14

<210> SEQ ID NO 603
<211> LENGTH: 14
<212> TYPE: DNA
<213> ORGANISM: Artificial Sequence
<220> FEATURE:
<223> OTHER INFORMATION: Synthetic Construct

<400> SEQUENCE: 603
cggttagggc gagg                                                14

<210> SEQ ID NO 604
<211> LENGTH: 14
<212> TYPE: DNA
<213> ORGANISM: Artificial Sequence
<220> FEATURE:
<223> OTHER INFORMATION: Synthetic Construct

<400> SEQUENCE: 604
ggttagggcg aggt                                                14

<210> SEQ ID NO 605
<211> LENGTH: 14
<212> TYPE: DNA
<213> ORGANISM: Artificial Sequence
<220> FEATURE:
<223> OTHER INFORMATION: Synthetic Construct

<400> SEQUENCE: 605
gttagggcga ggta                                                14

<210> SEQ ID NO 606
<211> LENGTH: 14
<212> TYPE: DNA
<213> ORGANISM: Artificial Sequence
<220> FEATURE:
<223> OTHER INFORMATION: Synthetic Construct

<400> SEQUENCE: 606
ttagggcgag gtaa                                                14

<210> SEQ ID NO 607
<211> LENGTH: 14
<212> TYPE: DNA

```
<213> ORGANISM: Artificial Sequence
<220> FEATURE:
<223> OTHER INFORMATION: Synthetic Construct

<400> SEQUENCE: 607
tagggcgagg taat                                                         14

<210> SEQ ID NO 608
<211> LENGTH: 14
<212> TYPE: DNA
<213> ORGANISM: Artificial Sequence
<220> FEATURE:
<223> OTHER INFORMATION: Synthetic Construct

<400> SEQUENCE: 608
agggcgaggt aatc                                                         14

<210> SEQ ID NO 609
<211> LENGTH: 14
<212> TYPE: DNA
<213> ORGANISM: Artificial Sequence
<220> FEATURE:
<223> OTHER INFORMATION: Synthetic Construct

<400> SEQUENCE: 609
gggcgaggta atcg                                                         14

<210> SEQ ID NO 610
<211> LENGTH: 14
<212> TYPE: DNA
<213> ORGANISM: Artificial Sequence
<220> FEATURE:
<223> OTHER INFORMATION: Synthetic Construct

<400> SEQUENCE: 610
ggcgaggtaa tcga                                                         14

<210> SEQ ID NO 611
<211> LENGTH: 14
<212> TYPE: DNA
<213> ORGANISM: Artificial Sequence
<220> FEATURE:
<223> OTHER INFORMATION: Synthetic Construct

<400> SEQUENCE: 611
gcgaggtaat cgat                                                         14

<210> SEQ ID NO 612
<211> LENGTH: 14
<212> TYPE: DNA
<213> ORGANISM: Artificial Sequence
<220> FEATURE:
<223> OTHER INFORMATION: Synthetic Construct

<400> SEQUENCE: 612
cgaggtaatc gata                                                         14

<210> SEQ ID NO 613
<211> LENGTH: 14
<212> TYPE: DNA
<213> ORGANISM: Artificial Sequence
<220> FEATURE:
<223> OTHER INFORMATION: Synthetic Construct

<400> SEQUENCE: 613
gaggtaatcg atat                                                         14
```

```
<210> SEQ ID NO 614
<211> LENGTH: 14
<212> TYPE: DNA
<213> ORGANISM: Artificial Sequence
<220> FEATURE:
<223> OTHER INFORMATION: Synthetic Construct

<400> SEQUENCE: 614
aggtaatcga tatt                                                         14

<210> SEQ ID NO 615
<211> LENGTH: 14
<212> TYPE: DNA
<213> ORGANISM: Artificial Sequence
<220> FEATURE:
<223> OTHER INFORMATION: Synthetic Construct

<400> SEQUENCE: 615
ggtaatcgat atta                                                         14

<210> SEQ ID NO 616
<211> LENGTH: 14
<212> TYPE: DNA
<213> ORGANISM: Artificial Sequence
<220> FEATURE:
<223> OTHER INFORMATION: Synthetic Construct

<400> SEQUENCE: 616
gtaatcgata ttac                                                         14

<210> SEQ ID NO 617
<211> LENGTH: 14
<212> TYPE: DNA
<213> ORGANISM: Artificial Sequence
<220> FEATURE:
<223> OTHER INFORMATION: Synthetic Construct

<400> SEQUENCE: 617
taatcgatat tacg                                                         14

<210> SEQ ID NO 618
<211> LENGTH: 14
<212> TYPE: DNA
<213> ORGANISM: Artificial Sequence
<220> FEATURE:
<223> OTHER INFORMATION: Synthetic Construct

<400> SEQUENCE: 618
aatcgatatt acgt                                                         14

<210> SEQ ID NO 619
<211> LENGTH: 14
<212> TYPE: DNA
<213> ORGANISM: Artificial Sequence
<220> FEATURE:
<223> OTHER INFORMATION: Synthetic Construct

<400> SEQUENCE: 619
atcgatatta cgtg                                                         14

<210> SEQ ID NO 620
<211> LENGTH: 14
<212> TYPE: DNA
<213> ORGANISM: Artificial Sequence
<220> FEATURE:
```

```
<223> OTHER INFORMATION: Synthetic Construct

<400> SEQUENCE: 620
tcgatattac gtgg                                                         14

<210> SEQ ID NO 621
<211> LENGTH: 14
<212> TYPE: DNA
<213> ORGANISM: Artificial Sequence
<220> FEATURE:
<223> OTHER INFORMATION: Synthetic Construct

<400> SEQUENCE: 621
cgatattacg tgga                                                         14

<210> SEQ ID NO 622
<211> LENGTH: 14
<212> TYPE: DNA
<213> ORGANISM: Artificial Sequence
<220> FEATURE:
<223> OTHER INFORMATION: Synthetic Construct

<400> SEQUENCE: 622
gatattacgt ggaa                                                         14

<210> SEQ ID NO 623
<211> LENGTH: 14
<212> TYPE: DNA
<213> ORGANISM: Artificial Sequence
<220> FEATURE:
<223> OTHER INFORMATION: Synthetic Construct

<400> SEQUENCE: 623
atattacgtg gaat                                                         14

<210> SEQ ID NO 624
<211> LENGTH: 14
<212> TYPE: DNA
<213> ORGANISM: Artificial Sequence
<220> FEATURE:
<223> OTHER INFORMATION: Synthetic Construct

<400> SEQUENCE: 624
tattacgtgg aatc                                                         14

<210> SEQ ID NO 625
<211> LENGTH: 14
<212> TYPE: DNA
<213> ORGANISM: Artificial Sequence
<220> FEATURE:
<223> OTHER INFORMATION: Synthetic Construct

<400> SEQUENCE: 625
attacgtgga atcg                                                         14

<210> SEQ ID NO 626
<211> LENGTH: 14
<212> TYPE: DNA
<213> ORGANISM: Artificial Sequence
<220> FEATURE:
<223> OTHER INFORMATION: Synthetic Construct

<400> SEQUENCE: 626
ttacgtggaa tcgt                                                         14
```

```
<210> SEQ ID NO 627
<211> LENGTH: 14
<212> TYPE: DNA
<213> ORGANISM: Artificial Sequence
<220> FEATURE:
<223> OTHER INFORMATION: Synthetic Construct

<400> SEQUENCE: 627
tacgtggaat cgta                                                         14

<210> SEQ ID NO 628
<211> LENGTH: 14
<212> TYPE: DNA
<213> ORGANISM: Artificial Sequence
<220> FEATURE:
<223> OTHER INFORMATION: Synthetic Construct

<400> SEQUENCE: 628
acgtggaatc gtag                                                         14

<210> SEQ ID NO 629
<211> LENGTH: 14
<212> TYPE: DNA
<213> ORGANISM: Artificial Sequence
<220> FEATURE:
<223> OTHER INFORMATION: Synthetic Construct

<400> SEQUENCE: 629
cgtggaatcg tagt                                                         14

<210> SEQ ID NO 630
<211> LENGTH: 14
<212> TYPE: DNA
<213> ORGANISM: Artificial Sequence
<220> FEATURE:
<223> OTHER INFORMATION: Synthetic Construct

<400> SEQUENCE: 630
gtggaatcgt agta                                                         14

<210> SEQ ID NO 631
<211> LENGTH: 14
<212> TYPE: DNA
<213> ORGANISM: Artificial Sequence
<220> FEATURE:
<223> OTHER INFORMATION: Synthetic Construct

<400> SEQUENCE: 631
tggaatcgta gtag                                                         14

<210> SEQ ID NO 632
<211> LENGTH: 14
<212> TYPE: DNA
<213> ORGANISM: Artificial Sequence
<220> FEATURE:
<223> OTHER INFORMATION: Synthetic Construct

<400> SEQUENCE: 632
ggaatcgtag tagg                                                         14

<210> SEQ ID NO 633
<211> LENGTH: 14
<212> TYPE: DNA
<213> ORGANISM: Artificial Sequence
<220> FEATURE:
<223> OTHER INFORMATION: Synthetic Construct
```

```
<400> SEQUENCE: 633
gaatcgtagt aggc                                                14

<210> SEQ ID NO 634
<211> LENGTH: 14
<212> TYPE: DNA
<213> ORGANISM: Artificial Sequence
<220> FEATURE:
<223> OTHER INFORMATION: Synthetic Construct

<400> SEQUENCE: 634
aatcgtagta ggcg                                                14

<210> SEQ ID NO 635
<211> LENGTH: 14
<212> TYPE: DNA
<213> ORGANISM: Artificial Sequence
<220> FEATURE:
<223> OTHER INFORMATION: Synthetic Construct

<400> SEQUENCE: 635
atcgtagtag gcga                                                14

<210> SEQ ID NO 636
<211> LENGTH: 14
<212> TYPE: DNA
<213> ORGANISM: Artificial Sequence
<220> FEATURE:
<223> OTHER INFORMATION: Synthetic Construct

<400> SEQUENCE: 636
tcgtagtagg cgat                                                14

<210> SEQ ID NO 637
<211> LENGTH: 14
<212> TYPE: DNA
<213> ORGANISM: Artificial Sequence
<220> FEATURE:
<223> OTHER INFORMATION: Synthetic Construct

<400> SEQUENCE: 637
cgtagtaggc gatt                                                14

<210> SEQ ID NO 638
<211> LENGTH: 14
<212> TYPE: DNA
<213> ORGANISM: Artificial Sequence
<220> FEATURE:
<223> OTHER INFORMATION: Synthetic Construct

<400> SEQUENCE: 638
gtagtaggcg attt                                                14

<210> SEQ ID NO 639
<211> LENGTH: 14
<212> TYPE: DNA
<213> ORGANISM: Artificial Sequence
<220> FEATURE:
<223> OTHER INFORMATION: Synthetic Construct

<400> SEQUENCE: 639
tagtaggcga tttt                                                14

<210> SEQ ID NO 640
<211> LENGTH: 14
```

```
<212> TYPE: DNA
<213> ORGANISM: Artificial Sequence
<220> FEATURE:
<223> OTHER INFORMATION: Synthetic Construct

<400> SEQUENCE: 640
agtaggcgat tttt                                                    14

<210> SEQ ID NO 641
<211> LENGTH: 14
<212> TYPE: DNA
<213> ORGANISM: Artificial Sequence
<220> FEATURE:
<223> OTHER INFORMATION: Synthetic Construct

<400> SEQUENCE: 641
gtaggcgatt tttt                                                    14

<210> SEQ ID NO 642
<211> LENGTH: 14
<212> TYPE: DNA
<213> ORGANISM: Artificial Sequence
<220> FEATURE:
<223> OTHER INFORMATION: Synthetic Construct

<400> SEQUENCE: 642
taggcgattt ttta                                                    14

<210> SEQ ID NO 643
<211> LENGTH: 14
<212> TYPE: DNA
<213> ORGANISM: Artificial Sequence
<220> FEATURE:
<223> OTHER INFORMATION: Synthetic Construct

<400> SEQUENCE: 643
aggcgatttt ttaa                                                    14

<210> SEQ ID NO 644
<211> LENGTH: 14
<212> TYPE: DNA
<213> ORGANISM: Artificial Sequence
<220> FEATURE:
<223> OTHER INFORMATION: Synthetic Construct

<400> SEQUENCE: 644
ggcgattttt taag                                                    14

<210> SEQ ID NO 645
<211> LENGTH: 14
<212> TYPE: DNA
<213> ORGANISM: Artificial Sequence
<220> FEATURE:
<223> OTHER INFORMATION: Synthetic Construct

<400> SEQUENCE: 645 gcgattttt aagg                                                     14

<210> SEQ ID NO 646
<211> LENGTH: 14
<212> TYPE: DNA
<213> ORGANISM: Artificial Sequence
<220> FEATURE:
<223> OTHER INFORMATION: Synthetic Construct

<400> SEQUENCE: 646
``` cgattttttta aggg 14

<210> SEQ ID NO 647
<211> LENGTH: 14
<212> TYPE: DNA
<213> ORGANISM: Artificial Sequence
<220> FEATURE:
<223> OTHER INFORMATION: Synthetic Construct

<400> SEQUENCE: 647 gatttttttaa gggg 14

<210> SEQ ID NO 648
<211> LENGTH: 14
<212> TYPE: DNA
<213> ORGANISM: Artificial Sequence
<220> FEATURE:
<223> OTHER INFORMATION: Synthetic Construct

<400> SEQUENCE: 648
attttttaag ggga 14

<210> SEQ ID NO 649
<211> LENGTH: 14
<212> TYPE: DNA
<213> ORGANISM: Artificial Sequence
<220> FEATURE:
<223> OTHER INFORMATION: Synthetic Construct

<400> SEQUENCE: 649 tttttttaagg ggat 14

<210> SEQ ID NO 650
<211> LENGTH: 14
<212> TYPE: DNA
<213> ORGANISM: Artificial Sequence
<220> FEATURE:
<223> OTHER INFORMATION: Synthetic Construct

<400> SEQUENCE: 650
tttttaaggg gata 14

<210> SEQ ID NO 651
<211> LENGTH: 14
<212> TYPE: DNA
<213> ORGANISM: Artificial Sequence
<220> FEATURE:
<223> OTHER INFORMATION: Synthetic Construct

<400> SEQUENCE: 651
ttttaagggg atat 14

<210> SEQ ID NO 652
<211> LENGTH: 14
<212> TYPE: DNA
<213> ORGANISM: Artificial Sequence
<220> FEATURE:
<223> OTHER INFORMATION: Synthetic Construct

<400> SEQUENCE: 652 tttaaggga tatt 14

<210> SEQ ID NO 653
<211> LENGTH: 14
<212> TYPE: DNA
<213> ORGANISM: Artificial Sequence

```
<220> FEATURE:
<223> OTHER INFORMATION: Synthetic Construct

<400> SEQUENCE: 653
ttaaggggat attg                                                        14

<210> SEQ ID NO 654
<211> LENGTH: 14
<212> TYPE: DNA
<213> ORGANISM: Artificial Sequence
<220> FEATURE:
<223> OTHER INFORMATION: Synthetic Construct

<400> SEQUENCE: 654
taaggggata ttgg                                                        14

<210> SEQ ID NO 655
<211> LENGTH: 14
<212> TYPE: DNA
<213> ORGANISM: Artificial Sequence
<220> FEATURE:
<223> OTHER INFORMATION: Synthetic Construct

<400> SEQUENCE: 655
aaggggatat tggg                                                        14

<210> SEQ ID NO 656
<211> LENGTH: 14
<212> TYPE: DNA
<213> ORGANISM: Artificial Sequence
<220> FEATURE:
<223> OTHER INFORMATION: Synthetic Construct

<400> SEQUENCE: 656
aggggatatt gggg                                                        14

<210> SEQ ID NO 657
<211> LENGTH: 14
<212> TYPE: DNA
<213> ORGANISM: Artificial Sequence
<220> FEATURE:
<223> OTHER INFORMATION: Synthetic Construct

<400> SEQUENCE: 657
ggggatattg gggg                                                        14

<210> SEQ ID NO 658
<211> LENGTH: 14
<212> TYPE: DNA
<213> ORGANISM: Artificial Sequence
<220> FEATURE:
<223> OTHER INFORMATION: Synthetic Construct

<400> SEQUENCE: 658
gggatattgg ggga                                                        14

<210> SEQ ID NO 659
<211> LENGTH: 14
<212> TYPE: DNA
<213> ORGANISM: Artificial Sequence
<220> FEATURE:
<223> OTHER INFORMATION: Synthetic Construct

<400> SEQUENCE: 659
ggatattggg ggag                                                        14
```

```
<210> SEQ ID NO 660
<211> LENGTH: 14
<212> TYPE: DNA
<213> ORGANISM: Artificial Sequence
<220> FEATURE:
<223> OTHER INFORMATION: Synthetic Construct

<400> SEQUENCE: 660
gatattgggg gagg                                                     14

<210> SEQ ID NO 661
<211> LENGTH: 14
<212> TYPE: DNA
<213> ORGANISM: Artificial Sequence
<220> FEATURE:
<223> OTHER INFORMATION: Synthetic Construct

<400> SEQUENCE: 661
atattggggg aggt                                                     14

<210> SEQ ID NO 662
<211> LENGTH: 14
<212> TYPE: DNA
<213> ORGANISM: Artificial Sequence
<220> FEATURE:
<223> OTHER INFORMATION: Synthetic Construct

<400> SEQUENCE: 662
tattggggga ggta                                                     14

<210> SEQ ID NO 663
<211> LENGTH: 14
<212> TYPE: DNA
<213> ORGANISM: Artificial Sequence
<220> FEATURE:
<223> OTHER INFORMATION: Synthetic Construct

<400> SEQUENCE: 663 attggggga g gtac                                                    14

<210> SEQ ID NO 664
<211> LENGTH: 14
<212> TYPE: DNA
<213> ORGANISM: Artificial Sequence
<220> FEATURE:
<223> OTHER INFORMATION: Synthetic Construct

<400> SEQUENCE: 664
ttgggggagg tacg                                                     14

<210> SEQ ID NO 665
<211> LENGTH: 14
<212> TYPE: DNA
<213> ORGANISM: Artificial Sequence
<220> FEATURE:
<223> OTHER INFORMATION: Synthetic Construct

<400> SEQUENCE: 665
tgggggaggt acgg                                                     14

<210> SEQ ID NO 666
<211> LENGTH: 14
<212> TYPE: DNA
<213> ORGANISM: Artificial Sequence
<220> FEATURE:
<223> OTHER INFORMATION: Synthetic Construct
```

<400> SEQUENCE: 666
gggggaggta cgga                                                        14

<210> SEQ ID NO 667
<211> LENGTH: 14
<212> TYPE: DNA
<213> ORGANISM: Artificial Sequence
<220> FEATURE:
<223> OTHER INFORMATION: Synthetic Construct

<400> SEQUENCE: 667
ggggaggtac ggaa                                                        14

<210> SEQ ID NO 668
<211> LENGTH: 14
<212> TYPE: DNA
<213> ORGANISM: Artificial Sequence
<220> FEATURE:
<223> OTHER INFORMATION: Synthetic Construct

<400> SEQUENCE: 668
gggaggtacg gaac                                                        14

<210> SEQ ID NO 669
<211> LENGTH: 14
<212> TYPE: DNA
<213> ORGANISM: Artificial Sequence
<220> FEATURE:
<223> OTHER INFORMATION: Synthetic Construct

<400> SEQUENCE: 669
ggaggtacgg aacg                                                        14

<210> SEQ ID NO 670
<211> LENGTH: 14
<212> TYPE: DNA
<213> ORGANISM: Artificial Sequence
<220> FEATURE:
<223> OTHER INFORMATION: Synthetic Construct

<400> SEQUENCE: 670
gaggtacgga acgc                                                        14

<210> SEQ ID NO 671
<211> LENGTH: 14
<212> TYPE: DNA
<213> ORGANISM: Artificial Sequence
<220> FEATURE:
<223> OTHER INFORMATION: Synthetic Construct

<400> SEQUENCE: 671
aggtacggaa cgcg                                                        14

<210> SEQ ID NO 672
<211> LENGTH: 14
<212> TYPE: DNA
<213> ORGANISM: Artificial Sequence
<220> FEATURE:
<223> OTHER INFORMATION: Synthetic Construct

<400> SEQUENCE: 672
ggtacggaac gcgt                                                        14

<210> SEQ ID NO 673

```
<211> LENGTH: 14
<212> TYPE: DNA
<213> ORGANISM: Artificial Sequence
<220> FEATURE:
<223> OTHER INFORMATION: Synthetic Construct

<400> SEQUENCE: 673
gtacggaacg cgtt                                                       14

<210> SEQ ID NO 674
<211> LENGTH: 14
<212> TYPE: DNA
<213> ORGANISM: Artificial Sequence
<220> FEATURE:
<223> OTHER INFORMATION: Synthetic Construct

<400> SEQUENCE: 674
tacggaacgc gttc                                                       14

<210> SEQ ID NO 675
<211> LENGTH: 14
<212> TYPE: DNA
<213> ORGANISM: Artificial Sequence
<220> FEATURE:
<223> OTHER INFORMATION: Synthetic Construct

<400> SEQUENCE: 675
acggaacgcg ttcg                                                       14

<210> SEQ ID NO 676
<211> LENGTH: 14
<212> TYPE: DNA
<213> ORGANISM: Artificial Sequence
<220> FEATURE:
<223> OTHER INFORMATION: Synthetic Construct

<400> SEQUENCE: 676
cggaacgcgt tcga                                                       14

<210> SEQ ID NO 677
<211> LENGTH: 14
<212> TYPE: DNA
<213> ORGANISM: Artificial Sequence
<220> FEATURE:
<223> OTHER INFORMATION: Synthetic Construct

<400> SEQUENCE: 677
ggaacgcgtt cgaa                                                       14

<210> SEQ ID NO 678
<211> LENGTH: 14
<212> TYPE: DNA
<213> ORGANISM: Artificial Sequence
<220> FEATURE:
<223> OTHER INFORMATION: Synthetic Construct

<400> SEQUENCE: 678
gaacgcgttc gaaa                                                       14

<210> SEQ ID NO 679
<211> LENGTH: 14
<212> TYPE: DNA
<213> ORGANISM: Artificial Sequence
<220> FEATURE:
<223> OTHER INFORMATION: Synthetic Construct

<400> SEQUENCE: 679
```
aacgcgttcg aaaa                                                       14

<210> SEQ ID NO 680
<211> LENGTH: 14
<212> TYPE: DNA
<213> ORGANISM: Artificial Sequence
<220> FEATURE:
<223> OTHER INFORMATION: Synthetic Construct

<400> SEQUENCE: 680
acgcgttcga aaat                                                       14

<210> SEQ ID NO 681
<211> LENGTH: 14
<212> TYPE: DNA
<213> ORGANISM: Artificial Sequence
<220> FEATURE:
<223> OTHER INFORMATION: Synthetic Construct

<400> SEQUENCE: 681
cgcgttcgaa aatg                                                       14

<210> SEQ ID NO 682
<211> LENGTH: 14
<212> TYPE: DNA
<213> ORGANISM: Artificial Sequence
<220> FEATURE:
<223> OTHER INFORMATION: Synthetic Construct

<400> SEQUENCE: 682
gcgttcgaaa atgt                                                       14

<210> SEQ ID NO 683
<211> LENGTH: 14
<212> TYPE: DNA
<213> ORGANISM: Artificial Sequence
<220> FEATURE:
<223> OTHER INFORMATION: Synthetic Construct

<400> SEQUENCE: 683
cgttcgaaaa tgtt                                                       14

<210> SEQ ID NO 684
<211> LENGTH: 14
<212> TYPE: DNA
<213> ORGANISM: Artificial Sequence
<220> FEATURE:
<223> OTHER INFORMATION: Synthetic Construct

<400> SEQUENCE: 684
gttcgaaaat gttg                                                       14

<210> SEQ ID NO 685
<211> LENGTH: 14
<212> TYPE: DNA
<213> ORGANISM: Artificial Sequence
<220> FEATURE:
<223> OTHER INFORMATION: Synthetic Construct

<400> SEQUENCE: 685
ttcgaaaatg ttgg                                                       14

<210> SEQ ID NO 686
<211> LENGTH: 14
<212> TYPE: DNA

```
<213> ORGANISM: Artificial Sequence
<220> FEATURE:
<223> OTHER INFORMATION: Synthetic Construct

<400> SEQUENCE: 686
tcgaaaatgt tggg                                                         14

<210> SEQ ID NO 687
<211> LENGTH: 14
<212> TYPE: DNA
<213> ORGANISM: Artificial Sequence
<220> FEATURE:
<223> OTHER INFORMATION: Synthetic Construct

<400> SEQUENCE: 687
cgaaaatgtt ggga                                                         14

<210> SEQ ID NO 688
<211> LENGTH: 14
<212> TYPE: DNA
<213> ORGANISM: Artificial Sequence
<220> FEATURE:
<223> OTHER INFORMATION: Synthetic Construct

<400> SEQUENCE: 688
gaaaatgttg ggac                                                         14

<210> SEQ ID NO 689
<211> LENGTH: 14
<212> TYPE: DNA
<213> ORGANISM: Artificial Sequence
<220> FEATURE:
<223> OTHER INFORMATION: Synthetic Construct

<400> SEQUENCE: 689
aaaatgttgg gacg                                                         14

<210> SEQ ID NO 690
<211> LENGTH: 14
<212> TYPE: DNA
<213> ORGANISM: Artificial Sequence
<220> FEATURE:
<223> OTHER INFORMATION: Synthetic Construct

<400> SEQUENCE: 690
aaatgttggg acgt                                                         14

<210> SEQ ID NO 691
<211> LENGTH: 14
<212> TYPE: DNA
<213> ORGANISM: Artificial Sequence
<220> FEATURE:
<223> OTHER INFORMATION: Synthetic Construct

<400> SEQUENCE: 691
aatgttggga cgtc                                                         14

<210> SEQ ID NO 692
<211> LENGTH: 14
<212> TYPE: DNA
<213> ORGANISM: Artificial Sequence
<220> FEATURE:
<223> OTHER INFORMATION: Synthetic Construct

<400> SEQUENCE: 692
atgtttggga ctcg                                                         14
```

<210> SEQ ID NO 693
<211> LENGTH: 14
<212> TYPE: DNA
<213> ORGANISM: Artificial Sequence
<220> FEATURE:
<223> OTHER INFORMATION: Synthetic Construct

<400> SEQUENCE: 693
tgttgggacg tcgg                                                        14

<210> SEQ ID NO 694
<211> LENGTH: 14
<212> TYPE: DNA
<213> ORGANISM: Artificial Sequence
<220> FEATURE:
<223> OTHER INFORMATION: Synthetic Construct

<400> SEQUENCE: 694
gttgggacgt cggt                                                        14

<210> SEQ ID NO 695
<211> LENGTH: 14
<212> TYPE: DNA
<213> ORGANISM: Artificial Sequence
<220> FEATURE:
<223> OTHER INFORMATION: Synthetic Construct

<400> SEQUENCE: 695
ttgggacgtc ggtt                                                        14

<210> SEQ ID NO 696
<211> LENGTH: 14
<212> TYPE: DNA
<213> ORGANISM: Artificial Sequence
<220> FEATURE:
<223> OTHER INFORMATION: Synthetic Construct

<400> SEQUENCE: 696
tgggacgtcg gtta                                                        14

<210> SEQ ID NO 697
<211> LENGTH: 14
<212> TYPE: DNA
<213> ORGANISM: Artificial Sequence
<220> FEATURE:
<223> OTHER INFORMATION: Synthetic Construct

<400> SEQUENCE: 697
gggacgtcgg ttat                                                        14

<210> SEQ ID NO 698
<211> LENGTH: 14
<212> TYPE: DNA
<213> ORGANISM: Artificial Sequence
<220> FEATURE:
<223> OTHER INFORMATION: Synthetic Construct

<400> SEQUENCE: 698
ggacgtcggt tatt                                                        14

<210> SEQ ID NO 699
<211> LENGTH: 14
<212> TYPE: DNA
<213> ORGANISM: Artificial Sequence
<220> FEATURE:

```
<223> OTHER INFORMATION: Synthetic Construct

<400> SEQUENCE: 699
gacgtcggtt attg                                                14

<210> SEQ ID NO 700
<211> LENGTH: 14
<212> TYPE: DNA
<213> ORGANISM: Artificial Sequence
<220> FEATURE:
<223> OTHER INFORMATION: Synthetic Construct

<400> SEQUENCE: 700
acgtcggtta ttgg                                                14

<210> SEQ ID NO 701
<211> LENGTH: 14
<212> TYPE: DNA
<213> ORGANISM: Artificial Sequence
<220> FEATURE:
<223> OTHER INFORMATION: Synthetic Construct

<400> SEQUENCE: 701
cgtcggttat tgga                                                14

<210> SEQ ID NO 702
<211> LENGTH: 14
<212> TYPE: DNA
<213> ORGANISM: Artificial Sequence
<220> FEATURE:
<223> OTHER INFORMATION: Synthetic Construct

<400> SEQUENCE: 702
gtcggttatt ggat                                                14

<210> SEQ ID NO 703
<211> LENGTH: 14
<212> TYPE: DNA
<213> ORGANISM: Artificial Sequence
<220> FEATURE:
<223> OTHER INFORMATION: Synthetic Construct

<400> SEQUENCE: 703
tcggttattg gatt                                                14

<210> SEQ ID NO 704
<211> LENGTH: 14
<212> TYPE: DNA
<213> ORGANISM: Artificial Sequence
<220> FEATURE:
<223> OTHER INFORMATION: Synthetic Construct

<400> SEQUENCE: 704
cggttattgg attt                                                14

<210> SEQ ID NO 705
<211> LENGTH: 14
<212> TYPE: DNA
<213> ORGANISM: Artificial Sequence
<220> FEATURE:
<223> OTHER INFORMATION: Synthetic Construct

<400> SEQUENCE: 705
ggttattgga tttt                                                14
```

```
<210> SEQ ID NO 706
<211> LENGTH: 14
<212> TYPE: DNA
<213> ORGANISM: Artificial Sequence
<220> FEATURE:
<223> OTHER INFORMATION: Synthetic Construct

<400> SEQUENCE: 706
gttattggat tttt                                                       14

<210> SEQ ID NO 707
<211> LENGTH: 14
<212> TYPE: DNA
<213> ORGANISM: Artificial Sequence
<220> FEATURE:
<223> OTHER INFORMATION: Synthetic Construct

<400> SEQUENCE: 707
ttattggatt ttta                                                       14

<210> SEQ ID NO 708
<211> LENGTH: 14
<212> TYPE: DNA
<213> ORGANISM: Artificial Sequence
<220> FEATURE:
<223> OTHER INFORMATION: Synthetic Construct

<400> SEQUENCE: 708
tattggattt ttag                                                       14

<210> SEQ ID NO 709
<211> LENGTH: 14
<212> TYPE: DNA
<213> ORGANISM: Artificial Sequence
<220> FEATURE:
<223> OTHER INFORMATION: Synthetic Construct

<400> SEQUENCE: 709
attggatttt tagt                                                       14

<210> SEQ ID NO 710
<211> LENGTH: 14
<212> TYPE: DNA
<213> ORGANISM: Artificial Sequence
<220> FEATURE:
<223> OTHER INFORMATION: Synthetic Construct

<400> SEQUENCE: 710
ttggattttt agtt                                                       14

<210> SEQ ID NO 711
<211> LENGTH: 14
<212> TYPE: DNA
<213> ORGANISM: Artificial Sequence
<220> FEATURE:
<223> OTHER INFORMATION: Synthetic Construct

<400> SEQUENCE: 711
tggattttta gttt                                                       14

<210> SEQ ID NO 712
<211> LENGTH: 14
<212> TYPE: DNA
<213> ORGANISM: Artificial Sequence
<220> FEATURE:
<223> OTHER INFORMATION: Synthetic Construct
```

<400> SEQUENCE: 712
ggatttttag tttt                                                                14

<210> SEQ ID NO 713
<211> LENGTH: 14
<212> TYPE: DNA
<213> ORGANISM: Artificial Sequence
<220> FEATURE:
<223> OTHER INFORMATION: Synthetic Construct

<400> SEQUENCE: 713 gattttagt tttg                                                                 14

<210> SEQ ID NO 714
<211> LENGTH: 14
<212> TYPE: DNA
<213> ORGANISM: Artificial Sequence
<220> FEATURE:
<223> OTHER INFORMATION: Synthetic Construct

<400> SEQUENCE: 714 attttagtt ttgc                                                                 14

<210> SEQ ID NO 715
<211> LENGTH: 14
<212> TYPE: DNA
<213> ORGANISM: Artificial Sequence
<220> FEATURE:
<223> OTHER INFORMATION: Synthetic Construct

<400> SEQUENCE: 715
tttttagttt tgcg                                                                14

<210> SEQ ID NO 716
<211> LENGTH: 14
<212> TYPE: DNA
<213> ORGANISM: Artificial Sequence
<220> FEATURE:
<223> OTHER INFORMATION: Synthetic Construct

<400> SEQUENCE: 716
ttttagtttt gcgg                                                                14

<210> SEQ ID NO 717
<211> LENGTH: 14
<212> TYPE: DNA
<213> ORGANISM: Artificial Sequence
<220> FEATURE:
<223> OTHER INFORMATION: Synthetic Construct

<400> SEQUENCE: 717
tttagttttg cggc                                                                14

<210> SEQ ID NO 718
<211> LENGTH: 14
<212> TYPE: DNA
<213> ORGANISM: Artificial Sequence
<220> FEATURE:
<223> OTHER INFORMATION: Synthetic Construct

<400> SEQUENCE: 718
ttagttttgc ggcg                                                                14

<210> SEQ ID NO 719
<211> LENGTH: 14

```
<212> TYPE: DNA
<213> ORGANISM: Artificial Sequence
<220> FEATURE:
<223> OTHER INFORMATION: Synthetic Construct

<400> SEQUENCE: 719
tagttttgcg gcga                                                    14

<210> SEQ ID NO 720
<211> LENGTH: 14
<212> TYPE: DNA
<213> ORGANISM: Artificial Sequence
<220> FEATURE:
<223> OTHER INFORMATION: Synthetic Construct

<400> SEQUENCE: 720
agttttgcgg cgat                                                    14

<210> SEQ ID NO 721
<211> LENGTH: 14
<212> TYPE: DNA
<213> ORGANISM: Artificial Sequence
<220> FEATURE:
<223> OTHER INFORMATION: Synthetic Construct

<400> SEQUENCE: 721
gttttgcggc gatt                                                    14

<210> SEQ ID NO 722
<211> LENGTH: 14
<212> TYPE: DNA
<213> ORGANISM: Artificial Sequence
<220> FEATURE:
<223> OTHER INFORMATION: Synthetic Construct

<400> SEQUENCE: 722
ttttgcggcg attt                                                    14

<210> SEQ ID NO 723
<211> LENGTH: 14
<212> TYPE: DNA
<213> ORGANISM: Artificial Sequence
<220> FEATURE:
<223> OTHER INFORMATION: Synthetic Construct

<400> SEQUENCE: 723
tttgcggcga tttt                                                    14

<210> SEQ ID NO 724
<211> LENGTH: 14
<212> TYPE: DNA
<213> ORGANISM: Artificial Sequence
<220> FEATURE:
<223> OTHER INFORMATION: Synthetic Construct

<400> SEQUENCE: 724
ttgcggcgat tttt                                                    14

<210> SEQ ID NO 725
<211> LENGTH: 14
<212> TYPE: DNA
<213> ORGANISM: Artificial Sequence
<220> FEATURE:
<223> OTHER INFORMATION: Synthetic Construct

<400> SEQUENCE: 725
```
tgcggcgatt tttt                                                    14

<210> SEQ ID NO 726
<211> LENGTH: 14
<212> TYPE: DNA
<213> ORGANISM: Artificial Sequence
<220> FEATURE:
<223> OTHER INFORMATION: Synthetic Construct

<400> SEQUENCE: 726
gcggcgattt tttt                                                    14

<210> SEQ ID NO 727
<211> LENGTH: 14
<212> TYPE: DNA
<213> ORGANISM: Artificial Sequence
<220> FEATURE:
<223> OTHER INFORMATION: Synthetic Construct

<400> SEQUENCE: 727
cggcgatttt tttt                                                    14

<210> SEQ ID NO 728
<211> LENGTH: 14
<212> TYPE: DNA
<213> ORGANISM: Artificial Sequence
<220> FEATURE:
<223> OTHER INFORMATION: Synthetic Construct

<400> SEQUENCE: 728
ggcgattttt tttt                                                    14

<210> SEQ ID NO 729
<211> LENGTH: 14
<212> TYPE: DNA
<213> ORGANISM: Artificial Sequence
<220> FEATURE:
<223> OTHER INFORMATION: Synthetic Construct

<400> SEQUENCE: 729
gcgatttttt tttc                                                    14

<210> SEQ ID NO 730
<211> LENGTH: 14
<212> TYPE: DNA
<213> ORGANISM: Artificial Sequence
<220> FEATURE:
<223> OTHER INFORMATION: Synthetic Construct

<400> SEQUENCE: 730
cgattttttt ttcg                                                    14

<210> SEQ ID NO 731
<211> LENGTH: 14
<212> TYPE: DNA
<213> ORGANISM: Artificial Sequence
<220> FEATURE:
<223> OTHER INFORMATION: Synthetic Construct

<400> SEQUENCE: 731 gattttttt tcgt                                                     14

<210> SEQ ID NO 732
<211> LENGTH: 14
<212> TYPE: DNA
<213> ORGANISM: Artificial Sequence

```
<220> FEATURE:
<223> OTHER INFORMATION: Synthetic Construct

<400> SEQUENCE: 732
attttttttt cgtt                                                        14

<210> SEQ ID NO 733
<211> LENGTH: 14
<212> TYPE: DNA
<213> ORGANISM: Artificial Sequence
<220> FEATURE:
<223> OTHER INFORMATION: Synthetic Construct

<400> SEQUENCE: 733
tttttttttc gttg                                                        14

<210> SEQ ID NO 734
<211> LENGTH: 14
<212> TYPE: DNA
<213> ORGANISM: Artificial Sequence
<220> FEATURE:
<223> OTHER INFORMATION: Synthetic Construct

<400> SEQUENCE: 734
ttttttttcg ttga                                                        14

<210> SEQ ID NO 735
<211> LENGTH: 14
<212> TYPE: DNA
<213> ORGANISM: Artificial Sequence
<220> FEATURE:
<223> OTHER INFORMATION: Synthetic Construct

<400> SEQUENCE: 735
tttttttcgt tgag                                                        14

<210> SEQ ID NO 736
<211> LENGTH: 14
<212> TYPE: DNA
<213> ORGANISM: Artificial Sequence
<220> FEATURE:
<223> OTHER INFORMATION: Synthetic Construct

<400> SEQUENCE: 736
ttttttcgtt gagg                                                        14

<210> SEQ ID NO 737
<211> LENGTH: 14
<212> TYPE: DNA
<213> ORGANISM: Artificial Sequence
<220> FEATURE:
<223> OTHER INFORMATION: Synthetic Construct

<400> SEQUENCE: 737
tttttcgttg aggg                                                        14

<210> SEQ ID NO 738
<211> LENGTH: 14
<212> TYPE: DNA
<213> ORGANISM: Artificial Sequence
<220> FEATURE:
<223> OTHER INFORMATION: Synthetic Construct

<400> SEQUENCE: 738
ttttcgttga gggg                                                        14
```

```
<210> SEQ ID NO 739
<211> LENGTH: 14
<212> TYPE: DNA
<213> ORGANISM: Artificial Sequence
<220> FEATURE:
<223> OTHER INFORMATION: Synthetic Construct

<400> SEQUENCE: 739
tttcgttgag gggt                                                        14

<210> SEQ ID NO 740
<211> LENGTH: 14
<212> TYPE: DNA
<213> ORGANISM: Artificial Sequence
<220> FEATURE:
<223> OTHER INFORMATION: Synthetic Construct

<400> SEQUENCE: 740
ttcgttgagg ggtg                                                        14

<210> SEQ ID NO 741
<211> LENGTH: 14
<212> TYPE: DNA
<213> ORGANISM: Artificial Sequence
<220> FEATURE:
<223> OTHER INFORMATION: Synthetic Construct

<400> SEQUENCE: 741
tcgttgaggg gtgg                                                        14

<210> SEQ ID NO 742
<211> LENGTH: 14
<212> TYPE: DNA
<213> ORGANISM: Artificial Sequence
<220> FEATURE:
<223> OTHER INFORMATION: Synthetic Construct

<400> SEQUENCE: 742
cgttgagggg tgga                                                        14

<210> SEQ ID NO 743
<211> LENGTH: 14
<212> TYPE: DNA
<213> ORGANISM: Artificial Sequence
<220> FEATURE:
<223> OTHER INFORMATION: Synthetic Construct

<400> SEQUENCE: 743
gttgaggggt ggag                                                        14

<210> SEQ ID NO 744
<211> LENGTH: 14
<212> TYPE: DNA
<213> ORGANISM: Artificial Sequence
<220> FEATURE:
<223> OTHER INFORMATION: Synthetic Construct

<400> SEQUENCE: 744
ttgaggggtg gagg                                                        14

<210> SEQ ID NO 745
<211> LENGTH: 14
<212> TYPE: DNA
<213> ORGANISM: Artificial Sequence
<220> FEATURE:
<223> OTHER INFORMATION: Synthetic Construct
```

```
<400> SEQUENCE: 745
tgaggggtgg aggt                                                        14

<210> SEQ ID NO 746
<211> LENGTH: 14
<212> TYPE: DNA
<213> ORGANISM: Artificial Sequence
<220> FEATURE:
<223> OTHER INFORMATION: Synthetic Construct

<400> SEQUENCE: 746
gaggggtgga ggtt                                                        14

<210> SEQ ID NO 747
<211> LENGTH: 14
<212> TYPE: DNA
<213> ORGANISM: Artificial Sequence
<220> FEATURE:
<223> OTHER INFORMATION: Synthetic Construct

<400> SEQUENCE: 747
aggggtggag gttg                                                        14

<210> SEQ ID NO 748
<211> LENGTH: 14
<212> TYPE: DNA
<213> ORGANISM: Artificial Sequence
<220> FEATURE:
<223> OTHER INFORMATION: Synthetic Construct

<400> SEQUENCE: 748
ggggtggagg ttgt                                                        14

<210> SEQ ID NO 749
<211> LENGTH: 14
<212> TYPE: DNA
<213> ORGANISM: Artificial Sequence
<220> FEATURE:
<223> OTHER INFORMATION: Synthetic Construct

<400> SEQUENCE: 749
gggtggaggt tgta                                                        14

<210> SEQ ID NO 750
<211> LENGTH: 14
<212> TYPE: DNA
<213> ORGANISM: Artificial Sequence
<220> FEATURE:
<223> OTHER INFORMATION: Synthetic Construct

<400> SEQUENCE: 750
ggtggaggtt gtat                                                        14

<210> SEQ ID NO 751
<211> LENGTH: 14
<212> TYPE: DNA
<213> ORGANISM: Artificial Sequence
<220> FEATURE:
<223> OTHER INFORMATION: Synthetic Construct

<400> SEQUENCE: 751
gtggaggttg tatc                                                        14

<210> SEQ ID NO 752
```

```
<211> LENGTH: 14
<212> TYPE: DNA
<213> ORGANISM: Artificial Sequence
<220> FEATURE:
<223> OTHER INFORMATION: Synthetic Construct

<400> SEQUENCE: 752
tggaggttgt atcg                                                      14

<210> SEQ ID NO 753
<211> LENGTH: 14
<212> TYPE: DNA
<213> ORGANISM: Artificial Sequence
<220> FEATURE:
<223> OTHER INFORMATION: Synthetic Construct

<400> SEQUENCE: 753
ggaggttgta tcgc                                                      14

<210> SEQ ID NO 754
<211> LENGTH: 14
<212> TYPE: DNA
<213> ORGANISM: Artificial Sequence
<220> FEATURE:
<223> OTHER INFORMATION: Synthetic Construct

<400> SEQUENCE: 754
gaggttgtat cgcg                                                      14

<210> SEQ ID NO 755
<211> LENGTH: 14
<212> TYPE: DNA
<213> ORGANISM: Artificial Sequence
<220> FEATURE:
<223> OTHER INFORMATION: Synthetic Construct

<400> SEQUENCE: 755
aggttgtatc gcgg                                                      14

<210> SEQ ID NO 756
<211> LENGTH: 14
<212> TYPE: DNA
<213> ORGANISM: Artificial Sequence
<220> FEATURE:
<223> OTHER INFORMATION: Synthetic Construct

<400> SEQUENCE: 756
ggttgtatcg cggg                                                      14

<210> SEQ ID NO 757
<211> LENGTH: 14
<212> TYPE: DNA
<213> ORGANISM: Artificial Sequence
<220> FEATURE:
<223> OTHER INFORMATION: Synthetic Construct

<400> SEQUENCE: 757
gttgtatcgc gggg                                                      14

<210> SEQ ID NO 758
<211> LENGTH: 14
<212> TYPE: DNA
<213> ORGANISM: Artificial Sequence
<220> FEATURE:
<223> OTHER INFORMATION: Synthetic Construct

<400> SEQUENCE: 758
```
ttgtatcgcg gggc                                                    14

<210> SEQ ID NO 759
<211> LENGTH: 14
<212> TYPE: DNA
<213> ORGANISM: Artificial Sequence
<220> FEATURE:
<223> OTHER INFORMATION: Synthetic Construct

<400> SEQUENCE: 759
tgtatcgcgg ggcg                                                    14

<210> SEQ ID NO 760
<211> LENGTH: 14
<212> TYPE: DNA
<213> ORGANISM: Artificial Sequence
<220> FEATURE:
<223> OTHER INFORMATION: Synthetic Construct

<400> SEQUENCE: 760
gtatcgcggg gcgt                                                    14

<210> SEQ ID NO 761
<211> LENGTH: 14
<212> TYPE: DNA
<213> ORGANISM: Artificial Sequence
<220> FEATURE:
<223> OTHER INFORMATION: Synthetic Construct

<400> SEQUENCE: 761
tatcgcgggg cgtt                                                    14

<210> SEQ ID NO 762
<211> LENGTH: 14
<212> TYPE: DNA
<213> ORGANISM: Artificial Sequence
<220> FEATURE:
<223> OTHER INFORMATION: Synthetic Construct

<400> SEQUENCE: 762
atcgcggggc gtta                                                    14

<210> SEQ ID NO 763
<211> LENGTH: 14
<212> TYPE: DNA
<213> ORGANISM: Artificial Sequence
<220> FEATURE:
<223> OTHER INFORMATION: Synthetic Construct

<400> SEQUENCE: 763
tcgcggggcg ttag                                                    14

<210> SEQ ID NO 764
<211> LENGTH: 14
<212> TYPE: DNA
<213> ORGANISM: Artificial Sequence
<220> FEATURE:
<223> OTHER INFORMATION: Synthetic Construct

<400> SEQUENCE: 764
cgcggggcgt tagg                                                    14

<210> SEQ ID NO 765
<211> LENGTH: 14
<212> TYPE: DNA

```
<213> ORGANISM: Artificial Sequence
<220> FEATURE:
<223> OTHER INFORMATION: Synthetic Construct

<400> SEQUENCE: 765
gcggggcgtt aggg                                              14

<210> SEQ ID NO 766
<211> LENGTH: 14
<212> TYPE: DNA
<213> ORGANISM: Artificial Sequence
<220> FEATURE:
<223> OTHER INFORMATION: Synthetic Construct

<400> SEQUENCE: 766
cggggcgtta ggga                                              14

<210> SEQ ID NO 767
<211> LENGTH: 14
<212> TYPE: DNA
<213> ORGANISM: Artificial Sequence
<220> FEATURE:
<223> OTHER INFORMATION: Synthetic Construct

<400> SEQUENCE: 767
ggggcgttag ggac                                              14

<210> SEQ ID NO 768
<211> LENGTH: 14
<212> TYPE: DNA
<213> ORGANISM: Artificial Sequence
<220> FEATURE:
<223> OTHER INFORMATION: Synthetic Construct

<400> SEQUENCE: 768
gggcgttagg gacg                                              14

<210> SEQ ID NO 769
<211> LENGTH: 14
<212> TYPE: DNA
<213> ORGANISM: Artificial Sequence
<220> FEATURE:
<223> OTHER INFORMATION: Synthetic Construct

<400> SEQUENCE: 769
ggcgttaggg acgg                                              14

<210> SEQ ID NO 770
<211> LENGTH: 14
<212> TYPE: DNA
<213> ORGANISM: Artificial Sequence
<220> FEATURE:
<223> OTHER INFORMATION: Synthetic Construct

<400> SEQUENCE: 770
gcgttaggga cggg                                              14

<210> SEQ ID NO 771
<211> LENGTH: 14
<212> TYPE: DNA
<213> ORGANISM: Artificial Sequence
<220> FEATURE:
<223> OTHER INFORMATION: Synthetic Construct

<400> SEQUENCE: 771
cgttagggac ggga                                              14
```

<210> SEQ ID NO 772
<211> LENGTH: 14
<212> TYPE: DNA
<213> ORGANISM: Artificial Sequence
<220> FEATURE:
<223> OTHER INFORMATION: Synthetic Construct

<400> SEQUENCE: 772
gttagggacg ggag                                                       14

<210> SEQ ID NO 773
<211> LENGTH: 14
<212> TYPE: DNA
<213> ORGANISM: Artificial Sequence
<220> FEATURE:
<223> OTHER INFORMATION: Synthetic Construct

<400> SEQUENCE: 773
ttagggacgg gagg                                                       14

<210> SEQ ID NO 774
<211> LENGTH: 14
<212> TYPE: DNA
<213> ORGANISM: Artificial Sequence
<220> FEATURE:
<223> OTHER INFORMATION: Synthetic Construct

<400> SEQUENCE: 774
tagggacggg agga                                                       14

<210> SEQ ID NO 775
<211> LENGTH: 14
<212> TYPE: DNA
<213> ORGANISM: Artificial Sequence
<220> FEATURE:
<223> OTHER INFORMATION: Synthetic Construct

<400> SEQUENCE: 775
agggacggga ggat                                                       14

<210> SEQ ID NO 776
<211> LENGTH: 14
<212> TYPE: DNA
<213> ORGANISM: Artificial Sequence
<220> FEATURE:
<223> OTHER INFORMATION: Synthetic Construct

<400> SEQUENCE: 776
gggacgggag gata                                                       14

<210> SEQ ID NO 777
<211> LENGTH: 14
<212> TYPE: DNA
<213> ORGANISM: Artificial Sequence
<220> FEATURE:
<223> OTHER INFORMATION: Synthetic Construct

<400> SEQUENCE: 777
ggacgggagg atat                                                       14

<210> SEQ ID NO 778
<211> LENGTH: 14
<212> TYPE: DNA
<213> ORGANISM: Artificial Sequence
<220> FEATURE:

<223> OTHER INFORMATION: Synthetic Construct

<400> SEQUENCE: 778
gacgggagga tatt                                                             14

<210> SEQ ID NO 779
<211> LENGTH: 14
<212> TYPE: DNA
<213> ORGANISM: Artificial Sequence
<220> FEATURE:
<223> OTHER INFORMATION: Synthetic Construct

<400> SEQUENCE: 779
acgggaggat attt                                                             14

<210> SEQ ID NO 780
<211> LENGTH: 14
<212> TYPE: DNA
<213> ORGANISM: Artificial Sequence
<220> FEATURE:
<223> OTHER INFORMATION: Synthetic Construct

<400> SEQUENCE: 780
cgggaggata tttt                                                             14

<210> SEQ ID NO 781
<211> LENGTH: 14
<212> TYPE: DNA
<213> ORGANISM: Artificial Sequence
<220> FEATURE:
<223> OTHER INFORMATION: Synthetic Construct

<400> SEQUENCE: 781
gggaggatat tttt                                                             14

<210> SEQ ID NO 782
<211> LENGTH: 14
<212> TYPE: DNA
<213> ORGANISM: Artificial Sequence
<220> FEATURE:
<223> OTHER INFORMATION: Synthetic Construct

<400> SEQUENCE: 782
ggaggatatt ttta                                                             14

<210> SEQ ID NO 783
<211> LENGTH: 14
<212> TYPE: DNA
<213> ORGANISM: Artificial Sequence
<220> FEATURE:
<223> OTHER INFORMATION: Synthetic Construct

<400> SEQUENCE: 783
gaggatattt ttat                                                             14

<210> SEQ ID NO 784
<211> LENGTH: 14
<212> TYPE: DNA
<213> ORGANISM: Artificial Sequence
<220> FEATURE:
<223> OTHER INFORMATION: Synthetic Construct

<400> SEQUENCE: 784
aggatatttt tata                                                             14

```
<210> SEQ ID NO 785
<211> LENGTH: 14
<212> TYPE: DNA
<213> ORGANISM: Artificial Sequence
<220> FEATURE:
<223> OTHER INFORMATION: Synthetic Construct

<400> SEQUENCE: 785
ggatattttt atag                                                         14

<210> SEQ ID NO 786
<211> LENGTH: 14
<212> TYPE: DNA
<213> ORGANISM: Artificial Sequence
<220> FEATURE:
<223> OTHER INFORMATION: Synthetic Construct

<400> SEQUENCE: 786
gatattttta tagg                                                         14

<210> SEQ ID NO 787
<211> LENGTH: 14
<212> TYPE: DNA
<213> ORGANISM: Artificial Sequence
<220> FEATURE:
<223> OTHER INFORMATION: Synthetic Construct

<400> SEQUENCE: 787
atatttttat agga                                                         14

<210> SEQ ID NO 788
<211> LENGTH: 14
<212> TYPE: DNA
<213> ORGANISM: Artificial Sequence
<220> FEATURE:
<223> OTHER INFORMATION: Synthetic Construct

<400> SEQUENCE: 788 tattttata ggag                                                          14

<210> SEQ ID NO 789
<211> LENGTH: 14
<212> TYPE: DNA
<213> ORGANISM: Artificial Sequence
<220> FEATURE:
<223> OTHER INFORMATION: Synthetic Construct

<400> SEQUENCE: 789 attttatag gagt                                                          14

<210> SEQ ID NO 790
<211> LENGTH: 14
<212> TYPE: DNA
<213> ORGANISM: Artificial Sequence
<220> FEATURE:
<223> OTHER INFORMATION: Synthetic Construct

<400> SEQUENCE: 790
tttttatagg agtt                                                         14

<210> SEQ ID NO 791
<211> LENGTH: 14
<212> TYPE: DNA
<213> ORGANISM: Artificial Sequence
<220> FEATURE:
<223> OTHER INFORMATION: Synthetic Construct
```

```
<400> SEQUENCE: 791
ttttatagga gtta                                                     14

<210> SEQ ID NO 792
<211> LENGTH: 14
<212> TYPE: DNA
<213> ORGANISM: Artificial Sequence
<220> FEATURE:
<223> OTHER INFORMATION: Synthetic Construct

<400> SEQUENCE: 792
tttataggag ttat                                                     14

<210> SEQ ID NO 793
<211> LENGTH: 14
<212> TYPE: DNA
<213> ORGANISM: Artificial Sequence
<220> FEATURE:
<223> OTHER INFORMATION: Synthetic Construct

<400> SEQUENCE: 793
ttataggagt tata                                                     14

<210> SEQ ID NO 794
<211> LENGTH: 14
<212> TYPE: DNA
<213> ORGANISM: Artificial Sequence
<220> FEATURE:
<223> OTHER INFORMATION: Synthetic Construct

<400> SEQUENCE: 794
tataggagtt atac                                                     14

<210> SEQ ID NO 795
<211> LENGTH: 14
<212> TYPE: DNA
<213> ORGANISM: Artificial Sequence
<220> FEATURE:
<223> OTHER INFORMATION: Synthetic Construct

<400> SEQUENCE: 795
ataggagtta tacg                                                     14

<210> SEQ ID NO 796
<211> LENGTH: 14
<212> TYPE: DNA
<213> ORGANISM: Artificial Sequence
<220> FEATURE:
<223> OTHER INFORMATION: Synthetic Construct

<400> SEQUENCE: 796
taggagttat acgg                                                     14

<210> SEQ ID NO 797
<211> LENGTH: 14
<212> TYPE: DNA
<213> ORGANISM: Artificial Sequence
<220> FEATURE:
<223> OTHER INFORMATION: Synthetic Construct

<400> SEQUENCE: 797
aggagttata cggg                                                     14

<210> SEQ ID NO 798
<211> LENGTH: 14
```

```
<212> TYPE: DNA
<213> ORGANISM: Artificial Sequence
<220> FEATURE:
<223> OTHER INFORMATION: Synthetic Construct

<400> SEQUENCE: 798
ggagttatac ggga                                                      14

<210> SEQ ID NO 799
<211> LENGTH: 14
<212> TYPE: DNA
<213> ORGANISM: Artificial Sequence
<220> FEATURE:
<223> OTHER INFORMATION: Synthetic Construct

<400> SEQUENCE: 799
gagttatacg ggag                                                      14

<210> SEQ ID NO 800
<211> LENGTH: 14
<212> TYPE: DNA
<213> ORGANISM: Artificial Sequence
<220> FEATURE:
<223> OTHER INFORMATION: Synthetic Construct

<400> SEQUENCE: 800
agttatacgg gagt                                                      14

<210> SEQ ID NO 801
<211> LENGTH: 14
<212> TYPE: DNA
<213> ORGANISM: Artificial Sequence
<220> FEATURE:
<223> OTHER INFORMATION: Synthetic Construct

<400> SEQUENCE: 801
gttatacggg agtg                                                      14

<210> SEQ ID NO 802
<211> LENGTH: 14
<212> TYPE: DNA
<213> ORGANISM: Artificial Sequence
<220> FEATURE:
<223> OTHER INFORMATION: Synthetic Construct

<400> SEQUENCE: 802
ttatacggga gtgt                                                      14

<210> SEQ ID NO 803
<211> LENGTH: 14
<212> TYPE: DNA
<213> ORGANISM: Artificial Sequence
<220> FEATURE:
<223> OTHER INFORMATION: Synthetic Construct

<400> SEQUENCE: 803
tatacgggag tgtc                                                      14

<210> SEQ ID NO 804
<211> LENGTH: 14
<212> TYPE: DNA
<213> ORGANISM: Artificial Sequence
<220> FEATURE:
<223> OTHER INFORMATION: Synthetic Construct

<400> SEQUENCE: 804
```

```
atacgggagt gtcg                                                    14
```

<210> SEQ ID NO 805
<211> LENGTH: 14
<212> TYPE: DNA
<213> ORGANISM: Artificial Sequence
<220> FEATURE:
<223> OTHER INFORMATION: Synthetic Construct

<400> SEQUENCE: 805

```
tacgggagtg tcgt                                                    14
```

<210> SEQ ID NO 806
<211> LENGTH: 14
<212> TYPE: DNA
<213> ORGANISM: Artificial Sequence
<220> FEATURE:
<223> OTHER INFORMATION: Synthetic Construct

<400> SEQUENCE: 806

```
acgggagtgt cgta                                                    14
```

<210> SEQ ID NO 807
<211> LENGTH: 14
<212> TYPE: DNA
<213> ORGANISM: Artificial Sequence
<220> FEATURE:
<223> OTHER INFORMATION: Synthetic Construct

<400> SEQUENCE: 807

```
cgggagtgtc gtaa                                                    14
```

<210> SEQ ID NO 808
<211> LENGTH: 14
<212> TYPE: DNA
<213> ORGANISM: Artificial Sequence
<220> FEATURE:
<223> OTHER INFORMATION: Synthetic Construct

<400> SEQUENCE: 808

```
gggagtgtcg taag                                                    14
```

<210> SEQ ID NO 809
<211> LENGTH: 14
<212> TYPE: DNA
<213> ORGANISM: Artificial Sequence
<220> FEATURE:
<223> OTHER INFORMATION: Synthetic Construct

<400> SEQUENCE: 809

```
ggagtgtcgt aagt                                                    14
```

<210> SEQ ID NO 810
<211> LENGTH: 14
<212> TYPE: DNA
<213> ORGANISM: Artificial Sequence
<220> FEATURE:
<223> OTHER INFORMATION: Synthetic Construct

<400> SEQUENCE: 810

```
gagtgtcgta agta                                                    14
```

<210> SEQ ID NO 811
<211> LENGTH: 14
<212> TYPE: DNA
<213> ORGANISM: Artificial Sequence

```
<220> FEATURE:
<223> OTHER INFORMATION: Synthetic Construct

<400> SEQUENCE: 811
agtgtcgtaa gtag                                                        14

<210> SEQ ID NO 812
<211> LENGTH: 14
<212> TYPE: DNA
<213> ORGANISM: Artificial Sequence
<220> FEATURE:
<223> OTHER INFORMATION: Synthetic Construct

<400> SEQUENCE: 812
gtgtcgtaag tagg                                                        14

<210> SEQ ID NO 813
<211> LENGTH: 14
<212> TYPE: DNA
<213> ORGANISM: Artificial Sequence
<220> FEATURE:
<223> OTHER INFORMATION: Synthetic Construct

<400> SEQUENCE: 813
tgtcgtaagt aggg                                                        14

<210> SEQ ID NO 814
<211> LENGTH: 14
<212> TYPE: DNA
<213> ORGANISM: Artificial Sequence
<220> FEATURE:
<223> OTHER INFORMATION: Synthetic Construct

<400> SEQUENCE: 814
gtcgtaagta gggc                                                        14

<210> SEQ ID NO 815
<211> LENGTH: 14
<212> TYPE: DNA
<213> ORGANISM: Artificial Sequence
<220> FEATURE:
<223> OTHER INFORMATION: Synthetic Construct

<400> SEQUENCE: 815
tcgtaagtag ggcg                                                        14

<210> SEQ ID NO 816
<211> LENGTH: 14
<212> TYPE: DNA
<213> ORGANISM: Artificial Sequence
<220> FEATURE:
<223> OTHER INFORMATION: Synthetic Construct

<400> SEQUENCE: 816
cgtaagtagg gcga                                                        14

<210> SEQ ID NO 817
<211> LENGTH: 14
<212> TYPE: DNA
<213> ORGANISM: Artificial Sequence
<220> FEATURE:
<223> OTHER INFORMATION: Synthetic Construct

<400> SEQUENCE: 817
gtaagtaggg cgag                                                        14
```

<210> SEQ ID NO 818
<211> LENGTH: 14
<212> TYPE: DNA
<213> ORGANISM: Artificial Sequence
<220> FEATURE:
<223> OTHER INFORMATION: Synthetic Construct

<400> SEQUENCE: 818
taagtagggc gagg                                                        14

<210> SEQ ID NO 819
<211> LENGTH: 14
<212> TYPE: DNA
<213> ORGANISM: Artificial Sequence
<220> FEATURE:
<223> OTHER INFORMATION: Synthetic Construct

<400> SEQUENCE: 819
aagtagggcg aggc                                                        14

<210> SEQ ID NO 820
<211> LENGTH: 14
<212> TYPE: DNA
<213> ORGANISM: Artificial Sequence
<220> FEATURE:
<223> OTHER INFORMATION: Synthetic Construct

<400> SEQUENCE: 820
agtagggcga ggcg                                                        14

<210> SEQ ID NO 821
<211> LENGTH: 14
<212> TYPE: DNA
<213> ORGANISM: Artificial Sequence
<220> FEATURE:
<223> OTHER INFORMATION: Synthetic Construct

<400> SEQUENCE: 821
gtagggcgag gcgg                                                        14

<210> SEQ ID NO 822
<211> LENGTH: 14
<212> TYPE: DNA
<213> ORGANISM: Artificial Sequence
<220> FEATURE:
<223> OTHER INFORMATION: Synthetic Construct

<400> SEQUENCE: 822
tagggcgagg cggg                                                        14

<210> SEQ ID NO 823
<211> LENGTH: 14
<212> TYPE: DNA
<213> ORGANISM: Artificial Sequence
<220> FEATURE:
<223> OTHER INFORMATION: Synthetic Construct

<400> SEQUENCE: 823
agggcgaggc gggg                                                        14

<210> SEQ ID NO 824
<211> LENGTH: 14
<212> TYPE: DNA
<213> ORGANISM: Artificial Sequence
<220> FEATURE:
<223> OTHER INFORMATION: Synthetic Construct

```
<400> SEQUENCE: 824
gggcgaggcg gggt                                                    14

<210> SEQ ID NO 825
<211> LENGTH: 14
<212> TYPE: DNA
<213> ORGANISM: Artificial Sequence
<220> FEATURE:
<223> OTHER INFORMATION: Synthetic Construct

<400> SEQUENCE: 825
ggcgaggcgg ggta                                                    14

<210> SEQ ID NO 826
<211> LENGTH: 14
<212> TYPE: DNA
<213> ORGANISM: Artificial Sequence
<220> FEATURE:
<223> OTHER INFORMATION: Synthetic Construct

<400> SEQUENCE: 826
gcgaggcggg gtac                                                    14

<210> SEQ ID NO 827
<211> LENGTH: 14
<212> TYPE: DNA
<213> ORGANISM: Artificial Sequence
<220> FEATURE:
<223> OTHER INFORMATION: Synthetic Construct

<400> SEQUENCE: 827
cgaggcgggg tacg                                                    14

<210> SEQ ID NO 828
<211> LENGTH: 14
<212> TYPE: DNA
<213> ORGANISM: Artificial Sequence
<220> FEATURE:
<223> OTHER INFORMATION: Synthetic Construct

<400> SEQUENCE: 828
gaggcggggt acgt                                                    14

<210> SEQ ID NO 829
<211> LENGTH: 14
<212> TYPE: DNA
<213> ORGANISM: Artificial Sequence
<220> FEATURE:
<223> OTHER INFORMATION: Synthetic Construct

<400> SEQUENCE: 829
aggcggggta cgtg                                                    14

<210> SEQ ID NO 830
<211> LENGTH: 14
<212> TYPE: DNA
<213> ORGANISM: Artificial Sequence
<220> FEATURE:
<223> OTHER INFORMATION: Synthetic Construct

<400> SEQUENCE: 830
ggcggggtac gtgt                                                    14

<210> SEQ ID NO 831
```

```
<211> LENGTH: 14
<212> TYPE: DNA
<213> ORGANISM: Artificial Sequence
<220> FEATURE:
<223> OTHER INFORMATION: Synthetic Construct

<400> SEQUENCE: 831
gcggggtacg tgtg                                                          14

<210> SEQ ID NO 832
<211> LENGTH: 14
<212> TYPE: DNA
<213> ORGANISM: Artificial Sequence
<220> FEATURE:
<223> OTHER INFORMATION: Synthetic Construct

<400> SEQUENCE: 832
cggggtacgt gtga                                                          14

<210> SEQ ID NO 833
<211> LENGTH: 14
<212> TYPE: DNA
<213> ORGANISM: Artificial Sequence
<220> FEATURE:
<223> OTHER INFORMATION: Synthetic Construct

<400> SEQUENCE: 833
ggggtacgtg tgat                                                          14

<210> SEQ ID NO 834
<211> LENGTH: 14
<212> TYPE: DNA
<213> ORGANISM: Artificial Sequence
<220> FEATURE:
<223> OTHER INFORMATION: Synthetic Construct

<400> SEQUENCE: 834
gggtacgtgt gata                                                          14

<210> SEQ ID NO 835
<211> LENGTH: 14
<212> TYPE: DNA
<213> ORGANISM: Artificial Sequence
<220> FEATURE:
<223> OTHER INFORMATION: Synthetic Construct

<400> SEQUENCE: 835
ggtacgtgtg atac                                                          14

<210> SEQ ID NO 836
<211> LENGTH: 14
<212> TYPE: DNA
<213> ORGANISM: Artificial Sequence
<220> FEATURE:
<223> OTHER INFORMATION: Synthetic Construct

<400> SEQUENCE: 836
gtacgtgtga tacg                                                          14

<210> SEQ ID NO 837
<211> LENGTH: 14
<212> TYPE: DNA
<213> ORGANISM: Artificial Sequence
<220> FEATURE:
<223> OTHER INFORMATION: Synthetic Construct

<400> SEQUENCE: 837
```
tacgtgtgat acgg                                                14

<210> SEQ ID NO 838
<211> LENGTH: 14
<212> TYPE: DNA
<213> ORGANISM: Artificial Sequence
<220> FEATURE:
<223> OTHER INFORMATION: Synthetic Construct

<400> SEQUENCE: 838
acgtgtgata cggc                                                14

<210> SEQ ID NO 839
<211> LENGTH: 14
<212> TYPE: DNA
<213> ORGANISM: Artificial Sequence
<220> FEATURE:
<223> OTHER INFORMATION: Synthetic Construct

<400> SEQUENCE: 839
cgtgtgatac ggcg                                                14

<210> SEQ ID NO 840
<211> LENGTH: 14
<212> TYPE: DNA
<213> ORGANISM: Artificial Sequence
<220> FEATURE:
<223> OTHER INFORMATION: Synthetic Construct

<400> SEQUENCE: 840
gtgtgatacg gcgt                                                14

<210> SEQ ID NO 841
<211> LENGTH: 14
<212> TYPE: DNA
<213> ORGANISM: Artificial Sequence
<220> FEATURE:
<223> OTHER INFORMATION: Synthetic Construct

<400> SEQUENCE: 841
tgtgatacgg cgtt                                                14

<210> SEQ ID NO 842
<211> LENGTH: 14
<212> TYPE: DNA
<213> ORGANISM: Artificial Sequence
<220> FEATURE:
<223> OTHER INFORMATION: Synthetic Construct

<400> SEQUENCE: 842
gtgatacggc gttc                                                14

<210> SEQ ID NO 843
<211> LENGTH: 14
<212> TYPE: DNA
<213> ORGANISM: Artificial Sequence
<220> FEATURE:
<223> OTHER INFORMATION: Synthetic Construct

<400> SEQUENCE: 843
tgatacggcg ttcg                                                14

<210> SEQ ID NO 844
<211> LENGTH: 14
<212> TYPE: DNA

```
<213> ORGANISM: Artificial Sequence
<220> FEATURE:
<223> OTHER INFORMATION: Synthetic Construct

<400> SEQUENCE: 844
gatacggcgt tcgg                                                         14

<210> SEQ ID NO 845
<211> LENGTH: 14
<212> TYPE: DNA
<213> ORGANISM: Artificial Sequence
<220> FEATURE:
<223> OTHER INFORMATION: Synthetic Construct

<400> SEQUENCE: 845
atacggcgtt cggt                                                         14

<210> SEQ ID NO 846
<211> LENGTH: 14
<212> TYPE: DNA
<213> ORGANISM: Artificial Sequence
<220> FEATURE:
<223> OTHER INFORMATION: Synthetic Construct

<400> SEQUENCE: 846
tacggcgttc ggtt                                                         14

<210> SEQ ID NO 847
<211> LENGTH: 14
<212> TYPE: DNA
<213> ORGANISM: Artificial Sequence
<220> FEATURE:
<223> OTHER INFORMATION: Synthetic Construct

<400> SEQUENCE: 847
acggcgttcg gttt                                                         14

<210> SEQ ID NO 848
<211> LENGTH: 14
<212> TYPE: DNA
<213> ORGANISM: Artificial Sequence
<220> FEATURE:
<223> OTHER INFORMATION: Synthetic Construct

<400> SEQUENCE: 848
cggcgttcgg tttc                                                         14

<210> SEQ ID NO 849
<211> LENGTH: 14
<212> TYPE: DNA
<213> ORGANISM: Artificial Sequence
<220> FEATURE:
<223> OTHER INFORMATION: Synthetic Construct

<400> SEQUENCE: 849
ggcgttcggt ttcg                                                         14

<210> SEQ ID NO 850
<211> LENGTH: 14
<212> TYPE: DNA
<213> ORGANISM: Artificial Sequence
<220> FEATURE:
<223> OTHER INFORMATION: Synthetic Construct

<400> SEQUENCE: 850
gcgttcggtt tcgg                                                         14
```

```
<210> SEQ ID NO 851
<211> LENGTH: 14
<212> TYPE: DNA
<213> ORGANISM: Artificial Sequence
<220> FEATURE:
<223> OTHER INFORMATION: Synthetic Construct

<400> SEQUENCE: 851
cgttcggttt cggg                                                     14

<210> SEQ ID NO 852
<211> LENGTH: 14
<212> TYPE: DNA
<213> ORGANISM: Artificial Sequence
<220> FEATURE:
<223> OTHER INFORMATION: Synthetic Construct

<400> SEQUENCE: 852
gttcggtttc gggt                                                     14

<210> SEQ ID NO 853
<211> LENGTH: 14
<212> TYPE: DNA
<213> ORGANISM: Artificial Sequence
<220> FEATURE:
<223> OTHER INFORMATION: Synthetic Construct

<400> SEQUENCE: 853
ttcggtttcg ggtc                                                     14

<210> SEQ ID NO 854
<211> LENGTH: 14
<212> TYPE: DNA
<213> ORGANISM: Artificial Sequence
<220> FEATURE:
<223> OTHER INFORMATION: Synthetic Construct

<400> SEQUENCE: 854
tcggtttcgg gtcg                                                     14

<210> SEQ ID NO 855
<211> LENGTH: 14
<212> TYPE: DNA
<213> ORGANISM: Artificial Sequence
<220> FEATURE:
<223> OTHER INFORMATION: Synthetic Construct

<400> SEQUENCE: 855
cggtttcggg tcgt                                                     14

<210> SEQ ID NO 856
<211> LENGTH: 14
<212> TYPE: DNA
<213> ORGANISM: Artificial Sequence
<220> FEATURE:
<223> OTHER INFORMATION: Synthetic Construct

<400> SEQUENCE: 856
ggtttcgggt cgtt                                                     14

<210> SEQ ID NO 857
<211> LENGTH: 14
<212> TYPE: DNA
<213> ORGANISM: Artificial Sequence
<220> FEATURE:
```

```
<223> OTHER INFORMATION: Synthetic Construct

<400> SEQUENCE: 857
gtttcgggtc gttt                                                       14

<210> SEQ ID NO 858
<211> LENGTH: 14
<212> TYPE: DNA
<213> ORGANISM: Artificial Sequence
<220> FEATURE:
<223> OTHER INFORMATION: Synthetic Construct

<400> SEQUENCE: 858
tttcgggtcg tttg                                                       14

<210> SEQ ID NO 859
<211> LENGTH: 14
<212> TYPE: DNA
<213> ORGANISM: Artificial Sequence
<220> FEATURE:
<223> OTHER INFORMATION: Synthetic Construct

<400> SEQUENCE: 859
ttcgggtcgt ttgg                                                       14

<210> SEQ ID NO 860
<211> LENGTH: 14
<212> TYPE: DNA
<213> ORGANISM: Artificial Sequence
<220> FEATURE:
<223> OTHER INFORMATION: Synthetic Construct

<400> SEQUENCE: 860
tcgggtcgtt tggt                                                       14

<210> SEQ ID NO 861
<211> LENGTH: 14
<212> TYPE: DNA
<213> ORGANISM: Artificial Sequence
<220> FEATURE:
<223> OTHER INFORMATION: Synthetic Construct

<400> SEQUENCE: 861
cgggtcgttt ggtc                                                       14

<210> SEQ ID NO 862
<211> LENGTH: 14
<212> TYPE: DNA
<213> ORGANISM: Artificial Sequence
<220> FEATURE:
<223> OTHER INFORMATION: Synthetic Construct

<400> SEQUENCE: 862
gggtcgtttg gtcg                                                       14

<210> SEQ ID NO 863
<211> LENGTH: 14
<212> TYPE: DNA
<213> ORGANISM: Artificial Sequence
<220> FEATURE:
<223> OTHER INFORMATION: Synthetic Construct

<400> SEQUENCE: 863
ggtcgtttgg tcgt                                                       14
```

```
<210> SEQ ID NO 864
<211> LENGTH: 14
<212> TYPE: DNA
<213> ORGANISM: Artificial Sequence
<220> FEATURE:
<223> OTHER INFORMATION: Synthetic Construct

<400> SEQUENCE: 864
gtcgtttggt cgtt                                                       14

<210> SEQ ID NO 865
<211> LENGTH: 14
<212> TYPE: DNA
<213> ORGANISM: Artificial Sequence
<220> FEATURE:
<223> OTHER INFORMATION: Synthetic Construct

<400> SEQUENCE: 865
tcgtttggtc gttg                                                       14

<210> SEQ ID NO 866
<211> LENGTH: 14
<212> TYPE: DNA
<213> ORGANISM: Artificial Sequence
<220> FEATURE:
<223> OTHER INFORMATION: Synthetic Construct

<400> SEQUENCE: 866
cgtttggtcg ttgg                                                       14

<210> SEQ ID NO 867
<211> LENGTH: 14
<212> TYPE: DNA
<213> ORGANISM: Artificial Sequence
<220> FEATURE:
<223> OTHER INFORMATION: Synthetic Construct

<400> SEQUENCE: 867
gtttggtcgt tggg                                                       14

<210> SEQ ID NO 868
<211> LENGTH: 14
<212> TYPE: DNA
<213> ORGANISM: Artificial Sequence
<220> FEATURE:
<223> OTHER INFORMATION: Synthetic Construct

<400> SEQUENCE: 868
tttggtcgtt gggg                                                       14

<210> SEQ ID NO 869
<211> LENGTH: 14
<212> TYPE: DNA
<213> ORGANISM: Artificial Sequence
<220> FEATURE:
<223> OTHER INFORMATION: Synthetic Construct

<400> SEQUENCE: 869
ttggtcgttg gggg                                                       14

<210> SEQ ID NO 870
<211> LENGTH: 14
<212> TYPE: DNA
<213> ORGANISM: Artificial Sequence
<220> FEATURE:
<223> OTHER INFORMATION: Synthetic Construct
```

```
<400> SEQUENCE: 870
tggtcgttgg ggga                                                14

<210> SEQ ID NO 871
<211> LENGTH: 14
<212> TYPE: DNA
<213> ORGANISM: Artificial Sequence
<220> FEATURE:
<223> OTHER INFORMATION: Synthetic Construct

<400> SEQUENCE: 871
ggtcgttggg ggat                                                14

<210> SEQ ID NO 872
<211> LENGTH: 14
<212> TYPE: DNA
<213> ORGANISM: Artificial Sequence
<220> FEATURE:
<223> OTHER INFORMATION: Synthetic Construct

<400> SEQUENCE: 872
gtcgttgggg gata                                                14

<210> SEQ ID NO 873
<211> LENGTH: 14
<212> TYPE: DNA
<213> ORGANISM: Artificial Sequence
<220> FEATURE:
<223> OTHER INFORMATION: Synthetic Construct

<400> SEQUENCE: 873
tcgttggggg atag                                                14

<210> SEQ ID NO 874
<211> LENGTH: 14
<212> TYPE: DNA
<213> ORGANISM: Artificial Sequence
<220> FEATURE:
<223> OTHER INFORMATION: Synthetic Construct

<400> SEQUENCE: 874
cgttggggga taga                                                14

<210> SEQ ID NO 875
<211> LENGTH: 14
<212> TYPE: DNA
<213> ORGANISM: Artificial Sequence
<220> FEATURE:
<223> OTHER INFORMATION: Synthetic Construct

<400> SEQUENCE: 875
gttgggggat agag                                                14

<210> SEQ ID NO 876
<211> LENGTH: 14
<212> TYPE: DNA
<213> ORGANISM: Artificial Sequence
<220> FEATURE:
<223> OTHER INFORMATION: Synthetic Construct

<400> SEQUENCE: 876
ttgggggata gagg                                                14

<210> SEQ ID NO 877
<211> LENGTH: 14
```

```
<212> TYPE: DNA
<213> ORGANISM: Artificial Sequence
<220> FEATURE:
<223> OTHER INFORMATION: Synthetic Construct

<400> SEQUENCE: 877
tgggggatag aggt                                                       14

<210> SEQ ID NO 878
<211> LENGTH: 14
<212> TYPE: DNA
<213> ORGANISM: Artificial Sequence
<220> FEATURE:
<223> OTHER INFORMATION: Synthetic Construct

<400> SEQUENCE: 878
gggggataga ggtt                                                       14

<210> SEQ ID NO 879
<211> LENGTH: 14
<212> TYPE: DNA
<213> ORGANISM: Artificial Sequence
<220> FEATURE:
<223> OTHER INFORMATION: Synthetic Construct

<400> SEQUENCE: 879
ggggatagag gttt                                                       14

<210> SEQ ID NO 880
<211> LENGTH: 14
<212> TYPE: DNA
<213> ORGANISM: Artificial Sequence
<220> FEATURE:
<223> OTHER INFORMATION: Synthetic Construct

<400> SEQUENCE: 880
gggatagagg tttt                                                       14

<210> SEQ ID NO 881
<211> LENGTH: 14
<212> TYPE: DNA
<213> ORGANISM: Artificial Sequence
<220> FEATURE:
<223> OTHER INFORMATION: Synthetic Construct

<400> SEQUENCE: 881
ggatagaggt tttt                                                       14

<210> SEQ ID NO 882
<211> LENGTH: 14
<212> TYPE: DNA
<213> ORGANISM: Artificial Sequence
<220> FEATURE:
<223> OTHER INFORMATION: Synthetic Construct

<400> SEQUENCE: 882
gatagaggtt tttt                                                       14

<210> SEQ ID NO 883
<211> LENGTH: 14
<212> TYPE: DNA
<213> ORGANISM: Artificial Sequence
<220> FEATURE:
<223> OTHER INFORMATION: Synthetic Construct

<400> SEQUENCE: 883
```

| | |
|---|---|
| atagaggttt tttt | 14 |

<210> SEQ ID NO 884
<211> LENGTH: 14
<212> TYPE: DNA
<213> ORGANISM: Artificial Sequence
<220> FEATURE:
<223> OTHER INFORMATION: Synthetic Construct

<400> SEQUENCE: 884

| | |
|---|---|
| tagaggtttt tttt | 14 |

<210> SEQ ID NO 885
<211> LENGTH: 14
<212> TYPE: DNA
<213> ORGANISM: Artificial Sequence
<220> FEATURE:
<223> OTHER INFORMATION: Synthetic Construct

<400> SEQUENCE: 885

| | |
|---|---|
| agaggttttt tttt | 14 |

<210> SEQ ID NO 886
<211> LENGTH: 14
<212> TYPE: DNA
<213> ORGANISM: Artificial Sequence
<220> FEATURE:
<223> OTHER INFORMATION: Synthetic Construct

<400> SEQUENCE: 886

| | |
|---|---|
| gaggtttttt tttc | 14 |

<210> SEQ ID NO 887
<211> LENGTH: 14
<212> TYPE: DNA
<213> ORGANISM: Artificial Sequence
<220> FEATURE:
<223> OTHER INFORMATION: Synthetic Construct

<400> SEQUENCE: 887

| | |
|---|---|
| aggttttttt ttcg | 14 |

<210> SEQ ID NO 888
<211> LENGTH: 14
<212> TYPE: DNA
<213> ORGANISM: Artificial Sequence
<220> FEATURE:
<223> OTHER INFORMATION: Synthetic Construct

<400> SEQUENCE: 888

| | |
|---|---|
| ggtttttttt tcgt | 14 |

<210> SEQ ID NO 889
<211> LENGTH: 14
<212> TYPE: DNA
<213> ORGANISM: Artificial Sequence
<220> FEATURE:
<223> OTHER INFORMATION: Synthetic Construct

<400> SEQUENCE: 889

| | |
|---|---|
| gtttttttt cgtt | 14 |

<210> SEQ ID NO 890
<211> LENGTH: 14
<212> TYPE: DNA
<213> ORGANISM: Artificial Sequence

```
<220> FEATURE:
<223> OTHER INFORMATION: Synthetic Construct

<400> SEQUENCE: 890
tttttttttc gtta                                                  14

<210> SEQ ID NO 891
<211> LENGTH: 14
<212> TYPE: DNA
<213> ORGANISM: Artificial Sequence
<220> FEATURE:
<223> OTHER INFORMATION: Synthetic Construct

<400> SEQUENCE: 891 tttttttcg ttac                                                   14

<210> SEQ ID NO 892
<211> LENGTH: 14
<212> TYPE: DNA
<213> ORGANISM: Artificial Sequence
<220> FEATURE:
<223> OTHER INFORMATION: Synthetic Construct

<400> SEQUENCE: 892
tttttttcgt tacg                                                  14

<210> SEQ ID NO 893
<211> LENGTH: 14
<212> TYPE: DNA
<213> ORGANISM: Artificial Sequence
<220> FEATURE:
<223> OTHER INFORMATION: Synthetic Construct

<400> SEQUENCE: 893 tttttcgtt acgt                                                   14

<210> SEQ ID NO 894
<211> LENGTH: 14
<212> TYPE: DNA
<213> ORGANISM: Artificial Sequence
<220> FEATURE:
<223> OTHER INFORMATION: Synthetic Construct

<400> SEQUENCE: 894
tttttcgtta cgtt                                                  14

<210> SEQ ID NO 895
<211> LENGTH: 14
<212> TYPE: DNA
<213> ORGANISM: Artificial Sequence
<220> FEATURE:
<223> OTHER INFORMATION: Synthetic Construct

<400> SEQUENCE: 895
ttttcgttac gttc                                                  14

<210> SEQ ID NO 896
<211> LENGTH: 14
<212> TYPE: DNA
<213> ORGANISM: Artificial Sequence
<220> FEATURE:
<223> OTHER INFORMATION: Synthetic Construct

<400> SEQUENCE: 896
tttcgttacg ttcg                                                  14
```

```
<210> SEQ ID NO 897
<211> LENGTH: 14
<212> TYPE: DNA
<213> ORGANISM: Artificial Sequence
<220> FEATURE:
<223> OTHER INFORMATION: Synthetic Construct

<400> SEQUENCE: 897
ttcgttacgt tcgt                                                    14

<210> SEQ ID NO 898
<211> LENGTH: 14
<212> TYPE: DNA
<213> ORGANISM: Artificial Sequence
<220> FEATURE:
<223> OTHER INFORMATION: Synthetic Construct

<400> SEQUENCE: 898
tcgttacgtt cgtt                                                    14

<210> SEQ ID NO 899
<211> LENGTH: 14
<212> TYPE: DNA
<213> ORGANISM: Artificial Sequence
<220> FEATURE:
<223> OTHER INFORMATION: Synthetic Construct

<400> SEQUENCE: 899
cgttacgttc gttt                                                    14

<210> SEQ ID NO 900
<211> LENGTH: 14
<212> TYPE: DNA
<213> ORGANISM: Artificial Sequence
<220> FEATURE:
<223> OTHER INFORMATION: Synthetic Construct

<400> SEQUENCE: 900
gttacgttcg tttt                                                    14

<210> SEQ ID NO 901
<211> LENGTH: 14
<212> TYPE: DNA
<213> ORGANISM: Artificial Sequence
<220> FEATURE:
<223> OTHER INFORMATION: Synthetic Construct

<400> SEQUENCE: 901
ttacgttcgt tttt                                                    14

<210> SEQ ID NO 902
<211> LENGTH: 14
<212> TYPE: DNA
<213> ORGANISM: Artificial Sequence
<220> FEATURE:
<223> OTHER INFORMATION: Synthetic Construct

<400> SEQUENCE: 902
tacgttcgtt tttt                                                    14

<210> SEQ ID NO 903
<211> LENGTH: 14
<212> TYPE: DNA
<213> ORGANISM: Artificial Sequence
<220> FEATURE:
<223> OTHER INFORMATION: Synthetic Construct
```

<400> SEQUENCE: 903
acgttcgttt tttt                                                     14

<210> SEQ ID NO 904
<211> LENGTH: 14
<212> TYPE: DNA
<213> ORGANISM: Artificial Sequence
<220> FEATURE:
<223> OTHER INFORMATION: Synthetic Construct

<400> SEQUENCE: 904
cgttcgtttt tttt                                                     14

<210> SEQ ID NO 905
<211> LENGTH: 14
<212> TYPE: DNA
<213> ORGANISM: Artificial Sequence
<220> FEATURE:
<223> OTHER INFORMATION: Synthetic Construct

<400> SEQUENCE: 905
gttcgttttt tttg                                                     14

<210> SEQ ID NO 906
<211> LENGTH: 14
<212> TYPE: DNA
<213> ORGANISM: Artificial Sequence
<220> FEATURE:
<223> OTHER INFORMATION: Synthetic Construct

<400> SEQUENCE: 906
ttcgtttttt ttgg                                                     14

<210> SEQ ID NO 907
<211> LENGTH: 14
<212> TYPE: DNA
<213> ORGANISM: Artificial Sequence
<220> FEATURE:
<223> OTHER INFORMATION: Synthetic Construct

<400> SEQUENCE: 907
tcgttttttt tggt                                                     14

<210> SEQ ID NO 908
<211> LENGTH: 14
<212> TYPE: DNA
<213> ORGANISM: Artificial Sequence
<220> FEATURE:
<223> OTHER INFORMATION: Synthetic Construct

<400> SEQUENCE: 908
cgtttttttt ggtt                                                     14

<210> SEQ ID NO 909
<211> LENGTH: 14
<212> TYPE: DNA
<213> ORGANISM: Artificial Sequence
<220> FEATURE:
<223> OTHER INFORMATION: Synthetic Construct

<400> SEQUENCE: 909 gtttttttg gttt                                                      14

<210> SEQ ID NO 910

```
<211> LENGTH: 14
<212> TYPE: DNA
<213> ORGANISM: Artificial Sequence
<220> FEATURE:
<223> OTHER INFORMATION: Synthetic Construct

<400> SEQUENCE: 910
tttttttggg tttt                                                    14

<210> SEQ ID NO 911
<211> LENGTH: 14
<212> TYPE: DNA
<213> ORGANISM: Artificial Sequence
<220> FEATURE:
<223> OTHER INFORMATION: Synthetic Construct

<400> SEQUENCE: 911
tttttttggt tttg                                                    14

<210> SEQ ID NO 912
<211> LENGTH: 14
<212> TYPE: DNA
<213> ORGANISM: Artificial Sequence
<220> FEATURE:
<223> OTHER INFORMATION: Synthetic Construct

<400> SEQUENCE: 912 tttttggtt ttgg                                                     14

<210> SEQ ID NO 913
<211> LENGTH: 14
<212> TYPE: DNA
<213> ORGANISM: Artificial Sequence
<220> FEATURE:
<223> OTHER INFORMATION: Synthetic Construct

<400> SEQUENCE: 913
tttttggttt tggc                                                    14

<210> SEQ ID NO 914
<211> LENGTH: 14
<212> TYPE: DNA
<213> ORGANISM: Artificial Sequence
<220> FEATURE:
<223> OTHER INFORMATION: Synthetic Construct

<400> SEQUENCE: 914
ttttggtttt ggcg                                                    14

<210> SEQ ID NO 915
<211> LENGTH: 14
<212> TYPE: DNA
<213> ORGANISM: Artificial Sequence
<220> FEATURE:
<223> OTHER INFORMATION: Synthetic Construct

<400> SEQUENCE: 915
tttggttttg gcgg                                                    14

<210> SEQ ID NO 916
<211> LENGTH: 14
<212> TYPE: DNA
<213> ORGANISM: Artificial Sequence
<220> FEATURE:
<223> OTHER INFORMATION: Synthetic Construct

<400> SEQUENCE: 916
```

```
ttggttttgg cggg                                                14
```

<210> SEQ ID NO 917
<211> LENGTH: 14
<212> TYPE: DNA
<213> ORGANISM: Artificial Sequence
<220> FEATURE:
<223> OTHER INFORMATION: Synthetic Construct

<400> SEQUENCE: 917

```
tggttttggc gggg                                                14
```

<210> SEQ ID NO 918
<211> LENGTH: 14
<212> TYPE: DNA
<213> ORGANISM: Artificial Sequence
<220> FEATURE:
<223> OTHER INFORMATION: Synthetic Construct

<400> SEQUENCE: 918

```
ggttttggcg gggc                                                14
```

<210> SEQ ID NO 919
<211> LENGTH: 14
<212> TYPE: DNA
<213> ORGANISM: Artificial Sequence
<220> FEATURE:
<223> OTHER INFORMATION: Synthetic Construct

<400> SEQUENCE: 919

```
gttttggcgg ggcg                                                14
```

<210> SEQ ID NO 920
<211> LENGTH: 14
<212> TYPE: DNA
<213> ORGANISM: Artificial Sequence
<220> FEATURE:
<223> OTHER INFORMATION: Synthetic Construct

<400> SEQUENCE: 920

```
ttttggcggg gcgt                                                14
```

<210> SEQ ID NO 921
<211> LENGTH: 14
<212> TYPE: DNA
<213> ORGANISM: Artificial Sequence
<220> FEATURE:
<223> OTHER INFORMATION: Synthetic Construct

<400> SEQUENCE: 921

```
tttggcgggg cgtt                                                14
```

<210> SEQ ID NO 922
<211> LENGTH: 14
<212> TYPE: DNA
<213> ORGANISM: Artificial Sequence
<220> FEATURE:
<223> OTHER INFORMATION: Synthetic Construct

<400> SEQUENCE: 922

```
ttggcggggc gttt                                                14
```

<210> SEQ ID NO 923
<211> LENGTH: 14
<212> TYPE: DNA

```
<213> ORGANISM: Artificial Sequence
<220> FEATURE:
<223> OTHER INFORMATION: Synthetic Construct

<400> SEQUENCE: 923
tggcggggcg tttt                                                         14

<210> SEQ ID NO 924
<211> LENGTH: 14
<212> TYPE: DNA
<213> ORGANISM: Artificial Sequence
<220> FEATURE:
<223> OTHER INFORMATION: Synthetic Construct

<400> SEQUENCE: 924
ggcggggcgt tttt                                                         14

<210> SEQ ID NO 925
<211> LENGTH: 14
<212> TYPE: DNA
<213> ORGANISM: Artificial Sequence
<220> FEATURE:
<223> OTHER INFORMATION: Synthetic Construct

<400> SEQUENCE: 925
gcggggcgtt tttg                                                         14

<210> SEQ ID NO 926
<211> LENGTH: 14
<212> TYPE: DNA
<213> ORGANISM: Artificial Sequence
<220> FEATURE:
<223> OTHER INFORMATION: Synthetic Construct

<400> SEQUENCE: 926
cggggcgttt ttgg                                                         14

<210> SEQ ID NO 927
<211> LENGTH: 14
<212> TYPE: DNA
<213> ORGANISM: Artificial Sequence
<220> FEATURE:
<223> OTHER INFORMATION: Synthetic Construct

<400> SEQUENCE: 927
ggggcgtttt tggg                                                         14

<210> SEQ ID NO 928
<211> LENGTH: 14
<212> TYPE: DNA
<213> ORGANISM: Artificial Sequence
<220> FEATURE:
<223> OTHER INFORMATION: Synthetic Construct

<400> SEQUENCE: 928
gggcgttttt gggg                                                         14

<210> SEQ ID NO 929
<211> LENGTH: 14
<212> TYPE: DNA
<213> ORGANISM: Artificial Sequence
<220> FEATURE:
<223> OTHER INFORMATION: Synthetic Construct

<400> SEQUENCE: 929
ggcgtttttg gggt                                                         14
```

```
<210> SEQ ID NO 930
<211> LENGTH: 14
<212> TYPE: DNA
<213> ORGANISM: Artificial Sequence
<220> FEATURE:
<223> OTHER INFORMATION: Synthetic Construct

<400> SEQUENCE: 930
gcgtttttgg ggtc                                                        14

<210> SEQ ID NO 931
<211> LENGTH: 14
<212> TYPE: DNA
<213> ORGANISM: Artificial Sequence
<220> FEATURE:
<223> OTHER INFORMATION: Synthetic Construct

<400> SEQUENCE: 931 cgttttggg gtcg                                                         14

<210> SEQ ID NO 932
<211> LENGTH: 14
<212> TYPE: DNA
<213> ORGANISM: Artificial Sequence
<220> FEATURE:
<223> OTHER INFORMATION: Synthetic Construct

<400> SEQUENCE: 932
gtttttgggg tcgg                                                        14

<210> SEQ ID NO 933
<211> LENGTH: 14
<212> TYPE: DNA
<213> ORGANISM: Artificial Sequence
<220> FEATURE:
<223> OTHER INFORMATION: Synthetic Construct

<400> SEQUENCE: 933
tttttggggt cggg                                                        14

<210> SEQ ID NO 934
<211> LENGTH: 14
<212> TYPE: DNA
<213> ORGANISM: Artificial Sequence
<220> FEATURE:
<223> OTHER INFORMATION: Synthetic Construct

<400> SEQUENCE: 934
ttttggggtc ggga                                                        14

<210> SEQ ID NO 935
<211> LENGTH: 14
<212> TYPE: DNA
<213> ORGANISM: Artificial Sequence
<220> FEATURE:
<223> OTHER INFORMATION: Synthetic Construct

<400> SEQUENCE: 935
tttggggtcg ggag                                                        14

<210> SEQ ID NO 936
<211> LENGTH: 14
<212> TYPE: DNA
<213> ORGANISM: Artificial Sequence
<220> FEATURE:
```

-continued

```
<223> OTHER INFORMATION: Synthetic Construct

<400> SEQUENCE: 936
ttggggtcgg gagg                                                 14

<210> SEQ ID NO 937
<211> LENGTH: 14
<212> TYPE: DNA
<213> ORGANISM: Artificial Sequence
<220> FEATURE:
<223> OTHER INFORMATION: Synthetic Construct

<400> SEQUENCE: 937
tggggtcggg agga                                                 14

<210> SEQ ID NO 938
<211> LENGTH: 14
<212> TYPE: DNA
<213> ORGANISM: Artificial Sequence
<220> FEATURE:
<223> OTHER INFORMATION: Synthetic Construct

<400> SEQUENCE: 938
ggggtcggga ggag                                                 14

<210> SEQ ID NO 939
<211> LENGTH: 14
<212> TYPE: DNA
<213> ORGANISM: Artificial Sequence
<220> FEATURE:
<223> OTHER INFORMATION: Synthetic Construct

<400> SEQUENCE: 939
gggtcgggag gagt                                                 14

<210> SEQ ID NO 940
<211> LENGTH: 14
<212> TYPE: DNA
<213> ORGANISM: Artificial Sequence
<220> FEATURE:
<223> OTHER INFORMATION: Synthetic Construct

<400> SEQUENCE: 940
ggtcgggagg agtt                                                 14

<210> SEQ ID NO 941
<211> LENGTH: 14
<212> TYPE: DNA
<213> ORGANISM: Artificial Sequence
<220> FEATURE:
<223> OTHER INFORMATION: Synthetic Construct

<400> SEQUENCE: 941
gtcgggagga gttt                                                 14

<210> SEQ ID NO 942
<211> LENGTH: 14
<212> TYPE: DNA
<213> ORGANISM: Artificial Sequence
<220> FEATURE:
<223> OTHER INFORMATION: Synthetic Construct

<400> SEQUENCE: 942
tcgggaggag tttc                                                 14
```

```
<210> SEQ ID NO 943
<211> LENGTH: 14
<212> TYPE: DNA
<213> ORGANISM: Artificial Sequence
<220> FEATURE:
<223> OTHER INFORMATION: Synthetic Construct

<400> SEQUENCE: 943
cgggaggagt ttcg                                                        14

<210> SEQ ID NO 944
<211> LENGTH: 14
<212> TYPE: DNA
<213> ORGANISM: Artificial Sequence
<220> FEATURE:
<223> OTHER INFORMATION: Synthetic Construct

<400> SEQUENCE: 944
gggaggagtt tcgt                                                        14

<210> SEQ ID NO 945
<211> LENGTH: 14
<212> TYPE: DNA
<213> ORGANISM: Artificial Sequence
<220> FEATURE:
<223> OTHER INFORMATION: Synthetic Construct

<400> SEQUENCE: 945
ggaggagttt cgtt                                                        14

<210> SEQ ID NO 946
<211> LENGTH: 14
<212> TYPE: DNA
<213> ORGANISM: Artificial Sequence
<220> FEATURE:
<223> OTHER INFORMATION: Synthetic Construct

<400> SEQUENCE: 946
gaggagtttc gttt                                                        14

<210> SEQ ID NO 947
<211> LENGTH: 14
<212> TYPE: DNA
<213> ORGANISM: Artificial Sequence
<220> FEATURE:
<223> OTHER INFORMATION: Synthetic Construct

<400> SEQUENCE: 947
aggagtttcg tttt                                                        14

<210> SEQ ID NO 948
<211> LENGTH: 14
<212> TYPE: DNA
<213> ORGANISM: Artificial Sequence
<220> FEATURE:
<223> OTHER INFORMATION: Synthetic Construct

<400> SEQUENCE: 948
ggagtttcgt tttc                                                        14

<210> SEQ ID NO 949
<211> LENGTH: 14
<212> TYPE: DNA
<213> ORGANISM: Artificial Sequence
<220> FEATURE:
<223> OTHER INFORMATION: Synthetic Construct
```

<400> SEQUENCE: 949
gagtttcgtt ttcg                                                              14

<210> SEQ ID NO 950
<211> LENGTH: 14
<212> TYPE: DNA
<213> ORGANISM: Artificial Sequence
<220> FEATURE:
<223> OTHER INFORMATION: Synthetic Construct

<400> SEQUENCE: 950
agtttcgttt tcgg                                                              14

<210> SEQ ID NO 951
<211> LENGTH: 14
<212> TYPE: DNA
<213> ORGANISM: Artificial Sequence
<220> FEATURE:
<223> OTHER INFORMATION: Synthetic Construct

<400> SEQUENCE: 951
gtttcgtttt cggc                                                              14

<210> SEQ ID NO 952
<211> LENGTH: 14
<212> TYPE: DNA
<213> ORGANISM: Artificial Sequence
<220> FEATURE:
<223> OTHER INFORMATION: Synthetic Construct

<400> SEQUENCE: 952
tttcgttttc ggcg                                                              14

<210> SEQ ID NO 953
<211> LENGTH: 14
<212> TYPE: DNA
<213> ORGANISM: Artificial Sequence
<220> FEATURE:
<223> OTHER INFORMATION: Synthetic Construct

<400> SEQUENCE: 953
ttcgttttcg gcgg                                                              14

<210> SEQ ID NO 954
<211> LENGTH: 14
<212> TYPE: DNA
<213> ORGANISM: Artificial Sequence
<220> FEATURE:
<223> OTHER INFORMATION: Synthetic Construct

<400> SEQUENCE: 954
tcgttttcgg cgga                                                              14

<210> SEQ ID NO 955
<211> LENGTH: 14
<212> TYPE: DNA
<213> ORGANISM: Artificial Sequence
<220> FEATURE:
<223> OTHER INFORMATION: Synthetic Construct

<400> SEQUENCE: 955
cgttttcggc ggag                                                              14

<210> SEQ ID NO 956
<211> LENGTH: 14

```
<212> TYPE: DNA
<213> ORGANISM: Artificial Sequence
<220> FEATURE:
<223> OTHER INFORMATION: Synthetic Construct

<400> SEQUENCE: 956
gttttcggcg gagc                                                      14

<210> SEQ ID NO 957
<211> LENGTH: 14
<212> TYPE: DNA
<213> ORGANISM: Artificial Sequence
<220> FEATURE:
<223> OTHER INFORMATION: Synthetic Construct

<400> SEQUENCE: 957
ttttcggcgg agcg                                                      14

<210> SEQ ID NO 958
<211> LENGTH: 14
<212> TYPE: DNA
<213> ORGANISM: Artificial Sequence
<220> FEATURE:
<223> OTHER INFORMATION: Synthetic Construct

<400> SEQUENCE: 958
tttcggcgga gcgt                                                      14

<210> SEQ ID NO 959
<211> LENGTH: 14
<212> TYPE: DNA
<213> ORGANISM: Artificial Sequence
<220> FEATURE:
<223> OTHER INFORMATION: Synthetic Construct

<400> SEQUENCE: 959
ttcggcggag cgtt                                                      14

<210> SEQ ID NO 960
<211> LENGTH: 14
<212> TYPE: DNA
<213> ORGANISM: Artificial Sequence
<220> FEATURE:
<223> OTHER INFORMATION: Synthetic Construct

<400> SEQUENCE: 960
tcggcggagc gttt                                                      14

<210> SEQ ID NO 961
<211> LENGTH: 14
<212> TYPE: DNA
<213> ORGANISM: Artificial Sequence
<220> FEATURE:
<223> OTHER INFORMATION: Synthetic Construct

<400> SEQUENCE: 961
cggcggagcg tttg                                                      14

<210> SEQ ID NO 962
<211> LENGTH: 14
<212> TYPE: DNA
<213> ORGANISM: Artificial Sequence
<220> FEATURE:
<223> OTHER INFORMATION: Synthetic Construct

<400> SEQUENCE: 962
```
ggcggagcgt ttgt                                                          14

<210> SEQ ID NO 963
<211> LENGTH: 14
<212> TYPE: DNA
<213> ORGANISM: Artificial Sequence
<220> FEATURE:
<223> OTHER INFORMATION: Synthetic Construct

<400> SEQUENCE: 963
gcggagcgtt tgtc                                                          14

<210> SEQ ID NO 964
<211> LENGTH: 14
<212> TYPE: DNA
<213> ORGANISM: Artificial Sequence
<220> FEATURE:
<223> OTHER INFORMATION: Synthetic Construct

<400> SEQUENCE: 964
cggagcgttt gtcg                                                          14

<210> SEQ ID NO 965
<211> LENGTH: 14
<212> TYPE: DNA
<213> ORGANISM: Artificial Sequence
<220> FEATURE:
<223> OTHER INFORMATION: Synthetic Construct

<400> SEQUENCE: 965
ggagcgtttg tcgg                                                          14

<210> SEQ ID NO 966
<211> LENGTH: 14
<212> TYPE: DNA
<213> ORGANISM: Artificial Sequence
<220> FEATURE:
<223> OTHER INFORMATION: Synthetic Construct

<400> SEQUENCE: 966
gagcgtttgt cggt                                                          14

<210> SEQ ID NO 967
<211> LENGTH: 14
<212> TYPE: DNA
<213> ORGANISM: Artificial Sequence
<220> FEATURE:
<223> OTHER INFORMATION: Synthetic Construct

<400> SEQUENCE: 967
agcgtttgtc ggta                                                          14

<210> SEQ ID NO 968
<211> LENGTH: 14
<212> TYPE: DNA
<213> ORGANISM: Artificial Sequence
<220> FEATURE:
<223> OTHER INFORMATION: Synthetic Construct

<400> SEQUENCE: 968
gcgtttgtcg gtat                                                          14

<210> SEQ ID NO 969
<211> LENGTH: 14
<212> TYPE: DNA
<213> ORGANISM: Artificial Sequence -continued
<220> FEATURE:
<223> OTHER INFORMATION: Synthetic Construct

<400> SEQUENCE: 969
cgtttgtcgg tatt                                                        14

<210> SEQ ID NO 970
<211> LENGTH: 14
<212> TYPE: DNA
<213> ORGANISM: Artificial Sequence
<220> FEATURE:
<223> OTHER INFORMATION: Synthetic Construct

<400> SEQUENCE: 970
gtttgtcggt attt                                                        14

<210> SEQ ID NO 971
<211> LENGTH: 14
<212> TYPE: DNA
<213> ORGANISM: Artificial Sequence
<220> FEATURE:
<223> OTHER INFORMATION: Synthetic Construct

<400> SEQUENCE: 971
tttgtcggta ttta                                                        14

<210> SEQ ID NO 972
<211> LENGTH: 14
<212> TYPE: DNA
<213> ORGANISM: Artificial Sequence
<220> FEATURE:
<223> OTHER INFORMATION: Synthetic Construct

<400> SEQUENCE: 972
ttgtcggtat ttag                                                        14

<210> SEQ ID NO 973
<211> LENGTH: 14
<212> TYPE: DNA
<213> ORGANISM: Artificial Sequence
<220> FEATURE:
<223> OTHER INFORMATION: Synthetic Construct

<400> SEQUENCE: 973
tgtcggtatt tagt                                                        14

<210> SEQ ID NO 974
<211> LENGTH: 14
<212> TYPE: DNA
<213> ORGANISM: Artificial Sequence
<220> FEATURE:
<223> OTHER INFORMATION: Synthetic Construct

<400> SEQUENCE: 974
gtcggtattt agtt                                                        14

<210> SEQ ID NO 975
<211> LENGTH: 14
<212> TYPE: DNA
<213> ORGANISM: Artificial Sequence
<220> FEATURE:
<223> OTHER INFORMATION: Synthetic Construct

<400> SEQUENCE: 975
tcggtattta gttt                                                        14

<210> SEQ ID NO 976
<211> LENGTH: 14
<212> TYPE: DNA
<213> ORGANISM: Artificial Sequence
<220> FEATURE:
<223> OTHER INFORMATION: Synthetic Construct

<400> SEQUENCE: 976
cggtatttag tttt                                                        14

<210> SEQ ID NO 977
<211> LENGTH: 14
<212> TYPE: DNA
<213> ORGANISM: Artificial Sequence
<220> FEATURE:
<223> OTHER INFORMATION: Synthetic Construct

<400> SEQUENCE: 977
ggtatttagt tttt                                                        14

<210> SEQ ID NO 978
<211> LENGTH: 14
<212> TYPE: DNA
<213> ORGANISM: Artificial Sequence
<220> FEATURE:
<223> OTHER INFORMATION: Synthetic Construct

<400> SEQUENCE: 978
gtatttagtt tttt                                                        14

<210> SEQ ID NO 979
<211> LENGTH: 14
<212> TYPE: DNA
<213> ORGANISM: Artificial Sequence
<220> FEATURE:
<223> OTHER INFORMATION: Synthetic Construct

<400> SEQUENCE: 979
tatttagttt tttt                                                        14

<210> SEQ ID NO 980
<211> LENGTH: 14
<212> TYPE: DNA
<213> ORGANISM: Artificial Sequence
<220> FEATURE:
<223> OTHER INFORMATION: Synthetic Construct

<400> SEQUENCE: 980
atttagtttt tttt                                                        14

<210> SEQ ID NO 981
<211> LENGTH: 14
<212> TYPE: DNA
<213> ORGANISM: Artificial Sequence
<220> FEATURE:
<223> OTHER INFORMATION: Synthetic Construct

<400> SEQUENCE: 981
tttagttttt tttt                                                        14

<210> SEQ ID NO 982
<211> LENGTH: 14
<212> TYPE: DNA
<213> ORGANISM: Artificial Sequence
<220> FEATURE:
<223> OTHER INFORMATION: Synthetic Construct

<400> SEQUENCE: 982 ttagttttttt tttt                                          14

<210> SEQ ID NO 983
<211> LENGTH: 14
<212> TYPE: DNA
<213> ORGANISM: Artificial Sequence
<220> FEATURE:
<223> OTHER INFORMATION: Synthetic Construct

<400> SEQUENCE: 983 tagtttttttt tttt                                          14

<210> SEQ ID NO 984
<211> LENGTH: 14
<212> TYPE: DNA
<213> ORGANISM: Artificial Sequence
<220> FEATURE:
<223> OTHER INFORMATION: Synthetic Construct

<400> SEQUENCE: 984
agtttttttt tttc                                           14

<210> SEQ ID NO 985
<211> LENGTH: 14
<212> TYPE: DNA
<213> ORGANISM: Artificial Sequence
<220> FEATURE:
<223> OTHER INFORMATION: Synthetic Construct

<400> SEQUENCE: 985 gtttttttttt ttcg                                          14

<210> SEQ ID NO 986
<211> LENGTH: 14
<212> TYPE: DNA
<213> ORGANISM: Artificial Sequence
<220> FEATURE:
<223> OTHER INFORMATION: Synthetic Construct

<400> SEQUENCE: 986
tttttttttt tcgt                                           14

<210> SEQ ID NO 987
<211> LENGTH: 14
<212> TYPE: DNA
<213> ORGANISM: Artificial Sequence
<220> FEATURE:
<223> OTHER INFORMATION: Synthetic Construct

<400> SEQUENCE: 987
tttttttttt cgtt                                           14

<210> SEQ ID NO 988
<211> LENGTH: 14
<212> TYPE: DNA
<213> ORGANISM: Artificial Sequence
<220> FEATURE:
<223> OTHER INFORMATION: Synthetic Construct

<400> SEQUENCE: 988 ttttttttttc gttt                                          14

<210> SEQ ID NO 989

```
<211> LENGTH: 14
<212> TYPE: DNA
<213> ORGANISM: Artificial Sequence
<220> FEATURE:
<223> OTHER INFORMATION: Synthetic Construct

<400> SEQUENCE: 989 tttttttcg tttt                                                         14

<210> SEQ ID NO 990
<211> LENGTH: 14
<212> TYPE: DNA
<213> ORGANISM: Artificial Sequence
<220> FEATURE:
<223> OTHER INFORMATION: Synthetic Construct

<400> SEQUENCE: 990
tttttttcgt tttg                                                        14

<210> SEQ ID NO 991
<211> LENGTH: 14
<212> TYPE: DNA
<213> ORGANISM: Artificial Sequence
<220> FEATURE:
<223> OTHER INFORMATION: Synthetic Construct

<400> SEQUENCE: 991 tttttcgtt ttgg                                                         14

<210> SEQ ID NO 992
<211> LENGTH: 14
<212> TYPE: DNA
<213> ORGANISM: Artificial Sequence
<220> FEATURE:
<223> OTHER INFORMATION: Synthetic Construct

<400> SEQUENCE: 992
tttttcgttt tggc                                                        14

<210> SEQ ID NO 993
<211> LENGTH: 14
<212> TYPE: DNA
<213> ORGANISM: Artificial Sequence
<220> FEATURE:
<223> OTHER INFORMATION: Synthetic Construct

<400> SEQUENCE: 993
ttttcgtttt ggcg                                                        14

<210> SEQ ID NO 994
<211> LENGTH: 14
<212> TYPE: DNA
<213> ORGANISM: Artificial Sequence
<220> FEATURE:
<223> OTHER INFORMATION: Synthetic Construct

<400> SEQUENCE: 994
tttcgttttg gcgg                                                        14

<210> SEQ ID NO 995
<211> LENGTH: 14
<212> TYPE: DNA
<213> ORGANISM: Artificial Sequence
<220> FEATURE:
<223> OTHER INFORMATION: Synthetic Construct

<400> SEQUENCE: 995
```
ttcgttttgg cggt                                                         14

<210> SEQ ID NO 996
<211> LENGTH: 14
<212> TYPE: DNA
<213> ORGANISM: Artificial Sequence
<220> FEATURE:
<223> OTHER INFORMATION: Synthetic Construct

<400> SEQUENCE: 996
tcgttttggc ggtg                                                         14

<210> SEQ ID NO 997
<211> LENGTH: 14
<212> TYPE: DNA
<213> ORGANISM: Artificial Sequence
<220> FEATURE:
<223> OTHER INFORMATION: Synthetic Construct

<400> SEQUENCE: 997
cgttttggcg gtgg                                                         14

<210> SEQ ID NO 998
<211> LENGTH: 14
<212> TYPE: DNA
<213> ORGANISM: Artificial Sequence
<220> FEATURE:
<223> OTHER INFORMATION: Synthetic Construct

<400> SEQUENCE: 998
gttttggcgg tggg                                                         14

<210> SEQ ID NO 999
<211> LENGTH: 14
<212> TYPE: DNA
<213> ORGANISM: Artificial Sequence
<220> FEATURE:
<223> OTHER INFORMATION: Synthetic Construct

<400> SEQUENCE: 999
ttttggcggt ggga                                                         14

<210> SEQ ID NO 1000
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1000
tttggcggtg ggaa                                                         14

<210> SEQ ID NO 1001
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1001
ttggcggtgg gaat                                                         14

<210> SEQ ID NO 1002
<211> LENGTH: 14
<212> TYPE: DNA

```
<213> ORGANISM: Artificial Sequence
<220> FEATURE:
<223> OTHER INFORMATION: Synthetic Construct

<400> SEQUENCE: 1002
tggcggtggg aatt                                                     14

<210> SEQ ID NO 1003
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1003
ggcggtggga attt                                                     14

<210> SEQ ID NO 1004
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1004
gcggtgggaa tttg                                                     14

<210> SEQ ID NO 1005
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1005
cggtgggaat ttga                                                     14

<210> SEQ ID NO 1006
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1006
ggtgggaatt tgat                                                     14

<210> SEQ ID NO 1007
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1007
gtgggaattt gatt                                                     14

<210> SEQ ID NO 1008
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1008
tgggaatttg attt                                                     14
```

```
<210> SEQ ID NO 1009
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1009
gggaatttga tttt                                                       14

<210> SEQ ID NO 1010
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1010
ggaatttgat tttt                                                       14

<210> SEQ ID NO 1011
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1011
gaatttgatt tttt                                                       14

<210> SEQ ID NO 1012
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1012
aatttgattt tttt                                                       14

<210> SEQ ID NO 1013
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1013
atttgatttt tttt                                                       14

<210> SEQ ID NO 1014
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1014
tttgattttt tttt                                                       14

<210> SEQ ID NO 1015
<211> LENGTH: 14
<212> TYPE: DNA
<213> ORGANISM: Artificial Sequence
<220> FEATURE:
```

<223> OTHER INFORMATION: Synthetic Construct

<400> SEQUENCE: 1015
ttgatttttt tttt                                                        14

<210> SEQ ID NO 1016
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1016
tgattttttt tttt                                                        14

<210> SEQ ID NO 1017
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1017 gattttttt tttg                                                         14

<210> SEQ ID NO 1018
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1018 atttttttt ttgg                                                         14

<210> SEQ ID NO 1019
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1019
tttttttttt tggt                                                        14

<210> SEQ ID NO 1020
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1020
tttttttttt ggtc                                                        14

<210> SEQ ID NO 1021
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1021 ttttttttg gtcg                                                         14

```
<210> SEQ ID NO 1022
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1022 tttttttttgg tcgc                                                         14

<210> SEQ ID NO 1023
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1023
tttttttggt cgcg                                                          14

<210> SEQ ID NO 1024
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1024 tttttggtc gcgt                                                           14

<210> SEQ ID NO 1025
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1025
tttttggtcg cgtt                                                          14

<210> SEQ ID NO 1026
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1026
ttttggtcgc gttt                                                          14

<210> SEQ ID NO 1027
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1027
tttggtcgcg tttc                                                          14

<210> SEQ ID NO 1028
<211> LENGTH: 14
<212> TYPE: DNA
<213> ORGANISM: Artificial Sequence
<220> FEATURE:
<223> OTHER INFORMATION: Synthetic Construct
```

```
<400> SEQUENCE: 1028
ttggtcgcgt ttcg                                                      14

<210> SEQ ID NO 1029
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1029
tggtcgcgtt tcgg                                                      14

<210> SEQ ID NO 1030
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1030
ggtcgcgttt cggg                                                      14

<210> SEQ ID NO 1031
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1031
gtcgcgtttc gggg                                                      14

<210> SEQ ID NO 1032
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1032
tcgcgtttcg gggg                                                      14

<210> SEQ ID NO 1033
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1033
cgcgtttcgg gggt                                                      14

<210> SEQ ID NO 1034
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1034
gcgtttcggg ggtt                                                      14

<210> SEQ ID NO 1035
<211> LENGTH: 14
```

```
<212> TYPE: DNA
<213> ORGANISM: Artificial Sequence
<220> FEATURE:
<223> OTHER INFORMATION: Synthetic Construct

<400> SEQUENCE: 1035
cgtttcgggg gttg                                             14

<210> SEQ ID NO 1036
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1036
gtttcggggg ttgg                                             14

<210> SEQ ID NO 1037
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1037 tttcggggt tgga                                              14

<210> SEQ ID NO 1038
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1038
ttcgggggtt ggag                                             14

<210> SEQ ID NO 1039
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1039 tcggggttg gagt                                              14

<210> SEQ ID NO 1040
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1040 cggggttgg agtt                                              14

<210> SEQ ID NO 1041
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1041
``` ggggttgga gttt                    14

<210> SEQ ID NO 1042
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1042
ggggttggag tttg                    14

<210> SEQ ID NO 1043
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1043
gggttggagt ttgt                    14

<210> SEQ ID NO 1044
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1044
ggttggagtt tgtt                    14

<210> SEQ ID NO 1045
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1045
gttggagttt gttt                    14

<210> SEQ ID NO 1046
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1046
ttggagtttg tttt                    14

<210> SEQ ID NO 1047
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1047
tggagtttgt tttt                    14

<210> SEQ ID NO 1048
<211> LENGTH: 14
<212> TYPE: DNA
<213> ORGANISM: Artificial Sequence

```
<220> FEATURE:
<223> OTHER INFORMATION: Synthetic Construct

<400> SEQUENCE: 1048
ggagtttgtt tttt                                                        14

<210> SEQ ID NO 1049
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1049
gagtttgttt tttt                                                        14

<210> SEQ ID NO 1050
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1050
agtttgtttt ttta                                                        14

<210> SEQ ID NO 1051
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1051
gtttgttttt ttac                                                        14

<210> SEQ ID NO 1052
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1052 tttgttttt tacg                                                         14

<210> SEQ ID NO 1053
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1053
ttgttttttt acgt                                                        14

<210> SEQ ID NO 1054
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1054
tgttttttta cgtc                                                        14
```

<210> SEQ ID NO 1055
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1055
gtttttttac gtcg                                                    14

<210> SEQ ID NO 1056
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1056 ttttttacg tcgt                                                     14

<210> SEQ ID NO 1057
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1057 tttttacgt cgtt                                                     14

<210> SEQ ID NO 1058
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1058
tttttacgtc gttt                                                    14

<210> SEQ ID NO 1059
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1059
ttttacgtcg ttta                                                    14

<210> SEQ ID NO 1060
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1060
tttacgtcgt ttaa                                                    14

<210> SEQ ID NO 1061
<211> LENGTH: 14
<212> TYPE: DNA
<213> ORGANISM: Artificial Sequence
<220> FEATURE:
<223> OTHER INFORMATION: Synthetic Construct

```
<400> SEQUENCE: 1061
ttacgtcgtt taat                                                       14

<210> SEQ ID NO 1062
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1062
tacgtcgttt aatg                                                       14

<210> SEQ ID NO 1063
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1063
acgtcgttta atga                                                       14

<210> SEQ ID NO 1064
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1064
cgtcgtttaa tgag                                                       14

<210> SEQ ID NO 1065
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1065
gtcgtttaat gagc                                                       14

<210> SEQ ID NO 1066
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1066
tcgtttaatg agcg                                                       14

<210> SEQ ID NO 1067
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1067
cgtttaatga gcgt                                                       14

<210> SEQ ID NO 1068
```

```
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1068
gtttaatgag cgtt                                                         14

<210> SEQ ID NO 1069
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1069
tttaatgagc gttt                                                         14

<210> SEQ ID NO 1070
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1070
ttaatgagcg tttt                                                         14

<210> SEQ ID NO 1071
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1071
taatgagcgt tttt                                                         14

<210> SEQ ID NO 1072
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1072
aatgagcgtt tttt                                                         14

<210> SEQ ID NO 1073
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1073
atgagcgttt ttta                                                         14

<210> SEQ ID NO 1074
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1074
```
tgagcgtttt ttaa                                                14

<210> SEQ ID NO 1075
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1075
gagcgttttt taaa                                                14

<210> SEQ ID NO 1076
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1076 agcgttttt aaag                                                 14

<210> SEQ ID NO 1077
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1077 gcgttttta aagg                                                 14

<210> SEQ ID NO 1078
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1078
cgttttttaa aggg                                                14

<210> SEQ ID NO 1079
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1079
gttttttaaa ggga                                                14

<210> SEQ ID NO 1080
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1080
ttttttaaag ggaa                                                14

<210> SEQ ID NO 1081
<211> LENGTH: 14
<212> TYPE: DNA

```
<213> ORGANISM: Artificial Sequence
<220> FEATURE:
<223> OTHER INFORMATION: Synthetic Construct

<400> SEQUENCE: 1081
tttttaaagg gaat                                                        14

<210> SEQ ID NO 1082
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1082
ttttaaaggg aatt                                                        14

<210> SEQ ID NO 1083
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1083
tttaaaggga attg                                                        14

<210> SEQ ID NO 1084
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1084
ttaaagggaa ttgt                                                        14

<210> SEQ ID NO 1085
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1085
taaagggaat tgtt                                                        14

<210> SEQ ID NO 1086
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1086
aaagggaatt gttt                                                        14

<210> SEQ ID NO 1087
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1087
aagggaattg tttt                                                        14
```

<210> SEQ ID NO 1088
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1088
agggaattgt tttt                                                         14

<210> SEQ ID NO 1089
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1089
gggaattgtt tttt                                                         14

<210> SEQ ID NO 1090
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1090
ggaattgttt tttt                                                         14

<210> SEQ ID NO 1091
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1091
gaattgtttt tttg                                                         14

<210> SEQ ID NO 1092
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1092
aattgttttt ttgg                                                         14

<210> SEQ ID NO 1093
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1093
attgtttttt tggt                                                         14

<210> SEQ ID NO 1094
<211> LENGTH: 14
<212> TYPE: DNA
<213> ORGANISM: Artificial Sequence
<220> FEATURE:

<223> OTHER INFORMATION: Synthetic Construct

<400> SEQUENCE: 1094
ttgttttttt ggtt                                                          14

<210> SEQ ID NO 1095
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1095 tgttttttg gttt                                                           14

<210> SEQ ID NO 1096
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1096 gttttttgg tttt                                                           14

<210> SEQ ID NO 1097
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1097 ttttttggt tttt                                                           14

<210> SEQ ID NO 1098
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1098 tttttggtt tttt                                                           14

<210> SEQ ID NO 1099
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1099 ttttggttt tttt                                                           14

<210> SEQ ID NO 1100
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1100
ttttggtttt tttt                                                          14

```
<210> SEQ ID NO 1101
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1101
tttggttttt tttc                                                      14

<210> SEQ ID NO 1102
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1102
ttggtttttt ttcg                                                      14

<210> SEQ ID NO 1103
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1103
tggttttttt tcgt                                                      14

<210> SEQ ID NO 1104
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1104
ggtttttttt cgtt                                                      14

<210> SEQ ID NO 1105
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1105
gttttttttc gttc                                                      14

<210> SEQ ID NO 1106
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1106
ttttttttcg ttcg                                                      14

<210> SEQ ID NO 1107
<211> LENGTH: 14
<212> TYPE: DNA
<213> ORGANISM: Artificial Sequence
<220> FEATURE:
<223> OTHER INFORMATION: Synthetic Construct
```

<400> SEQUENCE: 1107
tttttttcgt tcgt                                                14

<210> SEQ ID NO 1108
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1108 tttttttcgtt cgta                                               14

<210> SEQ ID NO 1109
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1109
tttttcgttc gtag                                                14

<210> SEQ ID NO 1110
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1110
ttttcgttcg tagt                                                14

<210> SEQ ID NO 1111
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1111
tttcgttcgt agtt                                                14

<210> SEQ ID NO 1112
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1112
ttcgttcgta gttg                                                14

<210> SEQ ID NO 1113
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1113
tcgttcgtag ttgt                                                14

<210> SEQ ID NO 1114
<211> LENGTH: 14

```
<212> TYPE: DNA
<213> ORGANISM: Artificial Sequence
<220> FEATURE:
<223> OTHER INFORMATION: Synthetic Construct

<400> SEQUENCE: 1114
cgttcgtagt tgtt                                                       14

<210> SEQ ID NO 1115
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1115
gttcgtagtt gttt                                                       14

<210> SEQ ID NO 1116
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1116
ttcgtagttg tttt                                                       14

<210> SEQ ID NO 1117
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1117
tcgtagttgt tttt                                                       14

<210> SEQ ID NO 1118
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1118
cgtagttgtt ttta                                                       14

<210> SEQ ID NO 1119
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1119
gtagttgttt ttat                                                       14

<210> SEQ ID NO 1120
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1120
```
tagttgtttt tatt                                                        14

<210> SEQ ID NO 1121
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1121
agttgttttt attt                                                        14

<210> SEQ ID NO 1122
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1122
gttgttttta tttg                                                        14

<210> SEQ ID NO 1123
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1123
ttgtttttat ttgg                                                        14

<210> SEQ ID NO 1124
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1124
tgttttattt tggg                                                        14

<210> SEQ ID NO 1125
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1125
gttttatttt gggc                                                        14

<210> SEQ ID NO 1126
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1126 ttttatttg ggcg                                                         14

<210> SEQ ID NO 1127
<211> LENGTH: 14
<212> TYPE: DNA
<213> ORGANISM: Artificial Sequence

```
<220> FEATURE:
<223> OTHER INFORMATION: Synthetic Construct

<400> SEQUENCE: 1127
ttttatttgg gcgt                                                            14

<210> SEQ ID NO 1128
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1128
tttatttggg cgtt                                                            14

<210> SEQ ID NO 1129
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1129
ttatttgggc gtta                                                            14

<210> SEQ ID NO 1130
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1130
tatttgggcg ttag                                                            14

<210> SEQ ID NO 1131
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1131
atttgggcgt tagg                                                            14

<210> SEQ ID NO 1132
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1132
tttgggcgtt agga                                                            14

<210> SEQ ID NO 1133
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1133
ttgggcgtta ggag                                                            14
```

<210> SEQ ID NO 1134
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1134
tgggcgttag gagt                                                         14

<210> SEQ ID NO 1135
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1135
gggcgttagg agtt                                                         14

<210> SEQ ID NO 1136
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1136
ggcgttagga gttt                                                         14

<210> SEQ ID NO 1137
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1137
gcgttaggag tttt                                                         14

<210> SEQ ID NO 1138
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1138
cgttaggagt tttg                                                         14

<210> SEQ ID NO 1139
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1139
gttaggagtt ttgt                                                         14

<210> SEQ ID NO 1140
<211> LENGTH: 14
<212> TYPE: DNA
<213> ORGANISM: Artificial Sequence
<220> FEATURE:
<223> OTHER INFORMATION: Synthetic Construct

```
<400> SEQUENCE: 1140
ttaggagttt tgtt                                                     14

<210> SEQ ID NO 1141
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1141
gaacgcattt atcc                                                     14

<210> SEQ ID NO 1142
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1142
aaataacgcc aacg                                                     14

<210> SEQ ID NO 1143
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1143
caaaaacctc tacg                                                     14

<210> SEQ ID NO 1144
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1144
ctccgtcctt ccca                                                     14

<210> SEQ ID NO 1145
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1145
cgaaataaaa ccgt                                                     14

<210> SEQ ID NO 1146
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1146
aataatatac gaaa                                                     14

<210> SEQ ID NO 1147
```

```
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1147
aaacactcgc gaat                                                   14

<210> SEQ ID NO 1148
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1148
attacctcgc ccta                                                   14

<210> SEQ ID NO 1149
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1149
gttccgtacc tccc                                                   14

<210> SEQ ID NO 1150
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1150
gaaaaaaaaa tcgc                                                   14

<210> SEQ ID NO 1151
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1151
aaaatatcct cccg                                                   14

<210> SEQ ID NO 1152
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1152
aacgccgtat caca                                                   14

<210> SEQ ID NO 1153
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1153
```
aaaaaacgaa cgta                                               14

<210> SEQ ID NO 1154
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1154
gacaaacgct ccgc                                               14

<210> SEQ ID NO 1155
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1155
acgcgaccaa aaaa                                               14

<210> SEQ ID NO 1156
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1156
tttaaaaaac gctc                                               14

<210> SEQ ID NO 1157
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1157
aaactcctaa cgcc                                               14

<210> SEQ ID NO 1158
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1158
aaacgaaatc taaa                                               14

<210> SEQ ID NO 1159
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1159
aaaaaacgta aaaa                                               14

<210> SEQ ID NO 1160
<211> LENGTH: 26
<212> TYPE: DNA

```
<213> ORGANISM: Artificial Sequence
<220> FEATURE:
<223> OTHER INFORMATION: Synthetic Construct

<400> SEQUENCE: 1160
tttaagtata tatcggagat tcgttg                                26

<210> SEQ ID NO 1161
<211> LENGTH: 26
<212> TYPE: DNA
<213> ORGANISM: Artificial Sequence
<220> FEATURE:
<223> OTHER INFORMATION: Synthetic Construct

<400> SEQUENCE: 1161
tttttttttt ttagaaaagc gttgtt                                26

<210> SEQ ID NO 1162
<211> LENGTH: 26
<212> TYPE: DNA
<213> ORGANISM: Artificial Sequence
<220> FEATURE:
<223> OTHER INFORMATION: Synthetic Construct

<400> SEQUENCE: 1162
tatcgagaat tgcggtttgg tttagt                                26

<210> SEQ ID NO 1163
<211> LENGTH: 26
<212> TYPE: DNA
<213> ORGANISM: Artificial Sequence
<220> FEATURE:
<223> OTHER INFORMATION: Synthetic Construct

<400> SEQUENCE: 1163
ttttcggcgg gttttgttgc gtggtt                                26

<210> SEQ ID NO 1164
<211> LENGTH: 26
<212> TYPE: DNA
<213> ORGANISM: Artificial Sequence
<220> FEATURE:
<223> OTHER INFORMATION: Synthetic Construct

<400> SEQUENCE: 1164
ggagtttggg tcgggttcgc gaggga                                26

<210> SEQ ID NO 1165
<211> LENGTH: 26
<212> TYPE: DNA
<213> ORGANISM: Artificial Sequence
<220> FEATURE:
<223> OTHER INFORMATION: Synthetic Construct

<400> SEQUENCE: 1165
tgatttggaa atttcggggt tttttt                                26

<210> SEQ ID NO 1166
<211> LENGTH: 26
<212> TYPE: DNA
<213> ORGANISM: Artificial Sequence
<220> FEATURE:
<223> OTHER INFORMATION: Synthetic Construct

<400> SEQUENCE: 1166
ggggagatgg gggttagatt taagag                                26
```

<210> SEQ ID NO 1167
<211> LENGTH: 26
<212> TYPE: DNA
<213> ORGANISM: Artificial Sequence
<220> FEATURE:
<223> OTHER INFORMATION: Synthetic Construct

<400> SEQUENCE: 1167
tttttttgtt tgatgttttt tgcggt                                          26

<210> SEQ ID NO 1168
<211> LENGTH: 26
<212> TYPE: DNA
<213> ORGANISM: Artificial Sequence
<220> FEATURE:
<223> OTHER INFORMATION: Synthetic Construct

<400> SEQUENCE: 1168
taggcgattt tttaagggga tattgg                                          26

<210> SEQ ID NO 1169
<211> LENGTH: 26
<212> TYPE: DNA
<213> ORGANISM: Artificial Sequence
<220> FEATURE:
<223> OTHER INFORMATION: Synthetic Construct

<400> SEQUENCE: 1169
tcggttattg gatttttagt tttgcg                                          26

<210> SEQ ID NO 1170
<211> LENGTH: 26
<212> TYPE: DNA
<213> ORGANISM: Artificial Sequence
<220> FEATURE:
<223> OTHER INFORMATION: Synthetic Construct

<400> SEQUENCE: 1170
gaggttgtat cgcggggcgt taggga                                          26

<210> SEQ ID NO 1171
<211> LENGTH: 26
<212> TYPE: DNA
<213> ORGANISM: Artificial Sequence
<220> FEATURE:
<223> OTHER INFORMATION: Synthetic Construct

<400> SEQUENCE: 1171
tcgtaagtag ggcgaggcgg ggtacg                                          26

<210> SEQ ID NO 1172
<211> LENGTH: 26
<212> TYPE: DNA
<213> ORGANISM: Artificial Sequence
<220> FEATURE:
<223> OTHER INFORMATION: Synthetic Construct

<400> SEQUENCE: 1172
ttgggggata gaggtttttt tttcgt                                          26

<210> SEQ ID NO 1173
<211> LENGTH: 26
<212> TYPE: DNA
<213> ORGANISM: Artificial Sequence
<220> FEATURE:

<223> OTHER INFORMATION: Synthetic Construct

<400> SEQUENCE: 1173
tggggtcggg aggagtttcg ttttcg                                              26

<210> SEQ ID NO 1174
<211> LENGTH: 26
<212> TYPE: DNA
<213> ORGANISM: Artificial Sequence
<220> FEATURE:
<223> OTHER INFORMATION: Synthetic Construct

<400> SEQUENCE: 1174
gttttggcgg tgggaatttg attttt                                              26

<210> SEQ ID NO 1175
<211> LENGTH: 26
<212> TYPE: DNA
<213> ORGANISM: Artificial Sequence
<220> FEATURE:
<223> OTHER INFORMATION: Synthetic Construct

<400> SEQUENCE: 1175
gagtttgttt ttttacgtcg tttaat                                              26

<210> SEQ ID NO 1176
<211> LENGTH: 26
<212> TYPE: DNA
<213> ORGANISM: Artificial Sequence
<220> FEATURE:
<223> OTHER INFORMATION: Synthetic Construct

<400> SEQUENCE: 1176
ttttcgttcg tagttgtttt tatttg                                              26

<210> SEQ ID NO 1177
<211> LENGTH: 26
<212> TYPE: DNA
<213> ORGANISM: Artificial Sequence
<220> FEATURE:
<223> OTHER INFORMATION: Synthetic Construct

<400> SEQUENCE: 1177
gttgggttag gtggaagttt gagtat                                              26

<210> SEQ ID NO 1178
<211> LENGTH: 26
<212> TYPE: DNA
<213> ORGANISM: Artificial Sequence
<220> FEATURE:
<223> OTHER INFORMATION: Synthetic Construct

<400> SEQUENCE: 1178
gtgcggttgt ttttggtttt tttggt                                              26

<210> SEQ ID NO 1179
<211> LENGTH: 25
<212> TYPE: DNA
<213> ORGANISM: Artificial Sequence
<220> FEATURE:
<223> OTHER INFORMATION: Synthetic Construct

<400> SEQUENCE: 1179
tagaaattaa taagtgagag ggcgt                                               25

```
<210> SEQ ID NO 1180
<211> LENGTH: 22
<212> TYPE: DNA
<213> ORGANISM: Artificial Sequence
<220> FEATURE:
<223> OTHER INFORMATION: Synthetic Construct

<400> SEQUENCE: 1180
gactcaaact cgaaaactcg aa                                              22
```